US010342829B2

(12) United States Patent
Smith et al.

(10) Patent No.: US 10,342,829 B2
(45) Date of Patent: Jul. 9, 2019

(54) MULTI-CHAIN CHIMERIC ANTIGEN RECEPTOR AND USES THEREOF

(71) Applicant: CELLECTIS, Paris (FR)

(72) Inventors: Julianne Smith, Le plessis Robinson (FR); Andrew Scharenberg, Seattle, WA (US); Cecile Mannioui, Villiers sur Marne (FR); Justin Eyquem, Paris (FR)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 14/018,021

(22) Filed: Sep. 4, 2013

(65) Prior Publication Data

US 2014/0134142 A1 May 15, 2014

Related U.S. Application Data

(63) Continuation-in-part of application No. 13/942,191, filed on Jul. 15, 2013, now abandoned, and a continuation-in-part of application No. 13/892,805, filed on May 13, 2013, and a continuation-in-part of application No. PCT/US2013/040766, filed on May 13, 2013, and a continuation-in-part of application No. PCT/US2013/040755, filed on May 13, 2013.

(60) Provisional application No. 61/696,612, filed on Sep. 4, 2012, provisional application No. 61/651,933, filed on May 25, 2012.

(51) Int. Cl.

| | |
|---|---|
| ***A61K 35/17*** | (2015.01) |
| ***A61K 38/00*** | (2006.01) |
| ***C07K 16/28*** | (2006.01) |
| ***C07K 14/705*** | (2006.01) |
| ***C07K 14/725*** | (2006.01) |
| ***C12N 5/0783*** | (2010.01) |

(52) U.S. Cl.

CPC .......... *A61K 35/17* (2013.01); *C07K 14/7051* (2013.01); *C07K 14/70517* (2013.01); *C07K 14/70521* (2013.01); *C07K 14/70578* (2013.01); *C07K 16/28* (2013.01); *C07K 16/2803* (2013.01); *C12N 5/0636* (2013.01); *A61K 38/00* (2013.01); *C07K 2317/14* (2013.01); *C07K 2317/24* (2013.01); *C07K 2317/569* (2013.01); *C07K 2317/622* (2013.01); *C07K 2319/00* (2013.01); *C07K 2319/03* (2013.01); *C07K 2319/74* (2013.01); *C12N 2501/39* (2013.01); *C12N 2501/51* (2013.01); *C12N 2501/515* (2013.01); *C12N 2501/599* (2013.01); *C12N 2502/99* (2013.01); *C12N 2510/00* (2013.01)

(58) Field of Classification Search

CPC .... A61K 35/17; C07K 14/7051; C07K 16/28; C07K 16/2803; C07K 14/70521; C07K 14/70517; C07K 14/70578; C07K 2317/569; C07K 2317/24; C07K 2317/62; C07K 2319/00; C07K 2319/03; C07K 2319/74; C12N 250/51; C12N 250/515

See application file for complete search history.

(56) References Cited

U.S. PATENT DOCUMENTS

| | | | | |
|---|---|---|---|---|
| 5,770,396 A * | 6/1998 | Kinet | C07K 16/283 435/252.3 |
| 8,946,385 B2 * | 2/2015 | Kawai | C07K 14/70535 530/350 |
| 2010/0035280 A1 * | 2/2010 | Kawai | C07K 14/70535 435/7.21 |
| 2015/0368342 A1 * | 12/2015 | Wu | C07K 16/2803 424/134.1 |

FOREIGN PATENT DOCUMENTS

| | | |
|---|---|---|
| EA | 009956 B1 | 4/2008 |
| JP | H07-506486 A | 7/1995 |
| WO | WO 93/19163 A1 | 9/1993 |
| WO | WO 93/21317 A1 | 10/1993 |
| WO | 03/020759 A2 | 3/2003 |
| WO | WO2010/027423 A2 | 3/2010 |
| WO | WO2010/027423 A3 | 3/2010 |
| WO | WO 2012/079000 A1 | 6/2012 |

OTHER PUBLICATIONS

International Search Report and Written Opinion dated Nov. 13, 2013 in PCT/US2013/058005.
Chisei Ra et al., "Complete Structure of the Mouse Mast Cell Receptor for IgE (FcεRI) and Surface Expression of Chimeric Receptors (Rat-Mouse-Human) on Transfected Cells", The Journal of Biological Chemistry, National Institute of Health, vol. 264, No. 26, XP-055086298, 1989, pp. 15323-15327.
Nicole M. Haynes et al., "Redirecting Mouse CTL Against Colon Carcinoma: Superior Signaling Efficacy of Single-Chain Variable Domain Chimeras Containing TCR-ζ vs FcεRI-γ", The Journal of Immunology, XP-055086325, Jan. 1, 2001, pp. 182-187 and Cover page.

(Continued)

*Primary Examiner* — Ruixiang Li

(74) *Attorney, Agent, or Firm* — Arrigo, Lee, Guttman & Mouta-Bellum LLP

(57) ABSTRACT

The present invention relates to a new generation of chimeric antigen receptors (CAR) referred to as multi-chain CARs. Such CARs, which aim to redirect immune cell specificity and reactivity toward a selected target exploiting the ligand-binding domain properties, comprise separate extracellular ligand binding and signaling domains in different transmembrane polypeptides. 91The signaling domains are designed to assemble in juxtamembrane position, which forms flexible architecture closer to natural receptors, that confers optimal signal transduction. The invention encompasses the polynucleotides, vectors encoding said multi-chain CAR and the isolated cells expressing them at their surface, in particularly for their use in immunotherapy. The invention opens the way to efficient adoptive immunotherapy strategies for treating cancer and viral infections.

6 Claims, 35 Drawing Sheets

Figure 1:
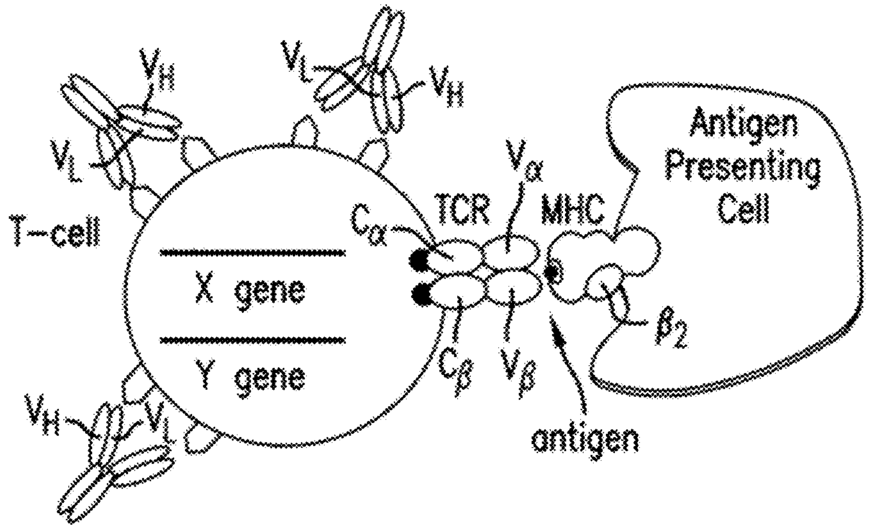

Specification includes a Sequence Listing.

(56) References Cited

OTHER PUBLICATIONS

International Search Report and Written Opinion dated Jul. 25, 2013 in PCT/US2013/040755.
A. Mizoguchi et al., "Pathogenic Role of IL-4, but not IFN-gamma in Colitis of TCRalpha Knockout Mice", Gastroenterology, vol. 114, XP-027469136, Apr. 15, 1998, p. A1041.
Hiroki Torikai et al., "A Foundation for Universal T-cell Based Immunotherapy: T-cells Engineered to Express a CD19-specific Chimeric-antigen-receptor and Eliminate Expression of Endogenous TCR", Blood, vol. 119, No. 24, XP-55071623, Jun. 14, 2012, pp. 5697-5705 and cover page.
Kyun-Do Kim et al., "Synergistic Inhibition of T-cell Activation by a Cell-permeable ZAP-70 Mutant and ctCTLA-4", Biochemical and Biophysical Research Communications, vol. 381, No. 3, XP-026422294, Apr. 10, 2009, pp. 355-360.
Magdy M. Mahfouz et al., "De Novo-engineered Transcription Activator-like Effector (TALE) Hybrid Nuclease with Novel DNA Binding Specificity Creates Double-strand Breaks", Proceedings of the National Academy of Sciences, vol. 108, No. 6, XP-055007615, Feb. 8, 2011, pp. 2623-2628.
A. Österborg et al., Clonal $CD8^+$and $CD52^-$ T Cells are Induced in Responding B Cell Lymphoma Patients Treated with Campath-1H* (anti-CD52), European Journal of Haematology, vol. 58, No. 1, XP-008067708, Jan. 1, 1997, pp. 5-13.
Rebecca J. Greenwald et al., "Negative Co-receptors on Lymphocytes", Current Opinion in Immunology, vol. 14, No. 3, XP-004350492, Jun. 1, 2002, pp. 391-396.
Cohen CJ et al., "Enhanced Antitumor Activity of T Cells Engineered to Express T Cell Receptors with a Second Disulfide Bond," Cancer Res., 2007; 67(8): 3898-3903.
Cooper GM., "Functions of Cell Surface Receptors," The Cell: A Molecular Approach. 2nd Ed., 2000, Sunderland (MA): Sinauer Associates (available at https://www.ncbi.nim.nih.gov/books/NBK9866).
Curran et al., "Chimeric Antigen Receptors for T cell Immunotherapy: Current Understanding and Future Direction," J. Gene Med., 2012, vol. 14(6):405-415.
Eshhar Z et al., "Specific activation and targeting of cytotoxic lymphocytes through chimeric single chains consisting of antibody-binding domains and the γ or ζ subunits of the immunoglobulin and T-cell receptors," Proc. Natl. Acad. Sci. USA 1993; 90(2): 720-724.
Kahlon KS et al. "Specific Recognition and Killing of Glioblastoma Multiforme by Interleukin 13-Zetakine Redirected Cytolytic T Cells," Cancer Res., 2004; 64:9160-9166.
Muniappan A et al., "Ligand-mediated cytolysis of tumor cells: use of heregulin-ζ chimeras to redirect cytotoxic T lymphocytes," Cancer Gene Ther., 2000; 7:128-134.
Niederman TM et al., "Antitumor activity of cytotoxic T lymphocytes engineered to target vascular endothelial growth factor receptors," Proc. Natl. Acad. Sci. USA, 2002; 99: 7009-7014.
Ramos CA et al., "Chimeric Antigen (CAR)—Engineered Lymphocytes for Cancer Therapy," Expert Opin. Biol. Ther. Jul. 2011; 11(7):855-873.
Sadelain M. et al ., "The Basic Principles of Chimeric Antigen Receptor Design," Cancer Discov., Apr. 2013; 3(4):1-11.
Shi et al., "Chimeric antigen receptor for adoptive immunotherapy of cancer: latest research and future prospects," Mol. Cancer, 2014, 13:219.
Wang et al., "Generation of Potent T-cell Immunotherapy for Cancer using DAP12-based, Multichain, Chimeric Immunoreceptors," Cancer Immunol. Res., 2015, vol. 3, pp. 815-826.
Bipulendu et al., "Redirecting T-cell specificity by introducing a tumor-specific chimeric antigen receptor," Blood, vol. 116(7), Aug. 2010, pp. 1035-1044.
Office Action issued in Eurasian Patent Application No. 2015112125/10 (018966) dated May 10, 2017 (11 pages).

* cited by examiner

| | LEFT HALF TARGET | Spacer size (bp) | RIGHT HALF TARGET | |
|---|---|---|---|---|
| TRAC | TTGTCCCACAGATATCC | 15 | CCGTGTACCCAGCTGAGA | |
| CD52 | TTCCTCCTACTCACCAT | 15 | GGTACAGGTAAGAGCA A | |
| Potential offsite targets | Left matched sequence | Spacer size (bp) | Right matched sequence | Mis-matc hes |
| 1 | ttgctctCaccAgtaTA | 25 | TTtTcaggtaagTgcaa | 8 |
| 2 | tCActcttacctgGacc | 19 | CCtacaggttaagGgcCa | 7 |
| 3 | tctcagAtgAtacacCC | 24 | AgtacaggCaTgagcCa | 8 |
| 4 | tGAtcccacagaAatAc | 18 | gCatTtctgtgggaTCa | 8 |
| 5 | ttCctctAacctgtaTT | 25 | gAtCcaggtaagGTcaa | 8 |
| 6 | tAgtcccCcagatatGA | 19 | aAggtgTgGaTgaggaa | 8 |
| 7 | ttgtcAcacaTataCcG | 21 | TgGtatTtgtgTgacaa | 8 |
| 8 | tAActcttacctgtaGT | 16 | AgatTtctCtgggGcaa | 8 |
| 9 | ttActccAactAacTat | 16 | ccgtTtaccGgctTaga | 7 |
| 10 | tGgctcAtacctgtaGT | 14 | aGgAtgagGTggaggaa | 8 |
| 11 | ttgctcAtacAtgtGcA | 21 | atgCtgTgtaggTggTa | 8 |
| 12 | ttgtcccacagaCatTc | 18 | ccACgtaGcagctgGga | 6 |
| 13 | tcAcaCctggtacaTAg | 27 | GtgTtTagtaggGggaa | 8 |
| 14 | ttgtcccacagCtaCcc | 29 | gAgtCtTtgtAggacaa | 6 |
| 15 | tctcaActgAAacaAgg | 23 | TgtaAtgTCaagagcaa | 8 |

FIG. 9A

| | Control transfection (no RNA) | | | CD52-TALEN+TRAC+TALEN transfection | | |
|---|---|---|---|---|---|---|
| | Nb seq analyzed | Nb indels | Frequency indels (less than) | Nb seq analyzed | Nb indels | Frequency indels (less than) |
| | 3965 | 0 | 2.52E-04 | 7560 | 3371 | 0.44 |
| | 1046 | 0 | 9.56E-04 | 2266 | 1056 | 0.47 |
| Matched sequence | | | | | | |
| CD52-R_TRAC-R | 7132 | 0 | 1.4E-04 | 7644 | 1 | 1.3E-04 |
| CD52-R_TRAC-R | 6431 | 0 | 1.6E-04 | 7377 | 2 | 2.7E-04 |
| CD52-R_TRAC-R | 2771 | 0 | 3.6E-04 | 2704 | 80 | 3.7E-04 |
| TRAC-L_CD52-L | 5525 | 0 | 1.8E-04 | 4739 | 0 | 2.1E-04 |
| CD52-R_TRAC-R | 27958 | 0 | 3.6E-05 | 16646 | 0 | 6.0E-05 |
| TRAC-L_CD52-L | 22456 | 0 | 4.5E-05 | 32912 | 10 | 3.0E-04 |
| TRAC-L_CD52-L | 8275 | 0 | 1.2E-04 | 5629 | 0 | 1.8E-04 |
| TRAC-L_CD52-R | 23253 | 0 | 4.3E-05 | 22054 | 16 | 7.3E-04 |
| CD52-L_TRAC-R | 13371 | 0 | 7.5E-05 | 13688 | 1 | 7.3E-05 |
| CD52 | 22856 | 0 | 4.4E-05 | 31292 | 0 | 3.2E-05 |
| CD52 | 3238 | 1 | 3.1E-04 | 3064 | 0 | 3.3E-04 |
| TRAC | 4530 | 0 | 2.2E-04 | 4652 | 0 | 2.1E-04 |
| CD52-L_TRAC-R | 17361 | 0 | 5.8E-05 | 14454 | 0 | 6.9E-05 |
| TRAC-L_CD52-L | 32823 | 0 | 3.0E-05 | 33911 | 1 | 2.9E-05 |
| CD52-R_TRAC-R | 6479 | 0 | 1.5E-04 | 6088 | 0 | 1.6E-04 |

FIG. 9B

MULTI-CHAIN CHIMERIC ANTIGEN RECEPTOR AND USES THEREOF

CROSS-REFERENCE TO RELATED APPLICATIONS

This application claims priority under 35 U.S.C. § 120:

to U.S. application Ser. No. 13/942,191, filed Jul. 15, 2013;

to U.S. application Ser. No. 13/892,805, filed May 13, 2013, PCT/US2013/040766, filed May 13, 2013, and to PCT/US2013/40755, filed May 13, 2013, all of which claim priority to U.S. 61/696,612, filed Sep. 4, 2012 and to U.S. 61/651,933 filed May 25, 2012; and to U.S. Provisional Application No. 61/696,612, filed Sep. 4, 2012; each of which is incorporated by reference in its entirety.

FIELD OF THE INVENTION

The present invention relates to chimeric antigen receptors (CAR). CARs are able to redirect immune cell specificity and reactivity toward a selected target exploiting the ligand-binding domain properties. In particular, the present invention relates to multi-chain Chimeric Antigen Receptor in which extracellular ligand binding and signaling domains are separate in different transmembrane polypeptides to improve their functions. The different transmembrane polypeptides composing the multi-chain CAR of the present invention, once assembled together can specifically bind to one or several ligand(s) in a target and induce activation of immune cells in which they are expressed and immune response. The present invention also relates to polynucleotides, vectors encoding such transmembrane polypeptides and isolated cells expressing said multi-chain CAR at their surface for immunotherapy. The present invention also relates to methods for engineering immune cells expressing multi-chain CAR at their surface. The invention opens the way to efficient adoptive immunotherapy strategies for treating cancer and viral infections.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

Present CAR architectures are built on a design in which all relevant domains are contained within a single polypeptide (U.S. Pat. No. 7,741,465). This design necessitates serial appending of signaling domains, thus necessitating moving some domains from their natural juxtamembrane positions, distal from the plasma membrane. Nevertheless, architectures in which ligands and signaling domains are separate in their normal juxtamembrane positions (i.e. adjacent to the cell membrane on the internal side of it) would be more desirable and deemed to allow improved function of costimulatory domains. The high affinity receptor for IgE (FcεRI), could afford such architecture. Indeed, FcεRI, which is present on mast cells and basophils, is a tetrameric complex consisting of a ligand binding alpha subunit, a beta subunit and a homodimer of two signal-transducing gamma subunits (Metzger, Alcaraz et al. 1986). FcεRI alpha domain consists of an extracellular domain containing two Ig-like domains that bind IgE, a transmembrane domain and a short cytoplasmic tail. Beta subunit contains four transmembrane segments separating amino and carboxy terminal cytoplasmic tails. The gamma chain consists essentially of a transmembrane region and cytoplasmic tail containing one immunoreceptor tyrosine-based activation motif (ITAM) (Cambier 1995).

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. In addition to lymphocyte infusion, the host may be manipulated in other ways that support the engraftment of the T cells or their participation in an immune response, for example pre-conditioning (with radiation or chemotherapy) and administration of lymphocyte growth factors (such as IL-2). Each patient receives an individually fabricated treatment, using the patient's own lymphocytes (i.e. an autologous therapy).

Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety. Ideally, one would like to use a standardized therapy in which allogeneic therapeutic cells could be pre-manufactured, characterized in detail, and available for immediate administration to patients. By allogeneic it is meant that the cells are obtained from individuals belonging to the same species but are genetically dissimilar. However, the use of allogeneic cells presently has many drawbacks. In immune-competent hosts allogeneic cells are rapidly rejected, a process termed host versus graft rejection (HvG), and this substantially limits the efficacy of the transferred cells. In immune-incompetent hosts, allogeneic cells are able to engraft, but their endogenous TCR specificities recognize the host tissue as foreign, resulting in graft versus host disease (GvHD), which can lead to serious tissue damage and death. In order to effectively use allogeneic cells, both of these problems must be overcome.

In immunocompetent hosts, allogeneic cells are rapidly rejected by the host immune system. It has been demonstrated that, allogeneic leukocytes present in non-irradiated blood products will persist for no more than 5 to 6 days. (Boni, Muranski et al. 2008). Thus, to prevent rejection of allogeneic cells, the host's immune system must be effectively suppressed. Glucocorticoidsteroids are widely used therapeutically for immunosuppression (Coutinho and Chapman 2011). This class of steroid hormones binds to the glucocorticoid receptor (GR) present in the cytosol of T cells resulting in the translocation into the nucleus and the binding of specific DNA motifs that regulate the expression of a number of genes involved in the immunologic process. Treatment of T cells with glucocorticoid steroids results in reduced levels of cytokine production leading to T cell anergy and interfering in T cell activation. Alemtuzumab, also known as CAMPATH1-H, is a humanized monoclonal antibody targeting CD52, a 12 amino acid glycosylphosphatidyl-inositol- (GPI) linked glycoprotein (Waldmann and Hale 2005). CD52 is expressed at high levels on T and B lymphocytes and lower levels on monocytes while being absent on granulocytes and bone marrow precursors. Treatment with Alemtuzumab, a humanized monoclonal antibody directed against CD52, has been shown to induce a rapid depletion of circulating lymphocytes and monocytes. It is frequently used in the treatment of T cell lymphomas and in certain cases as part of a conditioning regimen for transplantation. However, in the case of adoptive immunotherapy the use of immunosuppressive drugs will also have a detrimental effect on the introduced therapeutic T cells. Therefore, to effectively use an adoptive immunotherapy approach in these conditions, the introduced cells would need to be resistant to the immunosuppressive treatment.

On the other hand, T cell receptors (TCR) are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCRalpha or TCRbeta can result in the elimination of the TCR from the surface of T cells preventing recognition of alloantigen and thus GVHD. However, TCR disruption results in the elimination of the CD3 signaling component and alters the means of further T cell expansion.

T-cell mediated immunity includes multiple sequential steps regulated by a balance between co-stimulatory and inhibitory signals that fine-tune the immunity response. The inhibitory signals referred to as immune checkpoints are crucial for the maintenance of self-tolerance and also to limit immune-mediated collateral tissue damage. The expression of immune checkpoints protein can be deregulated by tumours. The ability of tumours to co-opt these inhibitory pathways represents an important mechanism in immune resistance and limits the success of immunotherapy. One of promising approaches to activating therapeutic T-cell immune response is the blockade of these immune checkpoints (Pardoll 2012). Immune checkpoints represent significant barriers to activation of functional cellular immunity in cancer, and antagonistic antibodies specific for inhibitory ligands on T cells including CTLA4 and programmed death-1 (PD-1) are examples of targeted agents being evaluated in the clinics.

Cytotoxic-T-lymphocyte-associated antigen 4 (CTLA-4; also known as CD152) down-regulates the amplitude of T cell activation and treatment with antagonist CTLA4 antibodies (ipilimumab) has shown a survival benefit in patients with melanoma (Robert and Mateus 2011). Programmed cell death protein 1 (PD1 or PDCD1 also known as CD279) represent another very promising target for immunotherapy (Pardoll and Drake 2012; Pardoll 2012). In contrast to CTLA-4, PD1 limits T cell effector functions in peripheral tissue at the time of an inflammatory response to infection and to limit autoimmunity. The first clinical trial with PD1 antibody shows some cases of tumour regression (Brahmer, Drake et al. 2010). Multiple additional immune checkpoint protein represent promising targets for therapeutic blockade based on recently studies.

In normal T-cells, T cell receptors emanate from the pre-T cell receptors (pTCR) which are expressed by immature thymocytes and are crucial for T cell development from the double negative (CD4− CD8−) to the double-positive (CD4+ CD8+) stages. Pre-T cells that succeed in productive rearrangements of the TCRbeta locus express a functional TCRbeta chain which pairs with an invariant preTalpha chain and CD3 signaling components to form the pre-TCR complex. The expression of the preTCR at the cell surface is necessary for triggering beta-selection, a process that induces the expansion of developing T cells, enforces allelic exclusion of the TCRbeta locus and results in the induction of rearrangements at the TCRalpha locus (von Boehmer 2005). After productive TCRalpha rearrangements and substitution of pTalpha by TCRalpha to form a mature TCR, thymocytes undergo a second step of selection, referred to as positive or TCRalpha/beta selection upon binding of self peptide MHC complexes expressed on thymic epithelial cells. Thus, mature T cells recognize and respond to the antigen/MHC complex through their TCR. The most immediate consequence of TCR activation is the initiation of signaling pathways via the associated CD3 subunits that result in multiple events including clonal expansion of T cells, upregulation of activation markers on the cell surface and induction of cytotoxicity or cytokine secretion.

Because of the nature of selection of TCRbeta chains through pairing with preTalpha during thymic development, in T cells in which TCRalpha has been inactivated, the heterologous introduction of the pTalpha transgene can result in the formation of a preTCR. This pTCR can serve as a means of T cell activation or stimulation in a manner that is non-MHC dependent, thus for example allowing continued expansion of alpha/beta T-cells following TCRalpha inactivation. Importantly, the pTCR complex displays a similar biochemical composition as the TCR in terms of associated CD3 subunits (Carrasco, Ramiro et al. 2001). In addition, in contrast to the TCR, pre-TCR signaling may occur in part by a ligand independent event. The crystal structure of the pTCR extracellular domain has provided a structural basis for the possible ligand-independence of pTCR signaling. The pTCR has been shown to form a head to tail dimer where two pTalpha-TCRbeta heterodimers associate (Pang, Berry et al. 2010).

In the context of developing therapeutic grade engineered immune cells that can target malignant or infected cells, the inventors have sought for improved CAR architectures, which would be closer to natural ones and likely to behave accordingly using any extracellular mono or multi-specific ligand binding domains.

As a result, they have designed a new generation of CARs involving separate polypeptide sub-units according to the present invention, referred to as "multi-chain CARs".

SUMMARY OF THE INVENTION

Chimeric Antigen Receptors (CAR) in the prior art present as single fusion molecules that necessitate serial appending of signaling domains. However, removing signaling domains from their natural juxtamembrane position interfere with their function. Thus, to overcome this drawback, the inventors have succeeded in designing so-called multi-chain CARs that allow juxtamembrane position of all relevant signaling domains. In the multi-chain CARs the signaling domains are placed on different polypeptide chains, in such that they seat in juxtamembrane positions. For example, multi-chain CAR can be derived from FcεRI, by replacing the high affinity IgE binding domain of FcεRI alpha chain by an extracellular ligand-binding domain such as scFv, whereas the N and/or C-termini tails of FcεRI beta and/or gamma chain are used to place signal transducing domain in normal juxtamembrane positions. The extracellular ligand binding domain has the role of redirecting T-cell specificity towards cell targets, while the signal transducing domains, left in juxtamembrane positions, activate the immune cell response.

The fact that the signaling domains in juxtamembrane position are present on polypeptide(s) distinct from that carrying the extracellular ligand binding domain, provides a more flexible architecture for CARs. Accordingly, additional signaling domains or co-stimulatory domains can be added or removed from the CAR depending on the intensity of interaction sought between the CAR's ligand binding domain and its receptor. This flexibility in the architecture of the CAR also permits to introduce additional extracellular ligand binding domain(s). This can be done by fusion of a second ligand binding domain to the polypeptide carrying the first ligand binding domain, or by introducing additional extracellular ligand binding domains. If this second ligand binding domain has a different specificity, this forms a bi-specific multi-chain CAR, and if there are additional ones, multi-specific multi-chain CAR. These are particularly advantageous in view of targeting a given cell or virus carrying two or more different receptors present at their surface. This increases the specificity of such multi-chain CAR towards said cell or virus. On another hand, the number of signaling domains may permit the modulation of the signal respectively to the different binding domains. In addition, each recombinant polypeptide forming the CAR can be expressed independently at different expression levels to further modulate activity of the CAR.

The present invention is drawn to this new CAR architecture, to the recombinant polynucleotides encoding thereof, as well as to the methods to engineer immune cells for specific cell recognition, whatever the purpose and nature of the immune cells.

The invention additionally provides methods for making such immune cells more suitable for immunotherapy purposes.

For instance, the immune cells can be further engineered to be non-alloreactive and/or resistant to immunosuppressive agents, in particular, by inactivating TCR alpha or beta genes in primary cells and/or by coupling the inactivation of genes encoding targets for different immunosuppressive agents, in particular CD52 and GR (Gluococorticoid Receptors) and further selecting the cells resistant to said immunosuppressive agents.

In addition to the above conception of genetically modified immune cells, the present invention also relates to embodiments where immune cells are engineered to allow proliferation when TCRalpha is inactivated, for instance by transiently expressing preTalpha in the cell thereby restoring a functional CD3 complex in the absence of a functional alpha/beta TCR.

In order to engineer genetically highly active modified immune cells, the invention also provides methods where immune checkpoints are blocked by lack of expression of genes such as PD1 and CTLA-4.

The present application further discloses engineered immune cells in particular T cells to be used as medicament, more particularly, for treating or preventing cancer by administrating such immune cells to a living organism.

BRIEF DESCRIPTION OF THE FIGURES AND TABLES

In addition to the preceding features, the invention further comprises other features which will emerge from the description which follows, as well as to the appended drawings. A more complete appreciation of the invention and many of the attendant advantages thereof will be readily obtained as the same becomes better understood by reference to the following Figures in conjunction with the detailed description below.

FIG. 1: Schematic representation of the normal relationship between T-cells and antigen presenting cell.

Figure 2:
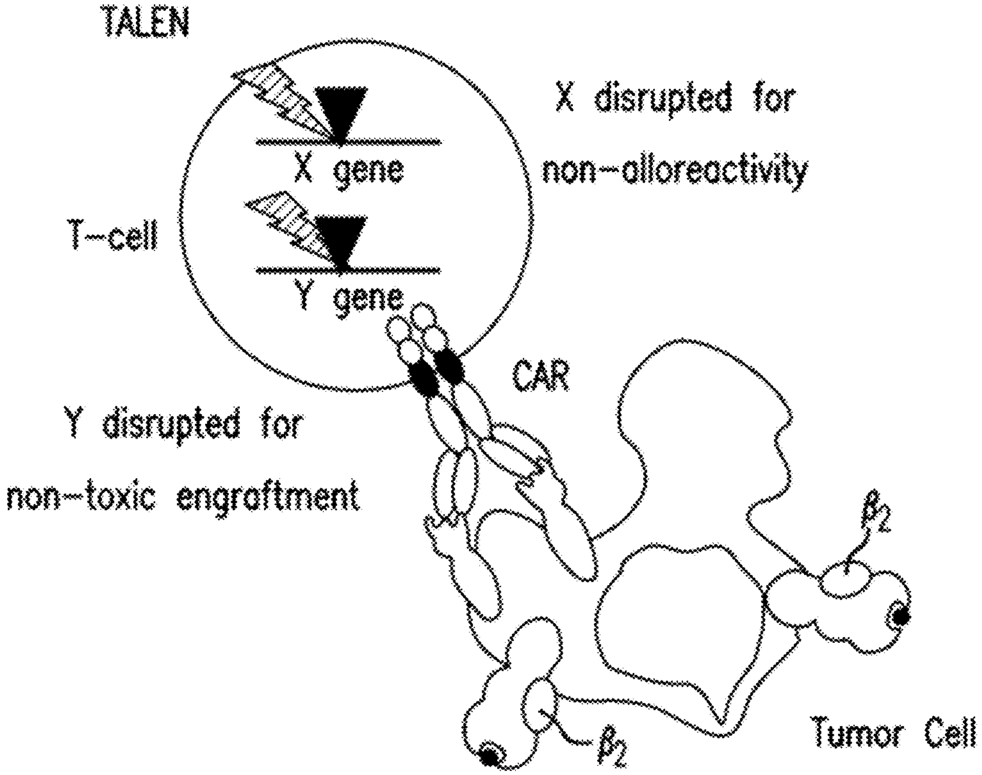

FIG. 2: Schematic representation of the genetically modified therapeutic T-cells according to the invention and the patient's tumor cells.

Figure 3:
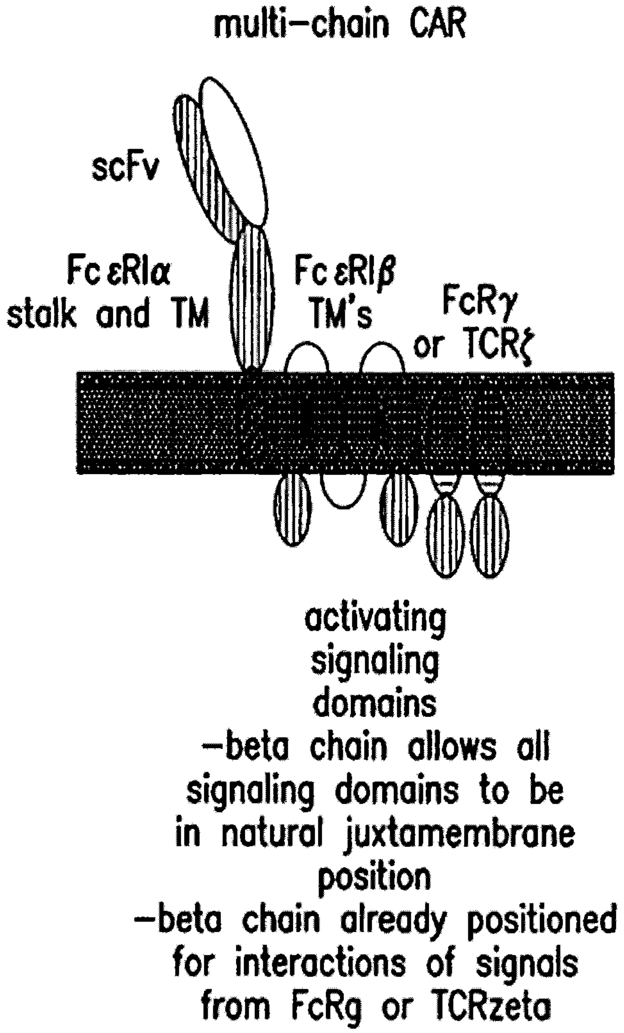

FIG. 3: Schematic representation of multi-chain CAR.

Figure 4A:
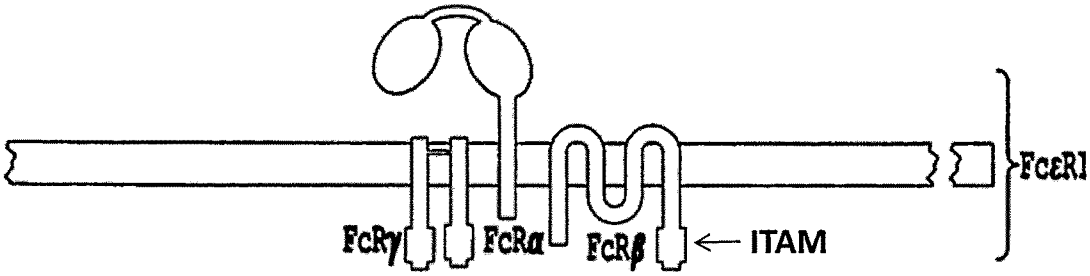
Figure 4B:
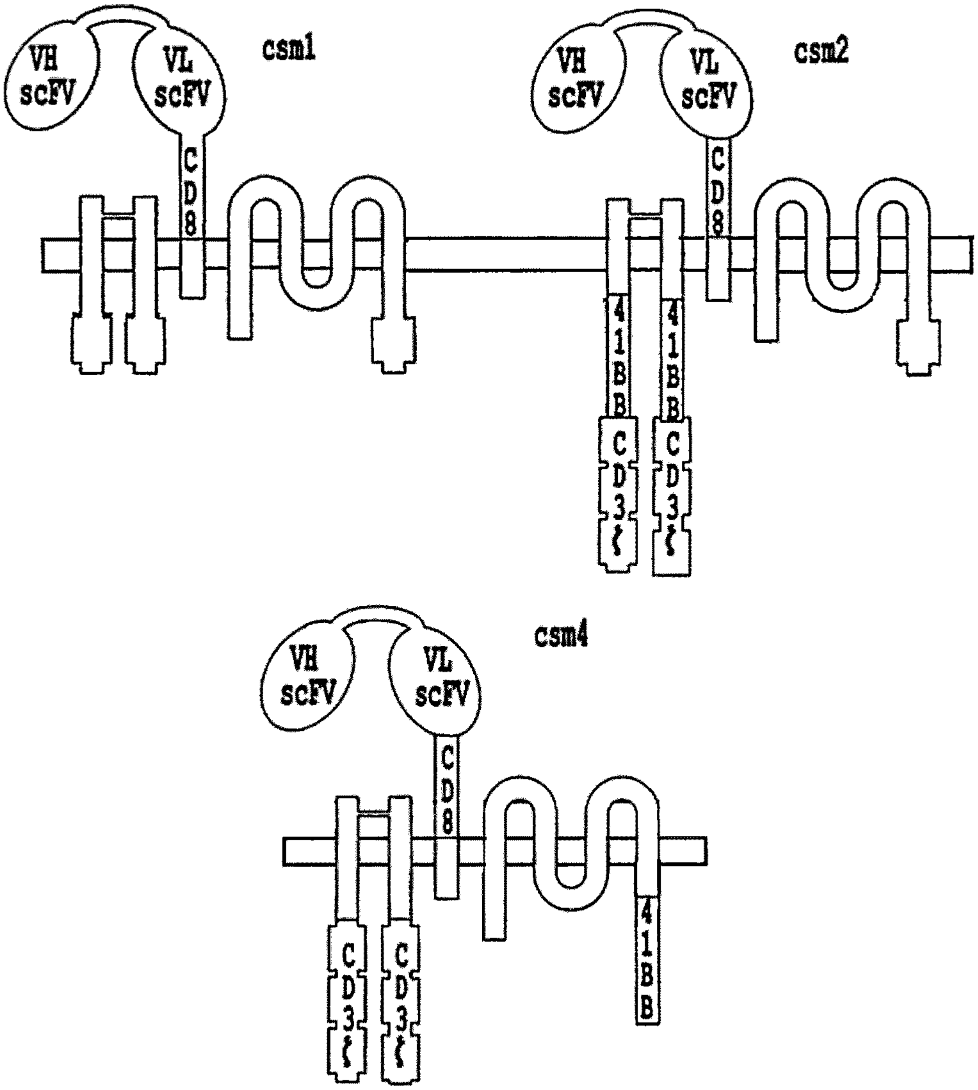
Figure 4C:
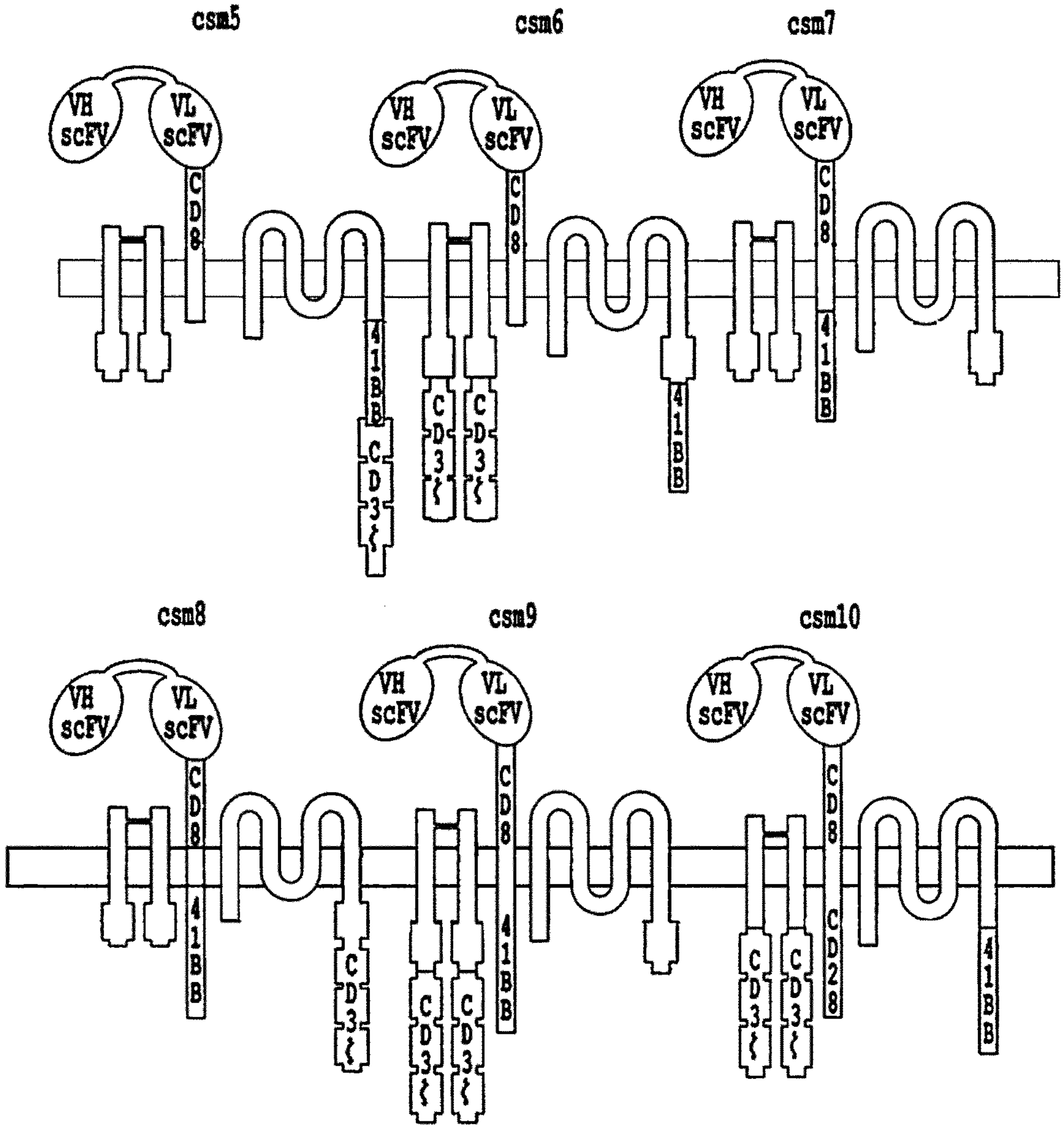

FIGS. 4 A, B and C: Schematic of different versions of multi-chain CARs. A. Schematic of the FcεRI receptor. B-C Different versions of multi-chain CARs (csm1 to csm10) comprising a scFv and a CD8 stalk region fused to the transmembrane domain of FcεRI alpha chain. At least one 41BB, CD28 and/or CD3 zeta domains can be fused to a FcεRI alpha, beta and/or gamma chain.

Figure 5:
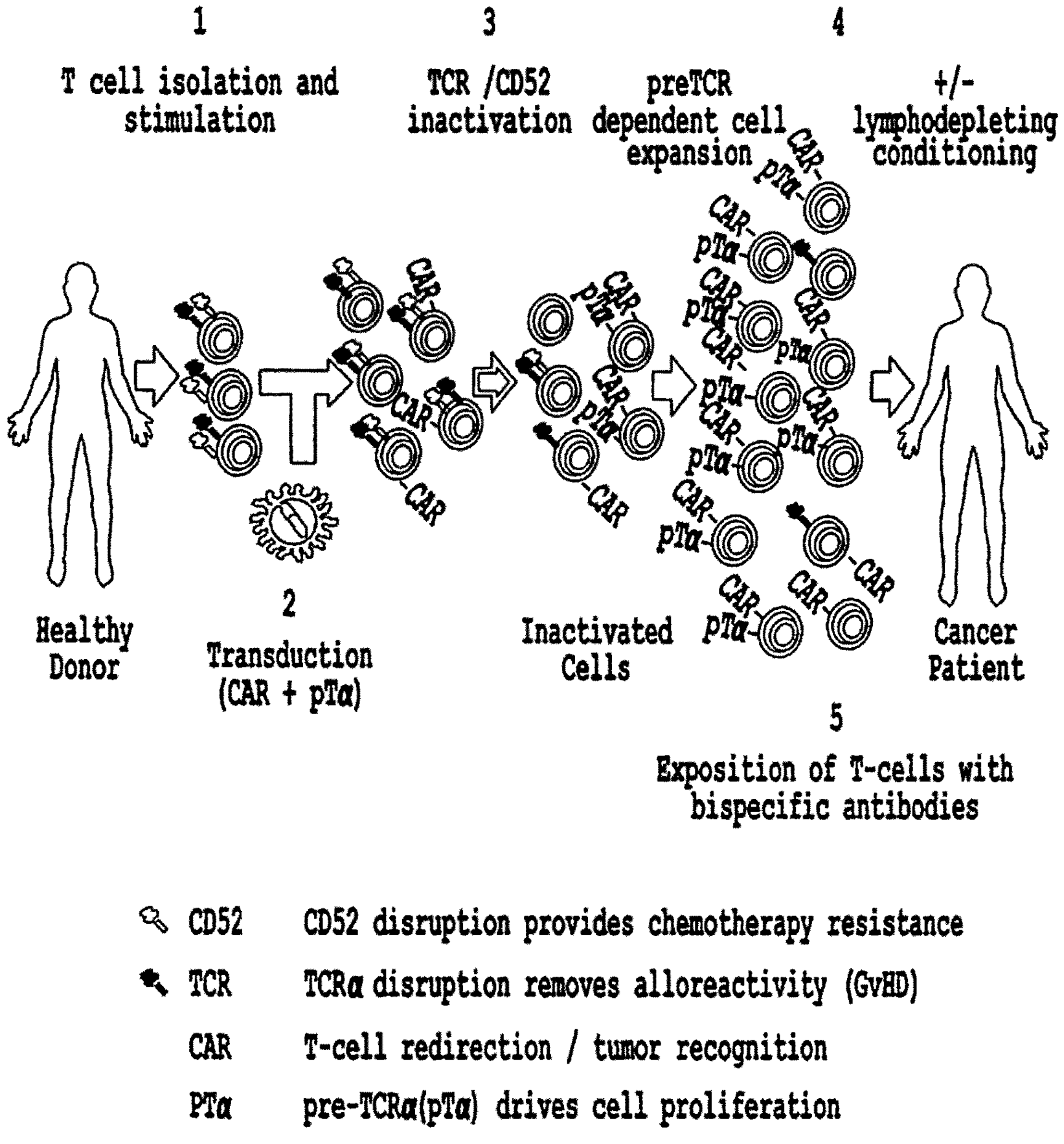

FIG. 5: Schematic representation of one example of the method of engineering human allogenic cells for immunotherapy.

Figure 6:
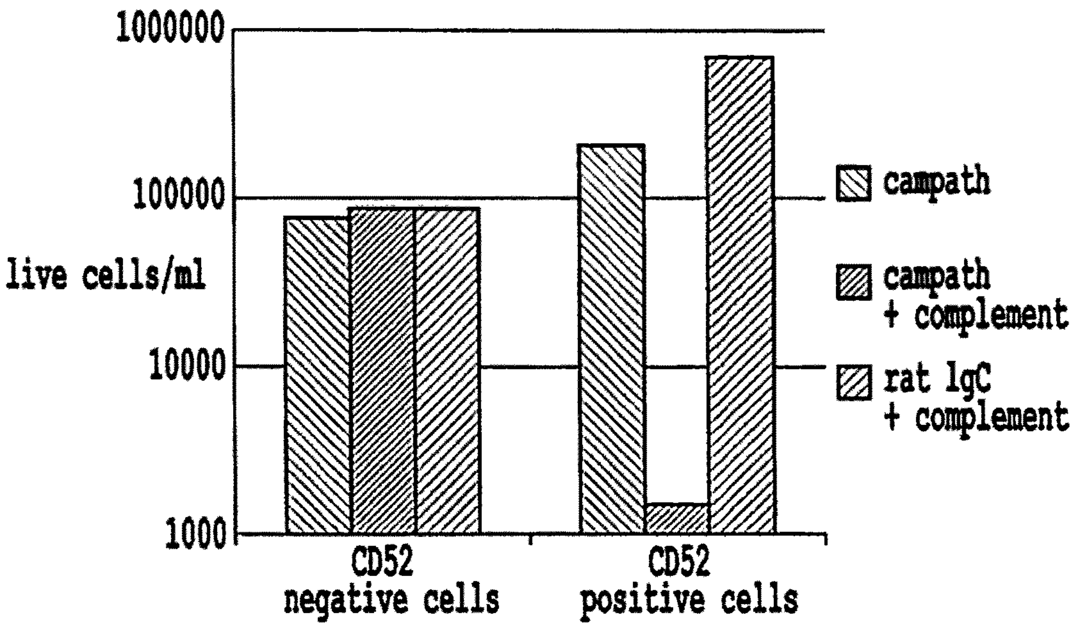

FIG. 6: Concentration in cells per milliliter of live CD52-positive or CD52-negative cells after treatment with anti-CD52 antibody (CAMPATH1-H) with complement or controls.

Figure 7:
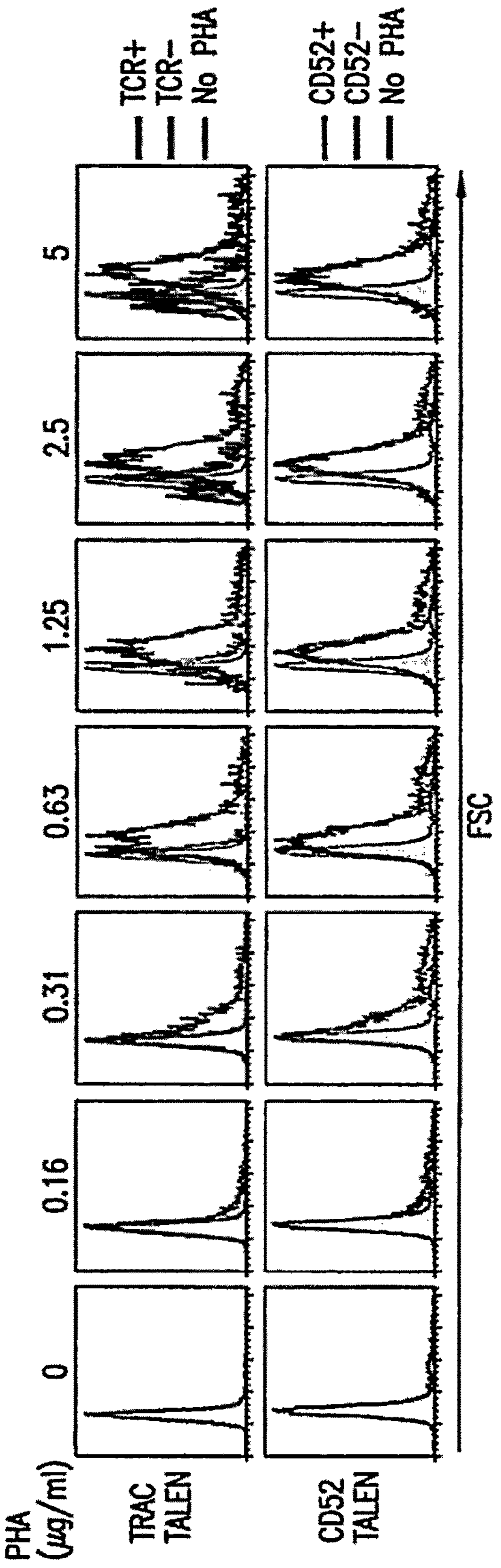
Figure 8A:
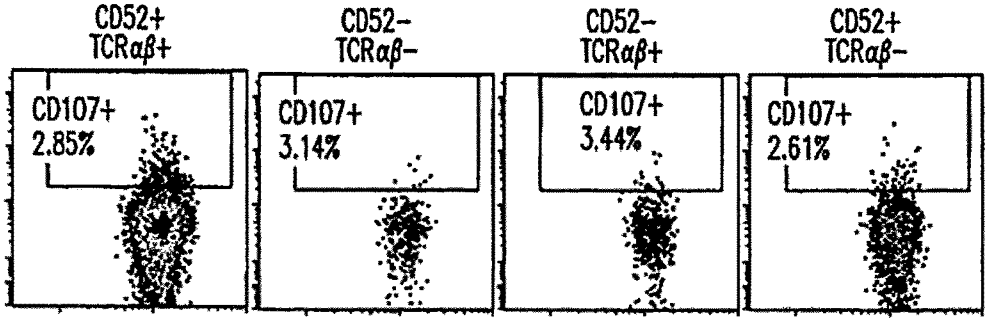
Figure 8B:
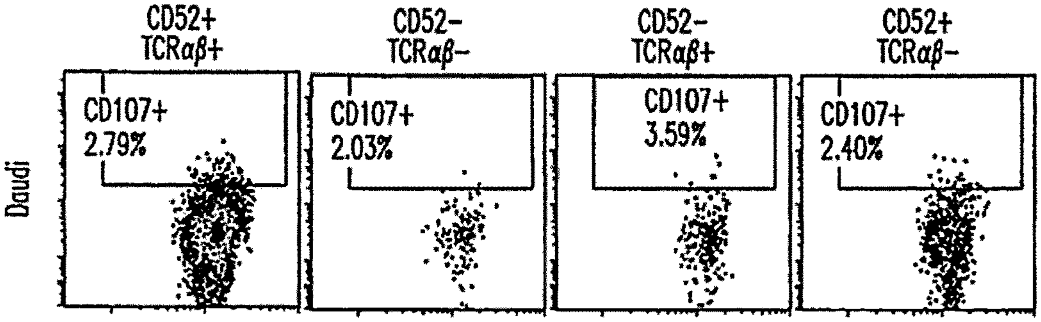
Figure 8C:
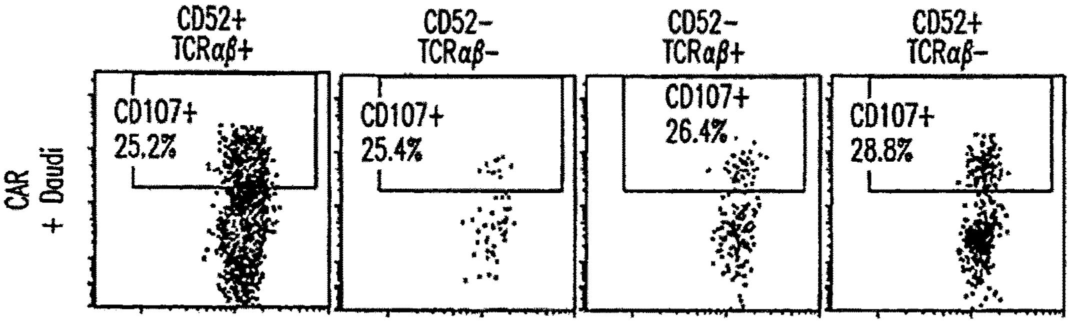
Figure 8D:
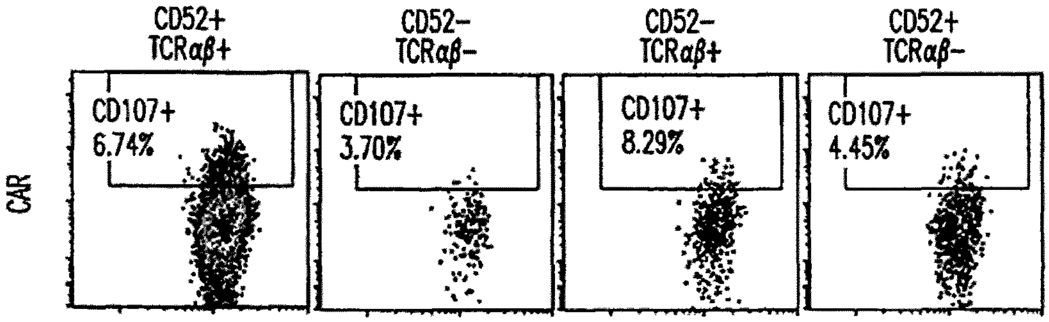
Figure 8E:
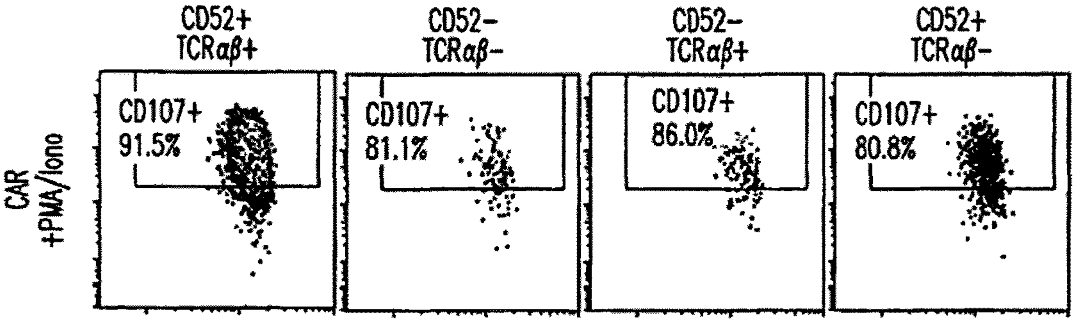

FIG. 7: Comparison of the forward side scatter (FSC) distribution, an indicator of cell size, between TCR-positive and TCR-negative cells, or between CD52-positive and CD52-negative cells, and non activated cells as control.

FIGS. 8 A, B, C, D and E: Flow cytometry analysis of CD107a expression (marker of degranulation) on targeted CD52 and TCRalpha inactivated T cells. CD107 expression is analyzed on CD52+TCRαβ+ cells (first column), CD52−TCRαβ− cells (second column), CD52−TCRαβ+ cells (third column) and CD52+TCRαβ− cells (fourth column) before (A) and after incubation with Daudi cells (B); C) represents flow cytometry analysis of T cells further transfected with a CAR and incubated with Daudi cells; D) represents flow cytometry analysis of T cells transfected with a CAR but not incubated with Daudi cells and E) represents flow cytometry analysis of T cells transfected with a CAR and treated to PMA/ionomycin (positive control).

FIGS. 9 A and B: Deep sequencing analysis of CD52 and TRAC TALE-nucleases potential off-site targets. FIG. 9 discloses "left half target" sequences as SEQ ID NOS: 149-165 and "right half target" sequences as SEQ ID NOS 166-182, all respectively, in order of appearance.

Figure 10:
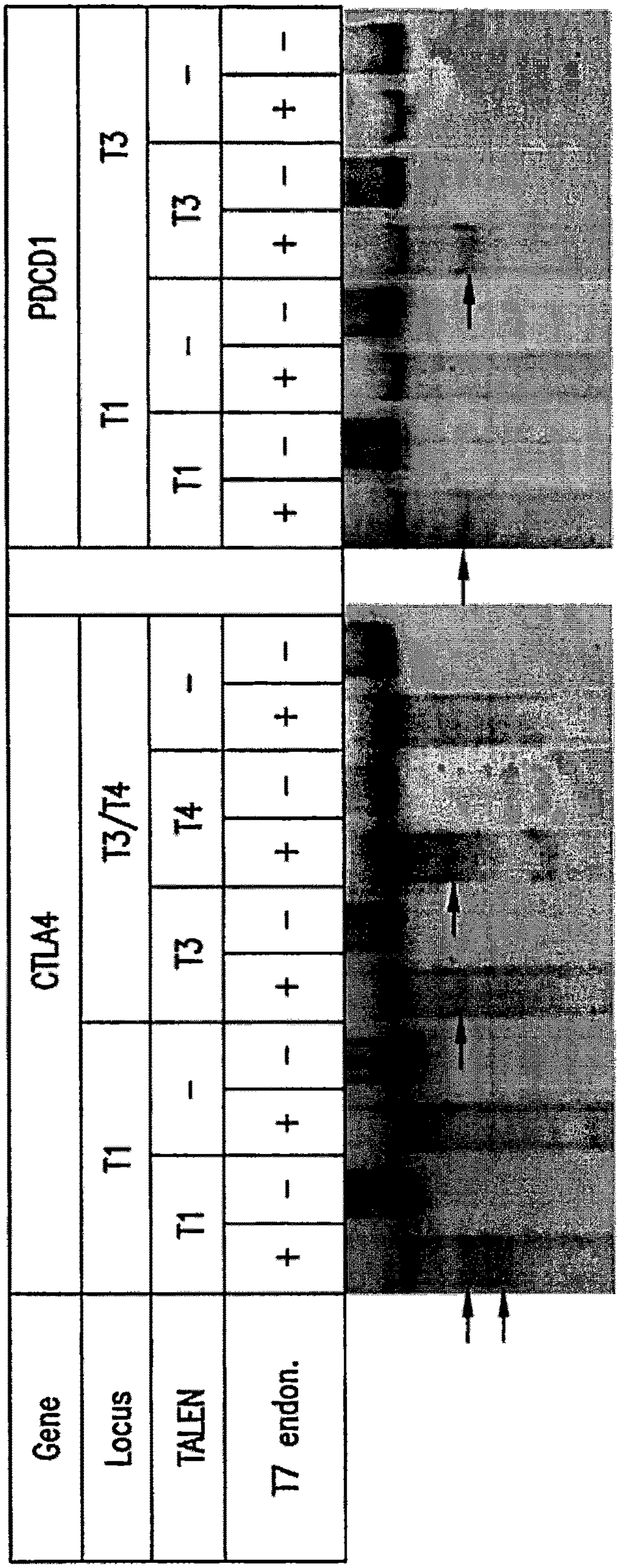

FIG. 10: Analysis of PDCD1 and CTLA-4 genomic locus by T7-endonuclease assay. Arrows point to digested PCR products.

Figure 11:
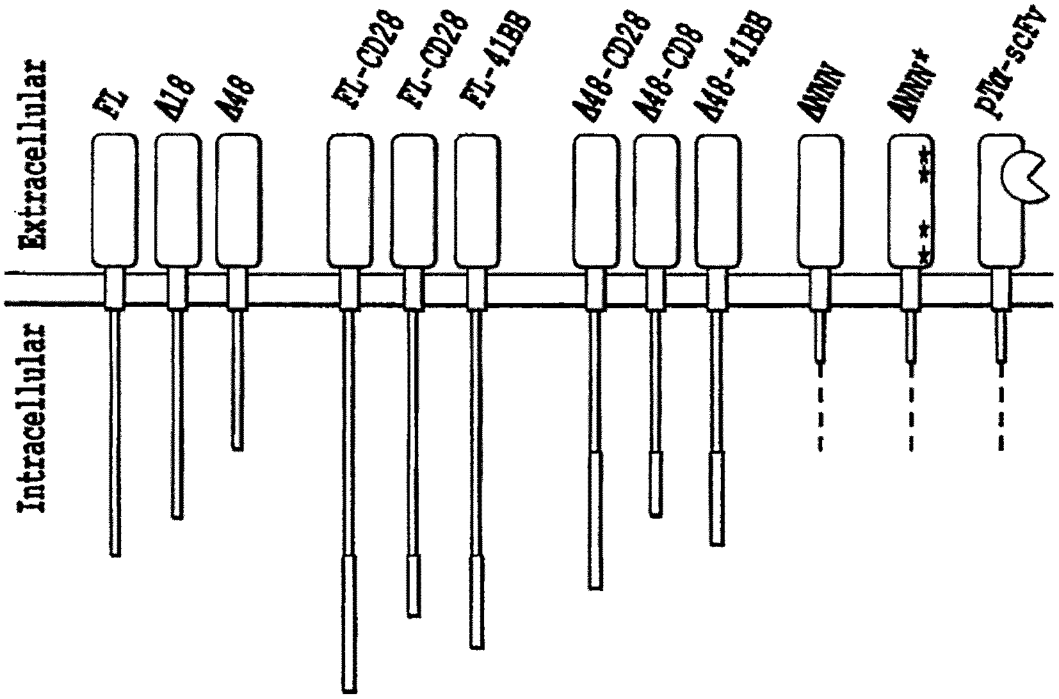

FIG. 11: Schematic representation of some examples of preTalpha constructs.

Figure 12:

FIG. 12: Flow cytometry analysis of transduction efficiency (% BFP+ cells) and activity of the FL, Δ18, Δ48 pTalpha constructs (% CD3 surface expression) in TCR alpha inactivated Jurkat cells.

Figure 13:
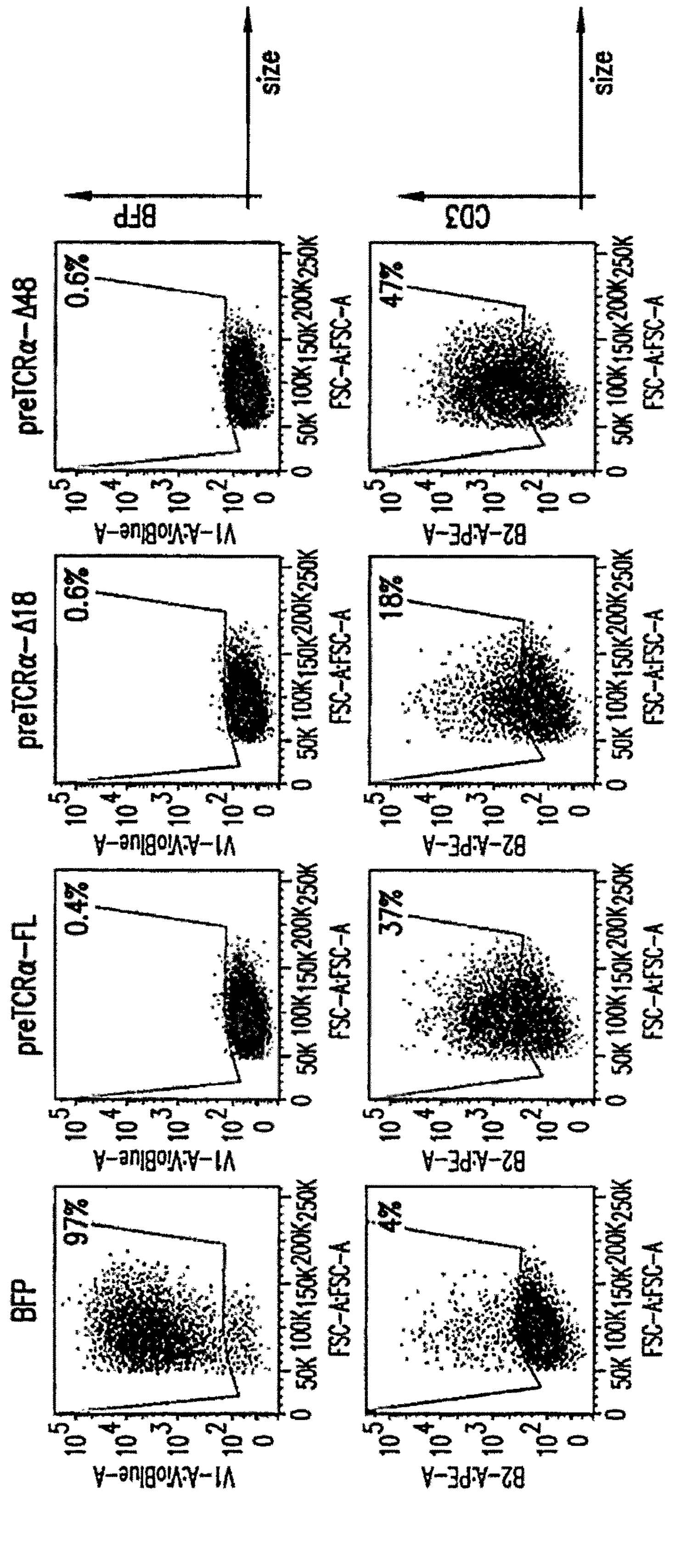

FIG. 13: Schematic representation of a lentiviral construct coding for pTalpha protein (preTCRα).

Figure 14A:
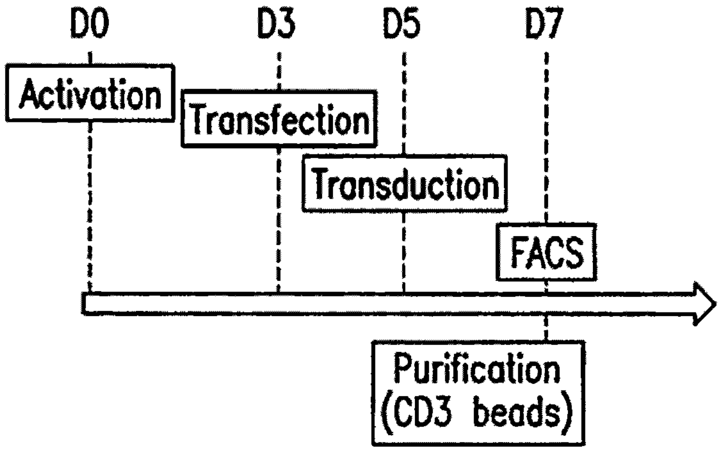
Figure 14B:
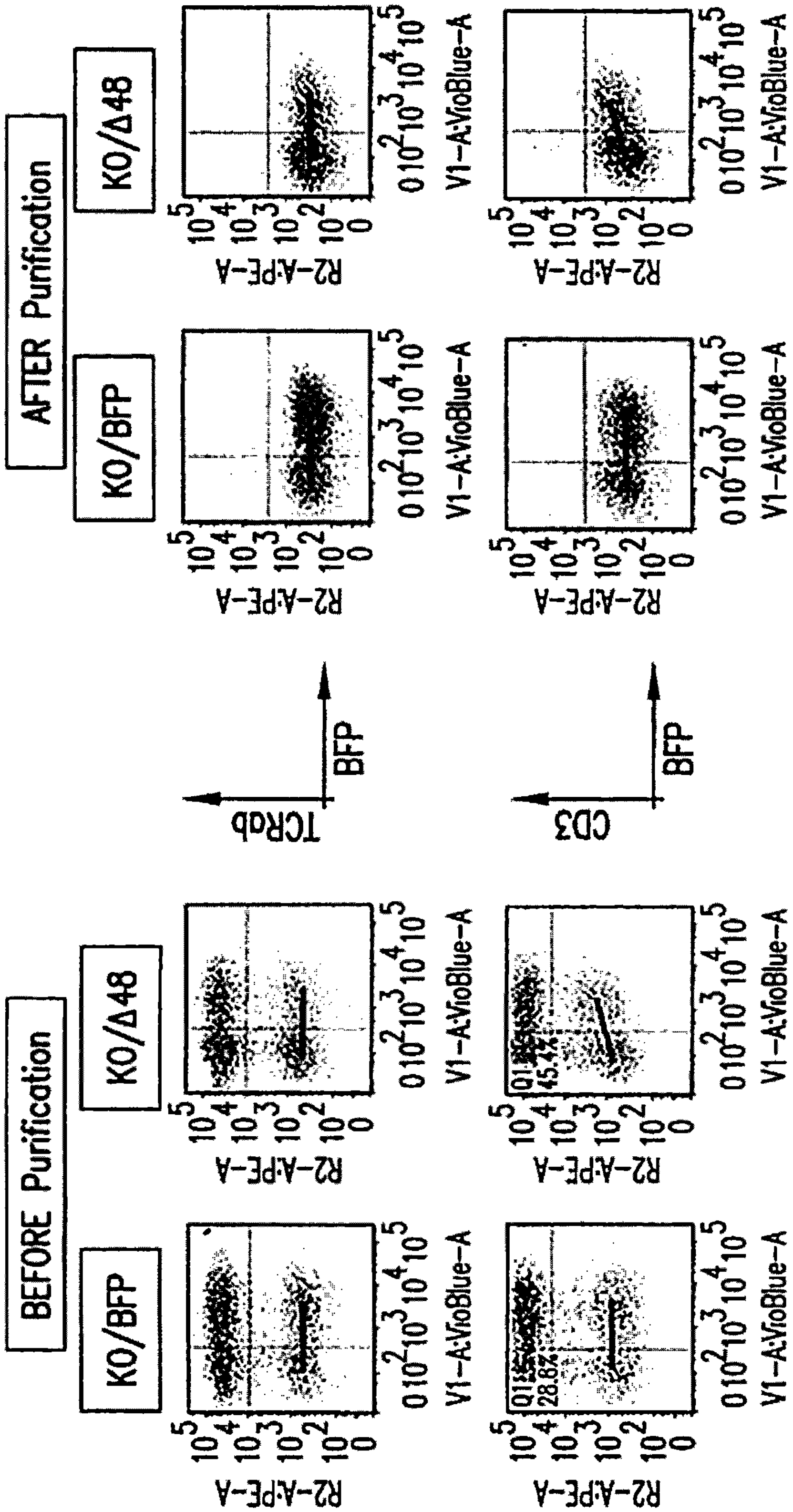
Figure 14C:
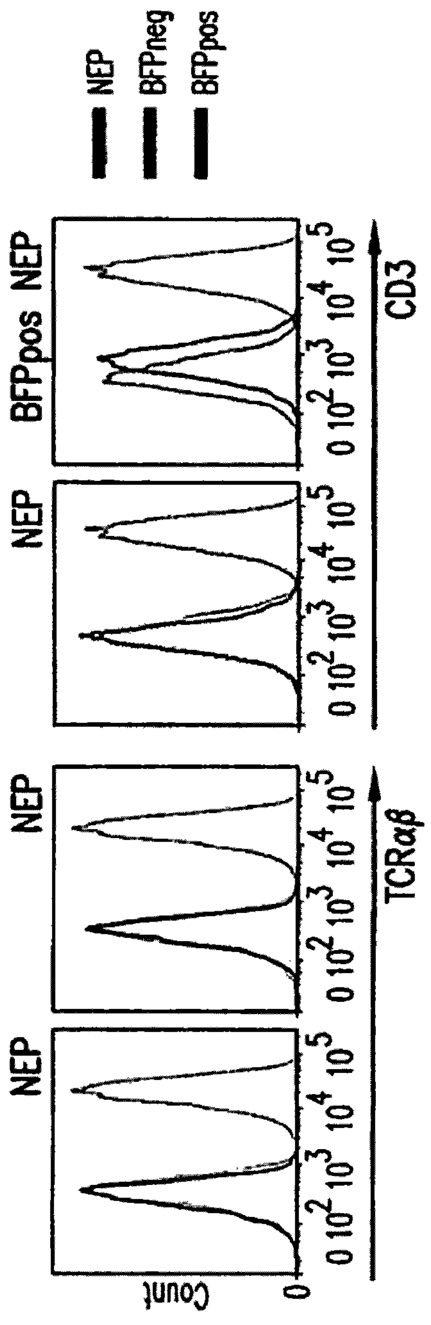

FIGS. 14 A, B and C: A. Representation of the experimental protocol. B. Flow cytometry analysis of TCR alpha/beta, CD3 expression and BFP expression on TCRalpha inactivated T cells (KO) transduced with either BFP-2A-pTalphaΔ48 (KO/Δ48) or control BFP lentiviral vector (KO/BFP) before and after purification. C. Flow cytometry analysis of TCR alpha/beta and CD3 expression on purified TCR alpha inactivated cells transduced (BFPpos) or not (BFPneg) with BFP-2A-pTalphaΔ48 lentiviral vector. NEP represents non electroporated cells with TRAC TALE-nucleases.

Figure 15A:
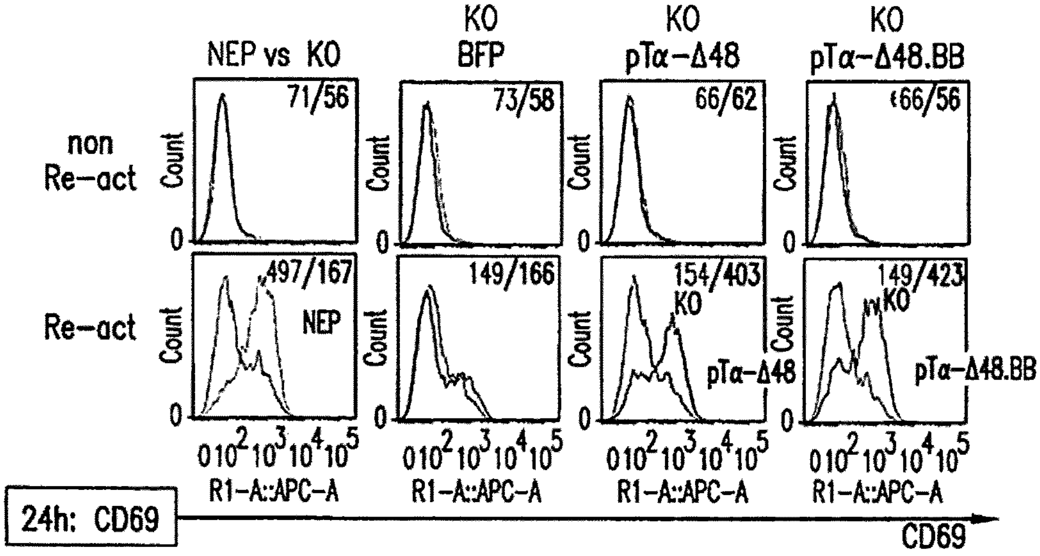

FIGS. 15A, B: and C Flow cytometry analysis of early activation marker CD69 (A), late activation marker CD25 (B) expression 24 and 48 hours after re-activation with anti-CD3/CD28 beads respectively on non electroporated cells (NEP) and TCRalpha inactivated cells (KO) transduced with BFP-2A-pTα-Δ48 lentiviral vector (pTα-Δ48), BFP-2A-pTα-Δ48.41BB lentiviral vector (pTα-Δ48.BB) or control BFP vector (BFP). pTα-Δ48 histograms correspond to the signal detected in TCR inactivated cells expressing pTα-Δ48 (BFP+ cells) while the KO histograms correspond to TCRalpha inactivated cells which do not express pTα-Δ48 (BFP− cells) pTα-Δ48.BB histograms correspond to the signal detected in TCR inactivated cells expressing pTα-Δ48.41BB (BFP+ cells) while the KO histograms correspond to TCRalpha inactivated cells which do not express pTα-Δ48.41BB (BFP− cells). NEP (non electroporated) histograms correspond to signal detected in non engineered cells. C. Flow cytometry analysis of the size of cells 72 hours after re-activation with anti-CD3/CD28 beads on non electroporated cells (NEP) and TCRalpha inactivated cells (KO) transduced with BFP-2A-pTα-Δ48 lentiviral vector (pTα-Δ48), BFP-2A-pTα-Δ48.41BB lentiviral vector (pTα-Δ48.BB) or control BFP vector (BFP). The values indicated in the upper part of each graph correspond to the geometrical mean of the fluorescence of each population.

Figure 16A:
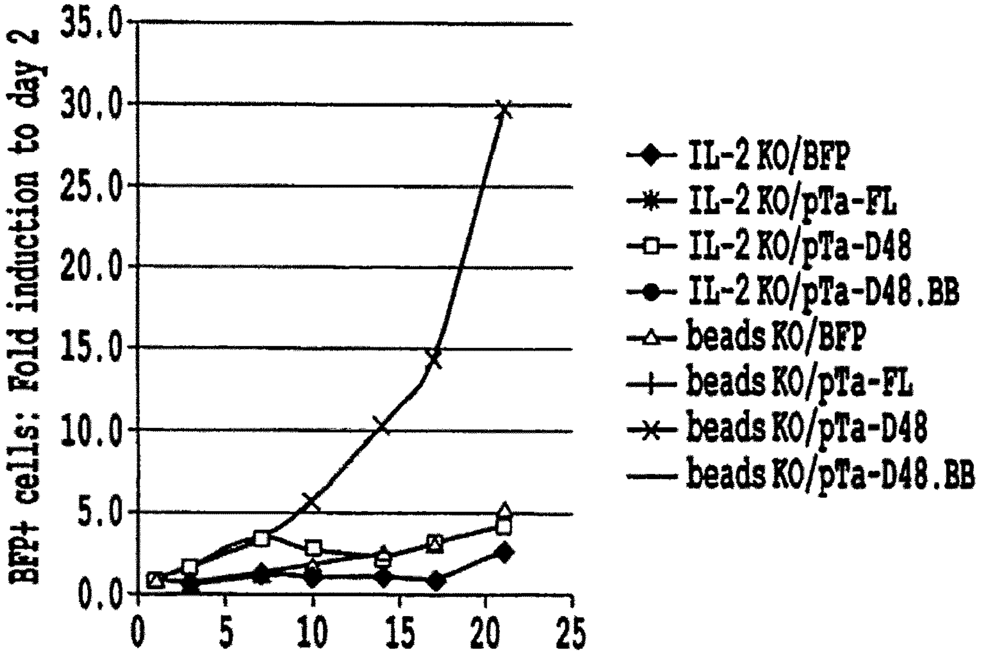
Figure 16B:
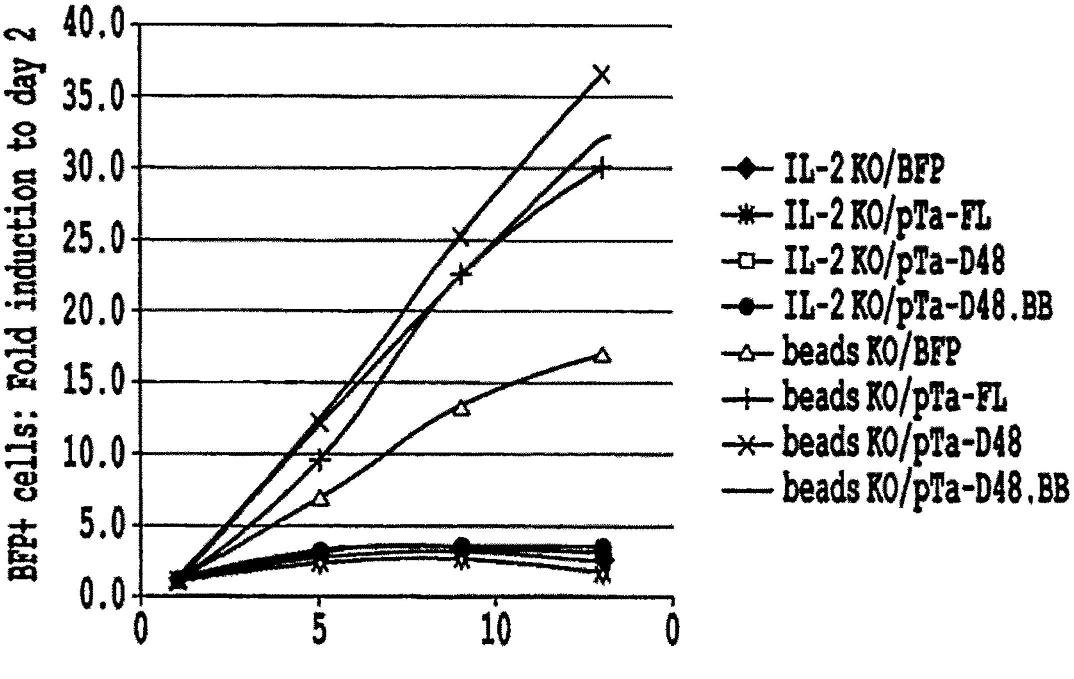

FIGS. 16 A and B: Cell growth analysis of TCR alpha inactivated cells (KO) transduced with pTalpha-Δ48 (pTaΔ48) or control BFP vector (BFP) maintained in IL2 or in IL2 with anti-CD3/CD28 beads at different time points (x-axis). The BFP+ cells number is estimated at different time points for each condition and the fold induction of these cells (y-axis) was estimated with respect to the value obtained at day 2 post re-activation. The results are obtained from two independent donors. For the second donor, cell growth was also determined for cells transduced with pTalpha-Δ48.41BB (pTα-Δ48.BB) and full-length pTalpha-(pTα-FL).

Figure 17A:
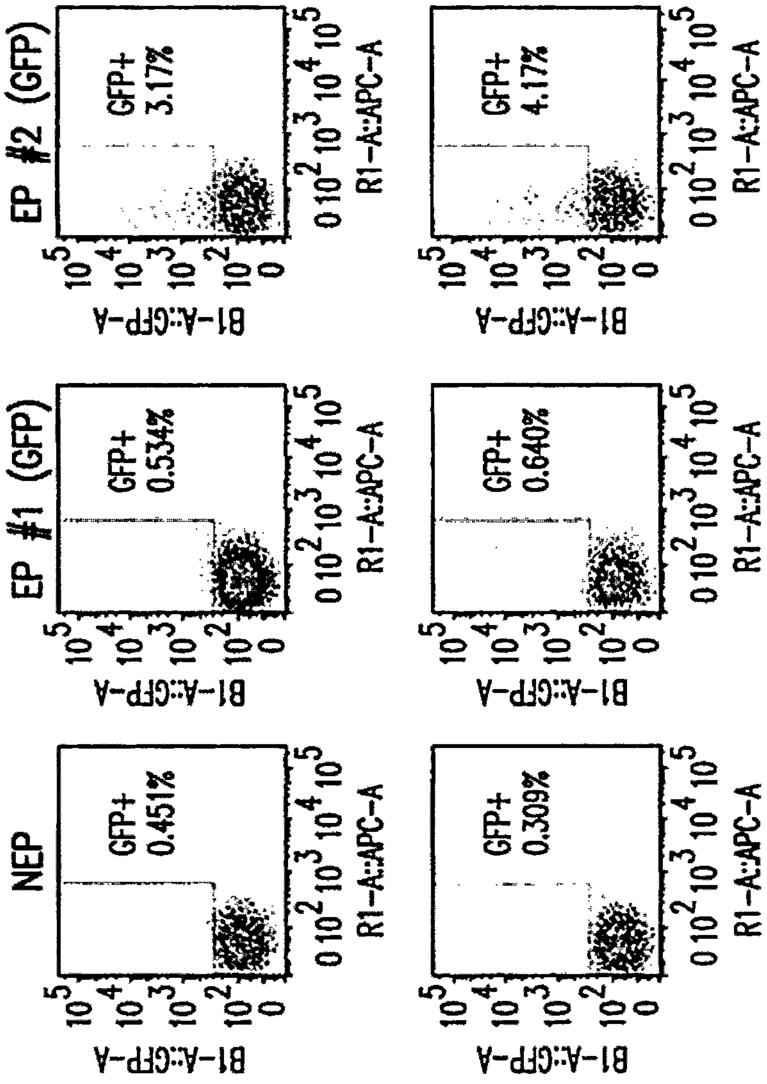
Figure 17B:
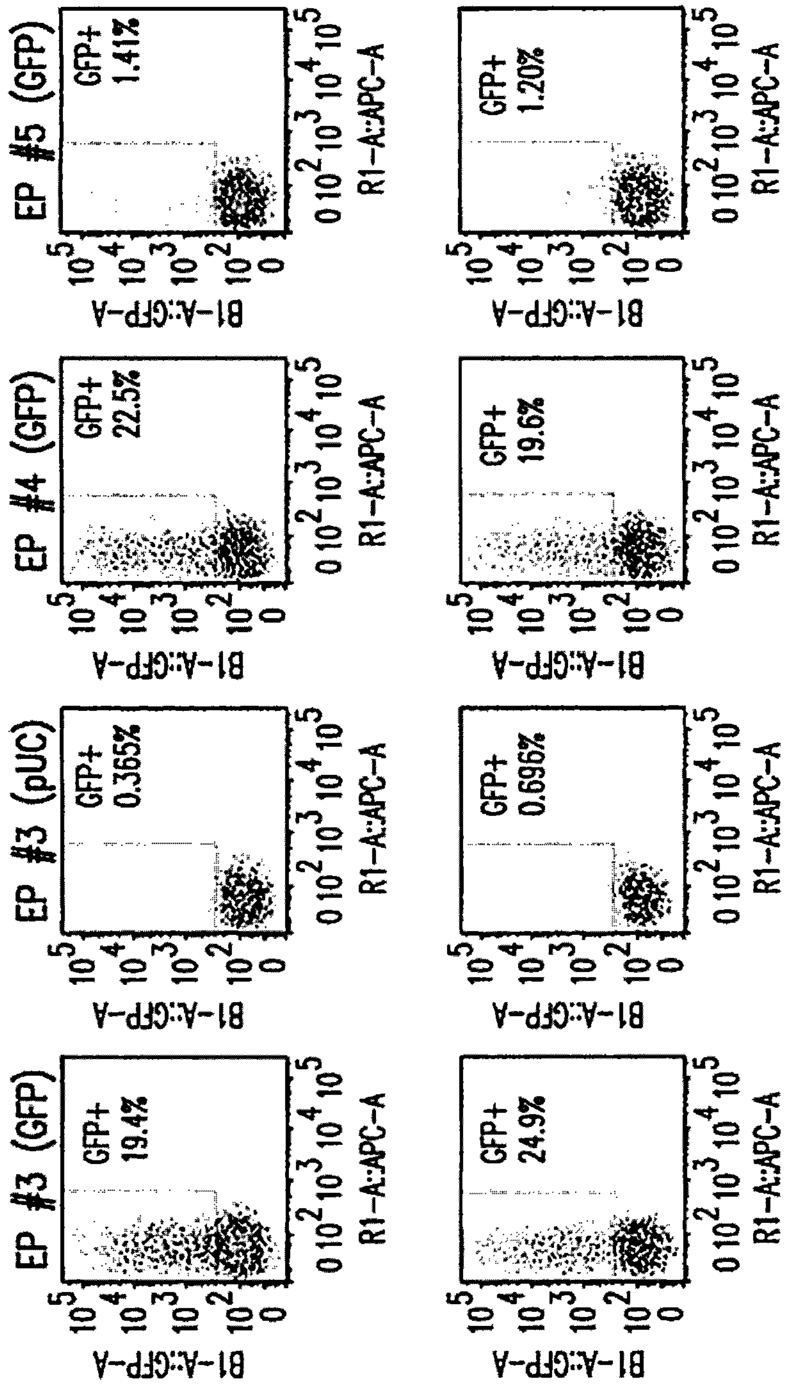

FIGS. 17 A and B: Flow cytometry analysis of GFP positive cells on PBMCs electroporated with the five different Cytopulse programs. A. NEP, EP#1 (GFP) and EP#2 (GFP); B. EP#3 (pUC), EP#4 (GFP) and EP#5 (GFP). The upper line corresponds to transfection of $6\times10^6$ cells per cuvette, while the lower line corresponds to transfection of $3\times10^6$ cells per cuvette.

Figure 18A:
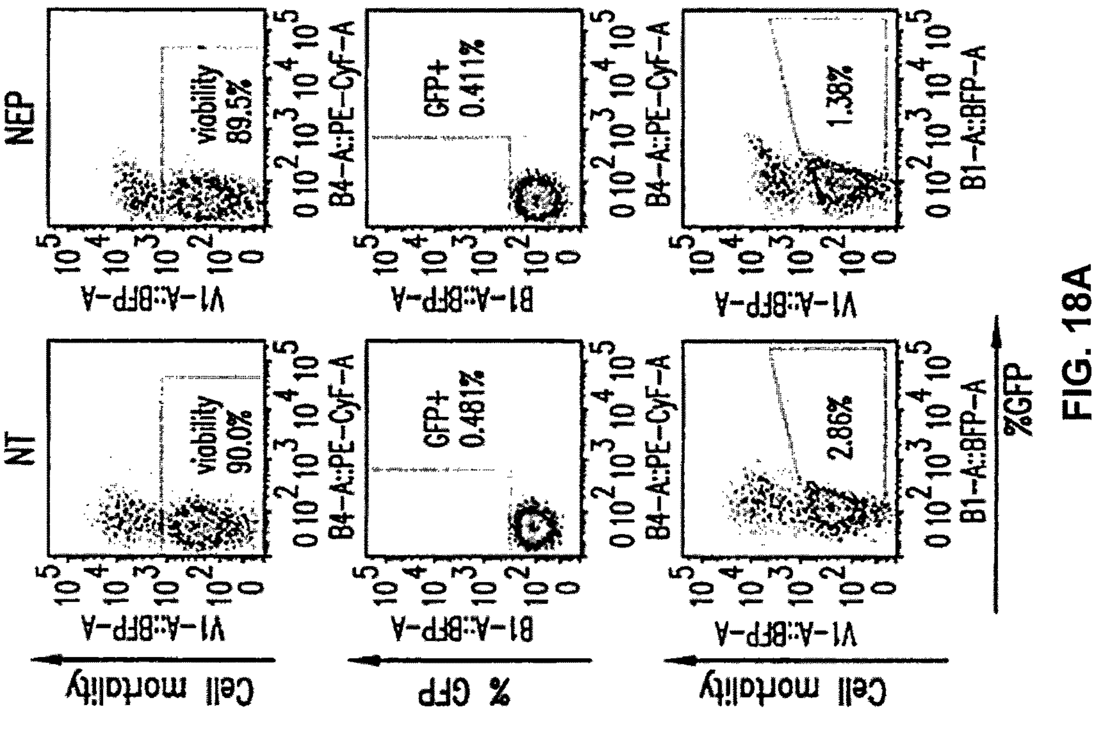
Figure 18B:
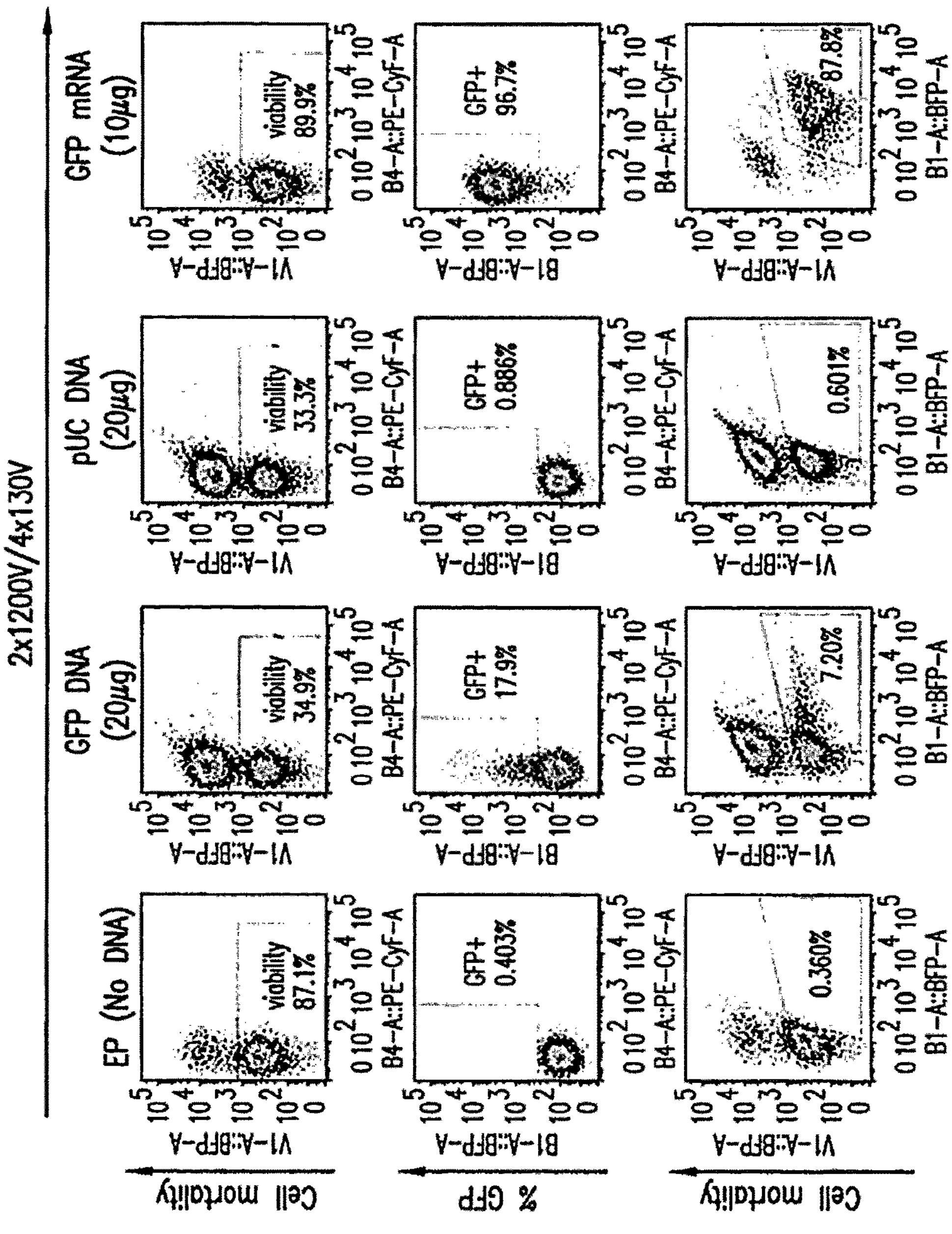

FIGS. 18 A and B: Flow cytometry analysis of purified T cell mortality using viability dye (eFluor-450) and of GFP positive cells among the viable population after electroporation with GFP mRNA, GFP DNA and control pUC DNA. A. NT and NEP; B. EP (no DNA) and GFP DNA; C. pUC DNA and GFP mRNA. NEP corresponds to cells that were maintained in electroporation buffer but were not electroporated and NT corresponds to non electroporated cells maintained in culture medium.

Figure 19:
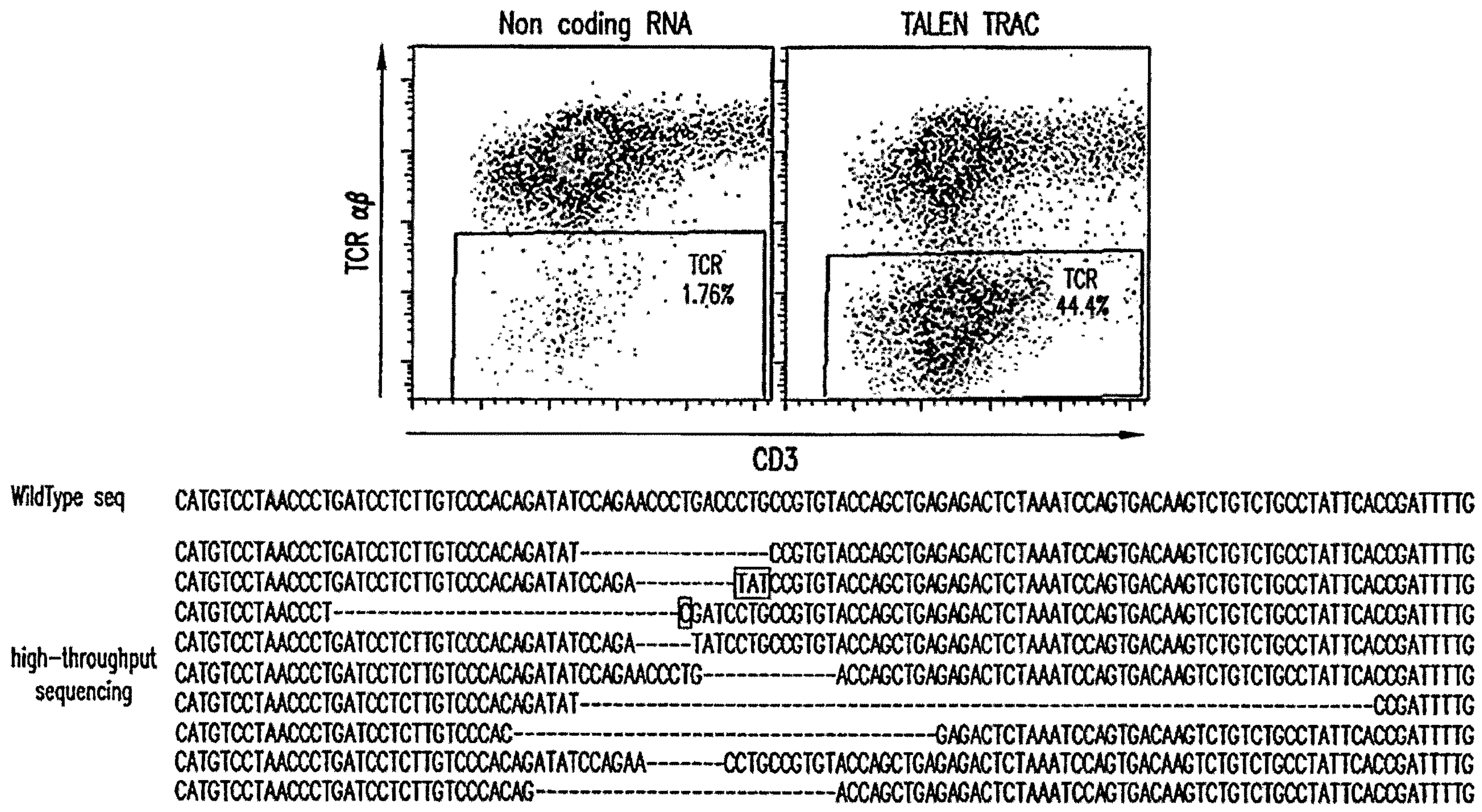

FIG. 19: Flow cytometry analysis of TCR alpha/beta and CD3 expression on human primary T cells following TRAC TALE-nuclease mRNA electroporation (top). Deep sequencing analysis of genomic DNA extracted from human primary T cells following TRAC TALE-nuclease mRNA electroporation (bottom) (SEQ ID NOS 183-192, respectively, in order of appearance).

Figure 20:
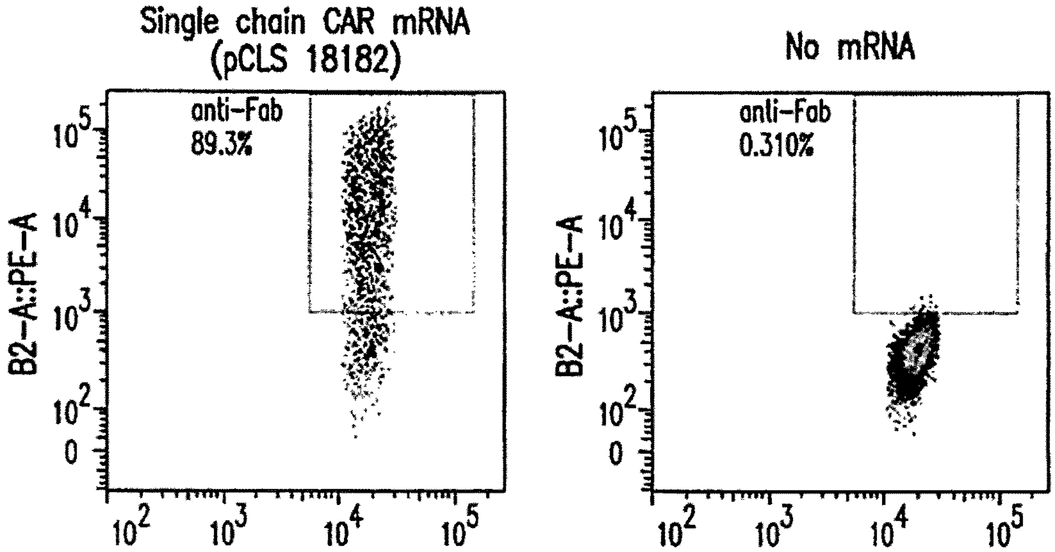
Figure 20:
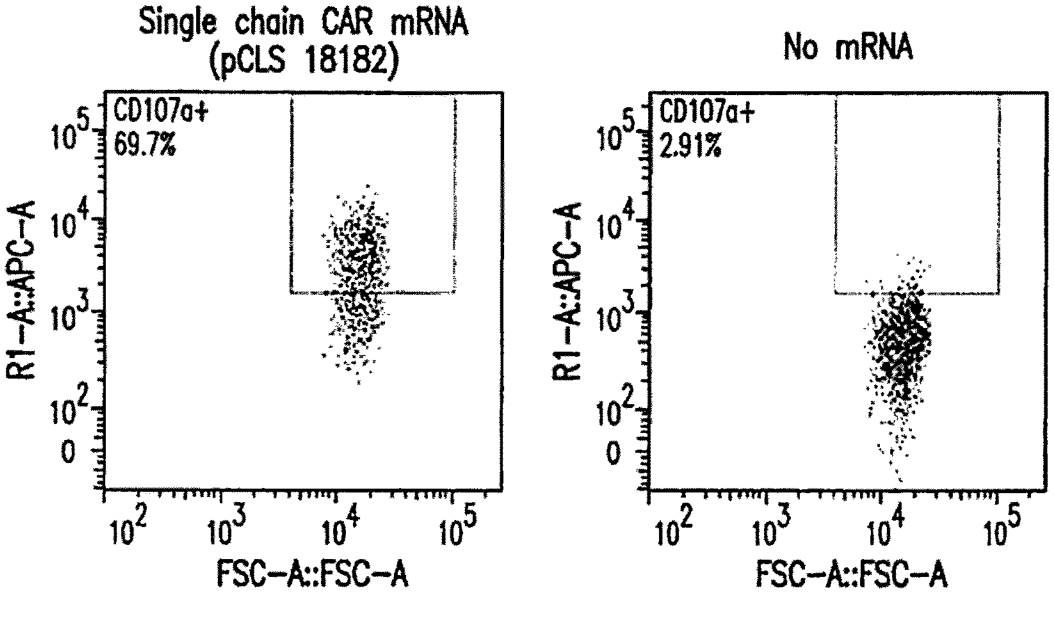

FIGS. 20 A and B: A. Flow cytometry analysis of CAR expression (anti F(ab')2) after electroporation of T cells with or without mRNA encoding a single chain CAR. B. Flow cytometry analysis of CD107a expression (marker of degranulation) on electroporated T cells cocultured with daudi cells.

Figure 21:
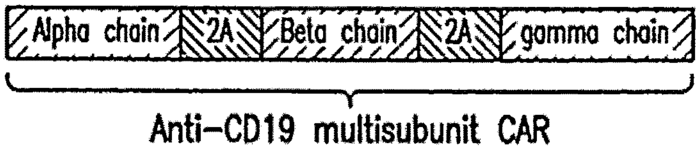
Figure 21:
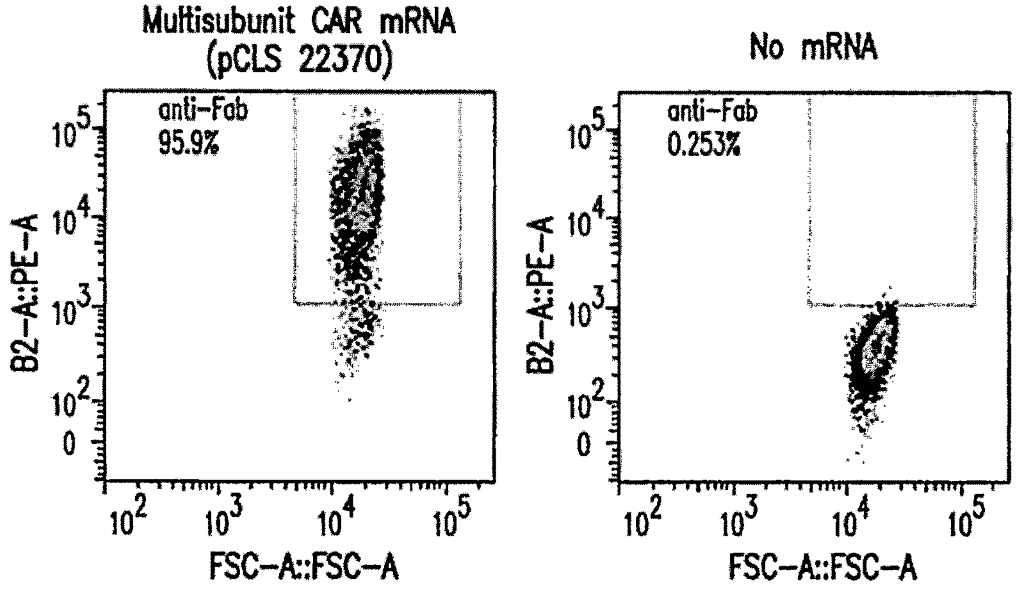
Figure 21:
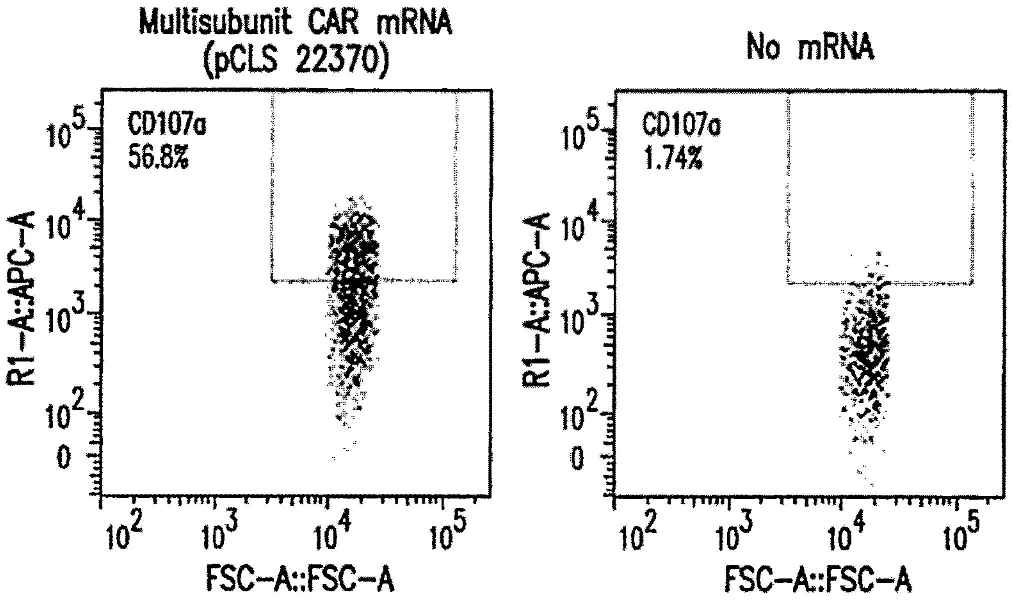

FIGS. 21A, B and C: A. Representation of mRNA encoding a multi-chain CAR. B. Flow cytometry analysis of CAR expression (anti F(ab')2) on viable T cells electroporated with or without a polycistronic mRNA encoding a multi-chain CAR. C. Flow cytometry analysis of CD107a expression (marker of degranulation) on electroporated T cells cocultured with daudi cells.

Figure 22:
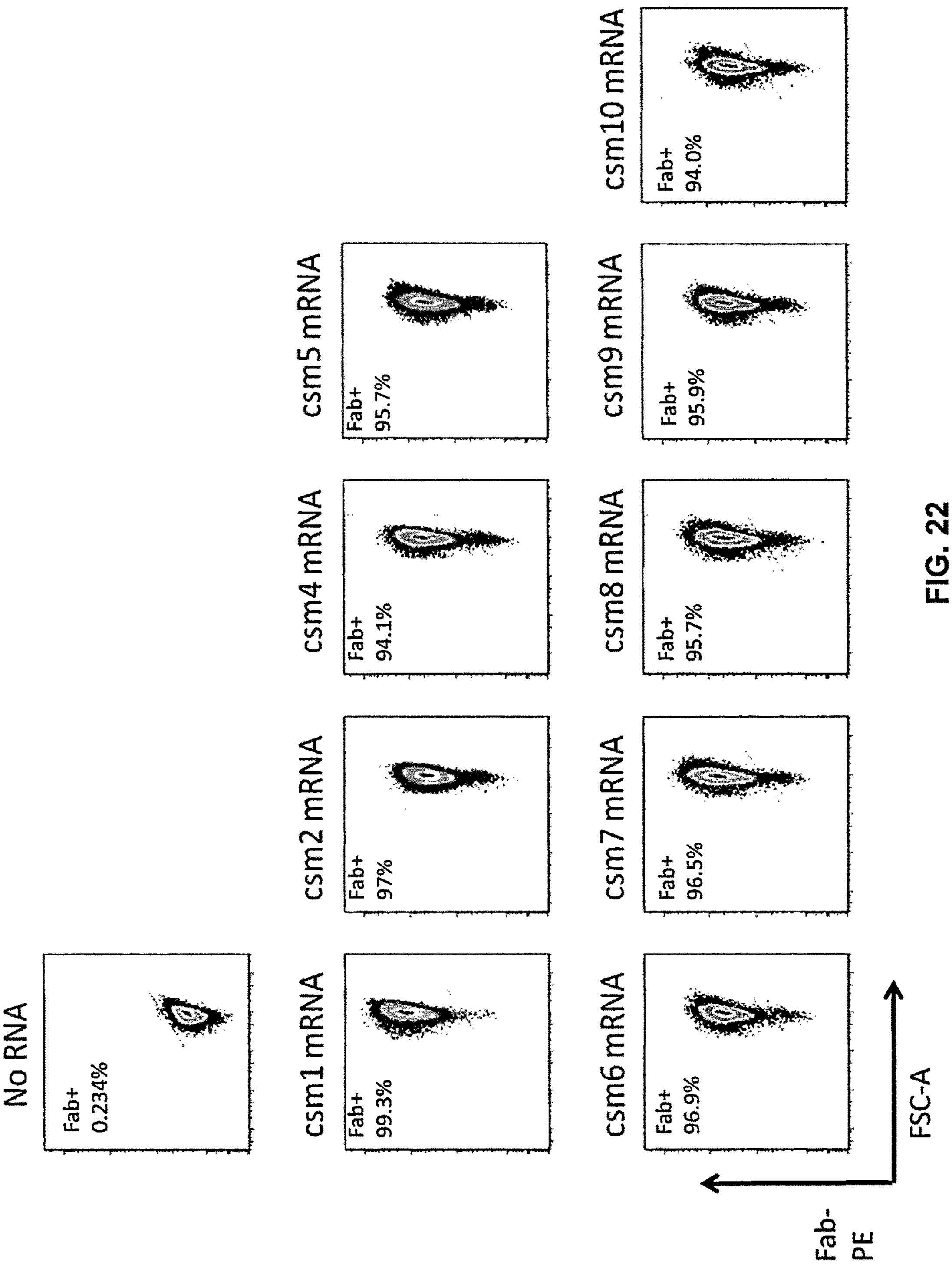

FIG. 22: Multi-chain CARs expression in human T cells after electroporation of polycistronic mRNAs.

Figure 23:
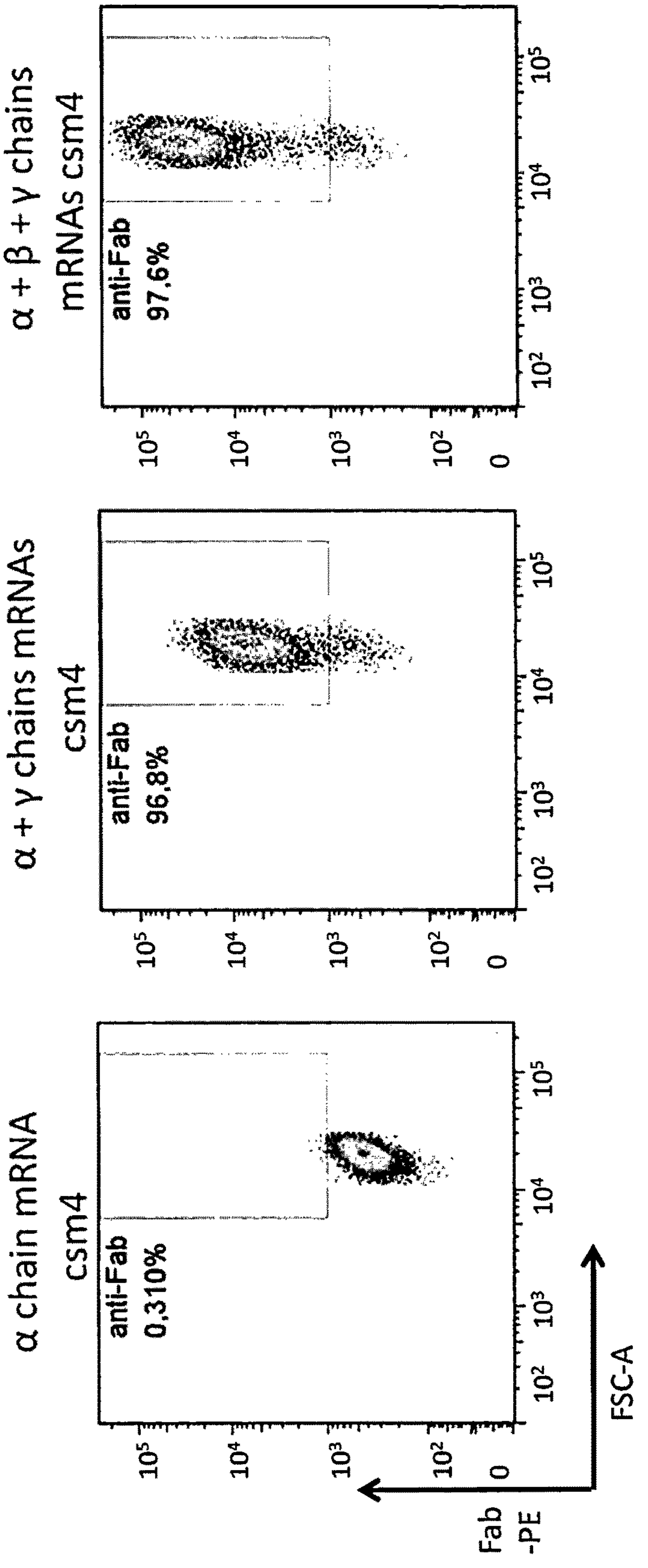

FIG. 23: The expression of the multi-subunit CARs is conditioned by the expression of the three chains: α, β and γ.

Figure 24A:
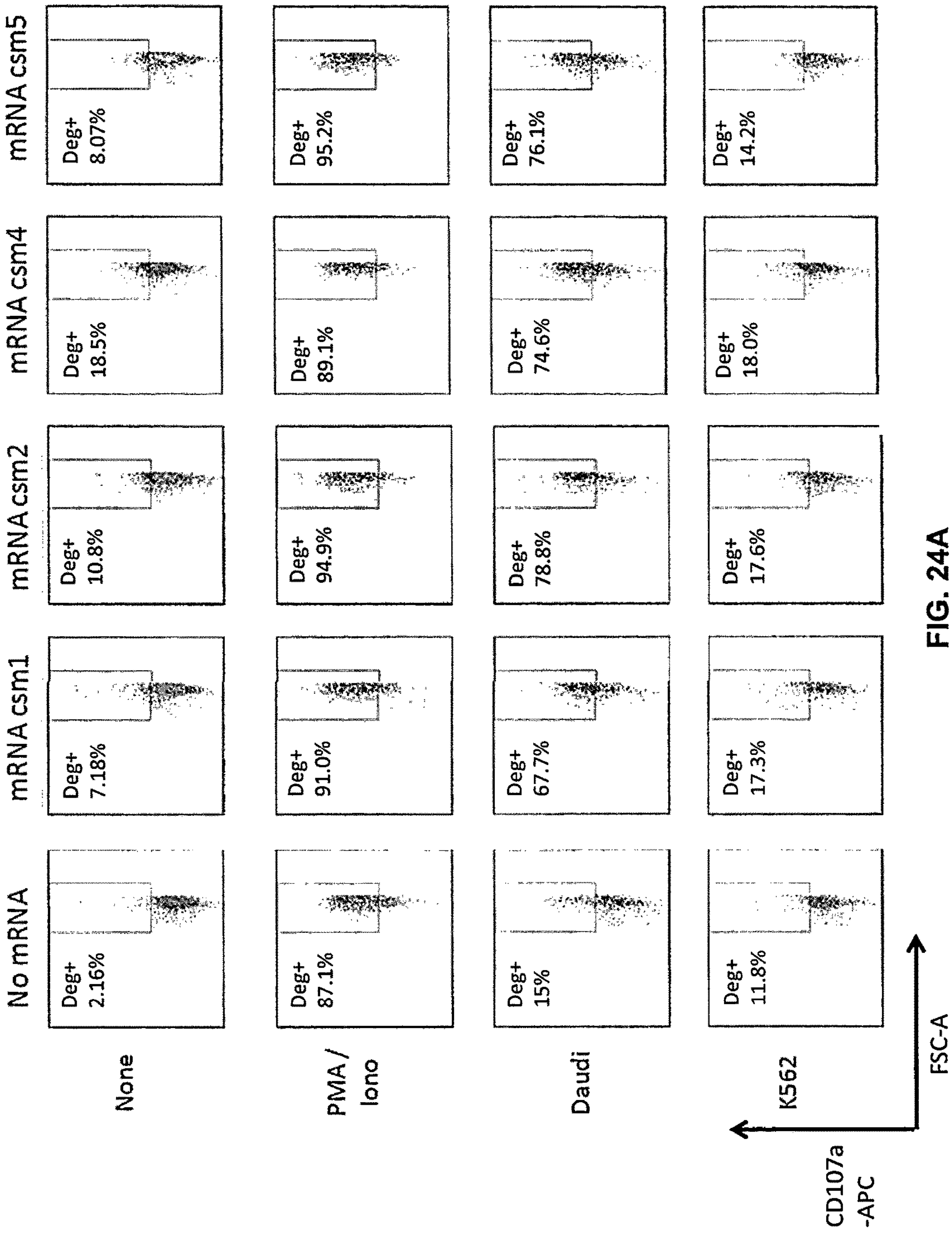
Figure 24B:
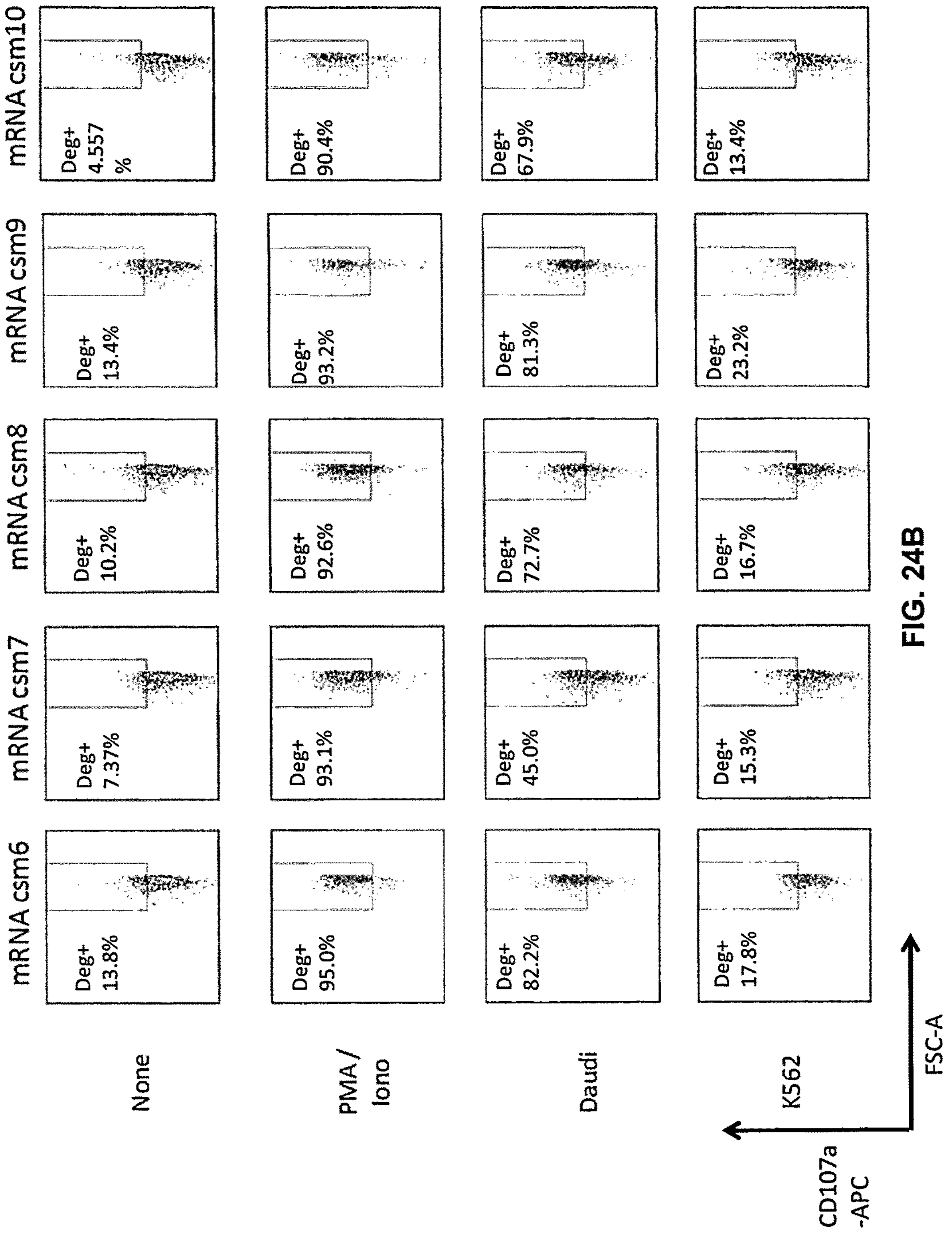

FIGS. 24 A and B: The human T cells transiently expressing the multi-chain CARs degranulate following coculture with target cells.

Figure 25A:
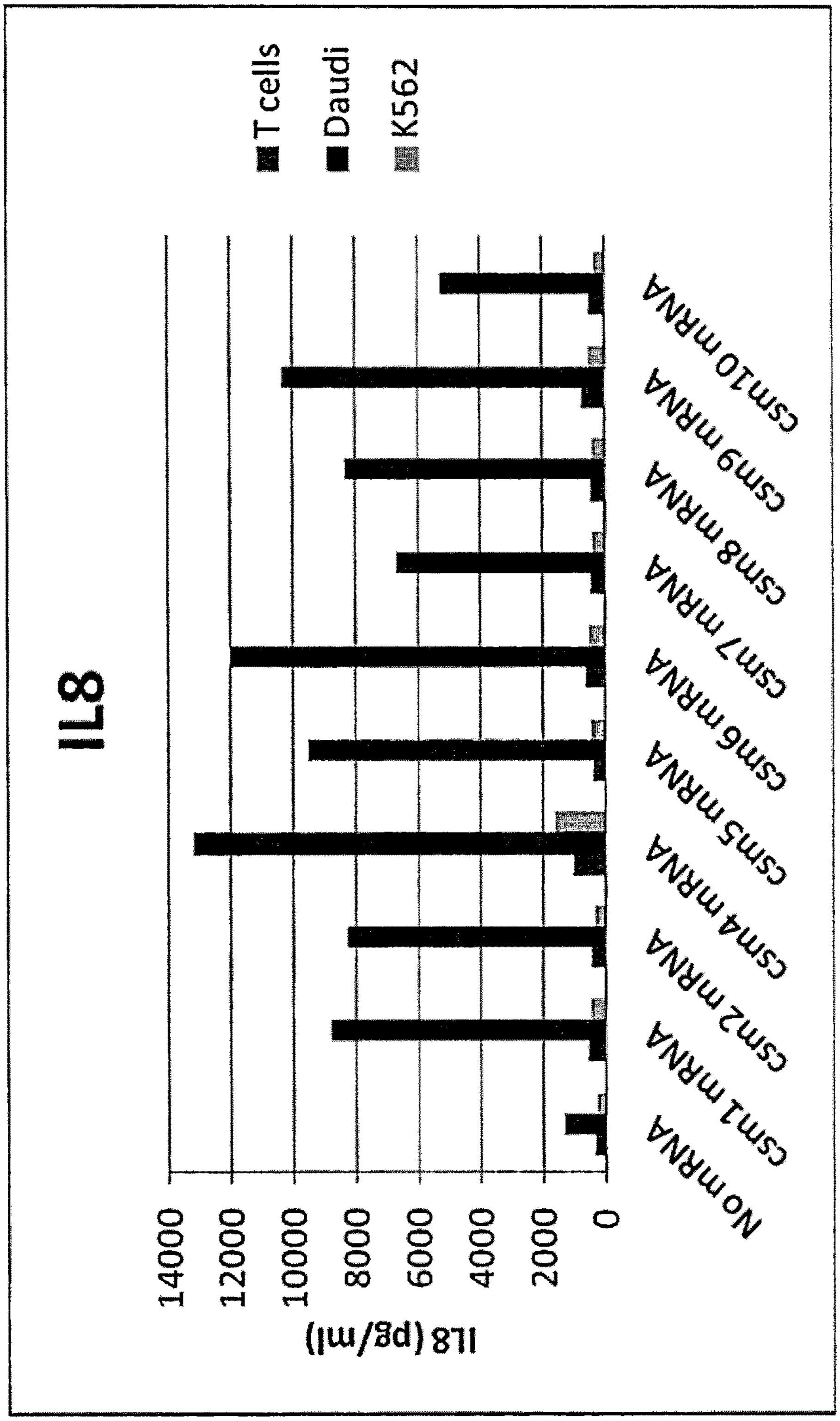
Figure 25B:
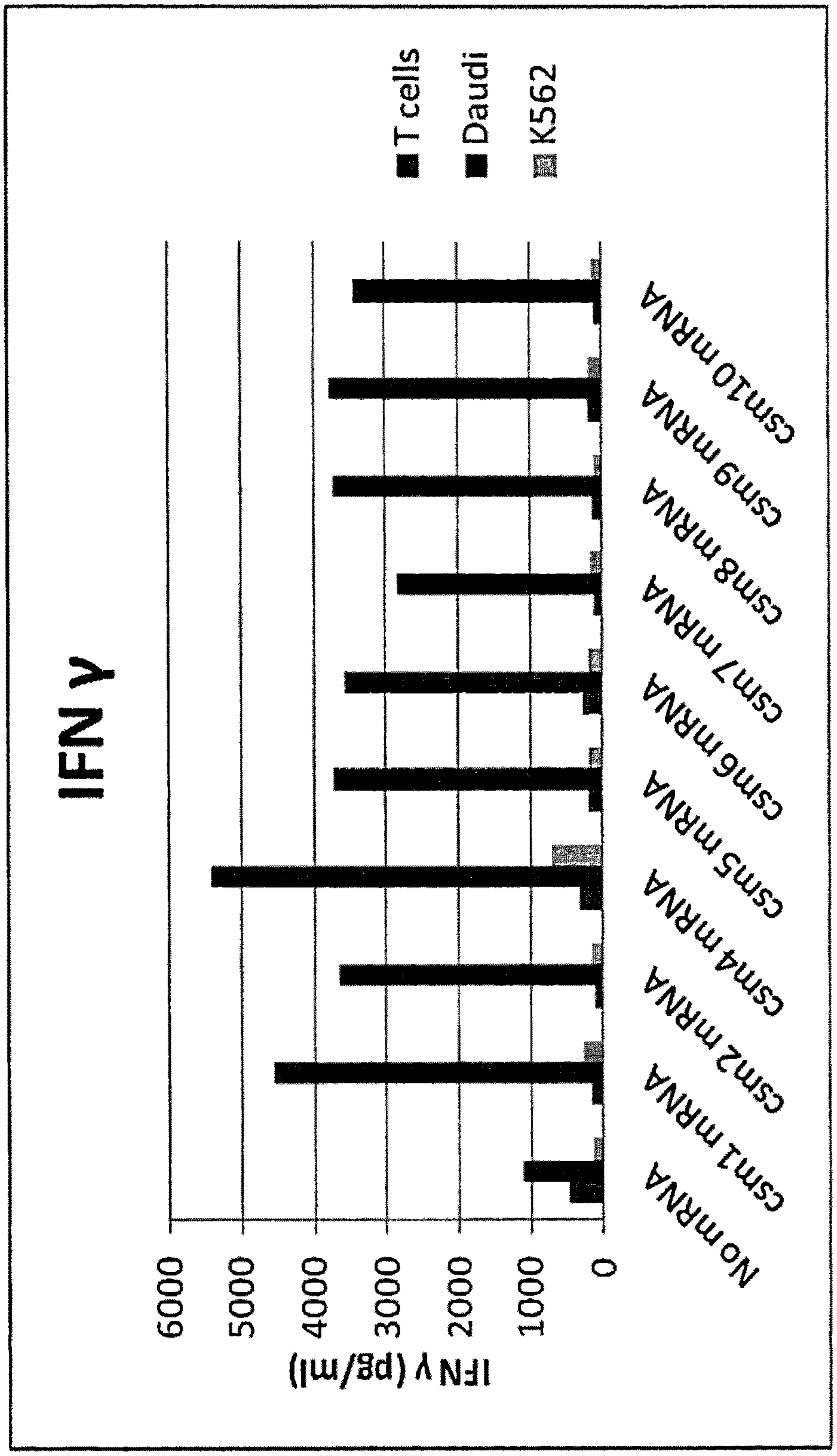
Figure 25C:
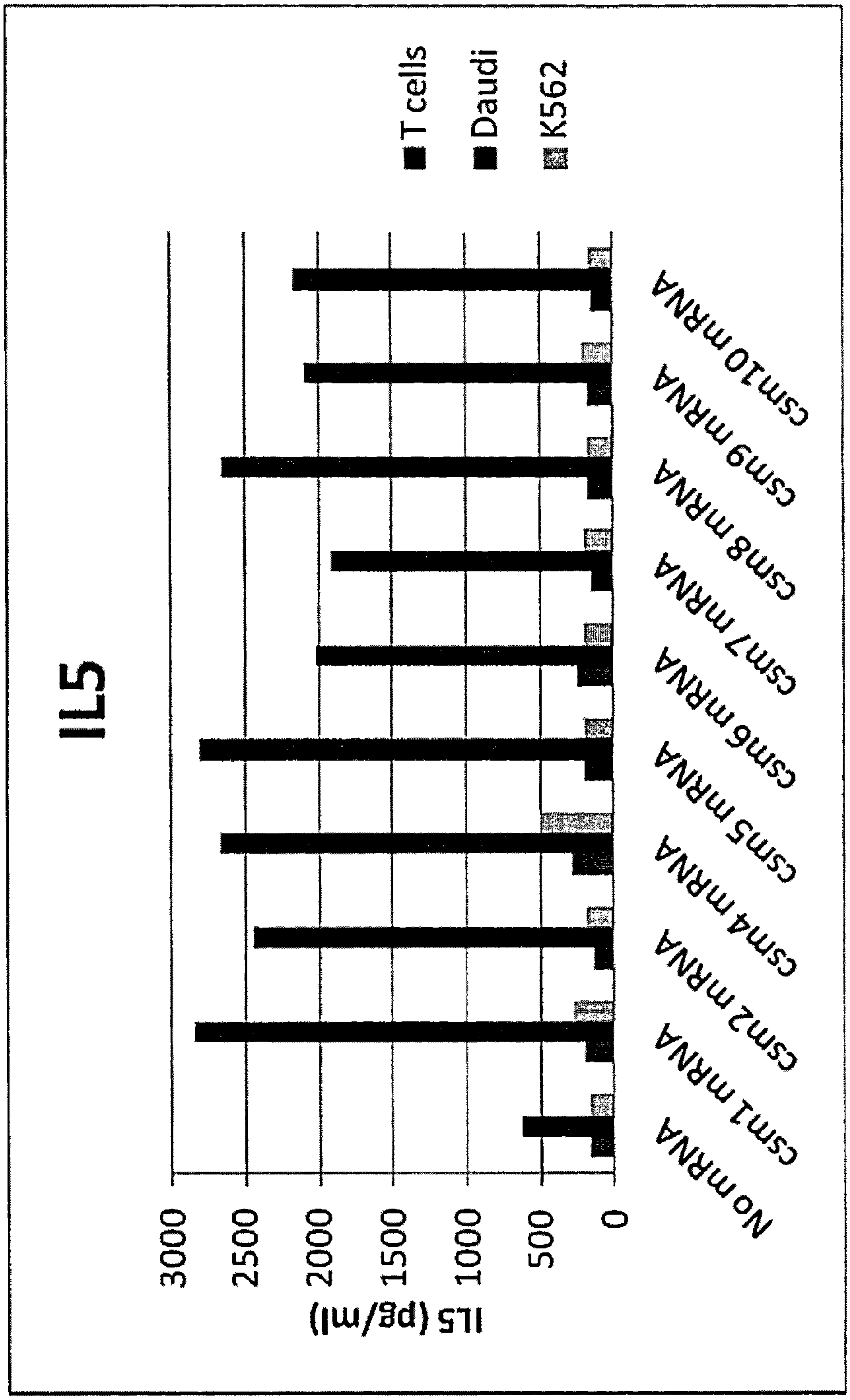

FIGS. 25 A, B and C: The human T cells transiently expressing the multi-chain CARs secrete cytokines following coculture with target cells.

Figure 26:
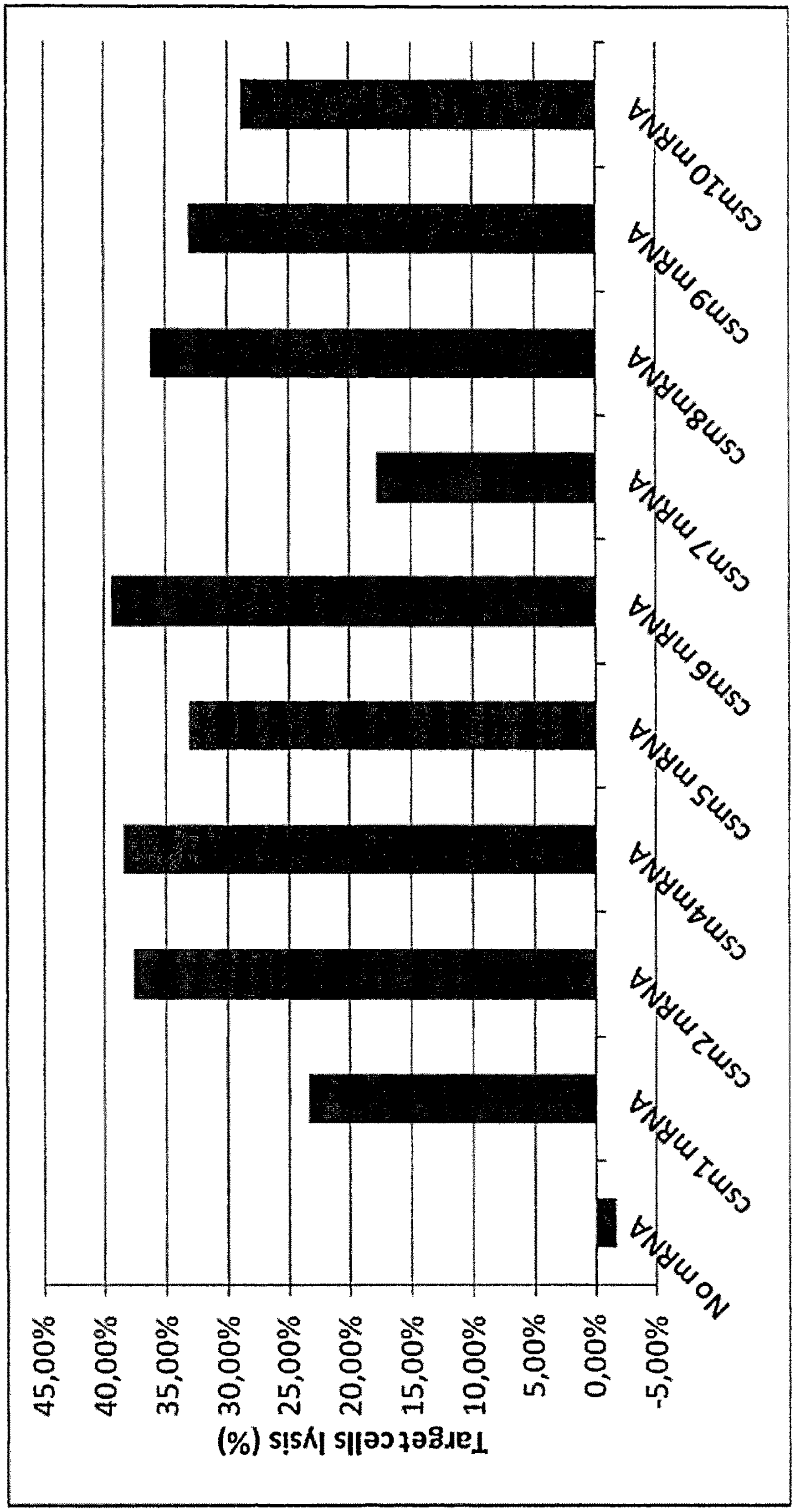

FIG. 26: The human T cells transiently expressing the multi-chain CARs lyse target cells.

Table 1: Description of the GR TALE-nucleases and sequences of the TALE-nucleases target sites in the human GR gene.

Table 2: Cleavage activity of the GR TALE-nucleases in yeast. Values are comprised between 0 and 1. Maximal value is 1.

Table 3: Percentage of targeted mutagenesis at endogenous TALE-nuclease target sites in 293 cells.

Table 4: Percentage of targeted mutagenesis at endogenous TALE-nuclease target sites in primary T lymphocytes.

Table 5: Description of the CD52, TRAC and TRBC TALE-nucleases and sequences of the TALE-nucleases target sites in the human corresponding genes.

Table 6: Additional target sequences for TRAC and CD52 TALE-nucleases.

Table 7: Percentage of indels for TALE-nuclease targeting CD52_T02, TRAC_T01, TRBC_T01 and TRBC_T02 targets.

Table 8: Percentages of CD52-negative, TCR-negative and CD52/TCR-double negative T lymphocytes after transfection of corresponding TALE-nuclease-expressing polynucleotides.

Table 9: Percentages of TCR-negative T lymphocytes after transfection of TRBC TALE-nuclease-expressing polynucleotides.

Table 10: Description of the CTLA4 and PDCD1 TALE-nucleases and sequences of the TALE-nucleases target sites in the human corresponding genes.

Table 11: Description of a subset of pTalpha constructs.

Table 12: Activity of the different pTalpha constructs in Jurkat TCR alpha inactivated cell. Activity was measured by flow cytometry analysis of CD3 expression on jurkat TCR alpha inactivated cell transfected with the different preTalpha constructs.

Table 13: Different cytopulse programs used to determine the minimal voltage required for electroporation in PBMC derived T-cells.

Table 14: Cytopulse program used to electroporate purified T-cells.

Table 15: Description of the FcR chains compositions of the multi-chain CARs versions.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Multi-chain Chimeric Antigen Receptor (CAR)

The present invention relates to a multi-chain chimeric antigen receptor (CAR) particularly adapted to immune cells used in immunotherapy.

The multi-chain CAR according to the invention generally comprises at least:

- one transmembrane polypeptide comprising at least one extracellular ligand-biding domain and;
- one transmembrane polypeptide comprising at least one signal-transducing domain;

such that said polypeptides assemble together to form a multi-chain Chimeric Antigen Receptor.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells. In particular, the extracellular ligand-binding domain can comprise an antigen binding domain derived from an antibody against an antigen of the target. As non limiting examples, the antigen of the target can be a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelia, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), endoglin, a major histocompatibility complex (MHC) molecule, BCMA (CD269, TNFRSF 17), or a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers.

The extracellular ligand-binding domain can also comprise a peptide binding an antigen of the target, a peptide or a protein binding an antibody that binds an antigen of the target, a peptide or a protein ligand such as a growth factor, a cytokine or a hormone as non limiting examples binding a receptor on the target, or a domain derived from a receptor such as a growth factor receptor, a cytokine receptor or a hormone receptor as non limiting examples, binding a peptide or a protein ligand on the target. Preferably the target is a cell or a virus.

In a preferred embodiment, said extracellular ligand-binding domain is a single chain antibody fragment (scFv) comprising the light ($V_L$) and the heavy ($V_H$) variable fragment of a target antigen specific monoclonal antibody joined by a flexible linker. In a preferred embodiment, said scFv is an anti-CD19 scFV, preferably scFV-4G7 (Peipp et al., J Immunol Methods. 2004 Feb. 15; 285(2):265-80) (VH: SEQ ID NO: 193 and VL: SEQ ID NO: 194, scFV: SEQ ID NO: 195).

Other binding domain than scFv can also be used for predefined targeting of lymphocytes, such as camelid single-domain antibody fragments or receptor ligands like a vascular endothelial growth factor polypeptide, an integrin-binding peptide, heregulin or an IL-13 mutein, antibody binding domains, antibody hypervariable loops or CDRs as non limiting examples.

In a preferred embodiment said transmembrane polypeptide further comprises a stalk region between said extracellular ligand-binding domain and said transmembrane domain. The term “stalk region” used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain (e.g. NP_001139345.1) (SEQ ID NO: 196).

Thus, the expression of multi-chain CAR in immune cells results in modified cells that selectively and eliminate defined targets, including but not limited to malignant cells carrying a respective tumor-associated surface antigen or virus infected cells carrying a virus-specific surface antigen, or target cells carrying a lineage-specific or tissue-specific surface antigen.

Downregulation or mutation of target antigens is commonly observed in cancer cells, creating antigen-loss escape variants. Thus, to offset tumor escape and render immune cell more specific to target, the multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR. In another embodiment, the present invention relates to a population of multi-chain CARs comprising each one different extracellular ligand binding domains. In a particular, the present invention relates to a method of engineering immune cells comprising providing an immune cell and expressing at the surface of said cell a population of multi-chain CAR each one comprising different extracellular ligand binding domains. In another particular embodiment, the present invention relates to a method of engineering an immune cell comprising providing an immune cell and introducing into said cell polynucleotides encoding polypeptides composing a population of multi-chain CAR each one comprising different extracellular ligand binding domains. In a particular embodiment the method of engineering an immune cell comprises expressing at the surface of the cell at least a part of FcεRI beta and/or gamma chain fused to a signal-transducing domain and several part of FcεRI alpha chains fused to different extracellular ligand binding domains. In a more particular embodiment, said method comprises introducing into said cell at least one polynucleotide which encodes a part of FcεRI beta and/or gamma chain fused to a signal-transducing domain and several FcεRI alpha chains fused to different extracellular ligand binding domains. By population of multi-chain CARs, it is meant at least two, three, four, five, six or more multi-chain CARs each one comprising different extracellular ligand binding domains. The different extracellular ligand binding domains according to the present invention can preferably simultaneously bind different elements in target thereby augmenting immune cell activation and function.

The present invention also relates to an isolated immune cell which comprises a population of multi-chain CARs each one comprising different extracellular ligand binding domains.

The signal transducing domain or intracellular signaling domain of the multi-chain CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines. Thus, the term “signal transducing domain” refers to the portion of a protein which transduces the effector signal function signal and directs the cell to perform a specialized function.

Preferred examples of signal transducing domain for use in multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases.

Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the FcεRI beta or gamma chains.

In particular embodiment the signal transduction domain of the multi-chain CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class 1 molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In another particular embodiment, said signal transducing domain is a TNFR-associated Factor 2 (TRAF2) binding motifs, intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

In a preferred embodiment, the signal transduction domain of the multi-chain CAR of the present invention comprises a part of co-stimulatory signal molecule selected from the group consisting of 4-1BB (GenBank: AAA53133.) and CD28 (NP_006130.1). In particular the signal transduction domain of the multi-chain CAR of the present invention comprises amino acid sequence selected from SEQ ID NO: 200 and SEQ ID NO: 201.

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the multi-chain CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein. As non limiting examples, the transmembrane polypeptide can be a subunit of the T cell receptor such as α, β, γ or δ, polypeptide constituting CD3 complex, IL2 receptor p55 (αchain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment, the transmembrane polypeptide derived from the Fcε receptor chains or variant thereof, in particular comprises a part of the FcεRI α (SEQ ID NO: 202), β (SEQ ID NO: 203) and/or γ chains (SEQ ID NO: 204) or variant thereof.

The term "derived from" means a polypeptide having an amino acid sequence which is equivalent to that an Fcε receptor which include one or more amino acid modification(s) of the sequence of the Fcε receptor. Such amino acid modification(s) may include amino acid substitution(s), deletion(s), addition(s) or a combination of any of those modifications, and may alter the biological activity of the Fc binding region relative to that of an Fc receptor. On the other hand, Fc binding regions derived from a particular Fc receptor may include one or more amino acid modification(s) which do not substantially alter the biological activity of the Fc binding region relative to that of an Fc receptor. Amino acid modification(s) of this kind will typically comprise conservative amino acid substitution(s).

In a particular embodiment, the multi-chain CAR comprises a transmembrane polypeptide derived from a FcεRI chain. In more particular embodiment FcεRI chain is a FcεRI α chain, in which the extracellular domain is replaced by an extracellular ligand-binding domain, preferably by a scFV, more preferably scFv-4G7 (SEQ ID NO: 195).

In more particular embodiment, said multi-chain CAR can comprise a part of FcεRI alpha chain and a part of FcεRI beta chain or variant thereof such that said FcεRI chains spontaneously dimerize together to form a dimeric Chimeric Antigen Receptor. In another embodiment, the multi-chain Chimeric Antigen can comprise a part of FcεRI alpha chain and a part of a FcεRI gamma chain or variant thereof such that said FcεRI chains spontaneously trimerize together to form a trimeric Chimeric Antigen Receptor, and in another embodiment the multi-chain Chimeric Antigen Receptor can comprise a part of FcεRI alpha chain, a part of FcεRI beta chain and a part of FcεRI gamma chain or variants thereof such that said FcεRI chains spontaneously tetramerize together to form a tetrameric Chimeric Antigen Receptor.

In other words, the multi-chain CAR comprising at least two of the following components:

a) one polypeptide comprising a part of FcεRI alpha chain and an extracellular ligand-binding domain,
b) one polypeptide comprising a part of FcεRI beta chain and/or
c) one polypeptide comprising a part FcεRI gamma chain, whereby different polypeptides multimerize together spontaneously to form dimeric, trimeric or tetrameric CAR.

In a preferred embodiment, the multi-chain CAR of the present invention comprise a part of a polypeptide with amino acid sequence selected from the group consisting of SEQ ID NO: 202 to SEQ ID NO: 204.

The term “a part of” used herein refers to any subset of the molecule, that is a shorter peptide. Alternatively, amino acid sequence functional variants of the polypeptide can be prepared by mutations in the DNA which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity. The functionality of the multi-chain CAR of the invention within a host cell is detectable in an assay suitable for demonstrating the signaling potential of said multi-chain CAR upon binding of a particular target. Such assays are available to the skilled person in the art. For example, this assay allows the detection of a signaling pathway, triggered upon binding of the target, such as an assay involving measurement of the increase of calcium ion release, intracellular tyrosine phosphorylation, inositol phosphate turnover, or interleukin (IL) 2, interferon γ, GM-CSF, IL-3, IL-4 production thus effected.

As non limiting example, different versions of multi-chain CAR are illustrated in FIG. 4. In a more preferred embodiment, the multi-chain CAR of the present invention comprises a polypeptide with amino acid sequence selected from the group consisting of SEQ ID NO: 206 to SEQ ID NO: 213. In a preferred embodiment the multi-chain CAR comprise a polypeptide with amino acid sequence that has at least 70%, preferably at least 80%, more preferably at least 90%, 95% 97% or 99% sequence identity with amino acid sequence selected from the group consisting of SEQ ID NO: 206 to SEQ ID NO: 213.

Polynucleotides, Vectors:

The present invention also relates to polynucleotides, vectors encoding the above described multi-chain CAR according to the invention. The present invention provides polynucleotides, including DNA and RNA molecules that encode the transmembrane polypeptides disclosed herein that can be included in the multi-chain CAR. In particular, the invention relates to a polynucleotide comprising a nucleic acid sequence encoding at least one transmembrane polypeptide composing the multi-chain CAR as described above. More particularly the invention relates to a polynucleotide comprising two or more nucleic acid sequences encoding transmembrane polypeptides composing the multi-chain CAR as described above. In a preferred embodiment, the present invention relates to a polynucleotide selected from the group consisting of: SEQ ID NO: 214 to SEQ ID NO: 223. In a preferred embodiment, the polynucleotide has at least 70%, preferably at least 80%, more preferably at least 90%, 95% 97% or 99% sequence identity with nucleic acid sequence selected from the group consisting of SEQ ID NO: 214 to SEQ ID NO: 223.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal “skip” from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By “codon” is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the different polypeptides of the multi-chain CAR. In a more preferred embodiment, the present invention relates to polynucleotides selected from the group consisting of: SEQ ID NO: 224 to SEQ ID NO: 232.

To direct, transmembrane polypeptide such as FcER into the secretory pathway of a host cell, a secretory signal sequence (also known as a leader sequence, prepro sequence or pre sequence) is provided in polynucleotide sequence or vector sequence. The secretory signal sequence may be that of FcER, or may be derived from another secreted protein (e.g., t-PA) or synthesized de novo. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the residues 1 to 25 of the FcεRI alpha chain (NP_001992.1) and has the amino acid sequence SEQ ID NO: 205.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

In a preferred embodiment, the polynucleotide according to the present invention comprises the nucleic acid sequence selected from the group consisting of: SEQ ID NO: 214 to SEQ ID NO: 223. The present invention relates to polynucleotides comprising a nucleic acid sequence that has at least 70%, preferably at least 80%, more preferably at least 90%, 95% 97% or 99% sequence identity with nucleic acid sequence selected from the group consisting of SEQ ID NO: 214 to SEQ ID NO: 222.

Methods of Engineering an Immune Cell:

In encompassed particular embodiment, the invention relates to a method of preparing immune cells for immunotherapy comprising introducing into said immune cells the polypeptides composing said multi-chain CAR and expanding said cells. In particular embodiment, the invention relates to a method of engineering an immune cell comprising providing a cell and expressing at the surface of said cell at least one multi-chain CAR as described above. In particular embodiment, the method comprises transforming the cell with at least one polynucleotide encoding polypeptides composing at least one multi-chain CAR as described above, and expressing said polynucleotides into said cell.

In another embodiment, the present invention relates to a method of preparing cells for immunotherapy comprising introducing into said cells the different polypeptides composing said multi-chain CAR and expanding said cells. In a preferred embodiment, said polynucleotides are included in lentiviral vectors in view of being stably expressed in the cells.

In another embodiment, said method further comprises a step of genetically modifying said cell by inactivating at least one gene expressing one component of the TCR, a target for an immunosuppressive agent, HLA gene and/or an immune checkpoint gene such as PDCD1 or CTLA-4. In a preferred embodiment, said gene is selected from the group consisting of TCRalpha, TCRbeta, CD52, GR, PD1 and CTLA-4. In a preferred embodiment said method further comprises introducing into said T cells a rare-cutting endonuclease able to selectively inactivate by DNA cleavage said genes. In a more preferred embodiment said rare-cutting endonuclease is TALE-nuclease. Preferred TALE-nucleases according to the invention are those recognizing and cleaving the target sequence selected from the group consisting of: SEQ ID NO: 1 to 6 (GR), SEQ ID NO: 37, 57 to 60 (TCRalpha), SEQ ID NO: 38 or 39 (TCRbeta), and SEQ ID NO: 40, SEQ ID NO: 61 to SEQ ID NO: 65 (CD52), SEQ ID NO: 74 to SEQ ID NO: 78 (PD1 and CTLA-4).

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e a mutagenesis event consecutive to an NHEJ event, has occurred can be identified and/or selected by well-known method in the art.

In another embodiment, additional catalytic domain can be further introduced into the cell with said rare-cutting endonuclease to increase mutagenesis in order to enhance their capacity to inactivate targeted genes described in the present disclosure. In particular, said additional catalytic domain is a DNA end processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise of a protein domain or catalytically active derivate of the protein domain selected from the group consisting of hExoI (EXO1_HUMAN), Yeast ExoI (EXO1_YEAST), *E. coli* ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain is TREX, more preferably TREX2 catalytic domain (WO2012/058458). In another preferred embodiment, said catalytic domain is encoded by a single chain TREX polypeptide. Said additional catalytic domain may be fused to a nuclease fusion protein or chimeric protein according to the invention optionally by a peptide linker.

Endonucleolytic breaks are known to stimulate the rate of homologous recombination. Thus, in another embodiment, the genetic modification step of the method further comprises a step of introduction into cells an exogeneous nucleic acid comprising at least a sequence homologous to a portion of the target nucleic acid sequence, such that homologous recombination occurs between the target nucleic acid sequence and the exogeneous nucleic acid. In particular embodiments, said exogenous nucleic acid comprises first and second portions which are homologous to region 5' and 3' of the target nucleic acid sequence, respectively. Said exogenous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogenous nucleic acid. Preferably, homologous sequences of at least 50 bp, preferably more than 100 bp and more preferably more than 200 bp are used within said donor matrix. Therefore, the exogenous nucleic acid is preferably from 200 bp to 6000 bp, more preferably from 1000 bp to 2000 bp. Indeed, shared nucleic acid homologies are located in regions flanking upstream and downstream the site of the break and the nucleic acid sequence to be introduced should be located between the two arms.

In particular, said exogenous nucleic acid successively comprises a first region of homology to sequences upstream of said cleavage, a sequence to inactivate one targeted gene selected from the group consisting of TCR alpha, TCR beta, CD52, GR, immune checkpoint genes and a second region of homology to sequences downstream of the cleavage. Said polynucleotide introduction step can be simultaneous, before or after the introduction or expression of said rare-cutting endonuclease. Depending on the location of the target nucleic acid sequence wherein break event has occurred, such exogenous nucleic acid can be used to knock-out a gene, e.g. when exogenous nucleic acid is located within the open reading frame of said gene, or to introduce new sequences or genes of interest. Sequence insertions by using such exogenous nucleic acid can be used to modify a targeted existing gene, by correction or replacement of said gene (allele swap as a non-limiting example), or to up- or down-regulate the expression of the targeted gene (promoter swap as non-limiting example), said targeted gene correction or replacement. In preferred embodiment, inactivation of genes from the group consisting of TCR alpha, TCR beta, CD52, GR, immune checkpoint genes can be done at a precise genomic location targeted by a specific TALE-nuclease, wherein said specific TALE-nuclease catalyzes a cleavage and wherein said exogenous nucleic acid successively comprising at least a region of homology and a sequence to inactivate one targeted gene selected from the group consisting of TCR alpha, TCR beta, CD52, GR, immune checkpoint genes which is integrated by homologous recombination. In another embodiment, several genes can be, successively or at the same time, inactivated by using several TALE-nucleases respectively and specifically targeting one defined gene and several specific polynucleotides for specific gene inactivation.

By additional genomic modification step, can be intended also the inactivation of another gene selected from the group consisting of TCR alpha, TCR beta, CD52, GR, immune checkpoint genes. As mentioned above, said additional genomic modification step can be an inactivation step comprising:

(a) introducing into said cells at least one rare-cutting endonuclease such that said rare-cutting endonuclease specifically catalyzes cleavage in one targeted sequence of the genome of said cell.

(b) Optionally introducing into said cells a exogenous nucleic acid successively comprising a first region of homology to sequences upstream of said cleavage, a sequence to be inserted in the genome of said cell and a second region of homology to sequences downstream of said cleavage, wherein said introduced exogenous nucleic acid inactivates a gene and integrates at least one exogenous polynucleotide sequence encoding at least one recombinant protein of interest. In another embodiment, said exogenous polynucleotide sequence is integrated within a gene selected from the group consisting of TCR alpha, TCR beta, CD52, GR, immune checkpoint genes.

Immunosuppressive Resistant T Cells:

In a particular aspect, one of the steps of genetically modifying cells can be a method comprising:

(a) modifying T-cells by inactivating at least one gene expressing a target for an immunosuppressive agent, and (b) Expanding said cells, optionally in presence of said immunosuppressive agent.

An immunosuppressive agent is an agent that suppresses immune function by one of several mechanisms of action. In other words, an immunosuppressive agent is a role played by a compound which is exhibited by a capability to diminish the extent and/or voracity of an immune response. As non limiting example, an immunosuppressive agent can be a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite. Classical cytotoxic immunosuppressants act by inhibiting DNA synthesis. Others may act through activation of T-cells or by inhibiting the activation of helper cells. The method according to the invention allows conferring immunosuppressive resistance to T cells for immunotherapy by inactivating the target of the immunosuppressive agent in T cells. As non limiting examples, targets for immunosuppressive agent can be a receptor for an immunosuppressive agent such as: CD52, glucocorticoid receptor (GR), a FKBP family gene member and a cyclophilin family gene member.

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. In a particular embodiment, said method to engineer cells comprises at least one of the following steps:

(a) Providing a T-cell, preferably from a cell culture or from a blood sample;

(b) Selecting a gene in said T-cell expressing a target for an immunosuppressive agent;

(c) Introducing into said T-cell a rare-cutting endonuclease able to selectively inactivate by DNA cleavage, preferably by double-strand break said gene encoding a target for said immunosuppressive agent, and (d) Expanding said cells, optionally in presence of said immunosuppressive agent.

In a more preferred embodiment, said method comprises:

(a) Providing a T-cell, preferably from a cell culture or from a blood sample;

(b) Selecting a gene in said T-cell expressing a target for an immunosuppressive agent;

(c) Transforming said T cell with nucleic acid encoding a rare-cutting endonuclease able to selectively inactivate by DNA cleavage, preferably by double-strand break said gene encoding a target for said immunosuppressive agent, and (d) Expressing said rare-cutting endonucleases into said T-cells;

(e) Expanding said cells, optionally in presence of said immunosuppressive agent.

In particular embodiment, said rare-cutting endonuclease specifically targets one gene selected from the group consisting of CD52, GR. In another embodiment, said gene of step (b), specific for an immunosuppressive treatment, is CD52 and the immunosuppressive treatment of step (d) or (e) comprises a humanized antibody targeting CD52 antigen.

In another embodiment, said gene of step (b), specific for an immunosuppressive treatment, is a glucocorticoid receptor (GR) and the immunosuppressive treatment of step d) or (e) comprises a corticosteroid such as dexamethasone.

In another embodiment, said target gene of step (b), specific for an immunosuppressive treatment, is a FKBP family gene member or a variant thereof and the immunosuppressive treatment of step (d) or (e) comprises FK506 also known as Tacrolimus or fujimycin. In another embodiment, said FKBP family gene member is FKBP12 or a variant thereof.

In another embodiment, said gene of step (b), specific for an immunosuppressive treatment, is a cyclophilin family gene member or a variant thereof and the immunosuppressive treatment of step (d) or (e) comprises cyclosporine.

In another embodiment, said rare-cutting endonuclease can be a meganuclease, a Zinc finger nuclease or a TALE-nuclease. In a preferred embodiment, said rare-cutting endonuclease is a TALE-nuclease. Preferred TALE-nucleases according to the invention are those recognizing and cleaving the target sequence selected from the group consisting of:

SEQ ID NO: 1 to 6 (GR), and

SEQ ID NO: 40, 61 to 65 (CD52)

Said TALE-nucleases preferably comprise a polypeptide sequence selected from SEQ ID NO: 7 to SEQ ID NO: 18 and SEQ ID NO: 47 to SEQ ID NO: 48, in order to cleave the respective target sequences SEQ ID NO: 1 to 6 and SEQ ID NO: 40.

Highly Active T Cells for Immunotherapy

In a particular aspect, one particular step of genetically modifying cell can be a method comprising:

(a) modifying T-cells by inactivating at least one immune checkpoint gene; and (b) expanding said cells.

T cell-mediated immunity includes multiple sequential steps involving the clonal selection of antigen specific cells, their activation and proliferation in secondary lymphoid tissue, their trafficking to sites of antigen and inflammation, the execution of direct effector function and the provision of help (through cytokines and membrane ligands) for a multitude of effector immune cells. Each of these steps is regulated by counterbalancing stimulatory and inhibitory signal that fine-tune the response. It will be understood by those of ordinary skill in the art, that the term "immune checkpoints" means a group of molecules expressed by T cells. These molecules effectively serve as "brakes" to down-modulate or inhibit an immune response. Immune checkpoint molecules include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as VSTM3, accession number: NM_173799), B7H5 (also known as C10orf54, homolog of mouse vista gene, accession number: NM_022153.1), LAIR1 (also known as CD305, GenBank accession number: CR542051.1), SIGLEC10 (GeneBank accession number: AY358337.1), 2B4 (also known as CD244, accession number: NM_001166664.1), which directly inhibit immune cells. For example, CTLA-4 is a cell-surface protein expressed on certain CD4 and CD8 T cells; when engaged by its ligands (B7-1 and B7-2) on antigen presenting cells, T-cell activation and effector function are inhibited. Thus the present invention relates to a method of engineering T-cells, especially for immunotherapy, comprising genetically modifying T-cells by inactivating at least one protein involved in the immune check-point, in particular PD1 and/or CTLA-4.

In a particular embodiment, said method to engineer cells comprises at least one of the following steps:

(a) providing a T-cell, preferably from a cell culture or from a blood sample;

(b) introducing into said T-cell a rare-cutting endonuclease able to selectively inactivate by DNA cleavage, preferably by double-strand break one gene encoding a immune checkpoint protein, (c) expanding said cells.

In a more preferred embodiment, said method comprises:

(a) providing a T-cell, preferably from a cell culture or from a blood sample;

(b) transforming said T cell with nucleic acid encoding a rare-cutting endonuclease able to selectively inactivate by DNA cleavage, preferably by double-strand break a gene encoding a immune checkpoint protein;

(c) expressing said rare-cutting endonucleases into said T-cells;

(d) expanding said cells.

In particular embodiment, said rare-cutting endonuclease specifically targets one gene selected from the group consisting of: PD1, CTLA-4, LAG3, Tim3, BTLA, BY55, TIGIT, B7H5, LAIR1, SIGLEC10, 2B4, TCR alpha and TCR beta. In another embodiment, said rare-cutting endonuclease can be a meganuclease, a Zinc finger nuclease or a TALE-nuclease. In a preferred embodiment, said rare-cutting endonuclease is a TALE-nuclease. By TALE-nuclease is intended a fusion protein consisting of a DNA-binding domain derived from a Transcription Activator Like Effector (TALE) and one nuclease catalytic domain to cleave a nucleic acid target sequence. (Boch, Scholze et al. 2009; Moscou and Bogdanove 2009; Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012; Mak, Bradley et al. 2012).

In the present invention new TALE-nucleases have been designed for precisely targeting relevant genes for adoptive immunotherapy strategies. Preferred TALE-nucleases according to the invention are those recognizing and cleaving the target sequence selected from the group consisting of: SEQ ID NO: 77 and SEQ ID NO: 78 (PD1), SEQ ID NO: 74 to SEQ ID NO: 76 (CTLA-4). The present invention also relates to TALE-nuclease polypeptides which comprise an amino acid sequence selected from the group consisting of SEQ ID NO: 79 to SEQ ID NO: 88.

The present invention also relates to polypeptides comprising an amino acid sequence that has at least 70%, preferably at least 80%, more preferably at least 90%, 95% 97% or 99% sequence identity with amino acid sequence selected from the group consisting of SEQ ID NO: 79 to SEQ ID NO: 88. Are also comprised in the scope of the present invention, polynucleotides, vectors encoding the above described rare-cutting endonucleases according to the invention. This method can be associated with any one of the different methods described in the present disclosure.

Non Alloreactive T Cells:

In another embodiment, the present invention can be particularly suitable for allogeneic immunotherapy. In this case, one of the steps of genetically modifying cells can be a method comprising:

(a) modifying T-cells by inactivating at least one gene encoding a component of the T-cell receptor (TCR)

(b) Expanding said cells.

In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. In a particular embodiment, said method to engineer cells comprises at least one of the following steps:

(a) Providing a T-cell, preferably from a cell culture or from a blood sample;

Introducing into said T-cell a rare-cutting endonuclease able to selectively inactivate by DNA cleavage, preferably by double-strand break at least one gene encoding a component of the T-cell receptor (TCR).

(b) Expanding said cells.

In a more preferred embodiment, said method comprises:

(a) Providing a T-cell, preferably from a cell culture or from a blood sample;

(b) Transforming said T cell with nucleic acid encoding a rare-cutting endonuclease able to selectively inactivate by DNA cleavage, preferably by double-strand break at least one gene encoding a component of the T-cell receptor (TCR);

(c) Expressing said rare-cutting endonucleases into said T-cells;

(d) Sorting the transformed T-cells, which do not express TCR on their cell surface;

(e) Expanding said cells.

In another embodiment, said rare-cutting endonuclease can be a meganuclease, a Zinc finger nuclease or a TALE-nuclease. In a preferred embodiment, said rare-cutting endonuclease is a TALE-nuclease. Preferred TALE-nucleases according to the invention are those recognizing and cleaving the target sequence selected from the group consisting of:

SEQ ID NO: 37, 57 to 60 (TCRalpha),

SEQ ID NO: 38 or 39 (TCRbeta),

Said TALE-nucleases preferably comprise a polypeptide sequence selected from SEQ ID NO: 41 to SEQ ID NO: 48, in order to cleave the respective target sequences SEQ ID NO: 37 to 39.

PreTalpha

In another aspect, one another step of genetically modifying cell can be a method of expanding TCR alpha deficient T-cell comprising introducing into said T-cell pTalpha (also named preTCRα) or a functional variant thereof and expanding said cells, optionally through stimulation of the CD3 complex. In a preferred embodiment, the method comprises:

a) Transforming said cells with nucleic acid encoding at least a fragment of pTalpha to support CD3 surface expression b) Expressing said pTalpha into said cells c) Expanding said cells, optionally through stimulation of the CD3 complex.

The invention also relates to a method of preparing T-cells for immunotherapy comprising steps of the method for expansion for T-cell.

In particular embodiment, the pTalpha polynucleotide sequence can be introduced randomly or else through homologous recombination, in particular the insertion could be associated with the inactivation of the TCRalpha gene.

According to the invention, different functional variants of pTalpha are used. A "functional variant" of the peptide refers to a molecule substantially similar to either the entire peptide or a fragment thereof. A "fragment" of the pTalpha or functional variant thereof of the present invention, refers to any subset of the molecule, that is, a shorter peptide. Preferred pTalpha or functional variants can be full length pTalpha or a C-terminal truncated pTalpha version. C-terminal truncated pTalpha lacks in C-terminal end one or more residues. As non limiting examples, C-terminal truncated pTalpha version lacks 18, 48, 62, 78, 92, 110 or 114 residues from the C-terminus of the protein (SEQ ID NO: 107 to SEQ ID NO: 114). Moreover, amino acid sequence variants of the peptide can be prepared by mutations in the DNA which encodes the peptide. Such functional variants include, for example, deletions from, or insertions or substitutions of, residues within the amino acid sequence. Any combination of deletion, insertion, and substitution may also be made to arrive at the final construct, provided that the final construct possesses the desired activity, in particular the restoration of a functional CD3 complex. In preferred embodiment, at least one mutation is introduced in the different pTalpha versions as described above to affect dimerization. As non limiting example, mutated residue can be at least W46R, D22A, K24A, R102A or R117A of the human pTalpha protein or aligned positions using CLUSTALW method on pTalpha family or homologue member. Preferably pTalpha or variant thereof as described above comprise the mutated residue W46R (SEQ ID NO:123) or the mutated residues D22A, K24A, R102A and R117A (SEQ ID NO: 124). In particular embodiment, said pTalpha or variants are also fused to a signal-transducing domain such as CD28, OX40, ICOS, CD27, CD137 (4-1BB) and CD8 as non limiting examples (SEQ ID NO: 115 to SEQ ID NO: 120). The extracellular domain of pTalpha or variants as described above can be fused to a fragment of the TCRalpha protein, particularly the transmembrane and intracellular domain of TCRalpha (SEQ ID NO: 122). pTalpha variants can also be fused to the intracellular domain of TCRalpha (SEQ ID NO:121).

In another embodiment, said pTalpha versions are fused to an extracellular ligand-binding domain and more preferably pTalpha or functional variant thereof is fused to a single chain antibody fragment (scFV) comprising the light ($V_L$) and the heavy ($V_H$) variable fragment of a target antigen specific monoclonal antibody joined by a flexible linker. As a non limiting example, amino acid sequence of pTalpha or functional variant thereof is selected from the group consisting of SEQ ID NO: 107 to SEQ ID NO: 124.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application.

The present invention is thus drawn to polypeptides comprising a polypeptide sequence that has at least 70%, preferably at least 80%, more preferably at least 90%, 95% 97% or 99% sequence identity with amino acid sequence selected from the group consisting of SEQ ID NO:107 to SEQ ID NO: 124.

By TCR alpha deficient T cell is intended an isolated T cell that lacks expression of a functional TCR alpha chain. This may be accomplished by different means, as non limiting examples, by engineering a T cell such that it does not express any functional TCR alpha on its cell surface or by engineering a T cell such that it produces very little functional TCR alpha chain on its surface or by engineering a T cell to express mutated or truncated form of TCR alpha chain.

TCR alpha deficient cells can no longer be expanded through CD3 complex. Thus, to overcome this problem and to allow proliferation of TCR alpha deficient cells, pTalpha or functional variant thereof is introduced into said cells, thus restoring a functional CD3 complex. In a preferred embodiment, the method further comprises introducing into said T cells rare-cutting endonucleases able to selectively inactivate by DNA cleavage one gene encoding one component of the T-cell receptor (TCR). In particular embodiment, said rare-cutting endonuclease is a TALE-nucleases. As non limiting examples, TALE-nuclease is directed against one of the gene target sequences of TCRalpha selected from the group consisting of SEQ ID NO: 37 and SEQ ID NO: 57 to 60. Preferably, TALE-nucleases are selected from the group consisting of SEQ ID NO: 41 and SEQ ID NO: 42.

Are also encompassed in the present invention polypeptides encoding pTalpha, particularly functional variants described above. In a preferred embodiment the invention relates to a pTalpha or functional variant thereof fused to a signal transducing domain such as CD28, OX40, ICOS, CD137 and CD8. More particularly, the invention relates to pTalpha functional variant comprising amino acid sequence selected form the group consisting of SEQ ID NO: 107 to SEQ ID NO: 124. Are also encompassed in the present invention polynucleotides, vectors encoding pTalpha or functional variants thereof described above.

In the scope of the present invention are also encompassed isolated cells or cell lines susceptible to be obtained by said method. In particular said isolated cells or cell lines are obtained by introducing into said cells a pTalpha or a functional variant thereof to support CD3 surface expression. In a preferred embodiment, said isolated cell or cell line are further genetically modified by inactivating TCRalpha gene. This gene is preferably inactivating by at least one rare-cutting endonuclease. In a preferred embodiment said rare-cutting endonuclease is TALE-nuclease.

In the scope of the present invention are also encompassed isolated cells or cell lines susceptible to be obtained by said method to engineer cells, in particular T cells, in which at least one gene selected from the group consisting of TCR alpha, TCR beta, CD52, GR, immune checkpoint genes has been inactivated.

Bispecific Antibodies

According to a further embodiment, engineered T cells obtained by the different methods as previously described can be further exposed with bispecific antibodies. Said T-cells could be exposed to bispecific antibodies ex vivo prior to administration to a patient or in vivo following administration to a patient. Said bispecific antibodies comprise two variable regions with distinct antigen properties that allow bringing the engineered cells into proximity to a target antigen. As a non limiting example, said bispecific antibody is directed against a tumor marker and lymphocyte antigen such as CD3 and has the potential to redirect and activate any circulating T cells against tumors.

Delivery Methods

The different methods described above involve introducing multi-chain CAR, pTalpha or functional variants thereof, rare cutting endonuclease, TALE-nuclease, CAR optionally with DNA-end processing enzyme or exogenous nucleic acid into a cell.

As non-limiting example, said multi-chain CAR, pTalpha or functional variant thereof, rare cutting endonucleases, TALE-nucleases or CAR optionally with DNA-end processing enzyme or exogenous nucleic acid can be introduced as transgenes encoded by one or as different plasmidic vectors. Different transgenes can be included in one vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the rare-cutting endonuclease and a DNA end-processing enzyme or the different polypeptides of the multi-chain CAR.

Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into animal cells are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Electroporation

In particular embodiment of the invention, polynucleotides encoding polypeptides according to the present invention can be mRNA which is introduced directly into the cells, for example by electroporation. The inventors determined the optimal condition for mRNA electroporation in T-cell.

The inventor used the cytoPulse technology which allows, by the use of pulsed electric fields, to transiently permeabilize living cells for delivery of material into the cells. The technology, based on the use of PulseAgile (Cellectis property) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow to move the polynucleotide into the cell. In one aspect of the present invention, the inventor describe the steps that led to achievement of >95% transfection efficiency of mRNA in T cells, and the use of the electroporation protocol to transiently express different kind of proteins in T cells. In particular the invention relates to a method of transforming T cell comprising contacting said T cell with RNA and applying to T cell an agile pulse sequence consisting of:

(a) one electrical pulse with a voltage range from 2250 to 3000 V per centimeter, a pulse width of 0.1 ms and a pulse interval of 0.2 to 10 ms between the electrical pulses of step (a) and (b);
(b) one electrical pulse with a voltage range from 2250 to 3000 V with a pulse width of 100 ms and a pulse interval of 100 ms between the electrical pulse of step (b) and the first electrical pulse of step (c); and
(c) 4 electrical pulses with a voltage of 325 V with a pulse width of 0.2 ms and a pulse interval of 2 ms between each of 4 electrical pulses.

In particular embodiment, the method of transforming T cell comprising contacting said T cell with RNA and applying to T cell an agile pulse sequence consisting of:

(a) one electrical pulse with a voltage of 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);

(b) one electrical pulse with a voltage range from 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

In particular embodiments, as non limiting examples, said RNA encodes a rare-cutting endonuclase, one monomer of the rare-cutting endonuclease such as Half-TALE-nuclease, a Chimeric Antigen Receptor, at least one component of the multi-chain chimeric antigen receptor, a pTalpha or functional variant thereof, an exogenous nucleic acid, one additional catalytic domain.

Modified T-cells

The present invention also relates to isolated cells or cell lines susceptible to be obtained by said method to engineer cells. In particular said isolated cell comprises at least one multi-chain CAR as described above. In another embodiment, said isolated cell comprises a population of multi-chain CARs each one comprising different extracellular ligand binding domains. In particular, said isolated cell comprises exogenous polynucleotide sequences encoding polypeptides composing at least one multi-chain CAR. Said cells can also further comprise at least one inactivated gene selected from the group consisting of CD52, GR, TCR alpha, TCR beta, HLA gene, immune check point genes such as PD1 and CTLA-4, or can express a pTalpha transgene.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptative immune response. Said immune cell according to the present invention can be derived from a stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

In another embodiment, said isolated cell according to the present invention comprises one inactivated gene selected from the group consisting of CD52, GR, PD1, CTLA-4, LAG3, Tim3, BTLA, BY55, TIGIT, B7H5, LAIR1, SIGLEC10, 2B4, HLA, TCR alpha and TCR beta and/or expresses a CAR, a multi-chain CAR and/or a pTalpha transgene. In another particular embodiment, said isolated cell comprises polynucleotides encoding said polypeptides composing the multi-chain CAR.

In another embodiment, said isolated cell according to the present invention comprises two inactivated genes selected from the group consisting of CD52 and GR, CD52 and TCR alpha, CDR52 and TCR beta, GR and TCR alpha, GR and TCR beta, TCR alpha and TCR beta, PD1 and TCR alpha, PD1 and TCR beta, CTLA-4 and TCR alpha, CTLA-4 and TCR beta, LAG3 and TCR alpha, LAG3 and TCR beta, Tim3 and TCR alpha, Tim3 and TCR beta, BTLA and TCR alpha, BTLA and TCR beta, BY55 and TCR alpha, BY55 and TCR beta, TIGIT and TCR alpha, TIGIT and TCR beta, B7H5 and TCR alpha, B7H5 and TCR beta, LAIR1 and TCR alpha, LAIR1 and TCR beta, SIGLEC10 and TCR alpha, SIGLEC10 and TCR beta, 2B4 and TCR alpha, 2B4 and TCR beta and/or expresses a CAR, a multi-chain CAR and/or a pTalpha transgene.

In another embodiment, TCR is rendered not functional in the cells according to the invention by inactivating TCR alpha gene and/or TCR beta gene(s). The above strategies are used more particularly to avoid GvHD. In a particular aspect of the present invention is a method to obtain modified cells derived from an individual, wherein said cells can proliferate independently of the Major Histocompatibility Complex signaling pathway. Said method comprises the following steps:

(a) Recovering cells from said individual;

(b) Genetically modifying said cells ex-vivo by inactivating TCR alpha or TCR beta genes;

(c) Cultivating genetically modified T-cells in vitro in appropriate conditions to amplify said cells.

Modified cells, which can proliferate independently of the Major Histocompatibility Complex signaling pathway, susceptible to be obtained by this method are encompassed in the scope of the present invention. Said modified cells can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Activation and Expansion of T Cells

Whether prior to or after genetic modification of the T cells, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869;

7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell.

For example, chemicals such as calcium ionophore A23187, phorbol 12-myristate 13-acetate (PMA), or mitogenic lectins like phytohemagglutinin (PHA) can be used to create an activation signal for the T-cell.

As non limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics.

In another particular embodiment, said cells can be expanded by co-culturing with tissue or cells. Said cells can also be expanded in vivo, for example in the subject's blood after administrating said cell into the subject.

Therapeutic Applications

In another embodiment, isolated cell obtained by the different methods or cell line derived from said isolated cell as previously described can be used as a medicament. In another embodiment, said medicament can be used for treating cancer or infections in a patient in need thereof. In another embodiment, said isolated cell according to the invention or cell line derived from said isolated cell can be used in the manufacture of a medicament for treatment of a cancer, viral infection or autoimmune disease in a patient in need thereof.

In another aspect, the present invention relies on methods for treating patients in need thereof, said method comprising at least one of the following steps:

(a) providing an immune-cell obtainable by any one of the methods previously described;

(b) Administrating said transformed immune cells to said patient,

On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product.

Cells that can be used with the disclosed methods are described in the previous section. Said treatment can be used to treat patients diagnosed with cancer, viral infection, autoimmune disorders or Graft versus Host Disease (GvHD). Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the multi-chain CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM PATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgeiy. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Example of Method to Engineer Human Allogeneic Cells for Immunotherapy

For a better understanding of the invention, one example of method to engineer human allogenic cells for immunotherapy is illustrated in FIG. 5. The method comprising a combination of one or several of the following steps:

1. Providing T-cells from a cell culture or from a blood sample from one individual patient or from blood bank and activating said T cells using anti-CD3/C28 activator beads. The beads provide both the primary and co-stimulatory signals that are required for activation and expansion of T cells.
2. a) Transducing said cells with pTalpha or functional variant thereof transgene to support CD3 surface expression and allow cell expansion through stimulation of CD3 complex. TCR disruption is expected to the elimination of the TCR complex and removes alloreactivity (GvHD) but may alter allogenic cells expansion due to the loss of CD3 signaling component. Transduced cells are expected to express pTalpha chain or functional variant thereof. This pTalpha chain pairs with TCRbeta chain and CD3 signaling components to form the preTCR complex and, thus restore a functional CD3 complex and support activation or stimulation of inactivated TCRalpha cells. Transduction of T-cells with pTalpha lentiviral vector can be realized before or after TCRalpha inactivation.
   b) Transducing said cells with multi-chain CARs allow redirecting T cells against antigens expressed at the surface of target cells from various malignancies including lymphomas and solid tumors. To improve the function of co-stimulatory domain, the inventors have designed a multi-chain CAR derived from FcεRI as previously described.

Transduction can be realized before or after the inactivation of TCRalpha and the other genes, such as CD52 genes.

3. Engineering non alloreactive and immunosuppressive resistant T cells:
   a) It is possible to Inactivate TCR alpha in said cells to eliminate the TCR from the surface of the cell and prevent recognition of host tissue as foreign by TCR of allogenic and thus to avoid GvHD.
   b) It is also possible to inactive one gene encoding target for immunosuppressive agent to render said cells resistant to immunosuppressive treatment to prevent graft rejection without affecting transplanted T cells. In this example, target of immunosuppressive agents is CD52 and immunosuppressive agent is a humanized monoclonal anti-CD52 antibody.

It has been shown by the inventors that the use of TALE-nuclease by allowing higher rates of DSB events within T-cells was particularly advantageous to achieve the above double inactivation in T-cells. Preferably, TCRalpha and CD52 genes are inactivated by electoporating T cells with mRNA coding for TALE-nuclease targeting said genes. It has been found by the inventors that using mRNA resulted into high transformation rate was less harmful to T-cells and so, was critical in the process of engineering T-cells. Then, inactivated T cells are sorted using magnetic beads. For example, T cells expressing CD52 are removed by fixation on a solid surface, and inactivated cells are not exposed of the stress of being passed through a column. This gentle method increases the concentration of properly engineered T-cells.

4. Expansion in vitro of engineered T-cells prior to administration to a patient or in vivo following administration to a patient through stimulation of CD3 complex. Before administration step, patients can be subjected to an immunosuppressive treatment such as CAMPATH1-H, a humanized monoclonal antibody anti-CD52.
5. Optionally exposed said cells with bispecific antibodies ex vivo prior to administration to a patient or in vivo following administration to a patient to bring the engineered cells into proximity to a target antigen.

Other Definitions

Unless otherwise specified, "a," "an," "the," and "at least one" are used interchangeably and mean one or more than one.

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by "polynucleotide successively comprising a first region of homology to sequences upstream of said double-stranded break, a sequence to be inserted in the genome of said cell and a second region of homology to sequences downstream of said double-stranded break" it is intended to mean a DNA construct or a matrix comprising a first and second portion that are homologous to regions 5' and 3' of a DNA target in situ. The DNA construct also comprises a third portion positioned between the first and second portion which comprise some homology with the corresponding DNA sequence in situ or alternatively comprise no homology with the regions 5' and 3' of the DNA target in situ. Following cleavage of the DNA target, a homologous recombination event is stimulated between the genome containing the targeted gene comprised in the locus of interest and this matrix, wherein the genomic sequence containing the DNA target is replaced by the third portion of the matrix and a variable part of the first and second portions of said matrix.

by "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of TALE-nuclease targets, targeted genomic sequences generally consist of two 17-bp long sequences (called half targets) separated by a 15-bp spacer. Each half-target is recognized by repeats of TALE-nucleases listed in tables 1, 5, 6 and 10 as non-limiting examples, encoded in plasmids, under the control of EF1-alpha promoter or T7 promoter. The nucleic acid target sequence is defined by the 5' to 3' sequence of one strand of said target, as indicated in tables 1, 5, 6 and 10.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity. One example of CAR used in the present invention is a CAR directing against CD19 antigen and can comprise as non limiting example the amino acid sequence: SEQ ID NO: 73

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

Rare-cutting endonucleases can also be for example TALE-nucleases, a new class of chimeric nucleases using a FokI catalytic domain and a DNA binding domain derived from Transcription Activator Like Effector (TALE), a family of proteins used in the infection process by plant pathogens of the *Xanthomonas* genus (Boch, Scholze et al. 2009; Moscou and Bogdanove 2009; Christian, Cermak et al. 2010; Li, Huang et al.). The functional layout of a FokI-based TALE-nuclease (TALE-nuclease) is essentially that of a ZFN, with the Zinc-finger DNA binding domain being replaced by the TALE domain. As such, DNA cleavage by a TALE-nuclease requires two DNA recognition regions flanking an unspecific central region. Rare-cutting endonucleases encompassed in the present invention can also be derived from TALE-nucleases.

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease ("LAGLIDADF" disclosed as SEQ ID NO: 127), to a HNH endonuclease, or to a GIY-YIG endonuclease. Preferred homing endonuclease according to the present invention can be an I-CreI variant.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al.). Engineered TAL-nucleases are commercially available under the trade name TALEN™ (Cellectis, 8 rue de la Croix Jarry, 75013 Paris, France).

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"similarity" describes the relationship between the amino acid sequences of two or more polypeptides. BLASTP may also be used to identify an amino acid sequence having at least 70%, 75%, 80%, 85%, 87.5%, 90%, 92.5%, 95%, 97.5%, 98%, 99% sequence similarity to a reference amino acid sequence using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means. For example, a functional variant of pTalpha can have 70%, 75%, 80%, 85%, 87.5%, 90%, 92.5%, 95%, 97.5%, 98%, 99% sequence similarity to the amino acid sequence of SEQ ID NO: 107. A polynucleotide encoding such a functional variant would be produced by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LIGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class 1 molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

"bispecific antibody" refers to an antibody that has binding sites for two different antigens within a single antibody molecule. It will be appreciated by those skilled in the art that other molecules in addition to the canonical antibody structure may be constructed with two binding specificities. It will further be appreciated that antigen binding by bispecific antibodies may be simultaneous or sequential. Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. As a non limiting example, each binding domain comprises at least one variable region from an antibody heavy chain ("VH or H region"), wherein the VH region of the first binding domain specifically binds to the lymphocyte marker such as CD3, and the VH region of the second binding domain specifically binds to tumor antigen.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

TALE-nucleases Cleaving the Human GR Gene 6 heterodimeric TALE-nucleases targeting exons of the human GR gene were designed and produced. Table 1 below indicates the target sequences cleaved by each TALE-nuclease. GR TALE-nuclease was composed of two independent entities (called half TALE-nucleases) each containing a repeat sequence engineered to bind and cleave GR target sequences consisting of two 17-bp long sequences (called half targets) separated by a 15-bp spacer.

was then ligated to the first and after SfaNI digestion a third bloc (tri-repeat) was coupled. The process was repeated using tri- or di-repeat blocks upon obtaining the desired repeat array. The product was then cloned in a classical pAPG10 cloning plasmid for amplification in *E. coli* and sequenced. The repeat array sequences thus obtained were subcloned in a yeast expression TALE vector using type IIS restriction enzymes BsmBI for the receiving plasmid and BbvI and SfaNI for the inserted repeat sequence. DNA coding for the half TALE-nuclease, containing a TALE derived DNA binding domain fused to the catalytic domain of the FokI restriction enzyme, was amplified in *E. coli*, recovered by standard miniprep techniques and sequenced to assess the integrity of the insert.

Activity of GR TALE-nucleases in Yeast:

Nuclease activity of the six GR-TALE-nucleases were tested at 37° C. and 30° C. in our yeast SSA assay previously described (International PCT Applications WO 2004/067736 and in (Epinat, Arnould et al. 2003; Chames, Epinat

TABLE 1

Description of the GR TALE-nucleases and sequences of the TALE-nucleases target sites in the human GR gene.

| Target name | Target sequence | Repeat sequence | Half TALE-nuclease sequence |
|---|---|---|---|
| GRex2 | TATTCACTGATGGACTC<br>caaagaatcattaac<br>TCCTGGTAGAGAAGAAA<br>(SEQ ID NO: 1) | Repeat GRex2-LPT9-L1<br>(SEQ ID NO: 7)<br>Repeat -GRex2-LPT9-R1<br>(SEQ ID NO: 8) | GRex2-L TALEN<br>(SEQ ID NO: 19)<br>GRex2-R TALEN<br>(SEQ ID NO: 20) |
| GRex3T2 | TGCCTGGTGTGCTCTGA<br>tgaagcttcaggatg<br>TCATTATGGAGTCTTAA<br>(SEQ ID NO: 2) | Repeat -GRex3T2-L1<br>(SEQ ID NO: 9)<br>Repeat -GRex3T2-R1<br>(SEQ ID NO: 10) | GRex3T2-L TALEN<br>(SEQ ID NO: 21)<br>GRex3T2-R TALEN<br>(SEQ ID NO: 22) |
| GRex3T4 | TGCTCTGATGAAGCTTC<br>aggatgtcattatgg<br>AGTCTTAACTTGTGGAA<br>(SEQ ID NO: 3) | Repeat -GRex3T4-L1<br>(SEQ ID NO: 11)<br>Repeat -GRex3T4-R1<br>(SEQ ID NO: 12) | GRex3T4-L TALEN<br>(SEQ ID NO: 23)<br>GRex3T4-R TALEN<br>(SEQ ID NO: 24) |
| GRex5T1 | TGGTGTCACTGTTGGAG<br>gttattgaacctgaa<br>GTGTTATATGCAGGATA<br>(SEQ ID NO: 4) | Repeat -GRex5T1-LPT8-L1<br>(SEQ ID NO: 13)<br>Repeat -GRex5T1-LPT8-R1<br>(SEQ ID NO: 14) | GRex5T1-L TALEN<br>(SEQ ID NO: 25)<br>GRex5T1-R TALEN<br>(SEQ ID NO: 26) |
| GRex5T2 | TATGATAGCTCTGTTCC<br>agactcaacttggag<br>GATCATGACTACGCTCA<br>(SEQ ID NO: 5) | Repeat -GRex5T2-L1<br>(SEQ ID NO: 15)<br>Repeat GRex5T2-R1<br>(SEQ ID NO: 16) | GRex5T2-L TALEN<br>(SEQ ID NO: 27)<br>GRex5T2-R TALEN<br>(SEQ ID NO: 28) |
| GRex5T3 | TTATATGCAGGATATGA<br>tagctctgttccaga<br>CTCAACTTGGAGGATCA<br>(SEQ ID NO: 6) | Repeat -GRex5T3-L1<br>(SEQ ID NO: 17)<br>Repeat -GRex5T3-R1<br>(SEQ ID NO: 18) | GRex5T3-L TALEN<br>(SEQ ID NO: 29)<br>GRex5T3-R TALEN<br>(SEQ ID NO: 30) |

The amino acid sequences of the N-terminal, C-terminal domains and repeat are based on the AvrBs3 TALE (ref: GenBank: X16130.1). The C-terminal and the N-terminal domains are separated by two BsmBI restriction sites. The repeat arrays (SEQ ID NO: 7 to 18), targeting the desired sequences (SEQ ID NO: 1 to 6) were synthesized using a solid support method composed of consecutive restriction/ligation/washing steps (International PCT application WO2013/017950). In brief, the first block (coding for a di-repeat) was immobilized on a solid support through biotin/streptavidin interaction, the second block (tri-repeat)

et al. 2005; Arnould, Chames et al. 2006; Smith, Grizot et al. 2006) on targets containing the two TALE target sequences facing each other on the DNA strand separated by a spacer of 15 bps resulting in SEQ ID NO: 1 to 6. All the yeast target reporter plasmids containing the TALE-nuclease DNA target sequences were constructed as previously described (International PCT Applications WO 2004/067736 and in (Epinat, Arnould et al. 2003; Chames, Epinat et al. 2005; Arnould, Chames et al. 2006; Smith, Grizot et al. 2006). TALE-nuclease cleavage activity levels, in yeast, of individual clones on the targets are presented in table 2.

TABLE 2

| Cleavage activity of the GR TALE-nucleases in yeast. | | | |
|---|---|---|---|
| Target | Half TALE-nuclease transfected | yeast gal37° C. | yeast gal30° C. |
| GRex2 | Grex2-L TALEN<br>Grex2-R TALEN | 1 | 1 |
| GRex3T2 | GRex3T2-L TALEN<br>GRex3T2-R TALEN | 0.92 | 0.87 |
| GRex3T4 | GRex3T4-L TALEN<br>GRex3T4-R TALEN | 0.94 | 0.87 |
| GRex5T1 | GRex5T1-L TALEN<br>GRex5T1-R TALEN | 0.48 | 0.36 |
| GRex5T2 | GRex5T2-L TALEN<br>GRex5T2-R TALEN | 0.97 | 0.91 |
| GRex5T3 | GRex5T3-L TALEN<br>GRex5T3-R TALEN | 1 | 0.98 |

Values are comprised between 0 and 1. Maximal value is 1.

Activity of GR TALE-nucleases in HEK293 Cells:

Each TALE-nuclease construct was subcloned using restriction enzyme digestion in a mammalian expression vector under the control of a pEF1alpha long promoter.

One million HEK293cells were seeded one day prior to transfection. Cells were co-transfected with 2.5 μg of each of two plasmids encoding left and right half of GRex2, GRex3T2, GRex3T4, GRex5T1, GRex5T2 or GRex5T3 TALE-nuclease recognizing the two half targets genomic sequences of interest in the GR gene under the control of EF1alpha promoter using 25 μL of lipofectamine (Invitrogen) according to the manufacturer's instructions. As a control, cells were co-transfected with 2.5 μg of each of the two plasmids encoding the left and the right half of TALE-nucleases targeting the T-cell receptor alpha constant chain region (TRAC_T01) target site ((TRAC_T01-L and -R TALE-nuclease (SEQ ID NO: 41 and SEQ ID NO: 42, TRAC_T01 target site (SEQ ID NO: 37)) under the control of EF1alpha promoter. The double strand break generated by TALE-nucleases in GR coding sequence induces non homologous end joining (NHEJ), which is an error-prone mechanism. Activity of TALE-nucleases is measured by the frequency of insertions or deletions at the genomic locus targeted.

2 or 7 days post transfection cells were harvested and locus specific PCRs were performed on genomic DNA extracted using the following composite primers: 5'-CCATCTCATCCCTGCGTGTCTCCGACTCAG-3' (forward adaptator sequence, SEQ ID NO: 126)-10N (TAG)-locus specific forward sequence for GR exon 2: 5'-GGTTCATTTAACAAGCTGCC-3' (SEQ ID NO: 127; composite primer disclosed as SEQ ID NO: 31), for GR exon 3: 5'-GCATTCTGACTATGAAGTGA-3' (SEQ ID NO: 128; composite primer disclosed as SEQ ID NO: 32) and for GR exon 5: 5'-TCAGCAGGCCACTACAGGAGTCTCACAAG-3' (SEQ ID NO: 129; composite primer disclosed as SEQ ID NO: 33) and the reverse composite primer 5'-CCTATCCCCTGTGTGCCTTGGCAGTCTCAG-3' (reverse adaptor sequence, SEQ ID No: 130))-locus specific reverse sequence for GR exon 2: 5'-AGCCAGTGAGGGTGAAGACG-3' (SEQ ID NO: 131; composite primer disclosed as SEQ ID NO: 34), for GR exon 3: 5'-GGGCTTTGCATATAATGGAA-3' (SEQ ID NO: 132; composite primer disclosed as SEQ ID NO: 35) and for GR exon 5: 5'-CTGACTCTCCCCTTCATAGTCCCCAGAAC-3' (SEQ ID NO: 133; composite primer disclosed as SEQ ID NO: 36).

PCR products were sequenced by a 454 sequencing system (454 Life Sciences). Approximately 10,000 sequences were obtained per PCR product and then analyzed for the presence of site-specific insertion or deletion events. Table 3 indicates the percentage of the sequences showing insertions or deletions at the TALE-nuclease target site among the total number of sequences in the sample. In table 3 are listed for GRex2, GRex3T2 and GRex3T4 the results of a representative experiment.

In all cases tested, the % of mutagenesis was similar at day 7 compared to the one of the sample at day 2 post transfection. The nature of the mutagenic events was also analyzed, revealing a majority of deletions in all cases compared to insertions.

TABLE 3

| Percentage of targeted mutagenesis at endogenous TALE-nuclease Target sites in HEK293 cells. | | | |
|---|---|---|---|
| Target | % Indels at 2 days with GR TALE-nuclease transfection | % Indels at 7 days with GR TALE-nuclease transfection | % Indels at 2 days with TRAC_T01 TALE-nuclease control transfection |
| GRex2 | 20.3 | 24.9 | 0.5 |
| GRex3T2 | 9.3 | 9.8 | 0 |
| GRex3T4 | 19 | 18.3 | 0.0 |
| GRex5T1 | 11.2 | NA | 0.7 |
| GRex5T2 | 3.4 | NA | 0 |
| GRex5T3 | 8.3 | NA | 0 |

Activity of GR TALE-nucleases in Primary T Lymphocytes:

Each TALE-nuclease construct was subcloned using restriction enzyme digestion in an expression vector under the control of a T7 promoter.

mRNA encoding TALE-nucleases cleaving GR genomic sequences were synthesized from each plasmid carrying the coding sequences downstream from the T7 promoter. T lymphocytes isolated from peripheral blood were activated for 5 days using anti-CD3/CD28 activator beads (Life technologies) and 5 million cells were transfected by electroporation with 10 μg of each of 2 mRNAs encoding both half TALE-nucleases using a CytoLVT-P instrument (BTX-Harvard apparatus). T cells transfected with 10 μg of each of the 2 mRNAs encoding both half TALE-nucleases targeting the CD52 gene (CD52_T02-L and -R TALEN (SEQ ID NO: 55 and 56), target sequence CD52_T02 SEQ ID NO: 40) are used as a control.

3 and 7 days after transfection, genomic DNA was isolated from transfected cells and locus specific PCRs were performed using the primers described previously. PCR products were sequenced by a 454 sequencing system (454 Life Sciences). Approximately 10,000 sequences were obtained per PCR product and then analyzed for the presence of site-specific insertion or deletion events; results are in Table 4.

TABLE 4

Percentage of targeted mutagenesis at endogenous TALE-nuclease target sites in primary T lymphocytes.

| Target | % Indels at day 3 with GR TALE-nuclease transfection | % Indels at day 7 with GR TALE-nuclease transfection | % Indels at day 3 with CD52 TALE-nuclease control transfection |
|---|---|---|---|
| GRex2 | 26.2 | 30.7 | 0.7 |
| GRex3T2 | 1.09 | 0.86 | 0.02 |
| GRex3T4 | 6.3 | 6.93 | 0 |
| GRex5T1 | 0.04 | 0.035 | 0.05 |
| GRex5T2 | 1.3 | 1.0 | 0.22 |
| GRex5T3 | 17.4 | NA | 0.41 |

Example 2

TALE-nucleases Cleaving the Human CD52 Gene, the Human T-cell Receptor Alpha Constant Chain (TRAC) and the Human T-cell Receptor Beta Constant Chains 1 and 2 (TRBC)

As described in example 1, heterodimeric TALE-nucleases targeting respectively CD52, TRAC and TRBC genes were designed and produced. The targeted genomic sequences consist of two 17-bp long sequences (called half targets) separated by an 11 or 15-bp spacer. Each half-target is recognized by repeats of half TALE-nucleases listed in table 5. The human genome contains two functional T-cell receptor beta chains (TRBC1 and TRBC2). During the development of alpha/beta T lymphocytes, one of these two constant chains is selected in each cell to be spliced to the variable region of TCR-beta and form a functional full length beta chain. The 2 TRBC targets were chosen in sequences conserved between TRBC1 and TRBC2 so that the corresponding TALE-nuclease would cleave both TRBC1 and TRBC2 at the same time.

TABLE 5

Description of the CD52, TRAC and TRBC TALE-nucleases and sequences of the TALE-nucleases target sites in the human corresponding genes.

| Target | Target sequence | Repeat sequence | Half TALE-nuclease |
|---|---|---|---|
| TRAC_T01 | TTGTCCCACAGATATCC Agaaccctgaccctg CCGTGTACCAGCTGAGA (SEQ ID NO: 37) | Repeat TRAC_T01-L (SEQ ID NO: 41) Repeat TRAC_T01-R (SEQ ID NO: 42) | TRAC_T01-L TALEN (SEQ ID NO: 49) TRAC_T01-R TALEN (SEQ ID NO: 50) |
| TRBC_T01 | TGTGTTTGAGCCATCAG aagcagagatctccc ACACCCAAAAGGCCACA (SEQ ID NO: 38) | Repeat TRBC_T01-L (SEQ ID NO: 43) Repeat TRBC_T01-R (SEQ ID NO: 44) | TRBC_T01-L TALEN (SEQ ID NO: 51) TRBC_T01-R TALEN (SEQ ID NO: 52) |
| TRBC_T02 | TTCCCACCCGAGGTCGC tgtgtttgagccatca GAAGCAGAGATCTCCCA (SEQ ID NO: 39) | Repeat TRBC_T02-L (SEQ ID NO: 45) Repeat TRBC_T02-R (SEQ ID NO: 46) | TRBC_T02-L TALEN (SEQ ID NO: 53) TRBC_T02-R TALEN (SEQ ID NO: 54) |
| CD52_T02 | TTCCTCCTACTCACCAT cagcctcctggttat GGTACAGGTAAGAGCAA (SEQ ID NO: 40) | Repeat CD52_T02-L (SEQ ID NO: 47) Repeat CD52_T02-R (SEQ ID NO: 48) | CD52_T02-L TALEN (SEQ ID NO: 55) CD52_T02-R TALEN (SEQ ID NO: 56) |

Other target sequences in TRAC and CD52 genes have been designed, which are displayed in Table 6.

TABLE 6

Additional target sequences for TRAC and CD52 TALE-nucleases.

| Target | Target sequence |
|---|---|
| TRAC_T02 | TTTAGAAAGTTCCTGTG atgtcaagctggtcg AGAAAAGCTTTGAAACA (SEQ ID NO: 57) |
| TRAC_T03 | TCCAGTGACAAGTCTGT ctgcctattcaccga TTTTGATTCTCAAACAA (SEQ ID NO: 58) |
| TRAC_T04 | TATATCACAGACAAAAC tgtgctagacatgag GTCTATGGACTTCAAGA (SEQ ID NO: 59) |
| TRAC_T05 | TGAGGTCTATGGACTTC aagagcaacagtgct GTGGCCTGGAGCAACAA (SEQ ID NO: 60) |
| CD52_T01 | TTCCTCTTCCTCCTAC caccatcagcctcct TTACCTGTACCATAAC (SEQ ID NO: 61) |
| CD52_T04 | TTCCTCCTACTCACCA cagcctcctgg TCTTACCTGTACCATA (SEQ ID NO: 62) |
| CD52_T05 | TCCTACTCACCATCAG ctcctggttat TTGCTCTTACCTGTAC (SEQ ID NO: 63) |

TABLE 6-continued

| Additional target sequences for TRAC and CD52 TALE-nucleases. | |
|---|---|
| Target | Target sequence |
| CD52_T06 | TTATCCCACTTCTCCT ctacagatacaaact TTTTGTCCTGAGAGTC (SEQ ID NO: 64) |
| CD52_T07 | TGGACTCTCAGGACAA acgacaccagccaaa TGCTGAGGGGCTGCTG (SEQ ID NO: 65) |

Activity of CD52-TALE-nuclease, TRAC-TALE-nuclease and TRBC-TALE-nuclease in HEK293 Cells Each TALE-nuclease construct was subcloned using restriction enzyme digestion in a mammalian expression vector under the control of pEF1alpha long promoter. One million HEK293 cells were seeded one day prior to transfection. Cells were co-transfected with 2.5 μg of each of the two plasmids encoding the TALE-nucleases recognizing the two half targets in the genomic sequence of interest in the CD52 gene, T-cell receptor alpha constant chain region (TRAC) or T-cell receptor beta constant chain region (TRBC) under the control of the EF1-alpha promoter or 5 μg of a control pUC vector (pCLS0003) using 25 μl of lipofectamine (Invitrogen) according to the manufacturer's instructions. The double stranded cleavage generated by TALE-nucleases in CD52 or TRAC coding sequences is repaired in live cells by non homologous end joining (NHEJ), which is an error-prone mechanism. Activity of TALE-nucleases in live cells is measured by the frequency of insertions or deletions at the genomic locus targeted. 48 hours after transfection, genomic DNA was isolated from transfected cells and locus specific PCRs were performed using the following composite primers: 5'-CCATCTCATC-CCTGCGTGTCTCCGACTCAG (forward adaptor sequence, SEQ ID NO: 126)-10N (TAG)-locus specific forward sequence for CD52: 5'-CAGATCTGCA-GAAAGGAAGC-3' (SEQ ID NO: 134; composite primer disclosed as SEQ ID NO: 66), for TRAC: 5'-ATCACTG-GCATCTGGACTCCA-3' (SEQ ID NO: 135; composite primer disclosed as SEQ ID NO: 67), for TRBC1: 5'-AGAGCCCCTACCAGAACCAGAC-3' (SEQ ID NO: 136; composite primer disclosed as SEQ ID NO: 68), or for TRBC2: 5'-GGACCTAGTAACATAATTGTGC-3' (SEQ ID NO: 137; composite primer disclosed as SEQ ID NO: 69), and the reverse composite primer 5'-CCTATCCCCTGTGT-GCCTTGGCAGTCTCAG (reverse adaptor sequence, SEQ ID NO: 130)-endogenous locus specific reverse sequence for CD52: 5'-CCTGTTGGAGTCCATCTGCTG-3' (SEQ ID NO: 138; composite primer disclosed as SEQ ID NO: 70), for TRAC: 5'-CCTCATGTCTAGCACAGTTT-3' (SEQ ID NO: 139; composite primer disclosed as SEQ ID NO: 71), for TRBC1 and TRBC2: 5'-ACCAGCTCAGCTC-CACGTGGT-3' (SEQ ID NO: 140; composite primer disclosed as SEQ ID NO: 72). PCR products were sequenced by a 454 sequencing system (454 Life Sciences). Approximately 10,000 sequences were obtained per PCR product and then analyzed for the presence of site-specific insertion or deletion events; results are in Table 7.

TABLE 7

Percentages of indels for TALE-nuclease targeting CD52_T02, TRAC_T01, TRBC_T01 and TRBC_T02 targets.

| Target | % Indels with TALE-nuclease transfection | % Indels with pUC control transfection |
|---|---|---|
| CD52_T02 | 28.0 | 0.9 |
| TRAC_T01 | 41.9 | 0.3 |
| TRBC_T01 in constant chain 1 | 3.81 | 0 |
| TRBC_T01 in constant chain 2 | 2.59 | 0 |
| TRBC_T02 in constant chain 1 | 14.7 | 0 |
| TRBC_T02 in constant chain 1 | 5.99 | 0 |

Activity of CD52-TALE-nuclease, TRBC-TALE-nuclease and TRAC-TALE-nuclease in Primary T Lymphocytes Each TALE-nuclease construct was subcloned using restriction enzyme digestion in a mammalian expression vector under the control of the T7 promoter.

mRNA encoding TALE-nuclease cleaving CD52 TRAC and TRBC genomic sequence were synthesized from plasmid carrying the coding sequences downstream from the T7 promoter. T lymphocytes isolated from peripheral blood were activated for 5 days using anti-CD3/CD28 activator beads (Life technologies) and 5 million cells were then transfected by electroporation with 10 μg of each of 2 mRNAs encoding both half TALE-nuclease (or non coding RNA as controls) using a CytoLVT-P instrument. As a consequence of the insertions and deletions induced by NHEJ, the coding sequence for CD52 and/or TRAC will be out of frame in a fraction of the cells resulting in non-functional genes. 5 days after electroporation, cells were labeled with fluorochrome-conjugated anti-CD52 or anti-TCR antibody by flow cytometry for the presence of CD52 or TCR at their cell surface. Since all T lymphocytes expanded from peripheral blood normally express CD52 and TCR, the proportion of CD52-negative or TCR-negative cells is a direct measure of TALE-nuclease activity. In table 8 are listed the results of a representative experiment. The table 9 shows the results of a representative experiment testing the efficiency of TRBC TALE-nucleases.

TABLE 8

Percentages of CD52-negative, TCR-negative and CD52/TCR-double negative T lymphocytes after transfection of corresponding TALE-nuclease-expressing polynucleotides.

| ARN transfected | % CD52-negative cells | % TCR-negative cells | % CD52/TCR double negative cells |
|---|---|---|---|
| non coding RNA | 1.21 | 1.531 | 0.111 |
| TALEN CD52_T02 | 49.2 | 1.6 | 0.78 |
| TALEN TRAC_T01 | 2.16 | 44.8 | 0.97 |
| TALEN CD52_T02 + TALEN TRAC_T01 | 29.3 | 39.6 | 15.5 |

TABLE 9

Percentages of TCR-negative T lymphocytes after transfection of TRBC TALE-nuclease-expressing polynucleotides.

| ARN transfected | % TCR-negative cells |
|---|---|
| no RNA | 1.22 |
| TALEN TRBC_T01 | 6.52 |
| TALEN TRBC_T02 | 23.5 |

Functional Analysis of T Cells with Targeted CD52 Gene

The goal of CD52 gene inactivation is to render T lymphocytes resistant to anti-CD52 antibody mediated immunosuppression. As described in the previous paragraph, T lymphocytes were transfected with mRNA encoding TALE-nuclease cleaving CD52. 7 days after transfection, cells were treated with 50 μg/ml anti-CD52 monoclonal antibody (or rat IgG as control) with or without 30% rabbit complement (Cedarlane). After 2 hours of incubation at 37° C., the cells were labeled with a fluorochrome-conjugated anti-CD52 antibody together with a fluorescent viability dye (eBioscience) and analyzed by flow cytometry to measure the frequency of CD52-positive and CD52-negative cells among live cells. FIG. 6 shows the result of a representative experiment, demonstrating that CD52-negative cells are completely resistant to complement-mediated anti-CD52 antibody toxicity.

Functional Analysis of T Cells with Targeted TRAC Gene

The goal of TRAC gene inactivation is to render T lymphocytes unresponsive to T-cell receptor stimulation. As described in the previous paragraph, T lymphocytes were transfected with mRNA encoding TALE-nuclease cleaving TRAC or CD52. 16 days after transfection, cells were treated with up to 5 μg/ml of phytohemagglutinin (PHA, Sigma-Aldrich), a T-cell mitogen acting through the T cell receptor. Cells with a functional T-cell receptor should increase in size following PHA treatment. After three days of incubation, cells were labeled with a fluorochrome-conjugated anti-CD52 or anti-TCR antibody and analyzed by flow cytometry to compare the cell size distribution between TCR-positive and TCR-negative cells, or between CD52-positive and CD52-negative cells. FIG. 7 shows that TCR-positive cells significantly increase in size after PHA treatment whereas TCR-negative cells have the same size as untreated cells indicating that TRAC inactivation rendered them unresponsive to TCR-signaling. By contrast, CD52-positive and CD52-negative increase in size to same extent.

Functional Analysis of T Cells with Targeted CD52 and TRAC Genes

To verify that genome engineering did not affect the ability of T cells to present anti-tumor activity when provided with a chimeric antigen receptor (CAR), we transfected T cells that had been targeted with CD52-TALE-nuclease and TRAC-TALE-nuclease with 10 μg of RNA encoding an anti-CD19 CAR (SEQ ID NO: 73). 24 hours later, T cells were incubated for 4 hours with CD19 expressing Daudi cells. The cell surface upregulation of CD107a, a marker of cytotoxic granule release by T lymphocytes (called degranulation) was measured by flow cytometry analysis (Betts, Brenchley et al. 2003). The results are included in FIG. 8 and show that CD52-negative/TCRαβ-negative cells and CD52-positive/TCRαβ-positive have the same ability to degranulate in response to PMA/ionomycin (positive control) or CD19+ Daudi cells. CD107 upregulation is dependent on the presence of a CD19+. These data suggest that genome engineering has no negative impact on the ability of T cells to mount a controlled anti-tumor response.

Genomic Safety of CD52-TALE-nuclease and TRAC-TALE-nuclease in Primary T Lymphocytes As our constructs include nuclease subunits, an important question is whether multiple TALE-nuclease transfection can lead to genotoxicity and off-target cleavage at 'close match' target sequences or by mispairing of half-TALE-nucleases. To estimate the impact of TRAC-TALE-nuclease and CD52-TALE-nuclease on the integrity of the cellular genomes, we listed sequences in the human genome that presented the potential for off-site cleavage. To generate this list, we identified all the sequences in the genome with up to 4 substitutions compared to the original half targets and then identified the pairs of potential half targets in a head to head orientation with a spacer of 9 to 30 bp from each other. This analysis included sites potentially targeted by homodimers of one half-TALE-nuclease molecule or heterodimers formed by one CD52 half TALE-nuclease and one TRAC half-TALE-nuclease. We scored the potential off-site targets based on the specificity data taking into account the cost of individual substitutions and the position of the substitutions (where mismatches are better tolerated for bases at the 3' end of the half target). We obtained 173 unique sequences with a score reflecting an estimation of the likelihood of cleavage. We selected the 15 top scores and analyzed by deep sequencing the frequency of mutations found at these loci in T cells simultaneously transfected with CD52 and TRAC TALE-nuclease and purified by magnetic separation as CD52-negative, TCRαβ-negative. Results are in FIG. 9. The highest frequency of insertion/deletion is $7\times10^{-4}$. These results make the putative offsite target at least 600 times less likely to be mutated than the intended targets. The TALE-nuclease reagents used in this study therefore appear extremely specific.

Example 3

TALE-nucleases Cleaving the Human CTLA4 Gene and the Human PDCD1 Gene

As described in example 1, heterodimeric TALE-nucleases targeting respectively PDCD1 and CTLA4 genes were designed and produced. The targeted genomic sequences consist of two 17-bp long sequences (called half targets) separated by an 11 or 15-bp spacer. Each half-target is recognized by repeats of half TALE-nucleases listed in table 10.

TABLE 10

Description of the CTLA4 and PDCD1 TALE-nucleases and sequences of the TALE-nucleases target sites in the human corresponding genes.

| Target | Target sequence | Repeat sequence | Half TALE-nuclease |
|---|---|---|---|
| CTLA4_T01 | TGGCCCTGCACTCTCCT<br>gtttttcttctctt<br>CATCCCTGTCTTCTGCA<br>(SEQ ID NO: 74) | Repeat CTLA4_T01-L<br>(SEQ ID NO: 79)<br>Repeat CTLA4_T01-R<br>(SEQ ID NO: 80) | CTLA4_T01-L TALEN<br>(SEQ ID NO: 89)<br>CTLA4_T01-R TALEN<br>(SEQ ID NO: 90) |
| CTLA4_T03 | TTTTCCATGCTAGCAAT<br>gcacgtggcccagcc<br>TGCTGTGGTACTGGCCA<br>(SEQ ID NO: 75) | Repeat CTLA4_T03-L<br>(SEQ ID NO: 81)<br>Repeat CTLA4_T03-R<br>(SEQ ID NO: 82) | CTLA4_T03-L TALEN<br>(SEQ ID NO: 91)<br>CTLA4_T03-R TALEN<br>(SEQ ID NO: 92) |

TABLE 10-continued

Description of the CTLA4 and PDCD1 TALE-nucleases and sequences of the TALE-nucleases target sites in the human corresponding genes.

| Target | Target sequence | Repeat sequence | Half TALE-nuclease |
|---|---|---|---|
| CTLA4_T04 | TCCATGCTAGCAATGCA cgtggcccagcctgc TGTGGTACTGGCCAGCA (SEQ ID NO: 76) | Repeat CTLA4_T04-L (SEQ ID NO: 84) Repeat CTLA4_T04-R (SEQ ID NO: 85) | CTLA4_T04-L TALEN (SEQ ID NO: 93) CTLA4_T04-R TALEN (SEQ ID NO: 94) |
| PDCD1_T01 | TTCTCCCCAGCCCTGCT cgtggtgaccgaagg GGACAACGCCACCTTCA (SEQ ID NO: 77) | Repeat PDCD1_T01-L (SEQ ID NO: 86) Repeat PDCD1_T01-R (SEQ ID NO: 87) | PDCD1_T01-L TALEN (SEQ ID NO: 95) PDCD1_T01-R TALEN (SEQ ID NO: 96) |
| PDCD1_T03 | TACCTCTGTGGGGCCAT ctccctggcccccaa GGCGCAGATCAAAGAGA (SEQ ID NO: 78) | Repeat PDCD1_T03-L (SEQ ID NO: 88) Repeat PDCD1_T03-R (SEQ ID NO: 89) | PDCD1_T03-L TALEN (SEQ ID NO: 97) PDCD1_T03-R TALEN (SEQ ID NO: 98 |

Activity of CTLA4-TALE-nuclease and PDCD1-TALE-nuclease in HEK293 Cells

Each TALE-nuclease construct was subcloned using restriction enzyme digestion in a mammalian expression vector under the control of the pEF1alpha long promoter. One million HEK293 cells were seeded one day prior to transfection. Cells were co-transfected with 2.5 μg of each of two plasmids encoding the TALE-nucleases recognizing the two half targets in the genomic sequence of interest in the PDCD1 and CTLA-4 gene under the control of the EF1-alpha promoter or 5 μg of a control pUC vector (pCLS0003) using 25 μl of lipofectamine (Invitrogen) according to the manufacturer's instructions. The double stranded cleavage generated by TALE-nucleases in PDCD1 or CTLA-4 coding sequences is repaired in live cells by non homologous end joining (NHEJ), which is an error-prone mechanism. Activity of TALE-nucleases in live cells is measured by the frequency of insertions or deletions at the genomic locus targeted. 48 hours after transfection, genomic DNA was isolated from transfected cells and locus specific PCRs were performed using the following composite primers: 5'-CCATCTCATCCCTGCGTGTCTCCGACTCAG (forward adaptor sequence, SEQ ID NO: 126)-10N (TAG)-locus specific forward sequence for CTLA4_T01: 5'-CTCTACTTCCTGAAGACCTG-3' (SEQ ID NO: 141; composite primer disclosed as SEQ ID NO: 99), for CTLA4_T03/T04: 5'-ACAGTTGAGAGATGGAGGGG-3' (SEQ ID NO: 142; composite primer disclosed as SEQ ID NO: 100), for PDCD1_T01: 5'-CCACAGAGGTAGGTGCCGC-3' (SEQ ID NO: 143; composite primer disclosed as SEQ ID NO: 101) or for PDCD1_T03: 5'-GACAGAGATGCCGGTCACCA-3' (SEQ ID NO: 144; composite primer disclosed as SEQ ID NO: 102) and the reverse composite primer 5'-CCTATCCCCTGTGTGCCTTGGCAGTCTCAG (reverse adaptor sequence, SEQ ID NO: 130)-endogenous locus specific reverse sequence for CTLA4_T01: 5'-TGGAATACAGAGCCAGCCAA-3' (SEQ ID NO: 145; composite primer disclosed as SEQ ID NO: 103), for CTLA4_T03/T04: 5'-GGTGCCCGTGCAGATGGAAT-3' (SEQ ID NO: 146; composite primer disclosed as SEQ ID NO: 104), for PDCD1_T01: 5'-GGCTCTGCAGTGGAGGCCAG-3' (SEQ ID NO: 147; composite primer disclosed as SEQ ID NO: 105) or for PDCD1_T03: 5'-GGACAACGCCACCTTCACCT-3' (SEQ ID NO: 148; composite primer disclosed as SEQ ID NO: 106).

PCR products were analyzed by T7-endonuclease assay: briefly, after denaturation and reannealing of the PCR product, T7 endonuclease will specifically digest mismatched DNA composed of wild type and mutated strands. The digestion product is then resolved by polyacrylamide gel electrophoresis. The presence of a digested product is indicative of mutated sequences induced by TALE-nuclease activity. Results are displayed in FIG. 10 where arrows point to the digested PCR products. They demonstrate that PDCD1_T1, PDCD1_T3, CTLA4_T1, CTLA4_T3 and CTLA4_T4 TALE-nucleases all exhibit mutagenic nuclease activity at their target sites.

Example 4 pTalpha Permits CD3 Surface Expression in Inactivated TCR Alpha T Lymphocytes Description of the Different preTalpha Versions:

The human pTalpha gene encodes a transmembrane glycoprotein comprising an extracellular Ig-like domain, a hydrophobic transmembrane domain and a large C-terminal intracytoplasmic tail. Different versions derived from human pTalpha glycoprotein have been designed and are described in Table 11 and represented in FIG. 11.

TABLE 11

Description of a subset of pTalpha constructs

| PTalpha versions | Description | SEQ ID |
|---|---|---|
| pTalpha-FL | Full-length of human pTalpha glycoprotein | 107 |
| pTalpha-Δ18 | Truncated Human pTalpha glycoprotein lacking 18 residues from the C-terminus. | 108 |
| pTalpha-Δ48 | Truncated Human pTalpha glycoprotein lacking 48 residues from the C-terminus. | 109 |
| pTalpha-Δ62 | Truncated Human pTalpha glycoprotein lacking 62 residues from the C-terminus. | 110 |

TABLE 11-continued

Description of a subset of pTalpha constructs

| PTalpha versions | Description | SEQ ID |
|---|---|---|
| pTalpha-Δ78 | Truncated Human pTalpha glycoprotein lacking 78 residues from the C-terminus. | 111 |
| pTalpha-Δ92 | Truncated Human pTalpha glycoprotein lacking 92 residues from the C-terminus. | 112 |
| pTalpha-Δ110 | Truncated Human pTalpha glycoprotein lacking 110 residues from the C-terminus. | 113 |
| pTalpha-Δ114 | Truncated Human pTalpha glycoprotein lacking 114 residues from the C-terminus. | 114 |
| pTalpha-FL-CD28 | Full-length of human pTalpha glycoprotein fused in C-terminus with CD28 activation domain. | 115 |
| pTalpha-FL-CD8 | Full-length of human pTalpha glycoprotein fused in C-terminus with CD8 activation domain. | 116 |
| pTalpha-FL-4-1BB | Full-length of human pTalpha glycoprotein fused in C-terminus with 4-1BB activation domain.. | 117 |
| pTalpha-Δ48-CD28 | pTalpha-Δ48 glycoprotein fused in C-terminus with CD28 activation domain. | 118 |
| pTalpha-Δ48-CD8 | pTalpha-Δ48 glycoprotein fused in C-terminus with CD8 activation domain. | 119 |
| pTalpha-Δ48-41BB | pTalpha-Δ48 glycoprotein fused in C-terminus with 4-1BB activation domain. | 120 |
| pTalpha-Δ114/TCRα.IC | pTalpha-Δ114 glycoprotein fused in C-terminus with the intracellular domain of TCRalpha | 121 |
| pTalpha-EC/TCRα.TM.IC | pTalpha extracellular domain fused in C-terminus with the transmembrane and intracellular domain of TCRalpha. | 122 |
| pTalpha-Δ48-1xMUT | pTalpha-Δ48 glycoprotein with mutated residue W46R. | 123 |
| preTalpha-Δ48-4xMUT | pTalpha-Δ48 glycoprotein with mutated residues D22A, K24A, R102A, R117A | 124 |

The different preTalpha constructs tested include:

1) pTalpha deletion mutants: Different deletions were generated in the intracellular cytoplasmic tail of the human pTalpha protein (which comprises 114 amino acids) (SEQ ID NO: 107). The constructs tested include the full length version of the protein (FL) and mutants in which 18, 48, 62, 78, 92, 110 and 114 amino acids were deleted from the C-terminus of the protein (SEQ ID NO: 108 to SEQ ID NO: 114).
2) pTalpha mutants containing intracellular activation domains: The FL and Δ48 variants where fused to the CD8, CD28 or 41BB intracellular activation domains at their C-terminus (SEQ ID NO: 115 to SEQ ID NO: 120).
3) pTalpha/TCRα chimeric mutants: In one of the constructs, the TCRα intracellular domain (IC) was fused to a tail-less version (Δ114) of pTalpha (SEQ ID NO: 121). A second construct was also generated in which the pTalpha extracellular domain was fused to the transmembrane (TM) and the IC domains from TCRα (SEQ ID NO: 122).
4) pTalpha dimerization mutants: Some mutations have been described in the literature as being capable to alter the oligomerisation/dimerisation ability of the preTCR complex. These mutants are proposed to allow preTCR expression at the cell surface, without inducing the constitutive signaling (supposed to be induced upon preTCR oligomerization). The mutations have been introduced in the pTalphaΔ48 variant and are:
   1×MUT: W46R (SEQ ID NO: 123)
   4×MUT: D22A, K24A, R102A, R117A (SEQ ID NO: 124)

Activity of Different preTalpha Constructs in TRAC Inactivated Jurkat Cells:

In order to screen different pTalpha variants for their ability to restore CD3 surface expression in TCRalpha inactivated cells, a cell line was generated in which the TCRalpha gene was disrupted using TALEN targeting TRAC. Jurkat cells (a T-cell leukemia cell line) were transfected with plasmids coding for the TALEN cleaving TRAC using CytoPulse electroporation, and the KO cells ($TCR_{\alpha/\beta}^{NEG}$; $CD3^{NEG}$) where then purified by negative selection using CD3 magnetic beads. The KO population (JKT_KOx3 cells) was amplified and used for screening of the different pTalpha variants. Screening was performed by transfection of one million of JKT_KOx3 cells with 15 μg of plasmid coding the different pTalpha variants under control of the EF1α promoter, followed by analysis by flow cytometry of CD3 cell surface expression 48 h after transfection. FIG. 12 is a representative example of the transfection efficiencies (% of BFP+ cells) and activity of the FL, Δ18 and Δ48 pTalpha constructs in JKT_KOx3 cells, based on the % of CD3+ cells, determined by flow cytometry. The results from the different constructs are grouped in Table 12.

TABLE 12

Activity of the different pTalpha constructs in Jurkat TCR alpha inactivated cells. Activity was measured by flow cytometry analysis of CD3 expression in jurkat TCR alpha inactivated cells transfected with the different preTalpha constructs.

| Mutant | ID | % $CD3_{Low}$ | SD |
|---|---|---|---|
| 0 | NEG | 4.69 | 1.53 |
| 1 | preTCRa-FL | 31.18 | 4.15 |
| 2 | preTCRα-Δ18 | 20.13 | 4.56 |
| 3 | preTCRα-Δ48 | 44.86 | 3.90 |
| 4 | preTCRα-Δ62 | 32.42 | 2.95 |
| 5 | preTCRα-Δ78 | 24.75 | 3.87 |
| 6 | preTCRα-Δ92 | 20.63 | 3.70 |
| 7 | preTCRα-Δ110 | 18.18 | 3.49 |
| 8 | preTCRα-Δ114 | 4.29 | 2.74 |
| 9 | preTCRα-FL-CD8 | 18.16 | 5.30 |
| 10 | preTCRα-FL-CD28 | 5.67 | 2.77 |

TABLE 12-continued

Activity of the different pTalpha constructs in Jurkat TCR alpha inactivated cells. Activity was measured by flow cytometry analysis of CD3 expression in jurkat TCR alpha inactivated cells transfected with the different preTalpha constructs.

| Mutant | ID | % $CD3_{Low}$ | SD |
|---|---|---|---|
| 11 | preTCRα-FL-41BB | 27.27 | 3.66 |
| 12 | preTCRα-Δ48-CD8 | 11.56 | 6.01 |
| 13 | preTCRα-Δ48-CD28 | 12.22 | 4.72 |
| 14 | preTCRα-Δ48-41BB | 35.93 | 4.55 |
| 15 | preTCRα-Δ114/TCRα.IC | 3.94 | 1.95 |
| 16 | preTCRα-EC/TCRα.TM.IC | 17.80 | 4.47 |
| 17 | preTCRα-Δ48-1xMUT | 26.88 | 4.37 |
| 18 | preTCRα-Δ48-4xMUT | 7.59 | 1.06 |

Activity of pTalpha-FL and pTalpha-Δ48 in TCR Alpha Inactivated Primary T Lymphocytes:

In order to test the ability of pTalpha-FL and pTalpha-Δ48 versions to induce CD3 surface expression in TCR alpha inactivated T lymphocytes, pTalpha-FL and pTalpha-Δ48 coding sequences were cloned into a self-inactivating pLV-SFFV-BFP-2A-PCTRA lentiviral vector that codes for Blue Fluorescent protein (BFP) under the SFFV promoter followed by the self-cleaving T2A peptide (FIG. 13).

T lymphocytes isolated from peripheral blood were activated for 72 hours using anti-CD3/CD28 activator beads (Life technologies) and 4.5 million cells were transfected by electroporation with 10 μg mRNA encoding the TALE-nuclease targeting TCR alpha constant chain region (TRAC) using a CytoLVT-S instrument (BTX-Harvard Harbour). Two days after electroporation, T cells were transduced with either the LV-SFFV-BFP-2A-pTalpha-Δ48 or LV-SFFV-BFP-2A-control lentiviral vectors. CD3 negative and CD3low T cells were then purified using anti-CD3 magnetic beads (Miltenyi Biotech). This experimental protocol is represented in FIG. 14A.

FIG. 14B represents flow cytometry analysis of TCRalpha/beta, CD3 cell surface expression, and BFP expression on TCRalpha inactivated T cells (KO) transduced with either BFP-2A-pTalphaΔ48 (KO/Δ48) or control BFP lentiviral vector (KO/BFP) before and after purification with CD3 beads. TCRalpha inactivated cells transduced with the BFP-T2A-pTalpha-Δ48 vector (BFP+ cells) show higher levels of CD3 compared to non transduced cells (BFP− cells). No differences are observed among cells transduced with the control BFP vector. These results indicate that pTalpha mediates restoration of CD3 expression at the cell surface of TCRalpha inactivated cells. In contrast, TCRalpha/beta staining remains, as expected, unchanged in cells transduced or not with the pTalpha-Δ48 expressing vector.

pTalpha-mediated CD3 Expression Supports Activation of TCR-deficient T-cells:

To determine the capacity of pTalpha to transduce cell activation signals, expression of early and later activation markers was analyzed on TCR alpha inactivated T cells transduced with pTalpha-Δ48 and pTalpha-Δ48.41BB. TCR alpha inactivated T cells transduced with pTalpha-Δ48 and pTalpha-Δ48.41BB were generated from primary human T-cells as described in previous section and in FIG. 14A.

Figure 15B:
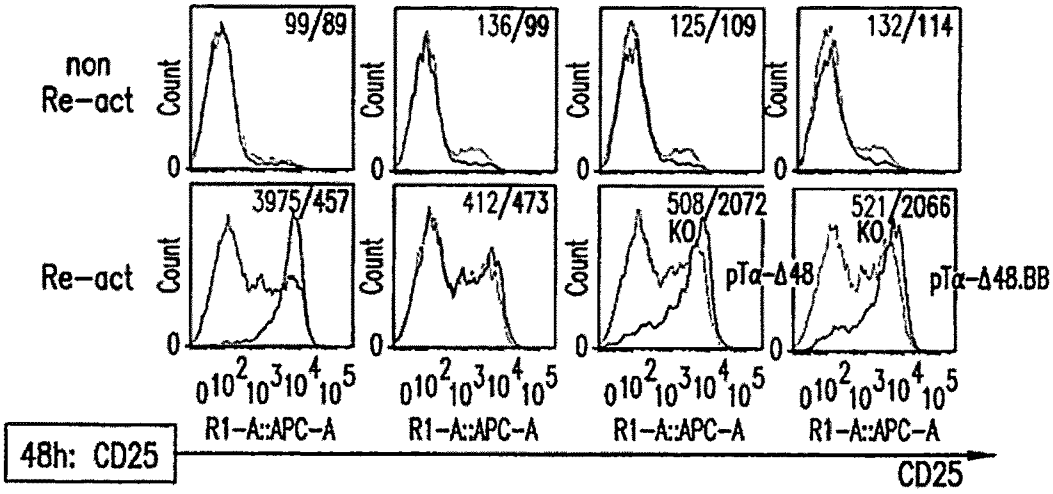

To detect signaling via CD3, cells were re-activated using anti-CD3/CD28-coated beads 3 days after purification of TCR alpha inactivated T cells with CD3 beads (FIG. 14A). Cells were stained with fluorochrome-conjugated anti-CD69 (early activation marker) and anti-CD25 (late activation marker), 24 and 48 hours after re-activation respectively and analyzed by flow cytometry (FIG. 15A-B). As represented in FIG. 15A-B, TCR alpha inactivated cells expressing pTalpha-Δ48 (KO/pTα-Δ48) or pTalpha-Δ48.41BB (KO/pTα-Δ48.BB) show upregulation of the activation markers, to levels similar to those observed in TCRalpha/beta expressing cells (NEP: non electroporated cells).

Figure 15C:
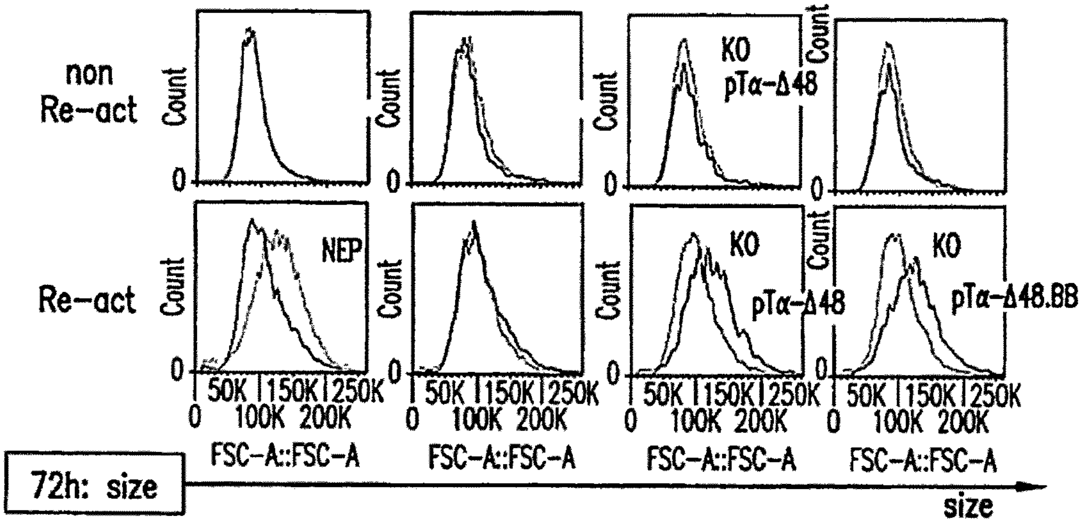

Another indicator of T cell activation is an increase in cell size which is sometimes referred to as “blasting”. The capacity of the preTCR complexes to induce “blasting” was measured by flow cytometry analysis of the cell size 72 hours after re-activation using anti-CD3/CD28-beads (FIG. 15C). Stimulation with anti-CD3/CD28 beads induced comparable increases in cell size in cells expressing TCRalpha/beta complexes vs. cells expressing pTalpha-Δ48 or pTalpha-Δ48.41BB. Taken together, these results suggest that preTCR complexes are competent to transduce signals that efficiently couple to the mechanisms mediating activation marker upregulation.

pTalpha Mediated CD3 Expression Supports Expansion of TCR-deficient Primary T-cells Using Stimulatory Anti-CD3/CD28 Antibodies To evaluate the capacity of preTCR complexes to support long term cell proliferation, proliferation of cells generated as previously described was measured. Ten days after the initial activation, cells were maintained in IL2 (non-Re-act) or in 112 with anti-CD3/CD28 beads (Re-act). For each condition, cells were counted and analyzed by flow cytometry at the different time points to estimate the number of BFP+ cells. The growth of TCRalpha inactivated cells (KO) transduced with BFP or BFP-T2A-preTCRα-Δ48 vectors was compared, and the fold induction of these cells was estimated with respect to the value obtained at day 2 post re-activation. FIG. 16 shows the results obtained with two independent donors. In both cases, TCRalpha inactivated cells expressing pTalpha-Δ48 displayed greater expansion than TCR alpha inactivated cells expressing only the BFP control vector. For the second donor, TCRalpha inactivated cells expressing pTalpha-Δ48.41BB or full-length pTalpha were also included, displaying also greater expansion than TCRalpha inactivated cells expressing only the BFP control vector.

Example 5

Optimization of mRNA Transfection in T Cells Using Cytopulse Technology

Determination of the Optimized Cytopulse Program

A first set of experiments were performed on non activated PBMCs in order to determine a voltage range in which cells could be transfected. Five different programs were tested as described in Table 13.

TABLE 13

Different cytopulse programs used to determine the minimal voltage required for electroporation in PBMC derived T-cells.

| Cyto- | Group 1 | | | | Group 2 | | | | Group 3 | | | |
|---|---|---|---|---|---|---|---|---|---|---|---|---|
| pulse program | Pulses | V | duration (ms) | Interval (ms) | Pulses | V | duration (ms) | Interval (ms) | Pulses | V | duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0.1 | 100 | 4 | 130 | 0.2 | 2 |

3 or 6 million of cells were electroporated in 0.4 cm gap cuvette (30 or $15\times10^6$ cells/ml) with 20 μg of plasmids encoding GFP and control plasmids pUC using the different Cytopulse programs. 24 hours post electroporation, GFP expression was analyzed in electroporated cells by flow cytometry to determine the efficiency of transfection. The data shown in FIG. 17 indicates the minimal voltage required for plasmid electroporation in PBMC derived T cells. These results demonstrate that the cytopulse program 3 and 4 allow an efficient transformation of T cells (EP#3 and #4).

Electroporation of mRNA of Purified Tcells Activated

After determining the best cytopulse program that allows an efficient DNA electroporation of T cells, we tested whether this method was applicable to the mRNA electroporation.

$5\times10^6$ purified T cells preactivated 6 days with PHA/IL2 were resuspended in cytoporation buffer T (BTX-Harvard apparatus) and electroporated in 0.4 cm cuvettes with 10 μg of mRNA encoding GFP or 20 μg of plasmids encoding GFP or pUC using the preferred cytopulse program as determined in the previous section (table 14).

TABLE 14

Cytopulse program used to electroporate purified T-cells.

| Cyto- | Group 1 | | | | Group 2 | | | | Group 3 | | | |
|---|---|---|---|---|---|---|---|---|---|---|---|---|
| pulse program | Pulse | V | duration (ms) | Interval (ms) | Pulse | V | duration (ms) | Interval (ms) | Pulse | V | duration (ms) | Interval (ms) |
| 3 | 1 | 1200 | 0.1 | 0.2 | 1 | 1200 | 0.1 | 100 | 4 | 130 | 0.2 | 2 |

48 h after transfection cells were stained with viability dye (eFluor-450) and the cellular viability and % of viable GFP+ cells was determined by flow cytometry analysis (FIG. 18).

The data shown in FIG. 18 indicates that the electroporation of RNA with the optimal condition determined here is no toxic and allows transfection of more than 95% of the viable cells.

In synthesis, the whole dataset shows that T-cells can be efficiently transfected either with DNA or RNA. In particular, RNA transfection has no impact on cellular viability and allows uniform expression levels of the transfected gene of interest in the cellular population.

Efficient transfection can be achieved early after cellular activation, independently of the activation method used (PHA/IL-2 or CD3/CD28-coated-beads). The inventors have succeeded in transfecting cells from 72 h after activation with efficiencies of >95%. In addition, efficient transfection of T cells after thawing and activation can also be obtained using the same electroporation protocol.

mRNA Electroporation in Primary Human T Cells for TALE-nuclease Functional Expression After demonstrating that mRNA electroporation allow efficient expression of GFP in primary human T cells, we tested whether this method was applicable to the expression of other proteins of interest. Transcription activator-like effector nucleases (TALE-nuclease) are site-specific nucleases generated by the fusion of a TAL DNA binding domain to a DNA cleavage domain. They are powerful genome editing tools as they induce double-strand breaks at practically any desired DNA sequence. These double-strand breaks activate Non-homologous end-joining (NHEJ), an error-prone DNA repair mechanism, potentially leading to inactivation of any desired gene of interest. Alternatively, if an adequate repair template is introduced into the cells at the same time, TALE-nuclease-induced DNA breaks can be repaired by homologous recombination, therefore offering the possibility of modifying at will the gene sequence.

We have used mRNA electroporation to express a TALE-nuclease designed to specifically cleave a sequence in the human gene coding for the alpha chain of the T cell antigen receptor (TRAC). Mutations induced in this sequence are expected to result in gene inactivation and loss of TCRαβ complex from the cell surface. TRAC TALE-nuclease RNA or non coding RNA as control are transfected into activated primary human T lymphocytes using Cytopulse technology. The electroporation sequence consisted in 2 pulses of 1200 V followed by four pulses of 130 V as described in Table 14.

By flow cytometry analysis of TCR surface expression 7 days post electroporation (FIG. 19, top panel), we observed that 44% of T cells lost the expression of TCRαβ. We analyzed the genomic DNA of the transfected cells by PCR amplification of the TRAC locus followed by 454 high throughput sequencing. 33% of alleles sequenced (727 out of 2153) contained insertion or deletion at the site of TALE-nuclease cleavage. FIG. 19 (bottom panel) shows examples of the mutated alleles.

These data indicate that electroporation of mRNA using cytopulse technology results in functional expression of TRAC TALE-nuclease.

Electroporation of T Cells with a Monocistronic mRNA Encoding for an Anti-CD19 Single Chain Chimeric Antigen Receptor (CAR):

$5\times10^6$ T cells preactivated several days (3-5) with anti-CD3/CD28 coated beads and IL2 were resuspended in cytoporation buffer T, and electroporated in 0.4 cm cuvettes without mRNA or with 10 μg of mRNA encoding a single chain CAR (SEQ ID NO: 73) using the program described in Table 14.

24 hours post electroporation, cells were stained with a fixable viability dye eFluor-780 and a PE-conjugated goat anti mouse IgG F(ab')2 fragment specific to assess the cell surface expression of the CAR on the live cells. The data is shown in the FIG. 20. It indicates that the vast majority of the live T cells electroporated with the monocitronic mRNA described previously express the CAR at their surface.

24 hours post electroporation, T cells were cocultured with Daudi ($CD19^+$) cells for 6 hours and analyzed by flow cytometry to detect the expression of the degranulation marker CD107a at their surface (Betts, Brenchley et al. 2003).

The data shown in FIG. 20 indicates that the majority of the cells electroporated with the monocistronic mRNA described previously degranulate in the presence of target cells expressing CD19. These results clearly demonstrate that the CAR expressed at the surface of electroporated T cells is active.

Electroporation of T Cells with a Polycistronic mRNA Encoding for an Anti-CD19 Multisubunit Chimeric Antigen Receptor (CAR):

$5\times10^6$ T cells preactivated several days (3-5) with anti CD3/CD28 coated beads and IL2 were electroporated in cytoporation buffer T, and electroporated in 0.4 cm cuvettes without mRNA or with 45 μg of mRNA encoding a multi-chain CAR (SEQ ID NO: 226), FIG. 21A and FIG. 4B (csm4)) using the program described in Table 14.

24 hours post electroporation, cells were stained with a fixable viability dye eFluor-780 and a PE-conjugated goat anti mouse IgG F(ab')2 fragment specific to assess the cell surface expression of the CAR on the live cells. The data shown in FIG. 21 indicates that the vast majority of the live T cells electroporated with the polycistronic mRNA described previously express the CAR at their surface.

24 hours post electroporation, T cells were cocultured with Daudi ($CD19^+$) for 6 hours and analyzed by flow cytometry to detect the expression of the degranulation marker CD107a at their surface. The data shown in FIG. 21 indicates that the majority of the cells electroporated with the polycistronic mRNA described previously degranulate in the presence of target cells expressing CD19. These results clearly demonstrate that the CAR expressed at the surface of electroporated T cells is active.

Example 6

Multi-chain CARs

A. Design of Multi-Chain CARs

Nine multi-chain CARs targeting the CD19 antigen were designed based on the high affinity receptor for IgE (FcεRI). The FcεRI expressed on mast cells and basophiles triggers allergic reactions. It is a tetrameric complex composed of a single α subunit (SEQ ID NO: 202), a single β subunit (SEQ ID NO: 203) and two disulfide-linked γ subunits (SEQ ID NO: 204). The α subunit contains the IgE-binding domain. The β and γ subunits contain ITAMs (SEQ ID NO: 198 and SEQ ID NO: 199) that mediate signal transduction FIG. 4A. The multi-chain CARs were designed as described in FIGS. 4B, C and Table 15. In every multi-chain CAR, the extra-cellular domain of the FcRα chain was deleted and replaced by the 4G7scFv and the CD8α hinge (SEQ ID NO: 206). In the multi-chain CARs csm2, csm4, csm5, csm8 and csm10, the ITAM of the FcRβ chain and/or the FcRγ chain was deleted. In the multi-chain CARs csm2, csm4, csm5, csm6, csm8, csm9 and csm10, the 3 ITAMs of CD3ζ (SEQ ID NO: 197) were added to the FcRβ chain or the FcRγ chain. In the multi-chain CARs csm2, csm4, csm5, csm6, csm7, csm8, csm9 and csm10, the 4-1BB intracellular domain (SEQ ID NO: 200) was added to the FcRα chain, the FcRβ chain or the FcRγ chain. In the multi-chain CAR csm10, the CD28 intracellular domain was added to the FcRα chain (SEQ ID NO: 201).

TABLE 15

Description of the chains compositions of the multi-chain CARs versions.

| Multi-chain CAR versions | alpha chain | beta chain | gamma chain |
|---|---|---|---|
| Csm1 | FcRα-4G7scFV-CD8 (SEQ ID NO: 206) | FcRβ (SEQ ID NO: 203) | FcRγ (SEQ ID NO: 204) |
| Csm2 | FcRα-4G7scFv-CD8 (SEQ ID NO: 206) | FcRβ (SEQ ID NO: 203) | FcRγ-ΔITAM-41BB-CD3ζ (SEQ ID NO: 212) |
| Csm4 | FcRα-4G7scFv-CD8 (SEQ ID NO: 206) | FcRβ-ΔITAM-41BB (SEQ ID NO: 208) | FcRγ-ΔITAM-CD3ζ (SEQ ID NO: 213) |
| Csm5 | FcRα-4G7scFv-CD8 (SEQ ID NO: 206) | FcRβ-ΔITAM-41BB-CD3ζ (SEQ ID NO: 209) | FcRγ (SEQ ID NO: 204) |
| Csm6 | FcRα-4G7scFv-CD8 (SEQ ID NO: 206) | FcRβ-41BB (SEQ ID NO: 210) | FcRγ-CD3ζ (SEQ ID NO: 214) |
| Csm7 | FcRα-4G7scFv-CD8-41BB (SEQ ID NO: 207) | FcRβ (SEQ ID NO: 203) | FcRγ (SEQ ID NO: 204) |
| Csm8 | FcRα-4G7scFv-CD8-41BB (SEQ ID NO: 207) | FcRβ-ΔITAM-CD3ζ (SEQ ID NO: 211) | FcRγ (SEQ ID NO: 204) |

TABLE 15-continued

Description of the chains compositions of the multi-chain CARs versions.

| Multi-chain CAR versions | alpha chain | beta chain | gamma chain |
|---|---|---|---|
| Csm9 | FcRα-4G7scFv-CD8-41BB (SEQ ID NO: 207) | FcRβ (SEQ ID NO: 203) | FcRγ-CD3ζ (SEQ ID NO: 214) |
| Csm10 | FcRα-4G7scFv-CD8-CD28 (SEQ ID NO: 206) | FcRβ-ΔITAM-41BB (SEQ ID NO: 208) | FcRγ-ΔITAM-CD3ζ (SEQ ID NO: 213) |

B. Transiently Expressed Multi-Chain CARs can Trigger T Cells Activation

Multi-chain CARs can be Expressed in Human T Cells after Electroporation of Polycistronic mRNA.

T cells were electroporated with capped and polyadenylated polycistronic mRNA (FIG. 21A), that were produced using the mMESSAGE mMACHINE kit and linearized plasmids as template. The plasmids used as template contained the T7 RNA polymerase promoter followed by a polycistronic DNA sequence encoding csm1, csm2, csm4, csm5, csm6, csm7, csm8, csm9 or csm10 (SEQ ID NO: 224 to 232).

The electroporation of the polycistronic mRNAs into the human T cells was done using the CytoLVT-S device (Cellectis), according to the following protocol: $5\times10^6$ T cells preactivated several days (3-5) with anti CD3/CD28 coated beads and IL2 were resuspended in cytoporation buffer T, and electroporated in 0.4 cm cuvettes with 45 μg of mRNA using the PBMC3 program Table 14.

24 hours post electroporation, human T cells engineered using polycistronic mRNAs encoding the multi-chain CARs were labeled with a fixable viability dye eFluor-780 and a PE-conjugated goat anti mouse IgG F(ab')2 fragment specific, and analysed by flow cytometry. The data shown in FIG. 22 indicate that the live T cells engineered using polycistronic mRNAs express the multi-chain CARs csm1, csm2, csm4, csm5, csm6, csm7, csm8, csm9 and csm 10.

As described in the literature for the FcεRI, the expression of the multi-subunit CARs is conditioned by the expression of the 3 chains. The α chain alone is less expressed than the α+γ chains complex, and the α+γ chains complex is less expressed than the α+β+γ chains complex FIG. 23.

The Human T Cells Transiently Expressing the Multi-chain CARs Degranulate Following Coculture with Target Cells 24 hours post electroporation, human T cells engineered using polycistronic mRNAs encoding the multi-chain CARs were co-cultured with target (Daudi) or control (K562) cells for 6 hours. The CD8+ T cells were then analyzed by flow cytometry to detect the expression of the degranulation marker CD107a at their surface. The data shown in FIG. 24 indicate that the human CD8+ T cells expressing the multi-chain CARs csm1, csm2, csm4, csm5, csm6, csm7, csm8, csm9 and csm10 degranulate in coculture with CD19 expressing target cells but not in coculture with control cells.

The Human T Cells Transiently Expressing the Multi-chain CARs Secrete Cytokines Following Coculture with Target Cells 24 hours post electroporation, human T cells engineered using polycistronic mRNAs encoding the multi-chain CARs were co-cultured with target (Daudi) or control (K562) cells for 24 hours. The supernatants were then harvested and analysed using the TH1/TH2 cytokine cytometric bead array kit to quantify the cytokines produced by the T cells. The data shown in FIG. 25A-C indicate that the human T cells expressing the multi-chain CARs csm1, csm2, csm4, csm5, csm6, csm7, csm8, csm9 and csm10 produce IFNγ, IL8 and IL5 in coculture with CD19 expressing target cells but not in coculture with control cells.

The Human T Cells Transiently Expressing the Multi-chain CARs Lyse Target Cells 24 hours post electroporation, human T cells engineered using polycistronic mRNAs encoding the multi-chain CARs were co-cultured with target (Daudi) or control (K562) cells for 4 hours. The target cells were then analysed by flow cytometry to analyse their viability. The data shown in FIG. 26 indicate that the cells expressing the multi-chain CARs csm1, csm2, csm4, csm5, csm6, csm7, csm8, csm9 and csm10 lyse the CD19 expressing target cells but not the control cells.

LIST OF REFERENCES CITED IN THE DESCRIPTION

Arimondo, P. B., C. J. Thomas, et al. (2006). "Exploring the cellular activity of camptothecin-triple-helix-forming oligonucleotide conjugates." *Mol Cell Biol* 26(1): 324-33.

Arnould, S., P. Chames, et al. (2006). "Engineering of large numbers of highly specific homing endonucleases that induce recombination on novel DNA targets." *J Mol Biol* 355(3): 443-58.

Ashwell, J. D. and R. D. Klusner (1990). "Genetic and mutational analysis of the T-cell antigen receptor." *Annu Rev Immunol* 8: 139-67.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Boch, J., H. Scholze, et al. (2009). "Breaking the code of DNA binding specificity of TAL-type III effectors." *Science* 326(5959): 1509-12.

Boni, A., P. Muranski, et al. (2008). "Adoptive transfer of allogeneic tumor-specific T cells mediates effective regression of large tumors across major histocompatibility barriers." *Blood* 112(12): 4746-54.

Brahmer, J. R., C. G. Drake, et al. (2010). "Phase I study of single-agent anti-programmed death-1 (MDX-1106) in refractory solid tumors: safety, clinical activity, pharmacodynamics, and immunologic correlates." *J Clin Oncol* 28(19): 3167-75.

Cambier, J. C. (1995). "Antigen and Fc receptor signaling. The awesome power of the immunoreceptor tyrosine-based activation motif (ITAM)." *J Immunol* 155(7): 3281-5.

Carrasco, Y. R., A. R. Ramiro, et al. (2001). "An endoplasmic reticulum retention function for the cytoplasmic tail of the human pre-T cell receptor (TCR) alpha chain: potential role in the regulation of cell surface pre-TCR expression levels." *J Exp Med* 193(9): 1045-58.

Cermak, T., E. L. Doyle, et al. (2011). "Efficient design and assembly of custom TALEN and other TAL effector-based constructs for DNA targeting." *Nucleic Acids Res* 39(12): e82.

Chames, P., J. C. Epinat, et al. (2005). "In vivo selection of engineered homing endonucleases using double-strand break induced homologous recombination." *Nucleic Acids Res* 33(20): e178.

Choulika, A., A. Perrin, et al. (1995). "Induction of homologous recombination in mammalian chromosomes by using the I-SceI system of *Saccharomyces cerevisiae.*" *Mol Cell Biol* 15(4): 1968-73.

Christian, M., T. Cermak, et al. (2010). "Targeting DNA double-strand breaks with TAL effector nucleases." *Genetics* 186(2): 757-61.

Coutinho, A. E. and K. E. Chapman (2011). "The anti-inflammatory and immunosuppressive effects of glucocorticoids, recent developments and mechanistic insights." *Mol Cell Endocrinol* 335(1): 2-13.

Critchlow, S. E. and S. P. Jackson (1998). "DNA end-joining: from yeast to man." *Trends Biochem Sci* 23(10): 394-8.

Deng, D., C. Yan, et al. (2012). "Structural basis for sequence-specific recognition of DNA by TAL effectors." *Science* 335(6069): 720-3.

Eisenschmidt, K., T. Lanio, et al. (2005). "Developing a programmed restriction endonuclease for highly specific DNA cleavage." *Nucleic Acids Res* 33(22): 7039-47.

Epinat, J. C., S. Arnould, et al. (2003). "A novel engineered meganuclease induces homologous recombination in yeast and mammalian cells." *Nucleic Acids Res* 31(11): 2952-62.

Geissler, R., H. Scholze, et al. (2011). "Transcriptional activators of human genes with programmable DNA-specificity." *PLoS One* 6(5): e19509.

Howard, F. D., H. R. Rodewald, et al. (1990). "CD3 zeta subunit can substitute for the gamma subunit of Fc epsilon receptor type I in assembly and functional expression of the high-affinity IgE receptor: evidence for interreceptor complementation." *Proc Natl Acad Sci USA* 87(18): 7015-9.

Huang, P., A. Xiao, et al. (2011). "Heritable gene targeting in zebrafish using customized TALENs." *Nat Biotechnol* 29(8): 699-700.

Jena, B., G. Dotti, et al. (2010). "Redirecting T-cell specificity by introducing a tumor-specific chimeric antigen receptor." *Blood* 116(7): 1035-44.

Kalish, J. M. and P. M. Glazer (2005). "Targeted genome modification via triple helix formation." *Ann N Y Acad Sci* 1058: 151-61.

Li, L., M. J. Piatek, et al. (2012). "Rapid and highly efficient construction of TALE-based transcriptional regulators and nucleases for genome modification." *Plant Mol Biol* 78(4-5): 407-16.

Li, T., S. Huang, et al. (2011). "TAL nucleases (TALNs): hybrid proteins composed of TAL effectors and FokI DNA-cleavage domain." *Nucleic Acids Res* 39(1): 359-72.

Li, T., S. Huang, et al. (2011). "Modularly assembled designer TAL effector nucleases for targeted gene knockout and gene replacement in eukaryotes." *Nucleic Acids Res* 39(14): 6315-25.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mahfouz, M. M., L. Li, et al. (2012). "Targeted transcriptional repression using a chimeric TALE-SRDX repressor protein." *Plant Mol Biol* 78(3): 311-21.

Mahfouz, M. M., L. Li, et al. (2011). "De novo-engineered transcription activator-like effector (TALE) hybrid nuclease with novel DNA binding specificity creates double-strand breaks." *Proc Natl Acad Sci USA* 108(6): 2623-8.

Mak, A. N., P. Bradley, et al. (2012). "The crystal structure of TAL effector PthXo1 bound to its DNA target." *Science* 335(6069): 716-9.

Metzger, H., G. Alcaraz, et al. (1986). "The receptor with high affinity for immunoglobulin E." *Annu Rev Immunol* 4: 419-70.

Miller, J. C., S. Tan, et al. (2011). "A TALE nuclease architecture for efficient genome editing." *Nat Biotechnol* 29(2): 143-8.

Morbitzer, R., P. Romer, et al. (2011). "Regulation of selected genome loci using de novo-engineered transcription activator-like effector (TALE)-type transcription factors." *Proc Natl Acad Sci USA* 107(50): 21617-22.

Moscou, M. J. and A. J. Bogdanove (2009). "A simple cipher governs DNA recognition by TAL effectors." *Science* 326(5959): 1501.

Mussolino, C., R. Morbitzer, et al. (2011). "A novel TALE nuclease scaffold enables high genome editing activity in combination with low toxicity." *Nucleic Acids Res* 39(21): 9283-93.

Pang, S. S., R. Berry, et al. (2010). "The structural basis for autonomous dimerization of the pre-T-cell antigen receptor." *Nature* 467(7317): 844-8.

Paques, F. and P. Duchateau (2007). "Meganucleases and DNA double-strand break-induced recombination: perspectives for gene therapy." *Curr Gene Ther* 7(1): 49-66.

Pardoll, D. and C. Drake (2012). "Immunotherapy earns its spot in the ranks of cancer therapy." *J Exp Med* 209(2): 201-9.

Pardoll, D. M. (2012). "The blockade of immune checkpoints in cancer immunotherapy." *Nat Rev Cancer* 12(4): 252-64.

Park, T. S., S. A. Rosenberg, et al. (2011). "Treating cancer with genetically engineered T cells." *Trends Biotechnol* 29(11): 550-7.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Robert, C. and C. Mateus (2011). "[Anti-CTLA-4 monoclonal antibody: a major step in the treatment of metastatic melanoma]." *Med Sci* (*Paris*) 27(10): 850-8.

Rouet, P., F. Smih, et al. (1994). "Introduction of double-strand breaks into the genome of mouse cells by expression of a rare-cutting endonuclease." *Mol Cell Biol* 14(12): 8096-106.

Saint-Ruf, C., O. Lechner, et al. (1998). "Genomic structure of the human pre-T cell receptor alpha chain and expression of two mRNA isoforms." *Eur J Immunol* 28(11): 3824-31.

Sander, J. D., L. Cade, et al. (2011). "Targeted gene disruption in somatic zebrafish cells using engineered TALENs." *Nat Biotechnol* 29(8): 697-8.

Smith, J., S. Grizot, et al. (2006). "A combinatorial approach to create artificial homing endonucleases cleaving chosen sequences." *Nucleic Acids Res* 34(22): e149.

Stoddard, B. L. (2005). "Homing endonuclease structure and function." *Q Rev Biophys* 38(1): 49-95.

Tesson, L., C. Usal, et al. (2011). "Knockout rats generated by embryo microinjection of TALENs." *Nat Biotechnol* 29(8): 695-6.

von Boehmer, H. (2005). "Unique features of the pre-T-cell receptor alpha-chain: not just a surrogate." *Nat Rev Immunol* 5(7): 571-7.

Waldmann, H. and G. Hale (2005). "CAMPATH: from concept to clinic." *Philos Trans R Soc Lond B Biol Sci* 360(1461): 1707-11.

Weber, E., R. Gruetzner, et al. (2011). "Assembly of designer TAL effectors by Golden Gate cloning." *PLoS One* 6(5): e19722.

Yamasaki, S., E. Ishikawa, et al. (2006). "Mechanistic basis of pre-T cell receptor-mediated autonomous signaling critical for thymocyte development." *Nat Immunol* 7(1): 67-75.

Zhang, F., L. Cong, et al. (2011). "Efficient construction of sequence-specific TAL effectors for modulating mammalian transcription." *Nat Biotechnol* 29(2): 149-53.

The invention claimed is:

1. A multi-chain Chimeric Antigen Receptor (CAR) including at least two different and separate transmembrane polypeptides expressed on an immune cell, comprising:

a first transmembrane polypeptide fused with an extracellular ligand-binding domain, the extracellular ligand-binding domain comprising a single-chain antibody fragment (scFv) that recognizes an antigen on a target cell, wherein the first transmembrane polypeptide comprises an alpha chain of Fc epsilon Receptor I (FcεRI) without its high affinity IgE binding domain, and at least a second transmembrane polypeptide comprising at least one intracellular signal transducing domain from a T cell Receptor (TCR) zeta chain;

wherein the first transmembrane polypeptide dimerizes with the second transmembrane polypeptide to form the multi-chain CAR on the immune cell.

2. The multi-chain CAR of claim 1, wherein the second transmembrane polypeptide lacks an extracellular ligand-binding domain.

3. The multi-chain CAR of claim 2, further comprising a costimulatory domain of CD28.

4. The multi-chain CAR of claim 2, further comprising a costimulatory domain of CD137.

5. The multi-chain CAR of claim 1, wherein said first transmembrane polypeptide further comprises a CD8 stalk region.

6. The multi-chain CAR of claim 2, wherein said first transmembrane polypeptide further comprises a CD8 stalk region.

* * * * *

SEQUENCE LISTING

```
<160> NUMBER OF SEQ ID NOS: 232

<210> SEQ ID NO 1
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: GRex2

<400> SEQUENCE: 1

tattcactga tggactccaa agaatcatta actcctggta gagaagaaa                   49


<210> SEQ ID NO 2
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: GRex3T2

<400> SEQUENCE: 2

tgcctggtgt gctctgatga agcttcagga tgtcattatg gagtcttaa                   49


<210> SEQ ID NO 3
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: GRex3T4

<400> SEQUENCE: 3

tgctctgatg aagcttcagg atgtcattat ggagtcttaa cttgtggaa                   49


<210> SEQ ID NO 4
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: GRex5T1

<400> SEQUENCE: 4

tggtgtcact gttggaggtt attgaacctg aagtgttata tgcaggata                   49


<210> SEQ ID NO 5
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
```

<223> OTHER INFORMATION: GRex5T2

<400> SEQUENCE: 5
tatgatagct ctgttccaga ctcaacttgg aggatcatga ctacgctca 49

<210> SEQ ID NO 6
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: GRex5T3

<400> SEQUENCE: 6
ttatatgcag gatatgatag ctctgttcca gactcaactt ggaggatca 49

<210> SEQ ID NO 7
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex2-LPT9-L1

<400> SEQUENCE: 7

```
Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255
```

Leu Glu Thr Val Gln Arg Leu Leu Pro Val Leu Cys Gln Ala His Gly
260 265 270

Leu Thr Pro Glu Gln Val Val Ala Ile Ala Ser Asn Ile Gly Gly Lys
275 280 285

Gln Ala Leu Glu Thr Val Gln Ala Leu Leu Pro Val Leu Cys Gln Ala
290 295 300

His Gly Leu Thr Pro Gln Gln Val Val Ala Ile Ala Ser Asn Gly Gly
305 310 315 320

Gly Lys Gln Ala Leu Glu Thr Val Gln Arg Leu Leu Pro Val Leu Cys
325 330 335

Gln Ala His Gly Leu Thr Pro Gln Gln Val Val Ala Ile Ala Ser Asn
340 345 350

Asn Gly Gly Lys Gln Ala Leu Glu Thr Val Gln Arg Leu Leu Pro Val
355 360 365

Leu Cys Gln Ala His Gly Leu Thr Pro Gln Gln Val Val Ala Ile Ala
370 375 380

Ser Asn Asn Gly Gly Lys Gln Ala Leu Glu Thr Val Gln Arg Leu Leu
385 390 395 400

Pro Val Leu Cys Gln Ala His Gly Leu Thr Pro Glu Gln Val Val Ala
405 410 415

Ile Ala Ser Asn Ile Gly Gly Lys Gln Ala Leu Glu Thr Val Gln Ala
420 425 430

Leu Leu Pro Val Leu Cys Gln Ala His Gly Leu Thr Pro Glu Gln Val
435 440 445

Val Ala Ile Ala Ser His Asp Gly Gly Lys Gln Ala Leu Glu Thr Val
450 455 460

Gln Arg Leu Leu Pro Val Leu Cys Gln Ala His Gly Leu Thr Pro Gln
465 470 475 480

Gln Val Val Ala Ile Ala Ser Asn Gly Gly Gly Lys Gln Ala Leu Glu
485 490 495

Thr Val Gln Arg Leu Leu Pro Val Leu Cys Gln Ala His Gly Leu Thr
500 505 510

Pro Gln Gln Val Val Ala Ile Ala Ser Asn Gly Gly Gly Arg Pro Ala
515 520 525

Leu Glu
530

<210> SEQ ID NO 8
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex2-LPT9-R1

<400> SEQUENCE: 8

Leu Thr Pro Gln Gln Val Val Ala Ile Ala Ser Asn Gly Gly Gly Lys
1 5 10 15

Gln Ala Leu Glu Thr Val Gln Arg Leu Leu Pro Val Leu Cys Gln Ala
20 25 30

His Gly Leu Thr Pro Gln Gln Val Val Ala Ile Ala Ser Asn Gly Gly
35 40 45

Gly Lys Gln Ala Leu Glu Thr Val Gln Arg Leu Leu Pro Val Leu Cys
50 55 60

-continued

```
Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
```

```
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 9
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex3T2-L1

<400> SEQUENCE: 9

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300
```

His Gly Leu Thr Pro Gln Gln Val Val Ala Ile Ala Ser Asn Asn Gly
305 310 315 320

Gly Lys Gln Ala Leu Glu Thr Val Gln Arg Leu Leu Pro Val Leu Cys
325 330 335

Gln Ala His Gly Leu Thr Pro Glu Gln Val Val Ala Ile Ala Ser His
340 345 350

Asp Gly Gly Lys Gln Ala Leu Glu Thr Val Gln Arg Leu Leu Pro Val
355 360 365

Leu Cys Gln Ala His Gly Leu Thr Pro Gln Gln Val Val Ala Ile Ala
370 375 380

Ser Asn Gly Gly Gly Lys Gln Ala Leu Glu Thr Val Gln Arg Leu Leu
385 390 395 400

Pro Val Leu Cys Gln Ala His Gly Leu Thr Pro Glu Gln Val Val Ala
405 410 415

Ile Ala Ser His Asp Gly Gly Lys Gln Ala Leu Glu Thr Val Gln Arg
420 425 430

Leu Leu Pro Val Leu Cys Gln Ala His Gly Leu Thr Pro Gln Gln Val
435 440 445

Val Ala Ile Ala Ser Asn Gly Gly Gly Lys Gln Ala Leu Glu Thr Val
450 455 460

Gln Arg Leu Leu Pro Val Leu Cys Gln Ala His Gly Leu Thr Pro Gln
465 470 475 480

Gln Val Val Ala Ile Ala Ser Asn Asn Gly Gly Lys Gln Ala Leu Glu
485 490 495

Thr Val Gln Arg Leu Leu Pro Val Leu Cys Gln Ala His Gly Leu Thr
500 505 510

Pro Gln Gln Val Val Ala Ile Ala Ser Asn Gly Gly Gly Arg Pro Ala
515 520 525

Leu Glu
530

<210> SEQ ID NO 10
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex3T2-R1

<400> SEQUENCE: 10

Leu Thr Pro Gln Gln Val Val Ala Ile Ala Ser Asn Gly Gly Gly Lys
1 5 10 15

Gln Ala Leu Glu Thr Val Gln Arg Leu Leu Pro Val Leu Cys Gln Ala
20 25 30

His Gly Leu Thr Pro Glu Gln Val Val Ala Ile Ala Ser Asn Ile Gly
35 40 45

Gly Lys Gln Ala Leu Glu Thr Val Gln Ala Leu Leu Pro Val Leu Cys
50 55 60

Gln Ala His Gly Leu Thr Pro Glu Gln Val Val Ala Ile Ala Ser Asn
65 70 75 80

Ile Gly Gly Lys Gln Ala Leu Glu Thr Val Gln Ala Leu Leu Pro Val
85 90 95

Leu Cys Gln Ala His Gly Leu Thr Pro Gln Gln Val Val Ala Ile Ala
100 105 110

-continued

```
Ser Asn Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
```

530

<210> SEQ ID NO 11
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex3T4-L1

<400> SEQUENCE: 11

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Gly Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Glu Gln Val Val Ala Ile Ala Ser Asn
            340                 345                 350

```
Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 12
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex3T4-R1

<400> SEQUENCE: 12

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160
```

-continued

```
Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

<210> SEQ ID NO 13
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex5T1-LPT8-L1

<400> SEQUENCE: 13

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400
```

```
Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 14
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex5T1-LPT8-R1

<400> SEQUENCE: 14

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205
```

-continued

Gln Val Val Ala Ile Ala Ser His Asp Gly Gly Lys Gln Ala Leu Glu
210 215 220

Thr Val Gln Arg Leu Leu Pro Val Leu Cys Gln Ala His Gly Leu Thr
225 230 235 240

Pro Glu Gln Val Val Ala Ile Ala Ser Asn Ile Gly Gly Lys Gln Ala
245 250 255

Leu Glu Thr Val Gln Ala Leu Leu Pro Val Leu Cys Gln Ala His Gly
260 265 270

Leu Thr Pro Gln Gln Val Val Ala Ile Ala Ser Asn Gly Gly Gly Lys
275 280 285

Gln Ala Leu Glu Thr Val Gln Arg Leu Leu Pro Val Leu Cys Gln Ala
290 295 300

His Gly Leu Thr Pro Glu Gln Val Val Ala Ile Ala Ser Asn Ile Gly
305 310 315 320

Gly Lys Gln Ala Leu Glu Thr Val Gln Ala Leu Leu Pro Val Leu Cys
325 330 335

Gln Ala His Gly Leu Thr Pro Gln Gln Val Val Ala Ile Ala Ser Asn
340 345 350

Gly Gly Gly Lys Gln Ala Leu Glu Thr Val Gln Arg Leu Leu Pro Val
355 360 365

Leu Cys Gln Ala His Gly Leu Thr Pro Glu Gln Val Val Ala Ile Ala
370 375 380

Ser Asn Ile Gly Gly Lys Gln Ala Leu Glu Thr Val Gln Ala Leu Leu
385 390 395 400

Pro Val Leu Cys Gln Ala His Gly Leu Thr Pro Glu Gln Val Val Ala
405 410 415

Ile Ala Ser Asn Ile Gly Gly Lys Gln Ala Leu Glu Thr Val Gln Ala
420 425 430

Leu Leu Pro Val Leu Cys Gln Ala His Gly Leu Thr Pro Glu Gln Val
435 440 445

Val Ala Ile Ala Ser His Asp Gly Gly Lys Gln Ala Leu Glu Thr Val
450 455 460

Gln Arg Leu Leu Pro Val Leu Cys Gln Ala His Gly Leu Thr Pro Glu
465 470 475 480

Gln Val Val Ala Ile Ala Ser Asn Ile Gly Gly Lys Gln Ala Leu Glu
485 490 495

Thr Val Gln Ala Leu Leu Pro Val Leu Cys Gln Ala His Gly Leu Thr
500 505 510

Pro Gln Gln Val Val Ala Ile Ala Ser Asn Gly Gly Gly Arg Pro Ala
515 520 525

Leu Glu
530

<210> SEQ ID NO 15
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex5T2-L1

<400> SEQUENCE: 15

Leu Thr Pro Glu Gln Val Val Ala Ile Ala Ser Asn Ile Gly Gly Lys
1 5 10 15

Gln Ala Leu Glu Thr Val Gln Ala Leu Leu Pro Val Leu Cys Gln Ala

-continued

```
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445
```

```
Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 16
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex5T2-R1

<400> SEQUENCE: 16

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255
```

```
Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 17
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex5T3-L1

<400> SEQUENCE: 17

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
```

```
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495
```

```
Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 18
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat-GRex5T3-R1

<400> SEQUENCE: 18

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300
```

-continued

```
His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

<210> SEQ ID NO 19
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex2-L TALEN

<400> SEQUENCE: 19

```
atgggcgatc ctaaaaagaa acgtaaggtc atcgattacc catacgatgt tccagattac     60

gctatcgata tcgccgatct acgcacgctc ggctacagcc agcagcaaca ggagaagatc    120

aaaccgaagg ttcgttcgac agtggcgcag caccacgagg cactggtcgg ccacgggttt    180

acacacgcgc acatcgttgc gttaagccaa cacccggcag cgttagggac cgtcgctgtc    240

aagtatcagg acatgatcgc agcgttgcca gaggcgacac acgaagcgat cgttggcgtc    300

ggcaaacagt ggtccggcgc acgcgctctg gaggccttgc tcacggtggc gggagagttg    360

agaggtccac cgttacagtt ggacacaggc caacttctca agattgcaaa acgtggcggc    420

gtgaccgcag tggaggcagt gcatgcatgg cgcaatgcac tgacgggtgc cccgctcaac    480

ttgaccccgg agcaggtggt ggccatcgcc agcaatattg gtggcaagca ggcgctggag    540

acggtgcagg cgctgttgcc ggtgctgtgc caggcccacg gcttgacccc ccagcaggtg    600

gtggccatcg ccagcaatgg cggtggcaag caggcgctgg agacggtcca gcggctgttg    660
```

-continued

```
ccggtgctgt gccaggccca cggcttgacc ccccagcagg tggtggccat cgccagcaat    720
ggcggtggca agcaggcgct ggagacggtc cagcggctgt tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag caatattggt ggcaagcagg cgctggagac ggtgcaggcg    960
ctgttgccgg tgctgtgcca ggcccacggc ttgaccccgg agcaggtggt ggccatcgcc   1020
agccacgatg gcggcaagca ggcgctggag acggtccagc ggctgttgcc ggtgctgtgc   1080
caggcccacg gcttgacccc ccagcaggtg gtggccatcg ccagcaatgg cggtggcaag   1140
caggcgctgg agacggtcca gcggctgttg ccggtgctgt gccaggccca cggcttgacc   1200
ccccagcagg tggtggccat cgccagcaat aatggtggca agcaggcgct ggagacggtc   1260
cagcggctgt tgccggtgct gtgccaggcc cacggcttga ccccggagca ggtggtggcc   1320
atcgccagca atattggtgg caagcaggcg ctggagacgg tgcaggcgct gttgccggtg   1380
ctgtgccagg cccacggctt gacccccccag caggtggtgg ccatcgccag caatggcggt   1440
ggcaagcagg cgctggagac ggtccagcgg ctgttgccgg tgctgtgcca ggcccacggc   1500
ttgacccccc agcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaataa tggtggcaag caggcgctgg agacggtcca gcggctgttg   1680
ccggtgctgt gccaggccca cggcttgacc ccggagcagg tggtggccat cgccagcaat   1740
attggtggca agcaggcgct ggagacggtg caggcgctgt tgccggtgct gtgccaggcc   1800
cacggcttga ccccggagca ggtggtggcc atcgccagcc acgatggcgg caagcaggcg   1860
ctggagacgg tccagcggct gttgccggtg ctgtgccagg cccacggctt gaccccccag   1920
caggtggtgg ccatcgccag caatggcggt ggcaagcagg cgctggagac ggtccagcgg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg gggatcccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg gccaggccga cgaaatgcag   2520
aggtacgtgg aggagaacca gaccaggaac aagcacatca accccaacga gtggtggaag   2580
gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gaccctggag   2760
gaggtgagga ggaagttcaa caacggcgag atcaacttcg cggccgactg ataa         2814
```

<210> SEQ ID NO 20
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex2-R TALEN

<400> SEQUENCE: 20

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccag caggtggtgg ccatcgccag caatggcggt    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccccagcagg tggtggccat cgccagcaat    840
ggcggtggca agcaggcgct ggagacggtc cagcggctgt tgccggtgct gtgccaggcc    900
cacggcttga ccccccagca ggtggtggcc atcgccagca atggcggtgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgacccccc agcaggtggt ggccatcgcc   1140
agcaatggcg gtggcaagca ggcgctggag acggtccagc ggctgttgcc ggtgctgtgc   1200
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
ccccagcagg tggtggccat cgccagcaat ggcggtggca agcaggcgct ggagacggtc   1380
cagcggctgt tgccggtgct gtgccaggcc cacggcttga ccccggagca ggtggtggcc   1440
atcgccagca atattggtgg caagcaggcg ctggagacgg tgcaggcgct gttgccggtg   1500
ctgtgccagg cccacggctt gaccccggag caggtggtgg ccatcgccag ccacgatggc   1560
ggcaagcagg cgctggagac ggtccagcgg ctgttgccgg tgctgtgcca ggcccacggc   1620
ttgaccccgg agcaggtggt ggccatcgcc agccacgatg gcggcaagca ggcgctggag   1680
acggtccagc ggctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccccagcagg tggtggccat cgccagcaat   1860
aatggtggca agcaggcgct ggagacggtc cagcggctgt tgccggtgct gtgccaggcc   1920
cacggcttga ccccccagca ggtggtggcc atcgccagca ataatggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
```

-continued agccgttccc agctggtgaa gtccgagctg gaggagaaga aatccgagtt gaggcacaag 2280
ctgaagtacg tgccccacga gtacatcgag ctgatcgaga tcgcccggaa cagcacccag 2340
gaccgtatcc tggagatgaa ggtgatggag ttcttcatga aggtgtacgg ctacaggggc 2400
aagcacctgg gcggctccag gaagcccgac ggcgccatct acaccgtggg ctcccccatc 2460
gactacggcg tgatcgtgga caccaaggcc tactccggcg gctacaacct gcccatcggc 2520
caggccgacg aaatgcagag gtacgtggag gagaaccaga ccaggaacaa gcacatcaac 2580
cccaacgagt ggtggaaggt gtacccctcc agcgtgaccg agttcaagtt cctgttcgtg 2640
tccggccact tcaagggcaa ctacaaggcc cagctgacca ggctgaacca catcaccaac 2700
tgcaacggcg ccgtgctgtc cgtggaggag ctcctgatcg gcggcgagat gatcaaggcc 2760
ggcaccctga ccctggagga ggtgaggagg aagttcaaca acggcgagat caacttcgcg 2820
gccgactgat aa 2832

<210> SEQ ID NO 21
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex3T2-L TALEN

<400> SEQUENCE: 21
atgggcgatc ctaaaaagaa acgtaaggtc atcgattacc catacgatgt tccagattac 60
gctatcgata tcgccgatct acgcacgctc ggctacagcc agcagcaaca ggagaagatc 120
aaaccgaagg ttcgttcgac agtggcgcag caccacgagg cactggtcgg ccacgggttt 180
acacacgcgc acatcgttgc gttaagccaa cacccggcag cgttagggac cgtcgctgtc 240
aagtatcagg acatgatcgc agcgttgcca gaggcgacac acgaagcgat cgttggcgtc 300
ggcaaacagt ggtccggcgc acgcgctctg gaggccttgc tcacggtggc gggagagttg 360
agaggtccac cgttacagtt ggacacaggc caacttctca agattgcaaa acgtggcggc 420
gtgaccgcag tggaggcagt gcatgcatgg cgcaatgcac tgacgggtgc cccgctcaac 480
ttgacccccc agcaggtggt ggccatcgcc agcaataatg gtggcaagca ggcgctggag 540
acggtccagc ggctgttgcc ggtgctgtgc caggcccacg gcttgacccc ggagcaggtg 600
gtggccatcg ccagccacga tggcggcaag caggcgctgg agacggtcca gcggctgttg 660
ccggtgctgt gccaggccca cggcttgacc ccggagcagg tggtggccat cgccagccac 720
gatggcggca agcaggcgct ggagacggtc cagcggctgt tgccggtgct gtgccaggcc 780
cacggcttga ccccccagca ggtggtggcc atcgccagca atggcggtgg caagcaggcg 840
ctggagacgg tccagcggct gttgccggtg ctgtgccagg cccacggctt gacccccag 900 caggtggtgg ccatcgccag caataatggt ggcaagcagg cgctggagac ggtccagcgg 960
ctgttgccgg tgctgtgcca ggcccacggc ttgacccccc agcaggtggt ggccatcgcc 1020
agcaataatg gtggcaagca ggcgctggag acggtccagc ggctgttgcc ggtgctgtgc 1080
caggcccacg gcttgacccc ccagcaggtg gtggccatcg ccagcaatgg cggtggcaag 1140
caggcgctgg agacggtcca gcggctgttg ccggtgctgt gccaggccca cggcttgacc 1200
ccccagcagg tggtggccat cgccagcaat aatggtggca agcaggcgct ggagacggtc 1260
cagcggctgt tgccggtgct gtgccaggcc cacggcttga ccccccagca ggtggtggcc 1320
atcgccagca atggcggtgg caagcaggcg ctggagacgg tccagcggct gttgccggtg 1380

-continued

```
ctgtgccagg cccacggctt gaccccccag caggtggtgg ccatcgccag caataatggt   1440

ggcaagcagg cgctggagac ggtccagcgg ctgttgccgg tgctgtgcca ggcccacggc   1500

ttgaccccgg agcaggtggt ggccatcgcc agccacgatg gcggcaagca ggcgctggag   1560

acggtccagc ggctgttgcc ggtgctgtgc caggcccacg gcttgacccc ccagcaggtg   1620

gtggccatcg ccagcaatgg cggtggcaag caggcgctgg agacggtcca gcggctgttg   1680

ccggtgctgt gccaggccca cggcttgacc ccggagcagg tggtggccat cgccagccac   1740

gatggcggca agcaggcgct ggagacggtc cagcggctgt tgccggtgct gtgccaggcc   1800

cacggcttga ccccccagca ggtggtggcc atcgccagca atggcggtgg caagcaggcg   1860

ctggagacgg tccagcggct gttgccggtg ctgtgccagg cccacggctt gaccccccag   1920

caggtggtgg ccatcgccag caataatggt ggcaagcagg cgctggagac ggtccagcgg   1980

ctgttgccgg tgctgtgcca ggcccacggc ttgacccctc agcaggtggt ggccatcgcc   2040

agcaatggcg gcggcaggcc ggcgctggag agcattgttg cccagttatc tcgccctgat   2100

ccggcgttgg ccgcgttgac caacgaccac ctcgtcgcct tggcctgcct cggcgggcgt   2160

cctgcgctgg atgcagtgaa aaagggattg gggatcccta tcagccgttc ccagctggtg   2220

aagtccgagc tggaggagaa gaaatccgag ttgaggcaca agctgaagta cgtgccccac   2280

gagtacatcg agctgatcga gatcgcccgg aacagcaccc aggaccgtat cctggagatg   2340

aaggtgatgg agttcttcat gaaggtgtac ggctacaggg gcaagcacct gggcggctcc   2400

aggaagcccg acggcgccat ctacaccgtg ggctccccca tcgactacgg cgtgatcgtg   2460

gacaccaagg cctactccgg cggctacaac ctgcccatcg gccaggccga cgaaatgcag   2520

aggtacgtgg aggagaacca gaccaggaac aagcacatca accccaacga gtggtggaag   2580

gtgtacccct ccagcgtgac cgagttcaag ttcctgttcg tgtccggcca cttcaagggc   2640

aactacaagg cccagctgac caggctgaac cacatcacca actgcaacgg cgccgtgctg   2700

tccgtggagg agctcctgat cggcggcgag atgatcaagg ccggcaccct gaccctggag   2760

gaggtgagga ggaagttcaa caacggcgag atcaacttcg cggccgactg ataa         2814
```

```
<210> SEQ ID NO 22
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex3T2-R TALEN

<400> SEQUENCE: 22
```

```
atgggcgatc ctaaaaagaa acgtaaggtc atcgataagg agaccgccgc tgccaagttc     60

gagagacagc acatggacag catcgatatc gccgatctac gcacgctcgg ctacagccag    120

cagcaacagg agaagatcaa accgaaggtt cgttcgacag tggcgcagca ccacgaggca    180

ctggtcggcc acgggtttac acacgcgcac atcgttgcgt taagccaaca cccggcagcg    240

ttagggaccg tcgctgtcaa gtatcaggac atgatcgcag cgttgccaga ggcgacacac    300

gaagcgatcg ttggcgtcgg caaacagtgg tccggcgcac gcgctctgga ggccttgctc    360

acggtggcgg gagagttgag aggtccaccg ttacagttgg acacaggcca acttctcaag    420

attgcaaaac gtggcggcgt gaccgcagtg gaggcagtgc atgcatggcg caatgcactg    480

acgggtgccc cgctcaactt gaccccccag caggtggtgg ccatcgccag caatggcggt    540
```

-continued

```
ggcaagcagg cgctggagac ggtccagcgg ctgttgccgg tgctgtgcca ggcccacggc    600
ttgaccccgg agcaggtggt ggccatcgcc agcaatattg gtggcaagca ggcgctggag    660
acggtgcagg cgctgttgcc ggtgctgtgc caggcccacg gcttgacccc ggagcaggtg    720
gtggccatcg ccagcaatat tggtggcaag caggcgctgg agacggtgca ggcgctgttg    780
ccggtgctgt gccaggccca cggcttgacc ccccagcagg tggtggccat cgccagcaat    840
aatggtggca agcaggcgct ggagacggtc cagcggctgt tgccggtgct gtgccaggcc    900
cacggcttga ccccggagca ggtggtggcc atcgccagca atattggtgg caagcaggcg    960
ctggagacgg tgcaggcgct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgacccccc agcaggtggt ggccatcgcc   1140
agcaatggcg gtggcaagca ggcgctggag acggtccagc ggctgttgcc ggtgctgtgc   1200
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
ccggagcagg tggtggccat cgccagccac gatggcggca agcaggcgct ggagacggtc   1380
cagcggctgt tgccggtgct gtgccaggcc cacggcttga ccccggagca ggtggtggcc   1440
atcgccagca atattggtgg caagcaggcg ctggagacgg tgcaggcgct gttgccggtg   1500
ctgtgccagg cccacggctt gacccccccag caggtggtgg ccatcgccag caatggcggt   1560
ggcaagcagg cgctggagac ggtccagcgg ctgttgccgg tgctgtgcca ggcccacggc   1620
ttgaccccgg agcaggtggt ggccatcgcc agcaatattg gtggcaagca ggcgctggag   1680
acggtgcagg cgctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccccagcagg tggtggccat cgccagcaat   1860
ggcggtggca agcaggcgct ggagacggtc cagcggctgt tgccggtgct gtgccaggcc   1920
cacggcttga ccccccagca ggtggtggcc atcgccagca ataatggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtacccctcc agcgtgaccg agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760
ggcaccctga ccctggagga ggtgaggagg aagttcaaca acggcgagat caacttcgcg   2820
gccgactgat aa                                                       2832
```

<210> SEQ ID NO 23
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex3T4-L TALEN

<400> SEQUENCE: 23
atgggcgatc ctaaaaagaa acgtaaggtc atcgattacc catacgatgt tccagattac 60
gctatcgata tcgccgatct acgcacgctc ggctacagcc agcagcaaca ggagaagatc 120
aaaccgaagg ttcgttcgac agtggcgcag caccacgagg cactggtcgg ccacgggttt 180
acacacgcgc acatcgttgc gttaagccaa cacccggcag cgttagggac cgtcgctgtc 240
aagtatcagg acatgatcgc agcgttgcca gaggcgacac acgaagcgat cgttggcgtc 300
ggcaaacagt ggtccggcgc acgcgctctg gaggccttgc tcacggtggc gggagagttg 360
agaggtccac cgttacagtt ggacacaggc caacttctca agattgcaaa acgtggcggc 420
gtgaccgcag tggaggcagt gcatgcatgg cgcaatgcac tgacgggtgc cccgctcaac 480
ttgacccccc agcaggtggt ggccatcgcc agcaataatg gtggcaagca ggcgctggag 540
acggtccagc ggctgttgcc ggtgctgtgc caggcccacg gcttgacccc ggagcaggtg 600
gtggccatcg ccagccacga tggcggcaag caggcgctgg agacggtcca gcggctgttg 660
ccggtgctgt gccaggccca cggcttgacc ccccagcagg tggtggccat cgccagcaat 720
ggcggtggca agcaggcgct ggagacggtc cagcggctgt tgccggtgct gtgccaggcc 780
cacggcttga ccccggagca ggtggtggcc atcgccagcc acgatggcgg caagcaggcg 840
ctggagacgg tccagcggct gttgccggtg ctgtgccagg cccacggctt gacccccag 900 caggtggtgg ccatcgccag caatggcggt ggcaagcagg cgctggagac ggtccagcgg 960
ctgttgccgg tgctgtgcca ggcccacggc ttgacccccc agcaggtggt ggccatcgcc 1020
agcaataatg gtggcaagca ggcgctggag acggtccagc ggctgttgcc ggtgctgtgc 1080
caggcccacg gcttgacccc ggagcaggtg gtggccatcg ccagcaatat tggtggcaag 1140
caggcgctgg agacggtgca ggcgctgttg ccggtgctgt gccaggccca cggcttgacc 1200
ccccagcagg tggtggccat cgccagcaat ggcggtggca agcaggcgct ggagacggtc 1260
cagcggctgt tgccggtgct gtgccaggcc cacggcttga ccccccagca ggtggtggcc 1320
atcgccagca ataatggtgg caagcaggcg ctggagacgg tccagcggct gttgccggtg 1380
ctgtgccagg cccacggctt gaccccggag caggtggtgg ccatcgccag caatattggt 1440
ggcaagcagg cgctggagac ggtgcaggcg ctgttgccgg tgctgtgcca ggcccacggc 1500
ttgaccccgg agcaggtggt ggccatcgcc agcaatattg gtggcaagca ggcgctggag 1560
acggtgcagg cgctgttgcc ggtgctgtgc caggcccacg gcttgacccc ccagcaggtg 1620
gtggccatcg ccagcaataa tggtggcaag caggcgctgg agacggtcca gcggctgttg 1680
ccggtgctgt gccaggccca cggcttgacc ccggagcagg tggtggccat cgccagccac 1740
gatggcggca agcaggcgct ggagacggtc cagcggctgt tgccggtgct gtgccaggcc 1800
cacggcttga ccccccagca ggtggtggcc atcgccagca atggcggtgg caagcaggcg 1860
ctggagacgg tccagcggct gttgccggtg ctgtgccagg cccacggctt gacccccag 1920 caggtggtgg ccatcgccag caatggcggt ggcaagcagg cgctggagac ggtccagcgg 1980
ctgttgccgg tgctgtgcca ggcccacggc ttgacccctc agcaggtggt ggccatcgcc 2040

-continued

```
agcaatggcg gcggcaggcc ggcgctggag agcattgttg cccagttatc tcgccctgat   2100

ccggcgttgg ccgcgttgac caacgaccac ctcgtcgcct tggcctgcct cggcgggcgt   2160

cctgcgctgg atgcagtgaa aaagggattg gggatcccta tcagccgttc ccagctggtg   2220

aagtccgagc tggaggagaa gaaatccgag ttgaggcaca agctgaagta cgtgccccac   2280

gagtacatcg agctgatcga gatcgcccgg aacagcaccc aggaccgtat cctggagatg   2340

aaggtgatgg agttcttcat gaaggtgtac ggctacaggg gcaagcacct gggcggctcc   2400

aggaagcccg acggcgccat ctacaccgtg ggctccccca tcgactacgg cgtgatcgtg   2460

gacaccaagg cctactccgg cggctacaac ctgcccatcg gccaggccga cgaaatgcag   2520

aggtacgtgg aggagaacca gaccaggaac aagcacatca accccaacga gtggtggaag   2580

gtgtacccct ccagcgtgac cgagttcaag ttcctgttcg tgtccggcca cttcaagggc   2640

aactacaagg cccagctgac caggctgaac cacatcacca actgcaacgg cgccgtgctg   2700

tccgtggagg agctcctgat cggcggcgag atgatcaagg ccggcaccct gaccctggag   2760

gaggtgagga ggaagttcaa caacggcgag atcaacttcg cggccgactg ataa         2814
```

<210> SEQ ID NO 24
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex3T4-R TALEN

<400> SEQUENCE: 24

```
atgggcgatc ctaaaaagaa acgtaaggtc atcgataagg agaccgccgc tgccaagttc     60

gagagacagc acatggacag catcgatatc gccgatctac gcacgctcgg ctacagccag    120

cagcaacagg agaagatcaa accgaaggtt cgttcgacag tggcgcagca ccacgaggca    180

ctggtcggcc acgggtttac acacgcgcac atcgttgcgt taagccaaca cccggcagcg    240

ttagggaccg tcgctgtcaa gtatcaggac atgatcgcag cgttgccaga ggcgacacac    300

gaagcgatcg ttggcgtcgg caaacagtgg tccggcgcac gcgctctgga ggccttgctc    360

acggtggcgg gagagttgag aggtccaccg ttacagttgg acacaggcca acttctcaag    420

attgcaaaac gtggcggcgt gaccgcagtg gaggcagtgc atgcatggcg caatgcactg    480

acgggtgccc cgctcaactt gacccccag caggtggtgg ccatcgccag caatggcggt    540

ggcaagcagg cgctggagac ggtccagcgg ctgttgccgg tgctgtgcca ggcccacggc    600

ttgaccccgg agcaggtggt ggccatcgcc agccacgatg gcggcaagca ggcgctggag    660

acggtccagc ggctgttgcc ggtgctgtgc caggcccacg gcttgacccc ggagcaggtg    720

gtggccatcg ccagccacga tggcggcaag caggcgctgg agacggtcca gcggctgttg    780

ccggtgctgt gccaggccca cggcttgacc ccggagcagg tggtggccat cgccagcaat    840

attggtggca agcaggcgct ggagacggtg caggcgctgt tgccggtgct gtgccaggcc    900

cacggcttga ccccggagca ggtggtggcc atcgccagcc acgatggcgg caagcaggcg    960

ctggagacgg tccagcggct gttgccggtg ctgtgccagg cccacggctt gaccccggag   1020

caggtggtgg ccatcgccag caatattggt ggcaagcagg cgctggagac ggtgcaggcg   1080

ctgttgccgg tgctgtgcca ggcccacggc ttgaccccgg agcaggtggt ggccatcgcc   1140

agcaatattg gtggcaagca ggcgctggag acggtgcagg cgctgttgcc ggtgctgtgc   1200

caggcccacg gcttgacccc ccagcaggtg gtggccatcg ccagcaataa tggtggcaag   1260
```

```
caggcgctgg agacggtcca gcggctgttg ccggtgctgt gccaggccca cggcttgacc   1320

ccccagcagg tggtggccat cgccagcaat ggcggtggca agcaggcgct ggagacggtc   1380

cagcggctgt tgccggtgct gtgccaggcc cacggcttga ccccccagca ggtggtggcc   1440

atcgccagca atggcggtgg caagcaggcg ctggagacgg tccagcggct gttgccggtg   1500

ctgtgccagg cccacggctt gaccccggag caggtggtgg ccatcgccag caatattggt   1560

ggcaagcagg cgctggagac ggtgcaggcg ctgttgccgg tgctgtgcca ggcccacggc   1620

ttgaccccgg agcaggtggt ggccatcgcc agcaatattg gtggcaagca ggcgctggag   1680

acggtgcagg cgctgttgcc ggtgctgtgc caggcccacg gcttgacccc ccagcaggtg   1740

gtggccatcg ccagcaataa tggtggcaag caggcgctgg agacggtcca gcggctgttg   1800

ccggtgctgt gccaggccca cggcttgacc ccggagcagg tggtggccat cgccagcaat   1860

attggtggca agcaggcgct ggagacggtg caggcgctgt tgccggtgct gtgccaggcc   1920

cacggcttga ccccggagca ggtggtggcc atcgccagcc acgatggcgg caagcaggcg   1980

ctggagacgg tccagcggct gttgccggtg ctgtgccagg cccacggctt gacccctcag   2040

caggtggtgg ccatcgccag caatggcggc ggcaggccgg cgctggagag cattgttgcc   2100

cagttatctc gccctgatcc ggcgttggcc gcgttgacca acgaccacct cgtcgccttg   2160

gcctgcctcg gcgggcgtcc tgcgctggat gcagtgaaaa agggattggg ggatcctatc   2220

agccgttccc agctggtgaa gtccgagctg gaggagaaga aatccgagtt gaggcacaag   2280

ctgaagtacg tgccccacga gtacatcgag ctgatcgaga tcgcccggaa cagcacccag   2340

gaccgtatcc tggagatgaa ggtgatggag ttcttcatga aggtgtacgg ctacaggggc   2400

aagcacctgg gcggctccag gaagcccgac ggcgccatct acaccgtggg ctcccccatc   2460

gactacggcg tgatcgtgga caccaaggcc tactccggcg gctacaacct gcccatcggc   2520

caggccgacg aaatgcagag gtacgtggag gagaaccaga ccaggaacaa gcacatcaac   2580

cccaacgagt ggtggaaggt gtacccctcc agcgtgaccg agttcaagtt cctgttcgtg   2640

tccggccact tcaagggcaa ctacaaggcc cagctgacca ggctgaacca catcaccaac   2700

tgcaacggcg ccgtgctgtc cgtggaggag ctcctgatcg gcggcgagat gatcaaggcc   2760

ggcaccctga ccctggagga ggtgaggagg aagttcaaca acggcgagat caacttcgcg   2820

gccgactgat aa                                                       2832
```

<210> SEQ ID NO 25
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex5T1-L TALEN

<400> SEQUENCE: 25

```
atgggcgatc ctaaaaagaa acgtaaggtc atcgattacc catacgatgt tccagattac     60

gctatcgata tcgccgatct acgcacgctc ggctacagcc agcagcaaca ggagaagatc    120

aaaccgaagg ttcgttcgac agtggcgcag caccacgagg cactggtcgg ccacgggttt    180

acacacgcgc acatcgttgc gttaagccaa cacccggcag cgttagggac cgtcgctgtc    240

aagtatcagg acatgatcgc agcgttgcca gaggcgacac acgaagcgat cgttggcgtc    300

ggcaaacagt ggtccggcgc acgcgctctg gaggccttgc tcacggtggc gggagagttg    360
```

-continued

```
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgacccccc agcaggtggt ggccatcgcc agcaataatg gtggcaagca ggcgctggag    540
acggtccagc ggctgttgcc ggtgctgtgc caggcccacg gcttgacccc ccagcaggtg    600
gtggccatcg ccagcaataa tggtggcaag caggcgctgg agacggtcca gcggctgttg    660
ccggtgctgt gccaggccca cggcttgacc ccccagcagg tggtggccat cgccagcaat    720
ggcggtggca agcaggcgct ggagacggtc cagcggctgt tgccggtgct gtgccaggcc    780
cacggcttga ccccccagca ggtggtggcc atcgccagca ataatggtgg caagcaggcg    840
ctggagacgg tccagcggct gttgccggtg ctgtgccagg cccacggctt gacccccccag    900
caggtggtgg ccatcgccag caatggcggt ggcaagcagg cgctggagac ggtccagcgg    960
ctgttgccgg tgctgtgcca ggcccacggc ttgaccccgg agcaggtggt ggccatcgcc   1020
agccacgatg gcggcaagca ggcgctggag acggtccagc ggctgttgcc ggtgctgtgc   1080
caggcccacg gcttgacccc ggagcaggtg gtggccatcg ccagcaatat tggtggcaag   1140
caggcgctgg agacggtgca ggcgctgttg ccggtgctgt gccaggccca cggcttgacc   1200
ccggagcagg tggtggccat cgccagccac gatggcggca agcaggcgct ggagacggtc   1260
cagcggctgt tgccggtgct gtgccaggcc cacggcttga ccccccagca ggtggtggcc   1320
atcgccagca atggcggtgg caagcaggcg ctggagacgg tccagcggct gttgccggtg   1380
ctgtgccagg cccacggctt gacccccccag caggtggtgg ccatcgccag caataatggt   1440
ggcaagcagg cgctggagac ggtccagcgg ctgttgccgg tgctgtgcca ggcccacggc   1500
ttgacccccc agcaggtggt ggccatcgcc agcaatggcg gtggcaagca ggcgctggag   1560
acggtccagc ggctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc ccccagcagg tggtggccat cgccagcaat   1740
aatggtggca agcaggcgct ggagacggtc cagcggctgt tgccggtgct gtgccaggcc   1800
cacggcttga ccccccagca ggtggtggcc atcgccagca ataatggtgg caagcaggcg   1860
ctggagacgg tccagcggct gttgccggtg ctgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg gggatcccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg gccaggccga cgaaatgcag   2520
aggtacgtgg aggagaacca gaccaggaac aagcacatca accccaacga gtggtggaag   2580
gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gaccctggag   2760
```

```
gaggtgagga ggaagttcaa caacggcgag atcaacttcg cggccgactg ataa         2814


<210> SEQ ID NO 26
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex5T1-R TALEN

<400> SEQUENCE: 26

atgggcgatc ctaaaaagaa acgtaaggtc atcgataagg agaccgccgc tgccaagttc     60

gagagacagc acatggacag catcgatatc gccgatctac gcacgctcgg ctacagccag    120

cagcaacagg agaagatcaa accgaaggtt cgttcgacag tggcgcagca ccacgaggca    180

ctggtcggcc acgggtttac acacgcgcac atcgttgcgt taagccaaca cccggcagcg    240

ttagggaccg tcgctgtcaa gtatcaggac atgatcgcag cgttgccaga ggcgacacac    300

gaagcgatcg ttggcgtcgg caaacagtgg tccggcgcac gcgctctgga ggccttgctc    360

acggtggcgg gagagttgag aggtccaccg ttacagttgg acacaggcca acttctcaag    420

attgcaaaac gtggcggcgt gaccgcagtg gaggcagtgc atgcatggcg caatgcactg    480

acgggtgccc cgctcaactt gaccccggag caggtggtgg ccatcgccag caatattggt    540

ggcaagcagg cgctggagac ggtgcaggcg ctgttgccgg tgctgtgcca ggcccacggc    600

ttgacccccc agcaggtggt ggccatcgcc agcaatggcg gtggcaagca ggcgctggag    660

acggtccagc ggctgttgcc ggtgctgtgc caggcccacg gcttgacccc ggagcaggtg    720

gtggccatcg ccagccacga tggcggcaag caggcgctgg agacggtcca gcggctgttg    780

ccggtgctgt gccaggccca cggcttgacc ccggagcagg tggtggccat cgccagccac    840

gatggcggca agcaggcgct ggagacggtc cagcggctgt tgccggtgct gtgccaggcc    900

cacggcttga ccccccagca ggtggtggcc atcgccagca atggcggtgg caagcaggcg    960

ctggagacgg tccagcggct gttgccggtg ctgtgccagg cccacggctt gacccccag   1020

caggtggtgg ccatcgccag caataatggt ggcaagcagg cgctggagac ggtccagcgg   1080

ctgttgccgg tgctgtgcca ggcccacggc ttgaccccgg agcaggtggt ggccatcgcc   1140

agccacgatg gcggcaagca ggcgctggag acggtccagc ggctgttgcc ggtgctgtgc   1200

caggcccacg gcttgacccc ggagcaggtg gtggccatcg ccagcaatat tggtggcaag   1260

caggcgctgg agacggtgca ggcgctgttg ccggtgctgt gccaggccca cggcttgacc   1320

ccccagcagg tggtggccat cgccagcaat ggcggtggca agcaggcgct ggagacggtc   1380

cagcggctgt tgccggtgct gtgccaggcc cacggcttga ccccggagca ggtggtggcc   1440

atcgccagca atattggtgg caagcaggcg ctggagacgg tgcaggcgct gttgccggtg   1500

ctgtgccagg cccacggctt gaccccccag caggtggtgg ccatcgccag caatggcggt   1560

ggcaagcagg cgctggagac ggtccagcgg ctgttgccgg tgctgtgcca ggcccacggc   1620

ttgaccccgg agcaggtggt ggccatcgcc agcaatattg gtggcaagca ggcgctggag   1680

acggtgcagg cgctgttgcc ggtgctgtgc caggcccacg gcttgacccc ggagcaggtg   1740

gtggccatcg ccagcaatat tggtggcaag caggcgctgg agacggtgca ggcgctgttg   1800

ccggtgctgt gccaggccca cggcttgacc ccggagcagg tggtggccat cgccagccac   1860

gatggcggca agcaggcgct ggagacggtc cagcggctgt tgccggtgct gtgccaggcc   1920
```

```
cacggcttga ccccggagca ggtggtggcc atcgccagca atattggtgg caagcaggcg   1980
ctggagacgg tgcaggcgct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtacccctcc agcgtgaccg agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760
ggcaccctga ccctggagga ggtgaggagg aagttcaaca acggcgagat caacttcgcg   2820
gccgactgat aa                                                       2832
```

<210> SEQ ID NO 27
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex5T2-L TALEN

<400> SEQUENCE: 27

```
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccccgg agcaggtggt ggccatcgcc agcaatattg gtggcaagca ggcgctggag    540
acggtgcagg cgctgttgcc ggtgctgtgc caggcccacg gcttgacccc ccagcaggtg    600
gtggccatcg ccagcaatgg cggtggcaag caggcgctgg agacggtcca gcggctgttg    660
ccggtgctgt gccaggccca cggcttgacc ccccagcagg tggtggccat cgccagcaat    720
aatggtggca agcaggcgct ggagacggtc cagcggctgt tgccggtgct gtgccaggcc    780
cacggcttga ccccggagca ggtggtggcc atcgccagca atattggtgg caagcaggcg    840
ctggagacgg tgcaggcgct gttgccggtg ctgtgccagg cccacggctt gacccccccag    900
caggtggtgg ccatcgccag caatggcggt ggcaagcagg cgctggagac ggtccagcgg    960
ctgttgccgg tgctgtgcca ggcccacggc ttgaccccgg agcaggtggt ggccatcgcc   1020
agcaatattg gtggcaagca ggcgctggag acggtgcagg cgctgttgcc ggtgctgtgc   1080
```

caggcccacg gcttgacccc ccagcaggtg gtggccatcg ccagcaataa tggtggcaag 1140
caggcgctgg agacggtcca gcggctgttg ccggtgctgt gccaggccca cggcttgacc 1200
ccggagcagg tggtggccat cgccagccac gatggcggca agcaggcgct ggagacggtc 1260
cagcggctgt tgccggtgct gtgccaggcc cacggcttga ccccccagca ggtggtggcc 1320
atcgccagca atggcggtgg caagcaggcg ctggagacgg tccagcggct gttgccggtg 1380
ctgtgccagg cccacggctt gaccccggag caggtggtgg ccatcgccag ccacgatggc 1440
ggcaagcagg cgctggagac ggtccagcgg ctgttgccgg tgctgtgcca ggcccacggc 1500
ttgacccccc agcaggtggt ggccatcgcc agcaatggcg gtggcaagca ggcgctggag 1560
acggtccagc ggctgttgcc ggtgctgtgc caggcccacg gcttgacccc ccagcaggtg 1620
gtggccatcg ccagcaataa tggtggcaag caggcgctgg agacggtcca gcggctgttg 1680
ccggtgctgt gccaggccca cggcttgacc ccccagcagg tggtggccat cgccagcaat 1740
ggcggtggca agcaggcgct ggagacggtc cagcggctgt tgccggtgct gtgccaggcc 1800
cacggcttga ccccccagca ggtggtggcc atcgccagca atggcggtgg caagcaggcg 1860
ctggagacgg tccagcggct gttgccggtg ctgtgccagg cccacggctt gaccccggag 1920
caggtggtgg ccatcgccag ccacgatggc ggcaagcagg cgctggagac ggtccagcgg 1980
ctgttgccgg tgctgtgcca ggcccacggc ttgacccctc agcaggtggt ggccatcgcc 2040
agcaatggcg gcggcaggcc ggcgctggag agcattgttg cccagttatc tcgccctgat 2100
ccggcgttgg ccgcgttgac caacgaccac ctcgtcgcct tggcctgcct cggcgggcgt 2160
cctgcgctgg atgcagtgaa aaagggattg gggatcccta tcagccgttc ccagctggtg 2220
aagtccgagc tggaggagaa gaaatccgag ttgaggcaca agctgaagta cgtgccccac 2280
gagtacatcg agctgatcga gatcgcccgg aacagcaccc aggaccgtat cctggagatg 2340
aaggtgatgg agttcttcat gaaggtgtac ggctacaggg gcaagcacct gggcggctcc 2400
aggaagcccg acggcgccat ctacaccgtg ggctccccca tcgactacgg cgtgatcgtg 2460
gacaccaagg cctactccgg cggctacaac ctgcccatcg gccaggccga cgaaatgcag 2520
aggtacgtgg aggagaacca gaccaggaac aagcacatca accccaacga gtggtggaag 2580
gtgtacccct ccagcgtgac cgagttcaag ttcctgttcg tgtccggcca cttcaagggc 2640
aactacaagg cccagctgac caggctgaac cacatcacca actgcaacgg cgccgtgctg 2700
tccgtggagg agctcctgat cggcggcgag atgatcaagg ccggcaccct gaccctggag 2760
gaggtgagga ggaagttcaa caacggcgag atcaacttcg cggccgactg ataa 2814

<210> SEQ ID NO 28
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex5T2-R TALEN

<400> SEQUENCE: 28
atgggcgatc ctaaaaagaa acgtaaggtc atcgataagg agaccgccgc tgccaagttc 60
gagagacagc acatggacag catcgatatc gccgatctac gcacgctcgg ctacagccag 120
cagcaacagg agaagatcaa accgaaggtt cgttcgacag tggcgcagca ccacgaggca 180
ctggtcggcc acgggtttac acacgcgcac atcgttgcgt taagccaaca cccggcagcg 240

-continued

```
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccccag caggtggtgg ccatcgccag caataatggt    540
ggcaagcagg cgctggagac ggtccagcgg ctgttgccgg tgctgtgcca ggcccacggc    600
ttgaccccgg agcaggtggt ggccatcgcc agcaatattg gtggcaagca ggcgctggag    660
acggtgcagg cgctgttgcc ggtgctgtgc caggcccacg gcttgacccc ccagcaggtg    720
gtggccatcg ccagcaataa tggtggcaag caggcgctgg agacggtcca gcggctgttg    780
ccggtgctgt gccaggccca cggcttgacc ccggagcagg tggtggccat cgccagccac    840
gatggcggca agcaggcgct ggagacggtc cagcggctgt tgccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gacccccag    1020
caggtggtgg ccatcgccag caatggcggt ggcaagcagg cgctggagac ggtccagcgg   1080
ctgttgccgg tgctgtgcca ggcccacggc ttgaccccgg agcaggtggt ggccatcgcc   1140
agcaatattg gtggcaagca ggcgctggag acggtgcagg cgctgttgcc ggtgctgtgc   1200
caggcccacg gcttgacccc ccagcaggtg gtggccatcg ccagcaataa tggtggcaag   1260
caggcgctgg agacggtcca gcggctgttg ccggtgctgt gccaggccca cggcttgacc   1320
ccccagcagg tggtggccat cgccagcaat ggcggtggca agcaggcgct ggagacggtc   1380
cagcggctgt tgccggtgct gtgccaggcc cacggcttga ccccggagca ggtggtggcc   1440
atcgccagcc acgatggcgg caagcaggcg ctggagacgg tccagcggct gttgccggtg   1500
ctgtgccagg cccacggctt gaccccggag caggtggtgg ccatcgccag caatattggt   1560
ggcaagcagg cgctggagac ggtgcaggcg ctgttgccgg tgctgtgcca ggcccacggc   1620
ttgacccccc agcaggtggt ggccatcgcc agcaatggcg gtggcaagca ggcgctggag   1680
acggtccagc ggctgttgcc ggtgctgtgc caggcccacg gcttgacccc ccagcaggtg   1740
gtggccatcg ccagcaataa tggtggcaag caggcgctgg agacggtcca gcggctgttg   1800
ccggtgctgt gccaggccca cggcttgacc ccggagcagg tggtggccat cgccagcaat   1860
attggtggca agcaggcgct ggagacggtg caggcgctgt tgccggtgct gtgccaggcc   1920
cacggcttga ccccccagca ggtggtggcc atcgccagca atggcggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtacccctcc agcgtgaccg agttcaagtt cctgttcgtg   2640
```

tccggccact tcaagggcaa ctacaaggcc cagctgacca ggctgaacca catcaccaac 2700
tgcaacggcg ccgtgctgtc cgtggaggag ctcctgatcg gcggcgagat gatcaaggcc 2760
ggcaccctga ccctggagga ggtgaggagg aagttcaaca acggcgagat caacttcgcg 2820
gccgactgat aa 2832

<210> SEQ ID NO 29
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex5T3-L TALEN

<400> SEQUENCE: 29
atgggcgatc ctaaaaagaa acgtaaggtc atcgattacc catacgatgt tccagattac 60
gctatcgata tcgccgatct acgcacgctc ggctacagcc agcagcaaca ggagaagatc 120
aaaccgaagg ttcgttcgac agtggcgcag caccacgagg cactggtcgg ccacgggttt 180
acacacgcgc acatcgttgc gttaagccaa cacccggcag cgttagggac cgtcgctgtc 240
aagtatcagg acatgatcgc agcgttgcca gaggcgacac acgaagcgat cgttggcgtc 300
ggcaaacagt ggtccggcgc acgcgctctg gaggccttgc tcacggtggc gggagagttg 360
agaggtccac cgttacagtt ggacacaggc caacttctca agattgcaaa acgtggcggc 420
gtgaccgcag tggaggcagt gcatgcatgg cgcaatgcac tgacgggtgc cccgctcaac 480
ttgacccccc agcaggtggt ggccatcgcc agcaatggcg gtggcaagca ggcgctggag 540
acggtccagc ggctgttgcc ggtgctgtgc caggcccacg gcttgacccc ggagcaggtg 600
gtggccatcg ccagcaatat tggtggcaag caggcgctgg agacggtgca ggcgctgttg 660
ccggtgctgt gccaggccca cggcttgacc ccccagcagg tggtggccat cgccagcaat 720
ggcggtggca agcaggcgct ggagacggtc cagcggctgt tgccggtgct gtgccaggcc 780
cacggcttga ccccggagca ggtggtggcc atcgccagca atattggtgg caagcaggcg 840
ctggagacgg tgcaggcgct gttgccggtg ctgtgccagg cccacggctt gacccccccag 900 caggtggtgg ccatcgccag caatggcggt ggcaagcagg cgctggagac ggtccagcgg 960
ctgttgccgg tgctgtgcca ggcccacggc ttgacccccc agcaggtggt ggccatcgcc 1020
agcaataatg gtggcaagca ggcgctggag acggtccagc ggctgttgcc ggtgctgtgc 1080
caggcccacg gcttgacccc ggagcaggtg gtggccatcg ccagccacga tggcggcaag 1140
caggcgctgg agacggtcca gcggctgttg ccggtgctgt gccaggccca cggcttgacc 1200
ccggagcagg tggtggccat cgccagcaat attggtggca agcaggcgct ggagacggtg 1260
caggcgctgt tgccggtgct gtgccaggcc cacggcttga ccccccagca ggtggtggcc 1320
atcgccagca ataatggtgg caagcaggcg ctggagacgg tccagcggct gttgccggtg 1380
ctgtgccagg cccacggctt gacccccccag caggtggtgg ccatcgccag caataatggt 1440
ggcaagcagg cgctggagac ggtccagcgg ctgttgccgg tgctgtgcca ggcccacggc 1500
ttgaccccgg agcaggtggt ggccatcgcc agcaatattg gtggcaagca ggcgctggag 1560
acggtgcagg cgctgttgcc ggtgctgtgc caggcccacg gcttgacccc ccagcaggtg 1620
gtggccatcg ccagcaatgg cggtggcaag caggcgctgg agacggtcca gcggctgttg 1680
ccggtgctgt gccaggccca cggcttgacc ccggagcagg tggtggccat cgccagcaat 1740

-continued attggtggca agcaggcgct ggagacggtg caggcgctgt tgccggtgct gtgccaggcc 1800
cacggcttga ccccccagca ggtggtggcc atcgccagca atggcggtgg caagcaggcg 1860
ctggagacgg tccagcggct gttgccggtg ctgtgccagg cccacggctt gacccccag 1920 caggtggtgg ccatcgccag caataatggt ggcaagcagg cgctggagac ggtccagcgg 1980
ctgttgccgg tgctgtgcca ggcccacggc ttgacccctc agcaggtggt ggccatcgcc 2040
agcaatggcg gcggcaggcc ggcgctggag agcattgttg cccagttatc tcgccctgat 2100
ccggcgttgg ccgcgttgac caacgaccac ctcgtcgcct tggcctgcct cggcgggcgt 2160
cctgcgctgg atgcagtgaa aaagggattg gggatcccta tcagccgttc ccagctggtg 2220
aagtccgagc tggaggagaa gaaatccgag ttgaggcaca agctgaagta cgtgccccac 2280
gagtacatcg agctgatcga gatcgcccgg aacagcaccc aggaccgtat cctggagatg 2340
aaggtgatgg agttcttcat gaaggtgtac ggctacaggg gcaagcacct gggcggctcc 2400
aggaagcccg acggcgccat ctacaccgtg ggctccccca tcgactacgg cgtgatcgtg 2460
gacaccaagg cctactccgg cggctacaac ctgcccatcg gccaggccga cgaaatgcag 2520
aggtacgtgg aggagaacca gaccaggaac aagcacatca accccaacga gtggtggaag 2580
gtgtacccct ccagcgtgac cgagttcaag ttcctgttcg tgtccggcca cttcaagggc 2640
aactacaagg cccagctgac caggctgaac cacatcacca actgcaacgg cgccgtgctg 2700
tccgtggagg agctcctgat cggcggcgag atgatcaagg ccggcaccct gaccctggag 2760
gaggtgagga ggaagttcaa caacggcgag atcaacttcg cggccgactg ataa 2814

<210> SEQ ID NO 30
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: GRex5T3-R TALEN

<400> SEQUENCE: 30
atgggcgatc ctaaaaagaa acgtaaggtc atcgataagg agaccgccgc tgccaagttc 60
gagagacagc acatggacag catcgatatc gccgatctac gcacgctcgg ctacagccag 120
cagcaacagg agaagatcaa accgaaggtt cgttcgacag tggcgcagca ccacgaggca 180
ctggtcggcc acgggtttac acacgcgcac atcgttgcgt taagccaaca cccggcagcg 240
ttagggaccg tcgctgtcaa gtatcaggac atgatcgcag cgttgccaga ggcgacacac 300
gaagcgatcg ttggcgtcgg caaacagtgg tccggcgcac gcgctctgga ggccttgctc 360
acggtggcgg gagagttgag aggtccaccg ttacagttgg acacaggcca acttctcaag 420
attgcaaaac gtggcggcgt gaccgcagtg gaggcagtgc atgcatggcg caatgcactg 480
acgggtgccc cgctcaactt gacccccag caggtggtgg ccatcgccag caataatggt 540
ggcaagcagg cgctggagac ggtccagcgg ctgttgccgg tgctgtgcca ggcccacggc 600
ttgaccccgg agcaggtggt ggccatcgcc agcaatattg gtggcaagca ggcgctggag 660
acggtgcagg cgctgttgcc ggtgctgtgc caggcccacg gcttgacccc ccagcaggtg 720
gtggccatcg ccagcaatgg cggtggcaag caggcgctgg agacggtcca gcggctgttg 780
ccggtgctgt gccaggccca cggcttgacc ccggagcagg tggtggccat cgccagccac 840
gatggcggca agcaggcgct ggagacggtc cagcggctgt tgccggtgct gtgccaggcc 900
cacggcttga ccccggagca ggtggtggcc atcgccagcc acgatggcgg caagcaggcg 960

-continued

```
ctggagacgg tccagcggct gttgccggtg ctgtgccagg cccacggctt gacccccccag   1020

caggtggtgg ccatcgccag caatggcggt ggcaagcagg cgctggagac ggtccagcgg   1080

ctgttgccgg tgctgtgcca ggcccacggc ttgaccccgg agcaggtggt ggccatcgcc   1140

agccacgatg gcggcaagca ggcgctggag acggtccagc ggctgttgcc ggtgctgtgc   1200

caggcccacg gcttgacccc ggagcaggtg gtggccatcg ccagccacga tggcggcaag   1260

caggcgctgg agacggtcca gcggctgttg ccggtgctgt gccaggccca cggcttgacc   1320

ccggagcagg tggtggccat cgccagcaat attggtggca agcaggcgct ggagacggtg   1380

caggcgctgt tgccggtgct gtgccaggcc cacggcttga ccccggagca ggtggtggcc   1440

atcgccagca atattggtgg caagcaggcg ctggagacgg tgcaggcgct gttgccggtg   1500

ctgtgccagg cccacggctt gacccccccag caggtggtgg ccatcgccag caataatggt   1560

ggcaagcagg cgctggagac ggtccagcgg ctgttgccgg tgctgtgcca ggcccacggc   1620

ttgacccccc agcaggtggt ggccatcgcc agcaatggcg gtggcaagca ggcgctggag   1680

acggtccagc ggctgttgcc ggtgctgtgc caggcccacg gcttgacccc ccagcaggtg   1740

gtggccatcg ccagcaatgg cggtggcaag caggcgctgg agacggtcca gcggctgttg   1800

ccggtgctgt gccaggccca cggcttgacc ccccagcagg tggtggccat cgccagcaat   1860

aatggtggca agcaggcgct ggagacggtc cagcggctgt tgccggtgct gtgccaggcc   1920

cacggcttga ccccggagca ggtggtggcc atcgccagca atattggtgg caagcaggcg   1980

ctggagacgg tgcaggcgct gttgccggtg ctgtgccagg cccacggctt gacccctcag   2040

caggtggtgg ccatcgccag caatggcggc ggcaggccgg cgctggagag cattgttgcc   2100

cagttatctc gccctgatcc ggcgttggcc gcgttgacca acgaccacct cgtcgccttg   2160

gcctgcctcg gcgggcgtcc tgcgctggat gcagtgaaaa agggattggg ggatcctatc   2220

agccgttccc agctggtgaa gtccgagctg gaggagaaga aatccgagtt gaggcacaag   2280

ctgaagtacg tgccccacga gtacatcgag ctgatcgaga tcgcccggaa cagcacccag   2340

gaccgtatcc tggagatgaa ggtgatggag ttcttcatga aggtgtacgg ctacaggggc   2400

aagcacctgg gcggctccag gaagcccgac ggcgccatct acaccgtggg ctcccccatc   2460

gactacggcg tgatcgtgga caccaaggcc tactccggcg gctacaacct gcccatcggc   2520

caggccgacg aaatgcagag gtacgtggag gagaaccaga ccaggaacaa gcacatcaac   2580

cccaacgagt ggtggaaggt gtacccctcc agcgtgaccg agttcaagtt cctgttcgtg   2640

tccggccact tcaagggcaa ctacaaggcc cagctgacca ggctgaacca catcaccaac   2700

tgcaacggcg ccgtgctgtc cgtggaggag ctcctgatcg gcggcgagat gatcaaggcc   2760

ggcaccctga ccctggagga ggtgaggagg aagttcaaca acggcgagat caacttcgcg   2820

gccgactgat aa                                                       2832
```

<210> SEQ ID NO 31
<211> LENGTH: 60
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer GR exon 2, including SEQ ID NO: 128, 10N and SEQ ID NO: 129
<220> FEATURE:
<221> NAME/KEY: modified_base
<222> LOCATION: (31)..(40)
<223> OTHER INFORMATION: a or c or t or g

<400> SEQUENCE: 31
ccatctcatc cctgcgtgtc tccgactcag nnnnnnnnnn ggttcattta acaagctgcc 60

<210> SEQ ID NO 32
<211> LENGTH: 60
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer GR exon 3, including SEQ ID NO: 128, 10N and SEQ ID NO: 130
<220> FEATURE:
<221> NAME/KEY: modified_base
<222> LOCATION: (31)..(40)
<223> OTHER INFORMATION: a or c or t or g

<400> SEQUENCE: 32
ccatctcatc cctgcgtgtc tccgactcag nnnnnnnnnn gcattctgac tatgaagtga 60

<210> SEQ ID NO 33
<211> LENGTH: 69
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer GR exon 5, including SEQ ID NO: 128, 10N and SEQ ID NO: 131
<220> FEATURE:
<221> NAME/KEY: modified_base
<222> LOCATION: (31)..(40)
<223> OTHER INFORMATION: a or c or t or g

<400> SEQUENCE: 33
ccatctcatc cctgcgtgtc tccgactcag nnnnnnnnnn tcagcaggcc actacaggag 60
tctcacaag 69

<210> SEQ ID NO 34
<211> LENGTH: 50
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Reverse composite primer GR exon 2, including SEQ ID NO: 132 and SEQ ID NO: 133

<400> SEQUENCE: 34
cctatcccct gtgtgccttg gcagtctcag agccagtgag ggtgaagacg 50

<210> SEQ ID NO 35
<211> LENGTH: 50
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Reverse composite primer GR exon 3, including SEQ ID NO: 132 and SEQ ID NO: 134

<400> SEQUENCE: 35
cctatcccct gtgtgccttg gcagtctcag gggctttgca tataatggaa 50

<210> SEQ ID NO 36
<211> LENGTH: 59
<212> TYPE: DNA

<213> ORGANISM: Artificial sequence
<220> FEATURE:
<223> OTHER INFORMATION: Synthetic oligonucleotide
<220> FEATURE:
<223> OTHER INFORMATION: Reverse composite primer GR exon 5,
including SEQ ID NO: 132 and SEQ ID NO: 135

<400> SEQUENCE: 36
cctatcccct gtgtgccttg gcagtctcag ctgactctcc ccttcatagt ccccagaac 59

<210> SEQ ID NO 37
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: TRAC_T01

<400> SEQUENCE: 37
ttgtcccaca gatatccaga accctgaccc tgccgtgtac cagctgaga 49

<210> SEQ ID NO 38
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: TRBC_T01

<400> SEQUENCE: 38
tgtgtttgag ccatcagaag cagagatctc ccacacccaa aaggccaca 49

<210> SEQ ID NO 39
<211> LENGTH: 50
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: TRBC_T02

<400> SEQUENCE: 39
ttcccacccg aggtcgctgt gtttgagcca tcagaagcag agatctccca 50

<210> SEQ ID NO 40
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: CD52_T02

<400> SEQUENCE: 40
ttcctcctac tcaccatcag cctcctggtt atggtacagg taagagcaa 49

<210> SEQ ID NO 41
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat TRAC_T01-L

<400> SEQUENCE: 41

-continued

```
Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
```

```
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 42
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat TRAC_T01-R

<400> SEQUENCE: 42

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240
```

```
Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

<210> SEQ ID NO 43
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat TRBC_T01-L

<400> SEQUENCE: 43

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45
```

```
Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
```

-continued

```
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 44
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat TRBC_T01-R

<400> SEQUENCE: 44

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Gly Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285
```

```
Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 45
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat TRBC_T02-L

<400> SEQUENCE: 45

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95
```

```
Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
```

515 520 525

Leu Glu
530

<210> SEQ ID NO 46
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat TRBC_T02-R

<400> SEQUENCE: 46

Leu Thr Pro Gln Gln Val Val Ala Ile Ala Ser Asn Asn Gly Gly Lys
1 5 10 15

Gln Ala Leu Glu Thr Val Gln Arg Leu Leu Pro Val Leu Cys Gln Ala
20 25 30

His Gly Leu Thr Pro Gln Gln Val Val Ala Ile Ala Ser Asn Asn Gly
35 40 45

Gly Lys Gln Ala Leu Glu Thr Val Gln Arg Leu Leu Pro Val Leu Cys
50 55 60

Gln Ala His Gly Leu Thr Pro Gln Gln Val Val Ala Ile Ala Ser Asn
65 70 75 80

Asn Gly Gly Lys Gln Ala Leu Glu Thr Val Gln Arg Leu Leu Pro Val
85 90 95

Leu Cys Gln Ala His Gly Leu Thr Pro Glu Gln Val Val Ala Ile Ala
100 105 110

Ser Asn Ile Gly Gly Lys Gln Ala Leu Glu Thr Val Gln Ala Leu Leu
115 120 125

Pro Val Leu Cys Gln Ala His Gly Leu Thr Pro Gln Gln Val Val Ala
130 135 140

Ile Ala Ser Asn Asn Gly Gly Lys Gln Ala Leu Glu Thr Val Gln Arg
145 150 155 160

Leu Leu Pro Val Leu Cys Gln Ala His Gly Leu Thr Pro Glu Gln Val
165 170 175

Val Ala Ile Ala Ser Asn Ile Gly Gly Lys Gln Ala Leu Glu Thr Val
180 185 190

Gln Ala Leu Leu Pro Val Leu Cys Gln Ala His Gly Leu Thr Pro Gln
195 200 205

Gln Val Val Ala Ile Ala Ser Asn Gly Gly Gly Lys Gln Ala Leu Glu
210 215 220

Thr Val Gln Arg Leu Leu Pro Val Leu Cys Gln Ala His Gly Leu Thr
225 230 235 240

Pro Glu Gln Val Val Ala Ile Ala Ser His Asp Gly Gly Lys Gln Ala
245 250 255

Leu Glu Thr Val Gln Arg Leu Leu Pro Val Leu Cys Gln Ala His Gly
260 265 270

Leu Thr Pro Gln Gln Val Val Ala Ile Ala Ser Asn Gly Gly Gly Lys
275 280 285

Gln Ala Leu Glu Thr Val Gln Arg Leu Leu Pro Val Leu Cys Gln Ala
290 295 300

His Gly Leu Thr Pro Glu Gln Val Val Ala Ile Ala Ser His Asp Gly
305 310 315 320

Gly Lys Gln Ala Leu Glu Thr Val Gln Arg Leu Leu Pro Val Leu Cys
325 330 335

```
Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 47
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat CD52_T02-L

<400> SEQUENCE: 47

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140
```

-continued

```
Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

<210> SEQ ID NO 48
<211> LENGTH: 530
<212> TYPE: PRT

-continued

```
<213> ORGANISM: Artificial sequence
<220> FEATURE:
<223> OTHER INFORMATION: Synthetic polypeptide
<220> FEATURE:
<223> OTHER INFORMATION: Repeat CD52_T02-R

<400> SEQUENCE: 48

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380
```

```
Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

<210> SEQ ID NO 49
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: TRAC_T01-L TALEN

<400> SEQUENCE: 49

```
atgggcgatc ctaaaaagaa acgtaaggtc atcgattacc catacgatgt tccagattac     60

gctatcgata tcgccgatct acgcacgctc ggctacagcc agcagcaaca ggagaagatc    120

aaaccgaagg ttcgttcgac agtggcgcag caccacgagg cactggtcgg ccacgggttt    180

acacacgcgc acatcgttgc gttaagccaa cacccggcag cgttagggac cgtcgctgtc    240

aagtatcagg acatgatcgc agcgttgcca gaggcgacac acgaagcgat cgttggcgtc    300

ggcaaacagt ggtccggcgc acgcgctctg gaggccttgc tcacggtggc gggagagttg    360

agaggtccac cgttacagtt ggacacaggc caacttctca agattgcaaa acgtggcggc    420

gtgaccgcag tggaggcagt gcatgcatgg cgcaatgcac tgacgggtgc cccgctcaac    480

ttgacccccc agcaggtggt ggccatcgcc agcaatggcg gtggcaagca ggcgctggag    540

acggtccagc ggctgttgcc ggtgctgtgc caggcccacg gcttgacccc ccagcaggtg    600

gtggccatcg ccagcaataa tggtggcaag caggcgctgg agacggtcca gcggctgttg    660

ccggtgctgt gccaggccca cggcttgacc ccccagcagg tggtggccat cgccagcaat    720

ggcggtggca agcaggcgct ggagacggtc cagcggctgt tgccggtgct gtgccaggcc    780

cacggcttga ccccggagca ggtggtggcc atcgccagcc acgatggcgg caagcaggcg    840

ctggagacgg tccagcggct gttgccggtg ctgtgccagg cccacggctt gaccccggag    900

caggtggtgg ccatcgccag ccacgatggc ggcaagcagg cgctggagac ggtccagcgg    960

ctgttgccgg tgctgtgcca ggcccacggc ttgaccccgg agcaggtggt ggccatcgcc   1020

agccacgatg gcggcaagca ggcgctggag acggtccagc ggctgttgcc ggtgctgtgc   1080
```

-continued

```
caggcccacg gcttgacccc ggagcaggtg gtggccatcg ccagcaatat tggtggcaag   1140

caggcgctgg agacggtgca ggcgctgttg ccggtgctgt gccaggccca cggcttgacc   1200

ccggagcagg tggtggccat cgccagccac gatggcggca agcaggcgct ggagacggtc   1260

cagcggctgt tgccggtgct gtgccaggcc cacggcttga ccccggagca ggtggtggcc   1320

atcgccagca atattggtgg caagcaggcg ctggagacgg tgcaggcgct gttgccggtg   1380

ctgtgccagg cccacggctt gaccccccag caggtggtgg ccatcgccag caataatggt   1440

ggcaagcagg cgctggagac ggtccagcgg ctgttgccgg tgctgtgcca ggcccacggc   1500

ttgaccccgg agcaggtggt ggccatcgcc agcaatattg gtggcaagca ggcgctggag   1560

acggtgcagg cgctgttgcc ggtgctgtgc caggcccacg gcttgacccc ccagcaggtg   1620

gtggccatcg ccagcaatgg cggtggcaag caggcgctgg agacggtcca gcggctgttg   1680

ccggtgctgt gccaggccca cggcttgacc ccggagcagg tggtggccat cgccagcaat   1740

attggtggca agcaggcgct ggagacggtg caggcgctgt tgccggtgct gtgccaggcc   1800

cacggcttga ccccccagca ggtggtggcc atcgccagca atggcggtgg caagcaggcg   1860

ctggagacgg tccagcggct gttgccggtg ctgtgccagg cccacggctt gaccccggag   1920

caggtggtgg ccatcgccag ccacgatggc ggcaagcagg cgctggagac ggtccagcgg   1980

ctgttgccgg tgctgtgcca ggcccacggc ttgacccctc agcaggtggt ggccatcgcc   2040

agcaatggcg gcggcaggcc ggcgctggag agcattgttg cccagttatc tcgccctgat   2100

ccggcgttgg ccgcgttgac caacgaccac ctcgtcgcct tggcctgcct cggcgggcgt   2160

cctgcgctgg atgcagtgaa aaagggattg gggatcccta tcagccgttc ccagctggtg   2220

aagtccgagc tggaggagaa gaaatccgag ttgaggcaca agctgaagta cgtgccccac   2280

gagtacatcg agctgatcga gatcgcccgg aacagcaccc aggaccgtat cctggagatg   2340

aaggtgatgg agttcttcat gaaggtgtac ggctacaggg gcaagcacct gggcggctcc   2400

aggaagcccg acggcgccat ctacaccgtg ggctccccca tcgactacgg cgtgatcgtg   2460

gacaccaagg cctactccgg cggctacaac ctgcccatcg gccaggccga cgaaatgcag   2520

aggtacgtgg aggagaacca gaccaggaac aagcacatca accccaacga gtggtggaag   2580

gtgtacccct ccagcgtgac cgagttcaag ttcctgttcg tgtccggcca cttcaagggc   2640

aactacaagg cccagctgac caggctgaac cacatcacca actgcaacgg cgccgtgctg   2700

tccgtggagg agctcctgat cggcggcgag atgatcaagg ccggcaccct gaccctggag   2760

gaggtgagga ggaagttcaa caacggcgag atcaacttcg cggccgactg ataa         2814
```

<210> SEQ ID NO 50
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: TRAC_T01-R TALEN

<400> SEQUENCE: 50

```
atgggcgatc ctaaaaagaa acgtaaggtc atcgataagg agaccgccgc tgccaagttc     60

gagagacagc acatggacag catcgatatc gccgatctac gcacgctcgg ctacagccag    120

cagcaacagg agaagatcaa accgaaggtt cgttcgacag tggcgcagca ccacgaggca    180

ctggtcggcc acgggtttac acacgcgcac atcgttgcgt taagccaaca cccggcagcg    240

ttagggaccg tcgctgtcaa gtatcaggac atgatcgcag cgttgccaga ggcgacacac    300
```

-continued

```
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccggag caggtggtgg ccatcgccag ccacgatggc    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagcaat    840
attggtggca agcaggcgct ggagacggtg caggcgctgt tgccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgacccccc agcaggtggt ggccatcgcc   1140
agcaatggcg gtggcaagca ggcgctggag acggtccagc ggctgttgcc ggtgctgtgc   1200
caggcccacg gcttgacccc ccagcaggtg gtggccatcg ccagcaataa tggtggcaag   1260
caggcgctgg agacggtcca gcggctgttg ccggtgctgt gccaggccca cggcttgacc   1320
ccccagcagg tggtggccat cgccagcaat aatggtggca agcaggcgct ggagacggtc   1380
cagcggctgt tgccggtgct gtgccaggcc cacggcttga ccccccagca ggtggtggcc   1440
atcgccagca atggcggtgg caagcaggcg ctggagacgg tccagcggct gttgccggtg   1500
ctgtgccagg cccacggctt gaccccggag caggtggtgg ccatcgccag caatattggt   1560
ggcaagcagg cgctggagac ggtgcaggcg ctgttgccgg tgctgtgcca ggcccacggc   1620
ttgaccccgg agcaggtggt ggccatcgcc agccacgatg gcggcaagca ggcgctggag   1680
acggtccagc ggctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccggagcagg tggtggccat cgccagccac   1860
gatggcggca agcaggcgct ggagacggtc cagcggctgt tgccggtgct gtgccaggcc   1920
cacggcttga ccccccagca ggtggtggcc atcgccagca ataatggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtacccctcc agcgtgaccg agttcaagtt cctgttcgtg   2640
```

```
tccggccact tcaagggcaa ctacaaggcc cagctgacca ggctgaacca catcaccaac   2700

tgcaacggcg ccgtgctgtc cgtggaggag ctcctgatcg gcggcgagat gatcaaggcc   2760

ggcaccctga ccctggagga ggtgaggagg aagttcaaca acggcgagat caacttcgcg   2820

gccgactgat aa                                                       2832


<210> SEQ ID NO 51
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: TRBC_T01-L TALEN

<400> SEQUENCE: 51

atgggcgatc ctaaaaagaa acgtaaggtc atcgattacc catacgatgt tccagattac     60

gctatcgata tcgccgatct acgcacgctc ggctacagcc agcagcaaca ggagaagatc    120

aaaccgaagg ttcgttcgac agtggcgcag caccacgagg cactggtcgg ccacgggttt    180

acacacgcgc acatcgttgc gttaagccaa cacccggcag cgttagggac cgtcgctgtc    240

aagtatcagg acatgatcgc agcgttgcca gaggcgacac acgaagcgat cgttggcgtc    300

ggcaaacagt ggtccggcgc acgcgctctg gaggccttgc tcacggtggc gggagagttg    360

agaggtccac cgttacagtt ggacacaggc caacttctca agattgcaaa acgtggcggc    420

gtgaccgcag tggaggcagt gcatgcatgg cgcaatgcac tgacgggtgc cccgctcaac    480

ttgacccccc agcaggtggt ggccatcgcc agcaataatg gtggcaagca ggcgctggag    540

acggtccagc ggctgttgcc ggtgctgtgc caggcccacg gcttgacccc ccagcaggtg    600

gtggccatcg ccagcaatgg cggtggcaag caggcgctgg agacggtcca gcggctgttg    660

ccggtgctgt gccaggccca cggcttgacc ccccagcagg tggtggccat cgccagcaat    720

aatggtggca agcaggcgct ggagacggtc cagcggctgt tgccggtgct gtgccaggcc    780

cacggcttga ccccccagca ggtggtggcc atcgccagca atggcggtgg caagcaggcg    840

ctggagacgg tccagcggct gttgccggtg ctgtgccagg cccacggctt gaccccccag    900

caggtggtgg ccatcgccag caatggcggt ggcaagcagg cgctggagac ggtccagcgg    960

ctgttgccgg tgctgtgcca ggcccacggc ttgacccccc agcaggtggt ggccatcgcc   1020

agcaatggcg gtggcaagca ggcgctggag acggtccagc ggctgttgcc ggtgctgtgc   1080

caggcccacg gcttgacccc ccagcaggtg gtggccatcg ccagcaataa tggtggcaag   1140

caggcgctgg agacggtcca gcggctgttg ccggtgctgt gccaggccca cggcttgacc   1200

ccggagcagg tggtggccat cgccagcaat attggtggca agcaggcgct ggagacggtg   1260

caggcgctgt tgccggtgct gtgccaggcc cacggcttga ccccccagca ggtggtggcc   1320

atcgccagca ataatggtgg caagcaggcg ctggagacgg tccagcggct gttgccggtg   1380

ctgtgccagg cccacggctt gaccccggag caggtggtgg ccatcgccag ccacgatggc   1440

ggcaagcagg cgctggagac ggtccagcgg ctgttgccgg tgctgtgcca ggcccacggc   1500

ttgaccccgg agcaggtggt ggccatcgcc agccacgatg gcggcaagca ggcgctggag   1560

acggtccagc ggctgttgcc ggtgctgtgc caggcccacg gcttgacccc ggagcaggtg   1620

gtggccatcg ccagcaatat tggtggcaag caggcgctgg agacggtgca ggcgctgttg   1680

ccggtgctgt gccaggccca cggcttgacc ccccagcagg tggtggccat cgccagcaat   1740

ggcggtggca agcaggcgct ggagacggtc cagcggctgt tgccggtgct gtgccaggcc   1800
```

```
cacggcttga ccccggagca ggtggtggcc atcgccagcc acgatggcgg caagcaggcg   1860
ctggagacgg tccagcggct gttgccggtg ctgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg gggatcccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg gccaggccga cgaaatgcag   2520
aggtacgtgg aggagaacca gaccaggaac aagcacatca accccaacga gtggtggaag   2580
gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gaccctggag   2760
gaggtgagga ggaagttcaa caacggcgag atcaacttcg cggccgactg ataa         2814
```

<210> SEQ ID NO 52
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: TRBC_T01-R TALEN

<400> SEQUENCE: 52

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccccag caggtggtgg ccatcgccag caataatggt    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ccagcaggtg    720
gtggccatcg ccagcaataa tggtggcaag caggcgctgg agacggtcca gcggctgttg    780
ccggtgctgt gccaggccca cggcttgacc ccccagcagg tggtggccat cgccagcaat    840
aatggtggca agcaggcgct ggagacggtc cagcggctgt tgccggtgct gtgccaggcc    900
cacggcttga ccccggagca ggtggtggcc atcgccagcc acgatggcgg caagcaggcg    960
```

-continued

```
ctggagacgg tccagcggct gttgccggtg ctgtgccagg cccacggctt gaccccggag   1020

caggtggtgg ccatcgccag ccacgatggc ggcaagcagg cgctggagac ggtccagcgg   1080

ctgttgccgg tgctgtgcca ggcccacggc ttgacccccc agcaggtggt ggccatcgcc   1140

agcaatggcg gtggcaagca ggcgctggag acggtccagc ggctgttgcc ggtgctgtgc   1200

caggcccacg gcttgacccc ccagcaggtg gtggccatcg ccagcaatgg cggtggcaag   1260

caggcgctgg agacggtcca gcggctgttg ccggtgctgt gccaggccca cggcttgacc   1320

ccccagcagg tggtggccat cgccagcaat ggcggtggca agcaggcgct ggagacggtc   1380

cagcggctgt tgccggtgct gtgccaggcc cacggcttga ccccccagca ggtggtggcc   1440

atcgccagca atggcggtgg caagcaggcg ctggagacgg tccagcggct gttgccggtg   1500

ctgtgccagg cccacggctt gacccccccag caggtggtgg ccatcgccag caataatggt   1560

ggcaagcagg cgctggagac ggtccagcgg ctgttgccgg tgctgtgcca ggcccacggc   1620

ttgacccccc agcaggtggt ggccatcgcc agcaataatg gtggcaagca ggcgctggag   1680

acggtccagc ggctgttgcc ggtgctgtgc caggcccacg gcttgacccc ccagcaggtg   1740

gtggccatcg ccagcaataa tggtggcaag caggcgctgg agacggtcca gcggctgttg   1800

ccggtgctgt gccaggccca cggcttgacc ccccagcagg tggtggccat cgccagcaat   1860

ggcggtggca agcaggcgct ggagacggtc cagcggctgt tgccggtgct gtgccaggcc   1920

cacggcttga ccccccagca ggtggtggcc atcgccagca ataatggtgg caagcaggcg   1980

ctggagacgg tccagcggct gttgccggtg ctgtgccagg cccacggctt gacccctcag   2040

caggtggtgg ccatcgccag caatggcggc ggcaggccgg cgctggagag cattgttgcc   2100

cagttatctc gccctgatcc ggcgttggcc gcgttgacca acgaccacct cgtcgccttg   2160

gcctgcctcg gcgggcgtcc tgcgctggat gcagtgaaaa agggattggg ggatcctatc   2220

agccgttccc agctggtgaa gtccgagctg gaggagaaga aatccgagtt gaggcacaag   2280

ctgaagtacg tgccccacga gtacatcgag ctgatcgaga tcgcccggaa cagcacccag   2340

gaccgtatcc tggagatgaa ggtgatggag ttcttcatga aggtgtacgg ctacaggggc   2400

aagcacctgg gcggctccag gaagcccgac ggcgccatct acaccgtggg ctcccccatc   2460

gactacggcg tgatcgtgga caccaaggcc tactccggcg gctacaacct gcccatcggc   2520

caggccgacg aaatgcagag gtacgtggag gagaaccaga ccaggaacaa gcacatcaac   2580

cccaacgagt ggtggaaggt gtacccctcc agcgtgaccg agttcaagtt cctgttcgtg   2640

tccggccact tcaagggcaa ctacaaggcc cagctgacca ggctgaacca catcaccaac   2700

tgcaacggcg ccgtgctgtc cgtggaggag ctcctgatcg gcggcgagat gatcaaggcc   2760

ggcaccctga ccctggagga ggtgaggagg aagttcaaca acggcgagat caacttcgcg   2820

gccgactgat aa                                                        2832
```

<210> SEQ ID NO 53
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: TRBC_T02-L TALEN

<400> SEQUENCE: 53

```
atgggcgatc ctaaaaagaa acgtaaggtc atcgattacc catacgatgt tccagattac     60

gctatcgata tcgccgatct acgcacgctc ggctacagcc agcagcaaca ggagaagatc    120
```

-continued

```
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccccgg agcaggtggt ggccatcgcc agccacgatg gcggcaagca ggcgctggag    540
acggtccagc ggctgttgcc ggtgctgtgc caggcccacg gcttgacccc ggagcaggtg    600
gtggccatcg ccagccacga tggcggcaag caggcgctgg agacggtcca gcggctgttg    660
ccggtgctgt gccaggccca cggcttgacc ccggagcagg tggtggccat cgccagccac    720
gatggcggca agcaggcgct ggagacggtc cagcggctgt tgccggtgct gtgccaggcc    780
cacggcttga ccccggagca ggtggtggcc atcgccagca atattggtgg caagcaggcg    840
ctggagacgg tgcaggcgct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccgg agcaggtggt ggccatcgcc   1020
agccacgatg gcggcaagca ggcgctggag acggtccagc ggctgttgcc ggtgctgtgc   1080
caggcccacg gcttgacccc ggagcaggtg gtggccatcg ccagccacga tggcggcaag   1140
caggcgctgg agacggtcca gcggctgttg ccggtgctgt gccaggccca cggcttgacc   1200
ccccagcagg tggtggccat cgccagcaat aatggtggca agcaggcgct ggagacggtc   1260
cagcggctgt tgccggtgct gtgccaggcc cacggcttga ccccggagca ggtggtggcc   1320
atcgccagca atattggtgg caagcaggcg ctggagacgg tgcaggcgct gttgccggtg   1380
ctgtgccagg cccacggctt gacccccag caggtggtgg ccatcgccag caataatggt   1440
ggcaagcagg cgctggagac ggtccagcgg ctgttgccgg tgctgtgcca ggcccacggc   1500
ttgaccccc agcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc ccggagcagg tggtggccat cgccagccac   1740
gatggcggca agcaggcgct ggagacggtc cagcggctgt tgccggtgct gtgccaggcc   1800
cacggcttga cccccagca ggtggtggcc atcgccagca ataatggtgg caagcaggcg   1860
ctggagacgg tccagcggct gttgccggtg ctgtgccagg cccacggctt gaccccggag   1920
caggtggtgg ccatcgccag ccacgatggc ggcaagcagg cgctggagac ggtccagcgg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg gggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctcccca tcgactacgg cgtgatcgtg   2460
```

gacaccaagg cctactccgg cggctacaac ctgcccatcg gccaggccga cgaaatgcag 2520
aggtacgtgg aggagaacca gaccaggaac aagcacatca accccaacga gtggtggaag 2580
gtgtacccct ccagcgtgac cgagttcaag ttcctgttcg tgtccggcca cttcaagggc 2640
aactacaagg cccagctgac caggctgaac cacatcacca actgcaacgg cgccgtgctg 2700
tccgtggagg agctcctgat cggcggcgag atgatcaagg ccggcaccct gaccctggag 2760
gaggtgagga ggaagttcaa caacggcgag atcaacttcg cggccgactg ataa 2814

<210> SEQ ID NO 54
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: TRBC_T02-R TALEN

<400> SEQUENCE: 54
atgggcgatc ctaaaaagaa acgtaaggtc atcgataagg agaccgccgc tgccaagttc 60
gagagacagc acatggacag catcgatatc gccgatctac gcacgctcgg ctacagccag 120
cagcaacagg agaagatcaa accgaaggtt cgttcgacag tggcgcagca ccacgaggca 180
ctggtcggcc acgggtttac acacgcgcac atcgttgcgt taagccaaca cccggcagcg 240
ttagggaccg tcgctgtcaa gtatcaggac atgatcgcag cgttgccaga ggcgacacac 300
gaagcgatcg ttggcgtcgg caaacagtgg tccggcgcac gcgctctgga ggccttgctc 360
acggtggcgg gagagttgag aggtccaccg ttacagttgg acacaggcca acttctcaag 420
attgcaaaac gtggcggcgt gaccgcagtg gaggcagtgc atgcatggcg caatgcactg 480
acgggtgccc cgctcaactt gaccccccag caggtggtgg ccatcgccag caataatggt 540
ggcaagcagg cgctggagac ggtccagcgg ctgttgccgg tgctgtgcca ggcccacggc 600
ttgacccccc agcaggtggt ggccatcgcc agcaataatg gtggcaagca ggcgctggag 660
acggtccagc ggctgttgcc ggtgctgtgc caggcccacg gcttgacccc ccagcaggtg 720
gtggccatcg ccagcaataa tggtggcaag caggcgctgg agacggtcca gcggctgttg 780
ccggtgctgt gccaggccca cggcttgacc ccggagcagg tggtggccat cgccagcaat 840
attggtggca agcaggcgct ggagacggtg caggcgctgt tgccggtgct gtgccaggcc 900
cacggcttga ccccccagca ggtggtggcc atcgccagca ataatggtgg caagcaggcg 960
ctggagacgg tccagcggct gttgccggtg ctgtgccagg cccacggctt gaccccggag 1020
caggtggtgg ccatcgccag caatattggt ggcaagcagg cgctggagac ggtgcaggcg 1080
ctgttgccgg tgctgtgcca ggcccacggc ttgacccccc agcaggtggt ggccatcgcc 1140
agcaatggcg gtggcaagca ggcgctggag acggtccagc ggctgttgcc ggtgctgtgc 1200
caggcccacg gcttgacccc ggagcaggtg gtggccatcg ccagccacga tggcggcaag 1260
caggcgctgg agacggtcca gcggctgttg ccggtgctgt gccaggccca cggcttgacc 1320
ccccagcagg tggtggccat cgccagcaat ggcggtggca agcaggcgct ggagacggtc 1380
cagcggctgt tgccggtgct gtgccaggcc cacggcttga ccccggagca ggtggtggcc 1440
atcgccagcc acgatggcgg caagcaggcg ctggagacgg tccagcggct gttgccggtg 1500
ctgtgccagg cccacggctt gaccccccag caggtggtgg ccatcgccag caatggcggt 1560
ggcaagcagg cgctggagac ggtccagcgg ctgttgccgg tgctgtgcca ggcccacggc 1620
ttgacccccc agcaggtggt ggccatcgcc agcaataatg gtggcaagca ggcgctggag 1680
acggtccagc ggctgttgcc ggtgctgtgc caggcccacg gcttgacccc ggagcaggtg 1740
gtggccatcg ccagccacga tggcggcaag caggcgctgg agacggtcca gcggctgttg 1800
ccggtgctgt gccaggccca cggcttgacc ccccagcagg tggtggccat cgccagcaat 1860
ggcggtggca agcaggcgct ggagacggtc cagcggctgt tgccggtgct gtgccaggcc 1920
cacggcttga ccccccagca ggtggtggcc atcgccagca atggcggtgg caagcaggcg 1980
ctggagacgg tccagcggct gttgccggtg ctgtgccagg cccacggctt gacccctcag 2040
caggtggtgg ccatcgccag caatggcggc ggcaggccgg cgctggagag cattgttgcc 2100
cagttatctc gccctgatcc ggcgttggcc gcgttgacca acgaccacct cgtcgccttg 2160
gcctgcctcg gcgggcgtcc tgcgctggat gcagtgaaaa agggattggg ggatcctatc 2220
agccgttccc agctggtgaa gtccgagctg gaggagaaga aatccgagtt gaggcacaag 2280
ctgaagtacg tgccccacga gtacatcgag ctgatcgaga tcgcccggaa cagcacccag 2340
gaccgtatcc tggagatgaa ggtgatggag ttcttcatga aggtgtacgg ctacaggggc 2400
aagcacctgg gcggctccag gaagcccgac ggcgccatct acaccgtggg ctcccccatc 2460
gactacggcg tgatcgtgga caccaaggcc tactccggcg gctacaacct gcccatcggc 2520
caggccgacg aaatgcagag gtacgtggag gagaaccaga ccaggaacaa gcacatcaac 2580
cccaacgagt ggtggaaggt gtacccctcc agcgtgaccg agttcaagtt cctgttcgtg 2640
tccggccact tcaagggcaa ctacaaggcc cagctgacca ggctgaacca catcaccaac 2700
tgcaacggcg ccgtgctgtc cgtggaggag ctcctgatcg gcggcgagat gatcaaggcc 2760
ggcaccctga ccctggagga ggtgaggagg aagttcaaca acggcgagat caacttcgcg 2820
gccgactgat aa 2832

<210> SEQ ID NO 55
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: CD52_T02-L TALEN

<400> SEQUENCE: 55
atgggcgatc ctaaaaagaa acgtaaggtc atcgattacc catacgatgt tccagattac 60
gctatcgata tcgccgatct acgcacgctc ggctacagcc agcagcaaca ggagaagatc 120
aaaccgaagg ttcgttcgac agtggcgcag caccacgagg cactggtcgg ccacgggttt 180
acacacgcgc acatcgttgc gttaagccaa cacccggcag cgttagggac cgtcgctgtc 240
aagtatcagg acatgatcgc agcgttgcca gaggcgacac acgaagcgat cgttggcgtc 300
ggcaaacagt ggtccggcgc acgcgctctg gaggccttgc tcacggtggc gggagagttg 360
agaggtccac cgttacagtt ggacacaggc caacttctca agattgcaaa acgtggcggc 420
gtgaccgcag tggaggcagt gcatgcatgg cgcaatgcac tgacgggtgc cccgctcaac 480
ttgacccccc agcaggtggt ggccatcgcc agcaatggcg gtggcaagca ggcgctggag 540
acggtccagc ggctgttgcc ggtgctgtgc caggcccacg gcttgacccc ggagcaggtg 600
gtggccatcg ccagccacga tggcggcaag caggcgctgg agacggtcca gcggctgttg 660
ccggtgctgt gccaggccca cggcttgacc ccggagcagg tggtggccat cgccagccac 720
gatggcggca agcaggcgct ggagacggtc cagcggctgt tgccggtgct gtgccaggcc 780

-continued

```
cacggcttga ccccccagca ggtggtggcc atcgccagca atggcggtgg caagcaggcg    840

ctggagacgg tccagcggct gttgccggtg ctgtgccagg cccacggctt gaccccggag    900

caggtggtgg ccatcgccag ccacgatggc ggcaagcagg cgctggagac ggtccagcgg    960

ctgttgccgg tgctgtgcca ggcccacggc ttgaccccgg agcaggtggt ggccatcgcc   1020

agccacgatg gcggcaagca ggcgctggag acggtccagc ggctgttgcc ggtgctgtgc   1080

caggcccacg gcttgacccc ccagcaggtg gtggccatcg ccagcaatgg cggtggcaag   1140

caggcgctgg agacggtcca gcggctgttg ccggtgctgt gccaggccca cggcttgacc   1200

ccggagcagg tggtggccat cgccagcaat attggtggca agcaggcgct ggagacggtg   1260

caggcgctgt tgccggtgct gtgccaggcc cacggcttga ccccggagca ggtggtggcc   1320

atcgccagcc acgatggcgg caagcaggcg ctggagacgg tccagcggct gttgccggtg   1380

ctgtgccagg cccacggctt gacccccag caggtggtgg ccatcgccag caatggcggt   1440

ggcaagcagg cgctggagac ggtccagcgg ctgttgccgg tgctgtgcca ggcccacggc   1500

ttgaccccgg agcaggtggt ggccatcgcc agccacgatg gcggcaagca ggcgctggag   1560

acggtccagc ggctgttgcc ggtgctgtgc caggcccacg gcttgacccc ggagcaggtg   1620

gtggccatcg ccagcaatat tggtggcaag caggcgctgg agacggtgca ggcgctgttg   1680

ccggtgctgt gccaggccca cggcttgacc ccggagcagg tggtggccat cgccagccac   1740

gatggcggca agcaggcgct ggagacggtc cagcggctgt tgccggtgct gtgccaggcc   1800

cacggcttga ccccggagca ggtggtggcc atcgccagcc acgatggcgg caagcaggcg   1860

ctggagacgg tccagcggct gttgccggtg ctgtgccagg cccacggctt gaccccggag   1920

caggtggtgg ccatcgccag caatattggt ggcaagcagg cgctggagac ggtgcaggcg   1980

ctgttgccgg tgctgtgcca ggcccacggc ttgacccctc agcaggtggt ggccatcgcc   2040

agcaatggcg gcggcaggcc ggcgctggag agcattgttg cccagttatc tcgccctgat   2100

ccggcgttgg ccgcgttgac caacgaccac ctcgtcgcct tggcctgcct cggcgggcgt   2160

cctgcgctgg atgcagtgaa aaagggattg gggatcccta tcagccgttc ccagctggtg   2220

aagtccgagc tggaggagaa gaaatccgag ttgaggcaca agctgaagta cgtgccccac   2280

gagtacatcg agctgatcga gatcgcccgg aacagcaccc aggaccgtat cctggagatg   2340

aaggtgatgg agttcttcat gaaggtgtac ggctacaggg gcaagcacct gggcggctcc   2400

aggaagcccg acggcgccat ctacaccgtg ggctccccca tcgactacgg cgtgatcgtg   2460

gacaccaagg cctactccgg cggctacaac ctgcccatcg gccaggccga cgaaatgcag   2520

aggtacgtgg aggagaacca gaccaggaac aagcacatca accccaacga gtggtggaag   2580

gtgtacccct ccagcgtgac cgagttcaag ttcctgttcg tgtccggcca cttcaagggc   2640

aactacaagg cccagctgac caggctgaac cacatcacca actgcaacgg cgccgtgctg   2700

tccgtggagg agctcctgat cggcggcgag atgatcaagg ccggcaccct gaccctggag   2760

gaggtgagga ggaagttcaa caacggcgag atcaacttcg cggccgactg ataa         2814
```

<210> SEQ ID NO 56
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: CD52_T02-R TALEN

<400> SEQUENCE: 56

-continued

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccccag caggtggtgg ccatcgccag caatggcggt    540
ggcaagcagg cgctggagac ggtccagcgg ctgttgccgg tgctgtgcca ggcccacggc    600
ttgacccccc agcaggtggt ggccatcgcc agcaataatg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccccagcagg tggtggccat cgccagcaat    840
ggcggtggca agcaggcgct ggagacggtc cagcggctgt tgccggtgct gtgccaggcc    900
cacggcttga ccccggagca ggtggtggcc atcgccagcc acgatggcgg caagcaggcg    960
ctggagacgg tccagcggct gttgccggtg ctgtgccagg cccacggctt gaccccccag   1020
caggtggtgg ccatcgccag caatggcggt ggcaagcagg cgctggagac ggtccagcgg   1080
ctgttgccgg tgctgtgcca ggcccacggc ttgacccccc agcaggtggt ggccatcgcc   1140
agcaatggcg gtggcaagca ggcgctggag acggtccagc ggctgttgcc ggtgctgtgc   1200
caggcccacg gcttgacccc ggagcaggtg gtggccatcg ccagcaatat tggtggcaag   1260
caggcgctgg agacggtgca ggcgctgttg ccggtgctgt gccaggccca cggcttgacc   1320
ccggagcagg tggtggccat cgccagccac gatggcggca agcaggcgct ggagacggtc   1380
cagcggctgt tgccggtgct gtgccaggcc cacggcttga ccccggagca ggtggtggcc   1440
atcgccagcc acgatggcgg caagcaggcg ctggagacgg tccagcggct gttgccggtg   1500
ctgtgccagg cccacggctt gaccccccag caggtggtgg ccatcgccag caatggcggt   1560
ggcaagcagg cgctggagac ggtccagcgg ctgttgccgg tgctgtgcca ggcccacggc   1620
ttgacccccc agcaggtggt ggccatcgcc agcaataatg gtggcaagca ggcgctggag   1680
acggtccagc ggctgttgcc ggtgctgtgc caggcccacg gcttgacccc ccagcaggtg   1740
gtggccatcg ccagcaatgg cggtggcaag caggcgctgg agacggtcca gcggctgttg   1800
ccggtgctgt gccaggccca cggcttgacc ccggagcagg tggtggccat cgccagcaat   1860
attggtggca agcaggcgct ggagacggtg caggcgctgt tgccggtgct gtgccaggcc   1920
cacggcttga ccccggagca ggtggtggcc atcgccagcc acgatggcgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcacccag   2340
```

-continued

```
gaccgtatcc tggagatgaa ggtgatggag ttcttcatga aggtgtacgg ctacaggggc   2400

aagcacctgg gcggctccag gaagcccgac ggcgccatct acaccgtggg ctcccccatc   2460

gactacggcg tgatcgtgga caccaaggcc tactccggcg gctacaacct gcccatcggc   2520

caggccgacg aaatgcagag gtacgtggag gagaaccaga ccaggaacaa gcacatcaac   2580

cccaacgagt ggtggaaggt gtacccctcc agcgtgaccg agttcaagtt cctgttcgtg   2640

tccggccact tcaagggcaa ctacaaggcc cagctgacca ggctgaacca catcaccaac   2700

tgcaacggcg ccgtgctgtc cgtggaggag ctcctgatcg gcggcgagat gatcaaggcc   2760

ggcaccctga ccctggagga ggtgaggagg aagttcaaca acggcgagat caacttcgcg   2820

gccgactgat aa                                                       2832


<210> SEQ ID NO 57
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: TRAC_T02

<400> SEQUENCE: 57

tttagaaagt tcctgtgatg tcaagctggt cgagaaaagc tttgaaaca                  49


<210> SEQ ID NO 58
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: TRAC_T03

<400> SEQUENCE: 58

tccagtgaca agtctgtctg cctattcacc gattttgatt ctcaaacaa                  49


<210> SEQ ID NO 59
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: TRAC_T04

<400> SEQUENCE: 59

tatatcacag acaaaactgt gctagacatg aggtctatgg acttcaaga                  49


<210> SEQ ID NO 60
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: TRAC_T05

<400> SEQUENCE: 60

tgaggtctat ggacttcaag agcaacagtg ctgtggcctg gagcaacaa                  49


<210> SEQ ID NO 61
<211> LENGTH: 47
<212> TYPE: DNA
<213> ORGANISM: Artificial sequence
```

<220> FEATURE:
<223> OTHER INFORMATION: Synthetic oligonucleotide
<220> FEATURE:
<223> OTHER INFORMATION: CD52_T01

<400> SEQUENCE: 61
ttcctcttcc tcctaccacc atcagcctcc tttacctgta ccataac 47

<210> SEQ ID NO 62
<211> LENGTH: 43
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: CD52_T04

<400> SEQUENCE: 62
ttcctcctac tcaccacagc ctcctggtct tacctgtacc ata 43

<210> SEQ ID NO 63
<211> LENGTH: 43
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: CD52_T05

<400> SEQUENCE: 63
tcctactcac catcagctcc tggttatttg ctcttacctg tac 43

<210> SEQ ID NO 64
<211> LENGTH: 47
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: CD52_T06

<400> SEQUENCE: 64
ttatcccact tctcctctac agatacaaac tttttgtcct gagagtc 47

<210> SEQ ID NO 65
<211> LENGTH: 47
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: CD52_T07

<400> SEQUENCE: 65
tggactctca ggacaaacga caccagccaa atgctgaggg gctgctg 47

<210> SEQ ID NO 66
<211> LENGTH: 60
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer for CD52
<220> FEATURE:
<221> NAME/KEY: modified_base
<222> LOCATION: (31)..(40)
<223> OTHER INFORMATION: a or c or t or g

<400> SEQUENCE: 66
ccatctcatc cctgcgtgtc tccgactcag nnnnnnnnnn cagatctgca gaaaggaagc 60

<210> SEQ ID NO 67
<211> LENGTH: 61
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer for TRAC
<220> FEATURE:
<221> NAME/KEY: modified_base
<222> LOCATION: (31)..(40)
<223> OTHER INFORMATION: a or c or t or g

<400> SEQUENCE: 67
ccatctcatc cctgcgtgtc tccgactcag nnnnnnnnnn atcactggca tctggactcc 60
a 61

<210> SEQ ID NO 68
<211> LENGTH: 62
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer for TRBC1
<220> FEATURE:
<221> NAME/KEY: modified_base
<222> LOCATION: (31)..(40)
<223> OTHER INFORMATION: a or c or t or g

<400> SEQUENCE: 68
ccatctcatc cctgcgtgtc tccgactcag nnnnnnnnnn agagccccta ccagaaccag 60
ac 62

<210> SEQ ID NO 69
<211> LENGTH: 62
<212> TYPE: DNA
<213> ORGANISM: Artificial sequence
<220> FEATURE:
<223> OTHER INFORMATION: Synthetic Oligonucleotide
<220> FEATURE:
<223> OTHER INFORMATION: Forward composite primer for TRBC2
<220> FEATURE:
<221> NAME/KEY: modified_base
<222> LOCATION: (31).. (40)
<223> OTHER INFORMATION: a or c or t or g

<400> SEQUENCE: 69
ccatctcatc cctgcgtgtc tccgactcag nnnnnnnnnn ggacctagta acataattgt 60
gc 62

<210> SEQ ID NO 70
<211> LENGTH: 51
<212> TYPE: DNA
<213> ORGANISM: Artificial sequence
<220> FEATURE:
<223> OTHER INFORMATION: Synthetic Oligonucleotide
<220> FEATURE:
<223> OTHER INFORMATION: Reverse composite primer for CD52

<400> SEQUENCE: 70
cctatcccct gtgtgccttg gcagtctcag cctgttggag tccatctgct g 51

<210> SEQ ID NO 71
<211> LENGTH: 50
<212> TYPE: DNA
<213> ORGANISM: Artificial sequence
<220> FEATURE:
<223> OTHER INFORMATION: Synthetic Oligonucleotide
<220> FEATURE:
<223> OTHER INFORMATION: Reverse composite primer for TRAC

<400> SEQUENCE: 71
cctatcccct gtgtgccttg gcagtctcag cctcatgtct agcacagttt 50

<210> SEQ ID NO 72
<211> LENGTH: 51
<212> TYPE: DNA
<213> ORGANISM: Artificial sequence
<220> FEATURE:
<223> OTHER INFORMATION: Synthetic Oligonucleotide
<220> FEATURE:
<223> OTHER INFORMATION: Reverse composite primer for TRBC1 and 2

<400> SEQUENCE: 72
cctatcccct gtgtgccttg gcagtctcag accagctcag ctccacgtgg t 51

<210> SEQ ID NO 73
<211> LENGTH: 495
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: anti-CD19 CAR

<400> SEQUENCE: 73

Met Glu Thr Asp Thr Leu Leu Leu Trp Val Leu Leu Leu Trp Val Pro
1 5 10 15

Gly Ser Thr Gly Glu Val Gln Leu Gln Gln Ser Gly Pro Glu Leu Ile
20 25 30

Lys Pro Gly Ala Ser Val Lys Met Ser Cys Lys Ala Ser Gly Tyr Thr
35 40 45

Phe Thr Ser Tyr Val Met His Trp Val Lys Gln Lys Pro Gly Gln Gly
50 55 60

Leu Glu Trp Ile Gly Tyr Ile Asn Pro Tyr Asn Asp Gly Thr Lys Tyr
65 70 75 80

Asn Glu Lys Phe Lys Gly Lys Ala Thr Leu Thr Ser Asp Lys Ser Ser
85 90 95

Ser Thr Ala Tyr Met Glu Leu Ser Ser Leu Thr Ser Glu Asp Ser Ala
100 105 110

Val Tyr Tyr Cys Ala Arg Gly Thr Tyr Tyr Tyr Gly Ser Arg Val Phe
115 120 125

Asp Tyr Trp Gly Gln Gly Thr Thr Leu Thr Val Ser Ser Gly Gly Gly
130 135 140

Gly Ser Gly Gly Gly Gly Ser Gly Gly Gly Gly Ser Asp Ile Val Met
145 150 155 160

Thr Gln Ala Ala Pro Ser Ile Pro Val Thr Pro Gly Glu Ser Val Ser
165 170 175

Ile Ser Cys Arg Ser Ser Lys Ser Leu Leu Asn Ser Asn Gly Asn Thr
180 185 190

Tyr Leu Tyr Trp Phe Leu Gln Arg Pro Gly Gln Ser Pro Gln Leu Leu
195 200 205

Ile Tyr Arg Met Ser Asn Leu Ala Ser Gly Val Pro Asp Arg Phe Ser

-continued

```
    210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495
```

<210> SEQ ID NO 74
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: CTLA4_T01

<400> SEQUENCE: 74
tggccctgca ctctcctgtt ttttcttctc ttcatccctg tcttctgca 49

<210> SEQ ID NO 75
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: CTLA4_T03

<400> SEQUENCE: 75
ttttccatgc tagcaatgca cgtggcccag cctgctgtgg tactggcca 49

<210> SEQ ID NO 76
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: CTLA4_T04

<400> SEQUENCE: 76
tccatgctag caatgcacgt ggcccagcct gctgtggtac tggccagca 49

<210> SEQ ID NO 77
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: PDCD1_T01

<400> SEQUENCE: 77
ttctccccag ccctgctcgt ggtgaccgaa ggggacaacg ccaccttca 49

<210> SEQ ID NO 78
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: PDCD1_T03

<400> SEQUENCE: 78
tacctctgtg gggccatctc cctggccccc aaggcgcaga tcaaagaga 49

<210> SEQ ID NO 79
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat CTLA4_T01-L

<400> SEQUENCE: 79

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

-continued

```
Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

<210> SEQ ID NO 80
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat CTLA4_T01-R

<400> SEQUENCE: 80

Leu Thr Pro Gln Gln Val Val Ala Ile Ala Ser Asn Asn Gly Gly Lys
1 5 10 15

Gln Ala Leu Glu Thr Val Gln Arg Leu Leu Pro Val Leu Cys Gln Ala
20 25 30

His Gly Leu Thr Pro Glu Gln Val Val Ala Ile Ala Ser His Asp Gly
35 40 45

Gly Lys Gln Ala Leu Glu Thr Val Gln Arg Leu Leu Pro Val Leu Cys
50 55 60

Gln Ala His Gly Leu Thr Pro Glu Gln Val Val Ala Ile Ala Ser Asn
65 70 75 80

Ile Gly Gly Lys Gln Ala Leu Glu Thr Val Gln Ala Leu Leu Pro Val
85 90 95

Leu Cys Gln Ala His Gly Leu Thr Pro Gln Gln Val Val Ala Ile Ala
100 105 110

Ser Asn Asn Gly Gly Lys Gln Ala Leu Glu Thr Val Gln Arg Leu Leu
115 120 125

Pro Val Leu Cys Gln Ala His Gly Leu Thr Pro Glu Gln Val Val Ala
130 135 140

Ile Ala Ser Asn Ile Gly Gly Lys Gln Ala Leu Glu Thr Val Gln Ala
145 150 155 160

Leu Leu Pro Val Leu Cys Gln Ala His Gly Leu Thr Pro Glu Gln Val
165 170 175

Val Ala Ile Ala Ser Asn Ile Gly Gly Lys Gln Ala Leu Glu Thr Val
180 185 190

Gln Ala Leu Leu Pro Val Leu Cys Gln Ala His Gly Leu Thr Pro Gln
195 200 205

Gln Val Val Ala Ile Ala Ser Asn Asn Gly Gly Lys Gln Ala Leu Glu
210 215 220

Thr Val Gln Arg Leu Leu Pro Val Leu Cys Gln Ala His Gly Leu Thr
225 230 235 240

Pro Glu Gln Val Val Ala Ile Ala Ser Asn Ile Gly Gly Lys Gln Ala
245 250 255

Leu Glu Thr Val Gln Ala Leu Leu Pro Val Leu Cys Gln Ala His Gly
260 265 270

Leu Thr Pro Glu Gln Val Val Ala Ile Ala Ser His Asp Gly Gly Lys
275 280 285

Gln Ala Leu Glu Thr Val Gln Arg Leu Leu Pro Val Leu Cys Gln Ala
290 295 300

His Gly Leu Thr Pro Glu Gln Val Val Ala Ile Ala Ser Asn Ile Gly
305 310 315 320

Gly Lys Gln Ala Leu Glu Thr Val Gln Ala Leu Leu Pro Val Leu Cys
325 330 335

Gln Ala His Gly Leu Thr Pro Gln Gln Val Val Ala Ile Ala Ser Asn
340 345 350

Asn Gly Gly Lys Gln Ala Leu Glu Thr Val Gln Arg Leu Leu Pro Val

```
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 81
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat CTLA4_T03-L

<400> SEQUENCE: 81

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175
```

Val Ala Ile Ala Ser Asn Ile Gly Gly Lys Gln Ala Leu Glu Thr Val
180 185 190

Gln Ala Leu Leu Pro Val Leu Cys Gln Ala His Gly Leu Thr Pro Gln
195 200 205

Gln Val Val Ala Ile Ala Ser Asn Gly Gly Gly Lys Gln Ala Leu Glu
210 215 220

Thr Val Gln Arg Leu Leu Pro Val Leu Cys Gln Ala His Gly Leu Thr
225 230 235 240

Pro Gln Gln Val Val Ala Ile Ala Ser Asn Asn Gly Gly Lys Gln Ala
245 250 255

Leu Glu Thr Val Gln Arg Leu Leu Pro Val Leu Cys Gln Ala His Gly
260 265 270

Leu Thr Pro Glu Gln Val Val Ala Ile Ala Ser His Asp Gly Gly Lys
275 280 285

Gln Ala Leu Glu Thr Val Gln Arg Leu Leu Pro Val Leu Cys Gln Ala
290 295 300

His Gly Leu Thr Pro Gln Gln Val Val Ala Ile Ala Ser Asn Gly Gly
305 310 315 320

Gly Lys Gln Ala Leu Glu Thr Val Gln Arg Leu Leu Pro Val Leu Cys
325 330 335

Gln Ala His Gly Leu Thr Pro Glu Gln Val Val Ala Ile Ala Ser Asn
340 345 350

Ile Gly Gly Lys Gln Ala Leu Glu Thr Val Gln Ala Leu Leu Pro Val
355 360 365

Leu Cys Gln Ala His Gly Leu Thr Pro Gln Gln Val Val Ala Ile Ala
370 375 380

Ser Asn Asn Gly Gly Lys Gln Ala Leu Glu Thr Val Gln Arg Leu Leu
385 390 395 400

Pro Val Leu Cys Gln Ala His Gly Leu Thr Pro Glu Gln Val Val Ala
405 410 415

Ile Ala Ser His Asp Gly Gly Lys Gln Ala Leu Glu Thr Val Gln Arg
420 425 430

Leu Leu Pro Val Leu Cys Gln Ala His Gly Leu Thr Pro Glu Gln Val
435 440 445

Val Ala Ile Ala Ser Asn Ile Gly Gly Lys Gln Ala Leu Glu Thr Val
450 455 460

Gln Ala Leu Leu Pro Val Leu Cys Gln Ala His Gly Leu Thr Pro Glu
465 470 475 480

Gln Val Val Ala Ile Ala Ser Asn Ile Gly Gly Lys Gln Ala Leu Glu
485 490 495

Thr Val Gln Ala Leu Leu Pro Val Leu Cys Gln Ala His Gly Leu Thr
500 505 510

Pro Gln Gln Val Val Ala Ile Ala Ser Asn Gly Gly Gly Arg Pro Ala
515 520 525

Leu Glu
530

<210> SEQ ID NO 82
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat CTLA4_T03-R

<400> SEQUENCE: 82

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
```

```
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

<210> SEQ ID NO 83
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat CTLA4_T04-L

<400> SEQUENCE: 83

```
Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220
```

Thr Val Gln Arg Leu Leu Pro Val Leu Cys Gln Ala His Gly Leu Thr
225 230 235 240

Pro Glu Gln Val Val Ala Ile Ala Ser Asn Ile Gly Gly Lys Gln Ala
245 250 255

Leu Glu Thr Val Gln Ala Leu Leu Pro Val Leu Cys Gln Ala His Gly
260 265 270

Leu Thr Pro Gln Gln Val Val Ala Ile Ala Ser Asn Asn Gly Gly Lys
275 280 285

Gln Ala Leu Glu Thr Val Gln Arg Leu Leu Pro Val Leu Cys Gln Ala
290 295 300

His Gly Leu Thr Pro Glu Gln Val Val Ala Ile Ala Ser His Asp Gly
305 310 315 320

Gly Lys Gln Ala Leu Glu Thr Val Gln Arg Leu Leu Pro Val Leu Cys
325 330 335

Gln Ala His Gly Leu Thr Pro Glu Gln Val Val Ala Ile Ala Ser Asn
340 345 350

Ile Gly Gly Lys Gln Ala Leu Glu Thr Val Gln Ala Leu Leu Pro Val
355 360 365

Leu Cys Gln Ala His Gly Leu Thr Pro Glu Gln Val Val Ala Ile Ala
370 375 380

Ser Asn Ile Gly Gly Lys Gln Ala Leu Glu Thr Val Gln Ala Leu Leu
385 390 395 400

Pro Val Leu Cys Gln Ala His Gly Leu Thr Pro Gln Gln Val Val Ala
405 410 415

Ile Ala Ser Asn Gly Gly Gly Lys Gln Ala Leu Glu Thr Val Gln Arg
420 425 430

Leu Leu Pro Val Leu Cys Gln Ala His Gly Leu Thr Pro Gln Gln Val
435 440 445

Val Ala Ile Ala Ser Asn Asn Gly Gly Lys Gln Ala Leu Glu Thr Val
450 455 460

Gln Arg Leu Leu Pro Val Leu Cys Gln Ala His Gly Leu Thr Pro Glu
465 470 475 480

Gln Val Val Ala Ile Ala Ser His Asp Gly Gly Lys Gln Ala Leu Glu
485 490 495

Thr Val Gln Arg Leu Leu Pro Val Leu Cys Gln Ala His Gly Leu Thr
500 505 510

Pro Gln Gln Val Val Ala Ile Ala Ser Asn Gly Gly Gly Arg Pro Ala
515 520 525

Leu Glu
530

<210> SEQ ID NO 84
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat CTLA4_T04-R

<400> SEQUENCE: 84

Leu Thr Pro Gln Gln Val Val Ala Ile Ala Ser Asn Asn Gly Gly Lys
1 5 10 15

Gln Ala Leu Glu Thr Val Gln Arg Leu Leu Pro Val Leu Cys Gln Ala
20 25 30

```
His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
```

```
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 85
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat PDCD1_T01-L

<400> SEQUENCE: 85

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270
```

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 86
<211> LENGTH: 529
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat PDCD1_T01-R

<400> SEQUENCE: 86

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Glu Gln Val Val Ala Ile Ala Ser Asn
65                  70                  75                  80

-continued

```
Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Gly Gly Lys Gln
        275                 280                 285

Ala Leu Glu Thr Val Gln Arg Leu Leu Pro Val Leu Cys Gln Ala His
    290                 295                 300

Gly Leu Thr Pro Gln Gln Val Val Ala Ile Ala Ser Asn Asn Gly Gly
305                 310                 315                 320

Lys Gln Ala Leu Glu Thr Val Gln Arg Leu Leu Pro Val Leu Cys Gln
                325                 330                 335

Ala His Gly Leu Thr Pro Gln Gln Val Val Ala Ile Ala Ser Asn Gly
            340                 345                 350

Gly Gly Lys Gln Ala Leu Glu Thr Val Gln Arg Leu Leu Pro Val Leu
        355                 360                 365

Cys Gln Ala His Gly Leu Thr Pro Gln Gln Val Val Ala Ile Ala Ser
    370                 375                 380

Asn Gly Gly Gly Lys Gln Ala Leu Glu Thr Val Gln Arg Leu Leu Pro
385                 390                 395                 400

Val Leu Cys Gln Ala His Gly Leu Thr Pro Gln Gln Val Val Ala Ile
                405                 410                 415

Ala Ser Asn Asn Gly Gly Lys Gln Ala Leu Glu Thr Val Gln Arg Leu
            420                 425                 430

Leu Pro Val Leu Cys Gln Ala His Gly Leu Thr Pro Gln Gln Val Val
        435                 440                 445

Ala Ile Ala Ser Asn Gly Gly Gly Lys Gln Ala Leu Glu Thr Val Gln
    450                 455                 460

Arg Leu Leu Pro Val Leu Cys Gln Ala His Gly Leu Thr Pro Glu Gln
465                 470                 475                 480

Val Val Ala Ile Ala Ser His Asp Gly Gly Lys Gln Ala Leu Glu Thr
                485                 490                 495

Val Gln Arg Leu Leu Pro Val Leu Cys Gln Ala His Gly Leu Thr Pro
```

```
            500                 505                 510

Gln Gln Val Val Ala Ile Ala Ser Asn Gly Gly Gly Arg Pro Ala Leu
        515                 520                 525

Glu


<210> SEQ ID NO 87
<211> LENGTH: 530
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat PDCD1_T03-L

<400> SEQUENCE: 87

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Gly Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Asn Gly
305                 310                 315                 320
```

```
Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 88
<211> LENGTH: 529
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: Repeat PDCD1_T03-R

<400> SEQUENCE: 88

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
```

-continued

```
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Gly Gly Lys Gln Ala Leu Glu Thr Val Gln Arg Leu
            420                 425                 430

Leu Pro Val Leu Cys Gln Ala His Gly Leu Thr Pro Gln Gln Val Val
        435                 440                 445

Ala Ile Ala Ser Asn Asn Gly Gly Lys Gln Ala Leu Glu Thr Val Gln
    450                 455                 460

Arg Leu Leu Pro Val Leu Cys Gln Ala His Gly Leu Thr Pro Glu Gln
465                 470                 475                 480

Val Val Ala Ile Ala Ser His Asp Gly Gly Lys Gln Ala Leu Glu Thr
                485                 490                 495

Val Gln Arg Leu Leu Pro Val Leu Cys Gln Ala His Gly Leu Thr Pro
            500                 505                 510

Gln Gln Val Val Ala Ile Ala Ser Asn Gly Gly Gly Arg Pro Ala Leu
        515                 520                 525

Glu
```

<210> SEQ ID NO 89
<211> LENGTH: 2814

<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: CTLA4_T01-L TALEN

<400> SEQUENCE: 89
atgggcgatc ctaaaaagaa acgtaaggtc atcgattacc catacgatgt tccagattac 60
gctatcgata tcgccgatct acgcacgctc ggctacagcc agcagcaaca ggagaagatc 120
aaaccgaagg ttcgttcgac agtggcgcag caccacgagg cactggtcgg ccacgggttt 180
acacacgcgc acatcgttgc gttaagccaa cacccggcag cgttagggac cgtcgctgtc 240
aagtatcagg acatgatcgc agcgttgcca gaggcgacac acgaagcgat cgttggcgtc 300
ggcaaacagt ggtccggcgc acgcgctctg gaggccttgc tcacggtggc gggagagttg 360
agaggtccac cgttacagtt ggacacaggc caacttctca agattgcaaa acgtggcggc 420
gtgaccgcag tggaggcagt gcatgcatgg cgcaatgcac tgacgggtgc cccgctcaac 480
ttgacccccc agcaggtggt ggccatcgcc agcaataatg gtggcaagca ggcgctggag 540
acggtccagc ggctgttgcc ggtgctgtgc caggcccacg gcttgacccc ccagcaggtg 600
gtggccatcg ccagcaataa tggtggcaag caggcgctgg agacggtcca gcggctgttg 660
ccggtgctgt gccaggccca cggcttgacc ccggagcagg tggtggccat cgccagccac 720
gatggcggca agcaggcgct ggagacggtc cagcggctgt tgccggtgct gtgccaggcc 780
cacggcttga ccccggagca ggtggtggcc atcgccagcc acgatggcgg caagcaggcg 840
ctggagacgg tccagcggct gttgccggtg ctgtgccagg cccacggctt gaccccggag 900
caggtggtgg ccatcgccag ccacgatggc ggcaagcagg cgctggagac ggtccagcgg 960
ctgttgccgg tgctgtgcca ggcccacggc ttgacccccc agcaggtggt ggccatcgcc 1020
agcaatggcg gtggcaagca ggcgctggag acggtccagc ggctgttgcc ggtgctgtgc 1080
caggcccacg gcttgacccc ccagcaggtg gtggccatcg ccagcaataa tggtggcaag 1140
caggcgctgg agacggtcca gcggctgttg ccggtgctgt gccaggccca cggcttgacc 1200
ccggagcagg tggtggccat cgccagccac gatggcggca agcaggcgct ggagacggtc 1260
cagcggctgt tgccggtgct gtgccaggcc cacggcttga ccccggagca ggtggtggcc 1320
atcgccagca atattggtgg caagcaggcg ctggagacgg tgcaggcgct gttgccggtg 1380
ctgtgccagg cccacggctt gaccccggag caggtggtgg ccatcgccag ccacgatggc 1440
ggcaagcagg cgctggagac ggtccagcgg ctgttgccgg tgctgtgcca ggcccacggc 1500
ttgacccccc agcaggtggt ggccatcgcc agcaatggcg gtggcaagca ggcgctggag 1560
acggtccagc ggctgttgcc ggtgctgtgc caggcccacg gcttgacccc ggagcaggtg 1620
gtggccatcg ccagccacga tggcggcaag caggcgctgg agacggtcca gcggctgttg 1680
ccggtgctgt gccaggccca cggcttgacc ccccagcagg tggtggccat cgccagcaat 1740
ggcggtggca agcaggcgct ggagacggtc cagcggctgt tgccggtgct gtgccaggcc 1800
cacggcttga ccccggagca ggtggtggcc atcgccagcc acgatggcgg caagcaggcg 1860
ctggagacgg tccagcggct gttgccggtg ctgtgccagg cccacggctt gaccccggag 1920
caggtggtgg ccatcgccag ccacgatggc ggcaagcagg cgctggagac ggtccagcgg 1980
ctgttgccgg tgctgtgcca ggcccacggc ttgacccctc agcaggtggt ggccatcgcc 2040
agcaatggcg gcggcaggcc ggcgctggag agcattgttg cccagttatc tcgccctgat 2100
ccggcgttgg ccgcgttgac caacgaccac ctcgtcgcct tggcctgcct cggcgggcgt 2160
cctgcgctgg atgcagtgaa aaagggattg gggatccta tcagccgttc ccagctggtg 2220
aagtccgagc tggaggagaa gaaatccgag ttgaggcaca agctgaagta cgtgccccac 2280
gagtacatcg agctgatcga gatcgcccgg aacagcaccc aggaccgtat cctggagatg 2340
aaggtgatgg agttcttcat gaaggtgtac ggctacaggg gcaagcacct gggcggctcc 2400
aggaagcccg acggcgccat ctacaccgtg ggctccccca tcgactacgg cgtgatcgtg 2460
gacaccaagg cctactccgg cggctacaac ctgcccatcg gccaggccga cgaaatgcag 2520
aggtacgtgg aggagaacca gaccaggaac aagcacatca accccaacga gtggtggaag 2580
gtgtacccct ccagcgtgac cgagttcaag ttcctgttcg tgtccggcca cttcaagggc 2640
aactacaagg cccagctgac caggctgaac cacatcacca actgcaacgg cgccgtgctg 2700
tccgtggagg agctcctgat cggcggcgag atgatcaagg ccggcaccct gaccctggag 2760
gaggtgagga ggaagttcaa caacggcgag atcaacttcg cggccgactg ataa 2814

<210> SEQ ID NO 90
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: CTLA4_T01-R TALEN

<400> SEQUENCE: 90
atgggcgatc ctaaaaagaa acgtaaggtc atcgataagg agaccgccgc tgccaagttc 60
gagagacagc acatggacag catcgatatc gccgatctac gcacgctcgg ctacagccag 120
cagcaacagg agaagatcaa accgaaggtt cgttcgacag tggcgcagca ccacgaggca 180
ctggtcggcc acgggtttac acacgcgcac atcgttgcgt taagccaaca cccggcagcg 240
ttagggaccg tcgctgtcaa gtatcaggac atgatcgcag cgttgccaga ggcgacacac 300
gaagcgatcg ttggcgtcgg caaacagtgg tccggcgcac gcgctctgga ggccttgctc 360
acggtggcgg gagagttgag aggtccaccg ttacagttgg acacaggcca acttctcaag 420
attgcaaaac gtggcggcgt gaccgcagtg gaggcagtgc atgcatggcg caatgcactg 480
acgggtgccc cgctcaactt gacccccag caggtggtgg ccatcgccag caataatggt 540
ggcaagcagg cgctggagac ggtccagcgg ctgttgccgg tgctgtgcca ggcccacggc 600
ttgaccccgg agcaggtggt ggccatcgcc agccacgatg gcggcaagca ggcgctggag 660
acggtccagc ggctgttgcc ggtgctgtgc caggcccacg gcttgacccc ggagcaggtg 720
gtggccatcg ccagcaatat tggtggcaag caggcgctgg agacggtgca ggcgctgttg 780
ccggtgctgt gccaggccca cggcttgacc ccccagcagg tggtggccat cgccagcaat 840
aatggtggca agcaggcgct ggagacggtc cagcggctgt tgccggtgct gtgccaggcc 900
cacggcttga ccccggagca ggtggtggcc atcgccagca atattggtgg caagcaggcg 960
ctggagacgg tgcaggcgct gttgccggtg ctgtgccagg cccacggctt gaccccggag 1020
caggtggtgg ccatcgccag caatattggt ggcaagcagg cgctggagac ggtgcaggcg 1080
ctgttgccgg tgctgtgcca ggcccacggc ttgacccccc agcaggtggt ggccatcgcc 1140
agcaataatg gtggcaagca ggcgctggag acggtccagc ggctgttgcc ggtgctgtgc 1200
caggcccacg gcttgacccc ggagcaggtg gtggccatcg ccagcaatat tggtggcaag 1260
caggcgctgg agacggtgca ggcgctgttg ccggtgctgt gccaggccca cggcttgacc 1320

-continued

```
ccggagcagg tggtggccat cgccagccac gatggcggca agcaggcgct ggagacggtc   1380

cagcggctgt tgccggtgct gtgccaggcc cacggcttga ccccggagca ggtggtggcc   1440

atcgccagca atattggtgg caagcaggcg ctggagacgg tgcaggcgct gttgccggtg   1500

ctgtgccagg cccacggctt gaccccccag caggtggtgg ccatcgccag caataatggt   1560

ggcaagcagg cgctggagac ggtccagcgg ctgttgccgg tgctgtgcca ggcccacggc   1620

ttgacccccc agcaggtggt ggccatcgcc agcaataatg gtggcaagca ggcgctggag   1680

acggtccagc ggctgttgcc ggtgctgtgc caggcccacg gcttgacccc ccagcaggtg   1740

gtggccatcg ccagcaataa tggtggcaag caggcgctgg agacggtcca gcggctgttg   1800

ccggtgctgt gccaggccca cggcttgacc ccggagcagg tggtggccat cgccagcaat   1860

attggtggca agcaggcgct ggagacggtg caggcgctgt tgccggtgct gtgccaggcc   1920

cacggcttga ccccccagca ggtggtggcc atcgccagca atggcggtgg caagcaggcg   1980

ctggagacgg tccagcggct gttgccggtg ctgtgccagg cccacggctt gacccctcag   2040

caggtggtgg ccatcgccag caatggcggc ggcaggccgg cgctggagag cattgttgcc   2100

cagttatctc gccctgatcc ggcgttggcc gcgttgacca acgaccacct cgtcgccttg   2160

gcctgcctcg gcgggcgtcc tgcgctggat gcagtgaaaa agggattggg ggatcctatc   2220

agccgttccc agctggtgaa gtccgagctg gaggagaaga aatccgagtt gaggcacaag   2280

ctgaagtacg tgccccacga gtacatcgag ctgatcgaga tcgcccggaa cagcacccag   2340

gaccgtatcc tggagatgaa ggtgatggag ttcttcatga aggtgtacgg ctacaggggc   2400

aagcacctgg gcggctccag gaagcccgac ggcgccatct acaccgtggg ctcccccatc   2460

gactacggcg tgatcgtgga caccaaggcc tactccggcg gctacaacct gcccatcggc   2520

caggccgacg aaatgcagag gtacgtggag gagaaccaga ccaggaacaa gcacatcaac   2580

cccaacgagt ggtggaaggt gtacccctcc agcgtgaccg agttcaagtt cctgttcgtg   2640

tccggccact tcaagggcaa ctacaaggcc cagctgacca ggctgaacca catcaccaac   2700

tgcaacggcg ccgtgctgtc cgtggaggag ctcctgatcg gcggcgagat gatcaaggcc   2760

ggcaccctga ccctggagga ggtgaggagg aagttcaaca acggcgagat caacttcgcg   2820

gccgactgat aa                                                       2832
```

<210> SEQ ID NO 91
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: CTLA4_T03-L TALEN

<400> SEQUENCE: 91

```
atgggcgatc ctaaaaagaa acgtaaggtc atcgattacc catacgatgt tccagattac     60

gctatcgata tcgccgatct acgcacgctc ggctacagcc agcagcaaca ggagaagatc    120

aaaccgaagg ttcgttcgac agtggcgcag caccacgagg cactggtcgg ccacgggttt    180

acacacgcgc acatcgttgc gttaagccaa cacccggcag cgttagggac cgtcgctgtc    240

aagtatcagg acatgatcgc agcgttgcca gaggcgacac acgaagcgat cgttggcgtc    300

ggcaaacagt ggtccggcgc acgcgctctg gaggccttgc tcacggtggc gggagagttg    360

agaggtccac cgttacagtt ggacacaggc caacttctca agattgcaaa acgtggcggc    420
```

-continued

```
gtgaccgcag tggaggcagt gcatgcatgg cgcaatgcac tgacgggtgc cccgctcaac    480
ttgaccccccc agcaggtggt ggccatcgcc agcaatggcg gtggcaagca ggcgctggag    540
acggtccagc ggctgttgcc ggtgctgtgc caggcccacg gcttgacccc ccagcaggtg    600
gtggccatcg ccagcaatgg cggtggcaag caggcgctgg agacggtcca gcggctgttg    660
ccggtgctgt gccaggccca cggcttgacc ccccagcagg tggtggccat cgccagcaat    720
ggcggtggca agcaggcgct ggagacggtc cagcggctgt tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccgg agcaggtggt ggccatcgcc   1020
agcaatattg gtggcaagca ggcgctggag acggtgcagg cgctgttgcc ggtgctgtgc   1080
caggcccacg gcttgacccc ccagcaggtg gtggccatcg ccagcaatgg cggtggcaag   1140
caggcgctgg agacggtcca gcggctgttg ccggtgctgt gccaggccca cggcttgacc   1200
ccccagcagg tggtggccat cgccagcaat aatggtggca agcaggcgct ggagacggtc   1260
cagcggctgt tgccggtgct gtgccaggcc cacggcttga ccccggagca ggtggtggcc   1320
atcgccagcc acgatggcgg caagcaggcg ctggagacgg tccagcggct gttgccggtg   1380
ctgtgccagg cccacggctt gacccccag caggtggtgg ccatcgccag caatggcggt   1440
ggcaagcagg cgctggagac ggtccagcgg ctgttgccgg tgctgtgcca ggcccacggc   1500
ttgaccccgg agcaggtggt ggccatcgcc agcaatattg gtggcaagca ggcgctggag   1560
acggtgcagg cgctgttgcc ggtgctgtgc caggcccacg gcttgacccc ccagcaggtg   1620
gtggccatcg ccagcaataa tggtggcaag caggcgctgg agacggtcca gcggctgttg   1680
ccggtgctgt gccaggccca cggcttgacc ccggagcagg tggtggccat cgccagccac   1740
gatggcggca agcaggcgct ggagacggtc cagcggctgt tgccggtgct gtgccaggcc   1800
cacggcttga ccccggagca ggtggtggcc atcgccagca atattggtgg caagcaggcg   1860
ctggagacgg tgcaggcgct gttgccggtg ctgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg gggatcccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg gccaggccga cgaaatgcag   2520
aggtacgtgg aggagaacca gaccaggaac aagcacatca accccaacga gtggtggaag   2580
gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gaccctggag   2760
gaggtgagga ggaagttcaa caacggcgag atcaacttcg cggccgactg ataa         2814
```

<210> SEQ ID NO 92
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: CTLA4_T03-RTALEN

<400> SEQUENCE: 92
atgggcgatc ctaaaaagaa acgtaaggtc atcgataagg agaccgccgc tgccaagttc 60
gagagacagc acatggacag catcgatatc gccgatctac gcacgctcgg ctacagccag 120
cagcaacagg agaagatcaa accgaaggtt cgttcgacag tggcgcagca ccacgaggca 180
ctggtcggcc acgggtttac acacgcgcac atcgttgcgt taagccaaca cccggcagcg 240
ttagggaccg tcgctgtcaa gtatcaggac atgatcgcag cgttgccaga ggcgacacac 300
gaagcgatcg ttggcgtcgg caaacagtgg tccggcgcac gcgctctgga ggccttgctc 360
acggtggcgg gagagttgag aggtccaccg ttacagttgg acacaggcca acttctcaag 420
attgcaaaac gtggcggcgt gaccgcagtg gaggcagtgc atgcatggcg caatgcactg 480
acgggtgccc cgctcaactt gaccccccag caggtggtgg ccatcgccag caataatggt 540
ggcaagcagg cgctggagac ggtccagcgg ctgttgccgg tgctgtgcca ggcccacggc 600
ttgacccccc agcaggtggt ggccatcgcc agcaataatg gtggcaagca ggcgctggag 660
acggtccagc ggctgttgcc ggtgctgtgc caggcccacg gcttgacccc ggagcaggtg 720
gtggccatcg ccagccacga tggcggcaag caggcgctgg agacggtcca gcggctgttg 780
ccggtgctgt gccaggccca cggcttgacc ccggagcagg tggtggccat cgccagccac 840
gatggcggca agcaggcgct ggagacggtc cagcggctgt tgccggtgct gtgccaggcc 900
cacggcttga ccccggagca ggtggtggcc atcgccagca atattggtgg caagcaggcg 960
ctggagacgg tgcaggcgct gttgccggtg ctgtgccagg cccacggctt gacccccag 1020 caggtggtgg ccatcgccag caataatggt ggcaagcagg cgctggagac ggtccagcgg 1080
ctgttgccgg tgctgtgcca ggcccacggc ttgacccccc agcaggtggt ggccatcgcc 1140
agcaatggcg gtggcaagca ggcgctggag acggtccagc ggctgttgcc ggtgctgtgc 1200
caggcccacg gcttgacccc ggagcaggtg gtggccatcg ccagcaatat tggtggcaag 1260
caggcgctgg agacggtgca ggcgctgttg ccggtgctgt gccaggccca cggcttgacc 1320
ccggagcagg tggtggccat cgccagccac gatggcggca agcaggcgct ggagacggtc 1380
cagcggctgt tgccggtgct gtgccaggcc cacggcttga ccccggagca ggtggtggcc 1440
atcgccagcc acgatggcgg caagcaggcg ctggagacgg tccagcggct gttgccggtg 1500
ctgtgccagg cccacggctt gaccccggag caggtggtgg ccatcgccag caatattggt 1560
ggcaagcagg cgctggagac ggtgcaggcg ctgttgccgg tgctgtgcca ggcccacggc 1620
ttgaccccgg agcaggtggt ggccatcgcc agccacgatg gcggcaagca ggcgctggag 1680
acggtccagc ggctgttgcc ggtgctgtgc caggcccacg gcttgacccc ggagcaggtg 1740
gtggccatcg ccagcaatat tggtggcaag caggcgctgg agacggtgca ggcgctgttg 1800
ccggtgctgt gccaggccca cggcttgacc ccccagcagg tggtggccat cgccagcaat 1860
aatggtggca agcaggcgct ggagacggtc cagcggctgt tgccggtgct gtgccaggcc 1920
cacggcttga ccccggagca ggtggtggcc atcgccagcc acgatggcgg caagcaggcg 1980
ctggagacgg tccagcggct gttgccggtg ctgtgccagg cccacggctt gacccctcag 2040
caggtggtgg ccatcgccag caatggcggc ggcaggccgg cgctggagag cattgttgcc 2100
cagttatctc gccctgatcc ggcgttggcc gcgttgacca acgaccacct cgtcgccttg 2160
gcctgcctcg gcgggcgtcc tgcgctggat gcagtgaaaa agggattggg ggatcctatc 2220
agccgttccc agctggtgaa gtccgagctg gaggagaaga aatccgagtt gaggcacaag 2280
ctgaagtacg tgccccacga gtacatcgag ctgatcgaga tcgcccggaa cagcacccag 2340
gaccgtatcc tggagatgaa ggtgatggag ttcttcatga aggtgtacgg ctacaggggc 2400
aagcacctgg gcggctccag gaagcccgac ggcgccatct acaccgtggg ctcccccatc 2460
gactacggcg tgatcgtgga caccaaggcc tactccggcg gctacaacct gcccatcggc 2520
caggccgacg aaatgcagag gtacgtggag gagaaccaga ccaggaacaa gcacatcaac 2580
cccaacgagt ggtggaaggt gtacccctcc agcgtgaccg agttcaagtt cctgttcgtg 2640
tccggccact tcaagggcaa ctacaaggcc cagctgacca ggctgaacca catcaccaac 2700
tgcaacggcg ccgtgctgtc cgtggaggag ctcctgatcg gcggcgagat gatcaaggcc 2760
ggcaccctga ccctggagga ggtgaggagg aagttcaaca acggcgagat caacttcgcg 2820
gccgactgat aa 2832

<210> SEQ ID NO 93
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: CTLA4_T04-L TALEN

<400> SEQUENCE: 93
atgggcgatc ctaaaaagaa acgtaaggtc atcgattacc catacgatgt tccagattac 60
gctatcgata tcgccgatct acgcacgctc ggctacagcc agcagcaaca ggagaagatc 120
aaaccgaagg ttcgttcgac agtggcgcag caccacgagg cactggtcgg ccacgggttt 180
acacacgcgc acatcgttgc gttaagccaa cacccggcag cgttagggac cgtcgctgtc 240
aagtatcagg acatgatcgc agcgttgcca gaggcgacac acgaagcgat cgttggcgtc 300
ggcaaacagt ggtccggcgc acgcgctctg gaggccttgc tcacggtggc gggagagttg 360
agaggtccac cgttacagtt ggacacaggc caacttctca agattgcaaa acgtggcggc 420
gtgaccgcag tggaggcagt gcatgcatgg cgcaatgcac tgacgggtgc cccgctcaac 480
ttgaccccgg agcaggtggt ggccatcgcc agccacgatg gcggcaagca ggcgctggag 540
acggtccagc ggctgttgcc ggtgctgtgc caggcccacg gcttgacccc ggagcaggtg 600
gtggccatcg ccagccacga tggcggcaag caggcgctgg agacggtcca gcggctgttg 660
ccggtgctgt gccaggccca cggcttgacc ccggagcagg tggtggccat cgccagcaat 720
attggtggca agcaggcgct ggagacggtg caggcgctgt tgccggtgct gtgccaggcc 780
cacggcttga ccccccagca ggtggtggcc atcgccagca atggcggtgg caagcaggcg 840
ctggagacgg tccagcggct gttgccggtg ctgtgccagg cccacggctt gacccccag 900 caggtggtgg ccatcgccag caataatggt ggcaagcagg cgctggagac ggtccagcgg 960
ctgttgccgg tgctgtgcca ggcccacggc ttgaccccgg agcaggtggt ggccatcgcc 1020
agccacgatg gcggcaagca ggcgctggag acggtccagc ggctgttgcc ggtgctgtgc 1080
caggcccacg gcttgacccc ccagcaggtg gtggccatcg ccagcaatgg cggtggcaag 1140
caggcgctgg agacggtcca gcggctgttg ccggtgctgt gccaggccca cggcttgacc 1200
ccggagcagg tggtggccat cgccagcaat attggtggca agcaggcgct ggagacggtg 1260
caggcgctgt tgccggtgct gtgccaggcc cacggcttga ccccccagca ggtggtggcc 1320
atcgccagca ataatggtgg caagcaggcg ctggagacgg tccagcggct gttgccggtg 1380
ctgtgccagg cccacggctt gaccccggag caggtggtgg ccatcgccag ccacgatggc 1440
ggcaagcagg cgctggagac ggtccagcgg ctgttgccgg tgctgtgcca ggcccacggc 1500
ttgaccccgg agcaggtggt ggccatcgcc agcaatattg gtggcaagca ggcgctggag 1560
acggtgcagg cgctgttgcc ggtgctgtgc caggcccacg gcttgacccc ggagcaggtg 1620
gtggccatcg ccagcaatat tggtggcaag caggcgctgg agacggtgca ggcgctgttg 1680
ccggtgctgt gccaggccca cggcttgacc ccccagcagg tggtggccat cgccagcaat 1740
ggcggtggca agcaggcgct ggagacggtc cagcggctgt tgccggtgct gtgccaggcc 1800
cacggcttga ccccccagca ggtggtggcc atcgccagca ataatggtgg caagcaggcg 1860
ctggagacgg tccagcggct gttgccggtg ctgtgccagg cccacggctt gaccccggag 1920
caggtggtgg ccatcgccag ccacgatggc ggcaagcagg cgctggagac ggtccagcgg 1980
ctgttgccgg tgctgtgcca ggcccacggc ttgacccctc agcaggtggt ggccatcgcc 2040
agcaatggcg gcggcaggcc ggcgctggag agcattgttg cccagttatc tcgccctgat 2100
ccggcgttgg ccgcgttgac caacgaccac ctcgtcgcct tggcctgcct cggcgggcgt 2160
cctgcgctgg atgcagtgaa aaagggattg gggggatccta tcagccgttc ccagctggtg 2220
aagtccgagc tggaggagaa gaaatccgag ttgaggcaca agctgaagta cgtgccccac 2280
gagtacatcg agctgatcga gatcgcccgg aacagcaccc aggaccgtat cctggagatg 2340
aaggtgatgg agttcttcat gaaggtgtac ggctacaggg gcaagcacct gggcggctcc 2400
aggaagcccg acggcgccat ctacaccgtg ggctccccca tcgactacgg cgtgatcgtg 2460
gacaccaagg cctactccgg cggctacaac ctgcccatcg gccaggccga cgaaatgcag 2520
aggtacgtgg aggagaacca gaccaggaac aagcacatca accccaacga gtggtggaag 2580
gtgtacccct ccagcgtgac cgagttcaag ttcctgttcg tgtccggcca cttcaagggc 2640
aactacaagg cccagctgac caggctgaac cacatcacca actgcaacgg cgccgtgctg 2700
tccgtggagg agctcctgat cggcggcgag atgatcaagg ccggcaccct gaccctggag 2760
gaggtgagga ggaagttcaa caacggcgag atcaacttcg cggccgactg ataa 2814

<210> SEQ ID NO 94
<211> LENGTH: 2832
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: CTLA4_T04-R TALEN

<400> SEQUENCE: 94
atgggcgatc ctaaaaagaa acgtaaggtc atcgataagg agaccgccgc tgccaagttc 60
gagagacagc acatggacag catcgatatc gccgatctac gcacgctcgg ctacagccag 120
cagcaacagg agaagatcaa accgaaggtt cgttcgacag tggcgcagca ccacgaggca 180
ctggtcggcc acgggtttac acacgcgcac atcgttgcgt taagccaaca cccggcagcg 240
ttagggaccg tcgctgtcaa gtatcaggac atgatcgcag cgttgccaga ggcgacacac 300

-continued

```
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccccag caggtggtgg ccatcgccag caataatggt    540
ggcaagcagg cgctggagac ggtccagcgg ctgttgccgg tgctgtgcca ggcccacggc    600
ttgaccccgg agcaggtggt ggccatcgcc agccacgatg gcggcaagca ggcgctggag    660
acggtccagc ggctgttgcc ggtgctgtgc caggcccacg gcttgacccc ccagcaggtg    720
gtggccatcg ccagcaatgg cggtggcaag caggcgctgg agacggtcca gcggctgttg    780
ccggtgctgt gccaggccca cggcttgacc ccccagcagg tggtggccat cgccagcaat    840
aatggtggca agcaggcgct ggagacggtc cagcggctgt tgccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgaccccgg agcaggtggt ggccatcgcc   1140
agccacgatg gcggcaagca ggcgctggag acggtccagc ggctgttgcc ggtgctgtgc   1200
caggcccacg gcttgacccc ggagcaggtg gtggccatcg ccagcaatat tggtggcaag   1260
caggcgctgg agacggtgca ggcgctgttg ccggtgctgt gccaggccca cggcttgacc   1320
ccccagcagg tggtggccat cgccagcaat aatggtggca agcaggcgct ggagacggtc   1380
cagcggctgt tgccggtgct gtgccaggcc cacggcttga ccccccagca ggtggtggcc   1440
atcgccagca atggcggtgg caagcaggcg ctggagacgg tccagcggct gttgccggtg   1500
ctgtgccagg cccacggctt gaccccggag caggtggtgg ccatcgccag caatattggt   1560
ggcaagcagg cgctggagac ggtgcaggcg ctgttgccgg tgctgtgcca ggcccacggc   1620
ttgaccccgg agcaggtggt ggccatcgcc agccacgatg gcggcaagca ggcgctggag   1680
acggtccagc ggctgttgcc ggtgctgtgc caggcccacg gcttgacccc ggagcaggtg   1740
gtggccatcg ccagccacga tggcggcaag caggcgctgg agacggtcca gcggctgttg   1800
ccggtgctgt gccaggccca cggcttgacc ccggagcagg tggtggccat cgccagcaat   1860
attggtggca agcaggcgct ggagacggtg caggcgctgt tgccggtgct gtgccaggcc   1920
cacggcttga ccccggagca ggtggtggcc atcgccagcc acgatggcgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtacccctcc agcgtgaccg agttcaagtt cctgttcgtg   2640
tccggccact tcaagggcaa ctacaaggcc cagctgacca ggctgaacca catcaccaac   2700
```

```
tgcaacggcg ccgtgctgtc cgtggaggag ctcctgatcg gcggcgagat gatcaaggcc   2760

ggcaccctga ccctggagga ggtgaggagg aagttcaaca acggcgagat caacttcgcg   2820

gccgactgat aa                                                       2832
```

<210> SEQ ID NO 95
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: PDCD1_T01-L TALEN

<400> SEQUENCE: 95

```
atgggcgatc ctaaaaagaa acgtaaggtc atcgattacc catacgatgt tccagattac     60

gctatcgata tcgccgatct acgcacgctc ggctacagcc agcagcaaca ggagaagatc    120

aaaccgaagg ttcgttcgac agtggcgcag caccacgagg cactggtcgg ccacgggttt    180

acacacgcgc acatcgttgc gttaagccaa cacccggcag cgttagggac cgtcgctgtc    240

aagtatcagg acatgatcgc agcgttgcca gaggcgacac acgaagcgat cgttggcgtc    300

ggcaaacagt ggtccggcgc acgcgctctg gaggccttgc tcacggtggc gggagagttg    360

agaggtccac cgttacagtt ggacacaggc caacttctca agattgcaaa acgtggcggc    420

gtgaccgcag tggaggcagt gcatgcatgg cgcaatgcac tgacgggtgc cccgctcaac    480

ttgacccccc agcaggtggt ggccatcgcc agcaatggcg gtggcaagca ggcgctggag    540

acggtccagc ggctgttgcc ggtgctgtgc caggcccacg gcttgacccc ggagcaggtg    600

gtggccatcg ccagccacga tggcggcaag caggcgctgg agacggtcca gcggctgttg    660

ccggtgctgt gccaggccca cggcttgacc ccccagcagg tggtggccat cgccagcaat    720

ggcggtggca agcaggcgct ggagacggtc cagcggctgt tgccggtgct gtgccaggcc    780

cacggcttga ccccggagca ggtggtggcc atcgccagcc acgatggcgg caagcaggcg    840

ctggagacgg tccagcggct gttgccggtg ctgtgccagg cccacggctt gaccccggag    900

caggtggtgg ccatcgccag ccacgatggc ggcaagcagg cgctggagac ggtccagcgg    960

ctgttgccgg tgctgtgcca ggcccacggc ttgaccccgg agcaggtggt ggccatcgcc   1020

agccacgatg gcggcaagca ggcgctggag acggtccagc ggctgttgcc ggtgctgtgc   1080

caggcccacg gcttgacccc ggagcaggtg gtggccatcg ccagccacga tggcggcaag   1140

caggcgctgg agacggtcca gcggctgttg ccggtgctgt gccaggccca cggcttgacc   1200

ccggagcagg tggtggccat cgccagcaat attggtggca agcaggcgct ggagacggtg   1260

caggcgctgt tgccggtgct gtgccaggcc cacggcttga ccccccagca ggtggtggcc   1320

atcgccagca ataatggtgg caagcaggcg ctggagacgg tccagcggct gttgccggtg   1380

ctgtgccagg cccacggctt gaccccggag caggtggtgg ccatcgccag ccacgatggc   1440

ggcaagcagg cgctggagac ggtccagcgg ctgttgccgg tgctgtgcca ggcccacggc   1500

ttgaccccgg agcaggtggt ggccatcgcc agccacgatg gcggcaagca ggcgctggag   1560

acggtccagc ggctgttgcc ggtgctgtgc caggcccacg gcttgacccc ggagcaggtg   1620

gtggccatcg ccagccacga tggcggcaag caggcgctgg agacggtcca gcggctgttg   1680

ccggtgctgt gccaggccca cggcttgacc ccccagcagg tggtggccat cgccagcaat   1740

ggcggtggca agcaggcgct ggagacggtc cagcggctgt tgccggtgct gtgccaggcc   1800
```

-continued

```
cacggcttga ccccccagca ggtggtggcc atcgccagca ataatggtgg caagcaggcg   1860

ctggagacgg tccagcggct gttgccggtg ctgtgccagg cccacggctt gaccccggag   1920

caggtggtgg ccatcgccag ccacgatggc ggcaagcagg cgctggagac ggtccagcgg   1980

ctgttgccgg tgctgtgcca ggcccacggc ttgacccctc agcaggtggt ggccatcgcc   2040

agcaatggcg gcggcaggcc ggcgctggag agcattgttg cccagttatc tcgccctgat   2100

ccggcgttgg ccgcgttgac caacgaccac ctcgtcgcct tggcctgcct cggcgggcgt   2160

cctgcgctgg atgcagtgaa aaagggattg gggatcccta tcagccgttc ccagctggtg   2220

aagtccgagc tggaggagaa gaaatccgag ttgaggcaca agctgaagta cgtgccccac   2280

gagtacatcg agctgatcga gatcgcccgg aacagcaccc aggaccgtat cctggagatg   2340

aaggtgatgg agttcttcat gaaggtgtac ggctacaggg gcaagcacct gggcggctcc   2400

aggaagcccg acggcgccat ctacaccgtg ggctccccca tcgactacgg cgtgatcgtg   2460

gacaccaagg cctactccgg cggctacaac ctgcccatcg gccaggccga cgaaatgcag   2520

aggtacgtgg aggagaacca gaccaggaac aagcacatca accccaacga gtggtggaag   2580

gtgtacccct ccagcgtgac cgagttcaag ttcctgttcg tgtccggcca cttcaagggc   2640

aactacaagg cccagctgac caggctgaac cacatcacca actgcaacgg cgccgtgctg   2700

tccgtggagg agctcctgat cggcggcgag atgatcaagg ccggcaccct gaccctggag   2760

gaggtgagga ggaagttcaa caacggcgag atcaacttcg cggccgactg ataa         2814
```

```
<210> SEQ ID NO 96
<211> LENGTH: 2829
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: PDCD1_T01-R TALEN

<400> SEQUENCE: 96
```

```
atgggcgatc ctaaaaagaa acgtaaggtc atcgataagg agaccgccgc tgccaagttc     60

gagagacagc acatggacag catcgatatc gccgatctac gcacgctcgg ctacagccag    120

cagcaacagg agaagatcaa accgaaggtt cgttcgacag tggcgcagca ccacgaggca    180

ctggtcggcc acgggtttac acacgcgcac atcgttgcgt taagccaaca cccggcagcg    240

ttagggaccg tcgctgtcaa gtatcaggac atgatcgcag cgttgccaga ggcgacacac    300

gaagcgatcg ttggcgtcgg caaacagtgg tccggcgcac gcgctctgga ggccttgctc    360

acggtggcgg gagagttgag aggtccaccg ttacagttgg acacaggcca acttctcaag    420

attgcaaaac gtggcggcgt gaccgcagtg gaggcagtgc atgcatggcg caatgcactg    480

acgggtgccc cgctcaactt gaccccccag caagtcgtcg caatcgccag caataacgga    540

gggaagcaag ccctcgaaac cgtgcagcgg ttgcttcctg tgctctgcca ggcccacggc    600

cttacccctg agcaggtggt ggccatcgca agtaacattg gaggaaagca agccttggag    660

acagtgcagg ccctgttgcc cgtgctgtgc caggcacacg gcctcacacc agagcaggtc    720

gtggccattg cctccaacat cggggggaaa caggctctgg agaccgtcca ggccctgctg    780

cccgtcctct gtcaagctca cggcctgact ccccaacaag tggtcgccat cgcctctaat    840

aacggcggga agcaggcact ggaaacagtg cagagactgc tccctgtgct ttgccaagct    900

catgggttga ccccccaaca ggtcgtcgct attgcctcaa acaacggggg caagcaggcc    960

cttgagactg tgcagaggct gttgccagtg ctgtgtcagg ctcacgggct cactccacaa   1020
```

```
caggtggtcg caattgccag caacggcggc ggaaagcaag ctcttgaaac cgtgcaacgc   1080

ctcctgcccg tgctctgtca ggctcatggc ctgacaccac aacaagtcgt ggccatcgcc   1140

agtaataatg gcgggaaaca ggctcttgag accgtccaga ggctgctccc agtgctctgc   1200

caggcacacg ggctgacccc ccagcaggtg gtggctatcg ccagcaataa tgggggcaag   1260

caggccctgg aaacagtcca gcgcctgctg ccagtgcttt gccaggctca cgggctcact   1320

cccgaacagg tcgtggcaat cgcctccaac ggagggaagc aggctctgga gaccgtgcag   1380

agactgctgc ccgtcttgtg ccaggcccac ggactcacac ctcagcaggt cgtcgccatt   1440

gcctctaaca acgggggcaa acaagccctg gagacagtgc agcggctgtt gcctgtgttg   1500

tgccaagccc acggcttgac tcctcaacaa gtggtcgcca tcgcctcaaa tggcggcgga   1560

aaacaagctc tggagacagt gcagaggttg ctgcccgtcc tctgccaagc ccacggcctg   1620

actccccaac aggtcgtcgc cattgccagc aacggcggag gaaagcaggc tctcgaaact   1680

gtgcagcggc tgcttcctgt gctgtgtcag gctcatgggc tgacccccca gcaagtggtg   1740

gctattgcct ctaacaatgg aggcaagcaa gcccttgaga cagtccagag gctgttgcca   1800

gtgctgtgcc aggcccacgg gctcacaccc cagcaggtgg tcgccatcgc cagtaacggc   1860

gggggcaaac aggcattgga aaccgtccag cgcctgcttc cagtgctctg ccaggcacac   1920

ggactgacac ccgaacaggt ggtggccatt gcatcccatg atgggggcaa gcaggccctg   1980

gagaccgtgc agagactcct gccagtgttg tgccaagctc acggcctcac ccctcagcaa   2040

gtcgtggcca tcgcctcaaa cggggggggc cggcctgcac tggagagcat tgttgcccag   2100

ttatctcgcc ctgatccggc gttggccgcg ttgaccaacg accacctcgt cgccttggcc   2160

tgcctcggcg ggcgtcctgc gctggatgca gtgaaaaagg gattggggga tcctatcagc   2220

cgttcccagc tggtgaagtc cgagctggag gagaagaaat ccgagttgag gcacaagctg   2280

aagtacgtgc cccacgagta catcgagctg atcgagatcg cccggaacag cacccaggac   2340

cgtatcctgg agatgaaggt gatggagttc ttcatgaagg tgtacggcta caggggcaag   2400

cacctgggcg gctccaggaa gcccgacggc gccatctaca ccgtgggctc ccccatcgac   2460

tacggcgtga tcgtggacac caaggcctac tccggcggct acaacctgcc catcggccag   2520

gccgacgaaa tgcagaggta cgtggaggag aaccagacca ggaacaagca catcaacccc   2580

aacgagtggt ggaaggtgta cccctccagc gtgaccgagt tcaagttcct gttcgtgtcc   2640

ggccacttca agggcaacta caaggcccag ctgaccaggc tgaaccacat caccaactgc   2700

aacggcgccg tgctgtccgt ggaggagctc ctgatcggcg gcgagatgat caaggccggc   2760

accctgaccc tggaggaggt gaggaggaag ttcaacaacg gcgagatcaa cttcgcggcc   2820

gactgataa                                                           2829
```

<210> SEQ ID NO 97
<211> LENGTH: 2814
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: PDCD1_T03-L TALEN

<400> SEQUENCE: 97

```
atgggcgatc ctaaaaagaa acgtaaggtc atcgattacc catacgatgt tccagattac     60

gctatcgata tcgccgatct acgcacgctc ggctacagcc agcagcaaca ggagaagatc    120
```

-continued

```
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccccgg agcaggtggt ggccatcgcc agcaatattg gtggcaagca ggcgctggag    540
acggtgcagg cgctgttgcc ggtgctgtgc caggcccacg gcttgacccc ggagcaggtg    600
gtggccatcg ccagccacga tggcggcaag caggcgctgg agacggtcca gcggctgttg    660
ccggtgctgt gccaggccca cggcttgacc ccggagcagg tggtggccat cgccagccac    720
gatggcggca agcaggcgct ggagacggtc cagcggctgt tgccggtgct gtgccaggcc    780
cacggcttga ccccccagca ggtggtggcc atcgccagca atggcggtgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgacccccc agcaggtggt ggccatcgcc   1020
agcaatggcg gtggcaagca ggcgctggag acggtccagc ggctgttgcc ggtgctgtgc   1080
caggcccacg gcttgacccc ccagcaggtg gtggccatcg ccagcaataa tggtggcaag   1140
caggcgctgg agacggtcca gcggctgttg ccggtgctgt gccaggccca cggcttgacc   1200
ccccagcagg tggtggccat cgccagcaat ggcggtggca agcaggcgct ggagacggtc   1260
cagcggctgt tgccggtgct gtgccaggcc cacggcttga ccccccagca ggtggtggcc   1320
atcgccagca ataatggtgg caagcaggcg ctggagacgg tccagcggct gttgccggtg   1380
ctgtgccagg cccacggctt gacccccccag caggtggtgg ccatcgccag caataatggt   1440
ggcaagcagg cgctggagac ggtccagcgg ctgttgccgg tgctgtgcca ggcccacggc   1500
ttgacccccc agcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaataa tggtggcaag caggcgctgg agacggtcca gcggctgttg   1680
ccggtgctgt gccaggccca cggcttgacc ccggagcagg tggtggccat cgccagccac   1740
gatggcggca agcaggcgct ggagacggtc cagcggctgt tgccggtgct gtgccaggcc   1800
cacggcttga ccccggagca ggtggtggcc atcgccagcc acgatggcgg caagcaggcg   1860
ctggagacgg tccagcggct gttgccggtg ctgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg gggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg gccaggccga cgaaatgcag   2520
```

aggtacgtgg aggagaacca gaccaggaac aagcacatca accccaacga gtggtggaag 2580
gtgtacccct ccagcgtgac cgagttcaag ttcctgttcg tgtccggcca cttcaagggc 2640
aactacaagg cccagctgac caggctgaac cacatcacca actgcaacgg cgccgtgctg 2700
tccgtggagg agctcctgat cggcggcgag atgatcaagg ccggcaccct gaccctggag 2760
gaggtgagga ggaagttcaa caacggcgag atcaacttcg cggccgactg ataa 2814

<210> SEQ ID NO 98
<211> LENGTH: 2829
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: PDCD1_T03-R TALEN

<400> SEQUENCE: 98
atgggcgatc ctaaaaagaa acgtaaggtc atcgataagg agaccgccgc tgccaagttc 60
gagagacagc acatggacag catcgatatc gccgatctac gcacgctcgg ctacagccag 120
cagcaacagg agaagatcaa accgaaggtt cgttcgacag tggcgcagca ccacgaggca 180
ctggtcggcc acgggtttac acacgcgcac atcgttgcgt taagccaaca cccggcagcg 240
ttagggaccg tcgctgtcaa gtatcaggac atgatcgcag cgttgccaga ggcgacacac 300
gaagcgatcg ttggcgtcgg caaacagtgg tccggcgcac gcgctctgga ggccttgctc 360
acggtggcgg gagagttgag aggtccaccg ttacagttgg acacaggcca acttctcaag 420
attgcaaaac gtggcggcgt gaccgcagtg gaggcagtgc atgcatggcg caatgcactg 480
acgggtgccc cgctcaactt gacccccgag caagtcgtcg caatcgccag ccatgatgga 540
gggaagcaag ccctcgaaac cgtgcagcgg ttgcttcctg tgctctgcca ggcccacggc 600
cttacccctc agcaggtggt ggccatcgca agtaacggag gaggaaagca agccttggag 660
acagtgcagc gcctgttgcc cgtgctgtgc caggcacacg gcctcacacc agagcaggtc 720
gtggccattg cctcccatga cgggggggaaa caggctctgg agaccgtcca gaggctgctg 780
cccgtcctct gtcaagctca cggcctgact ccccaacaag tggtcgccat cgcctctaat 840
ggcggcggga agcaggcact ggaaacagtg cagagactgc tccctgtgct ttgccaagct 900
catgggttga ccccccaaca ggtcgtcgct attgcctcaa acgggggggg caagcaggcc 960
cttgagactg tgcagaggct gttgccagtg ctgtgtcagg ctcacgggct cactccacaa 1020
caggtggtcg caattgccag caacggcggc ggaaagcaag ctcttgaaac cgtgcaacgc 1080
ctcctgcccg tgctctgtca ggctcatggc ctgacaccac aacaagtcgt ggccatcgcc 1140
agtaataatg gcgggaaaca ggctcttgag accgtccaga ggctgctccc agtgctctgc 1200
caggcacacg ggctgacccc cgagcaggtg gtggctatcg ccagcaatat tgggggcaag 1260
caggccctgg aaacagtcca ggccctgctg ccagtgcttt gccaggctca cgggctcact 1320
ccccagcagg tcgtggcaat cgcctccaac ggcggaggga agcaggctct ggagaccgtg 1380
cagagactgc tgcccgtctt gtgccaggcc cacggactca cacctgaaca ggtcgtcgcc 1440
attgcctctc acgatggggg caaacaagcc ctggagacag tgcagcggct gttgcctgtg 1500
ttgtgccaag cccacggctt gactcctcaa caagtggtcg ccatcgcctc aaatggcggc 1560
ggaaaacaag ctctggagac agtgcagagg ttgctgcccg tcctctgcca agcccacggc 1620
ctgactcccc aacaggtcgt cgccattgcc agcaacaacg gaggaaagca ggctctcgaa 1680

-continued actgtgcagc ggctgcttcc tgtgctgtgt caggctcatg ggctgacccc cgagcaagtg 1740
gtggctattg cctctaatgg aggcaagcaa gcccttgaga cagtccagag gctgttgcca 1800
gtgctgtgcc aggcccacgg gctcacaccc cagcaggtgg tcgccatcgc cagtaacaac 1860
gggggcaaac aggcattgga aaccgtccag cgcctgcttc cagtgctctg ccaggcacac 1920
ggactgacac ccgaacaggt ggtggccatt gcatcccatg atgggggcaa gcaggccctg 1980
gagaccgtgc agagactcct gccagtgttg tgccaagctc acggcctcac ccctcagcaa 2040
gtcgtggcca tcgcctcaaa cggggggggc cggcctgcac tggagagcat tgttgcccag 2100
ttatctcgcc ctgatccggc gttggccgcg ttgaccaacg accacctcgt cgccttggcc 2160
tgcctcggcg ggcgtcctgc gctggatgca gtgaaaaagg gattggggga tcctatcagc 2220
cgttcccagc tggtgaagtc cgagctggag gagaagaaat ccgagttgag gcacaagctg 2280
aagtacgtgc cccacgagta catcgagctg atcgagatcg cccggaacag cacccaggac 2340
cgtatcctgg agatgaaggt gatggagttc ttcatgaagg tgtacggcta caggggcaag 2400
cacctgggcg gctccaggaa gcccgacggc gccatctaca ccgtgggctc ccccatcgac 2460
tacggcgtga tcgtggacac caaggcctac tccggcggct acaacctgcc catcggccag 2520
gccgacgaaa tgcagaggta cgtggaggag aaccagacca ggaacaagca catcaacccc 2580
aacgagtggt ggaaggtgta cccctccagc gtgaccgagt tcaagttcct gttcgtgtcc 2640
ggccacttca agggcaacta caaggcccag ctgaccaggc tgaaccacat caccaactgc 2700
aacggcgccg tgctgtccgt ggaggagctc ctgatcggcg gcgagatgat caaggccggc 2760
accctgaccc tggaggaggt gaggaggaag ttcaacaacg gcgagatcaa cttcgcggcc 2820
gactgataa 2829

<210> SEQ ID NO 99
<211> LENGTH: 60
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer for CTLA4_T01
<220> FEATURE:
<221> NAME/KEY: modified_base
<222> LOCATION: (31)..(40)
<223> OTHER INFORMATION: a or c or t or g

<400> SEQUENCE: 99
ccatctcatc cctgcgtgtc tccgactcag nnnnnnnnnn ctctacttcc tgaagacctg 60

<210> SEQ ID NO 100
<211> LENGTH: 60
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer for CTLA4_T03/T04
<220> FEATURE:
<221> NAME/KEY: modified_base
<222> LOCATION: (31)..(40)
<223> OTHER INFORMATION: a or c or t or g

<400> SEQUENCE: 100
ccatctcatc cctgcgtgtc tccgactcag nnnnnnnnnn acagttgaga gatggagggg 60

<210> SEQ ID NO 101
<211> LENGTH: 59

<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer for PDCD1_T01
<220> FEATURE:
<221> NAME/KEY: modified_base
<222> LOCATION: (31)..(40)
<223> OTHER INFORMATION: a or c or t or g

<400> SEQUENCE: 101
ccatctcatc cctgcgtgtc tccgactcag nnnnnnnnnn ccacagaggt aggtgccgc 59

<210> SEQ ID NO 102
<211> LENGTH: 60
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward composite primer for PDCD1_T03
<220> FEATURE:
<221> NAME/KEY: modified_base
<222> LOCATION: (31)..(40)
<223> OTHER INFORMATION: a or c or t or g

<400> SEQUENCE: 102
ccatctcatc cctgcgtgtc tccgactcag nnnnnnnnnn gacagagatg ccggtcacca 60

<210> SEQ ID NO 103
<211> LENGTH: 50
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Reverse composite primer for CTLA4_T01

<400> SEQUENCE: 103
cctatcccct gtgtgccttg gcagtctcag tggaatacag agccagccaa 50

<210> SEQ ID NO 104
<211> LENGTH: 50
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Reverse composite primer for CTLA4_T03/04

<400> SEQUENCE: 104
cctatcccct gtgtgccttg gcagtctcag ggtgcccgtg cagatggaat 50

<210> SEQ ID NO 105
<211> LENGTH: 50
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Reverse composite primer for PDCD1_T01, including SEQ ID NO: 132 and SEQ ID NO: 149

<400> SEQUENCE: 105
cctatcccct gtgtgccttg gcagtctcag ggctctgcag tggaggccag 50

<210> SEQ ID NO 106
<211> LENGTH: 50

```
<212> TYPE: DNA
<213> ORGANISM: Artificial sequence
<220> FEATURE:
<223> OTHER INFORMATION: Reverse composite primer for PDCD1_T03

<400> SEQUENCE: 106

cctatcccct gtgtgccttg gcagtctcag ggacaacgcc accttcacct                50


<210> SEQ ID NO 107
<211> LENGTH: 281
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-FL

<400> SEQUENCE: 107

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Ser Leu Gly Ala Phe Phe Arg Gly Asp Leu
            260                 265                 270

Pro Pro Pro Leu Gln Ala Gly Ala Ala
        275                 280


<210> SEQ ID NO 108
<211> LENGTH: 263
<212> TYPE: PRT
```

<213> ORGANISM: Artificial sequence
<220> FEATURE:
<223> OTHER INFORMATION: Synthetic polypeptide
<220> FEATURE:
<223> OTHER INFORMATION: pTalpha-Delta18

<400> SEQUENCE: 108

```
Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Ser
            260
```

<210> SEQ ID NO 109
<211> LENGTH: 233
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-Delta48

<400> SEQUENCE: 109

```
Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45
```

```
Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val
225                 230


<210> SEQ ID NO 110
<211> LENGTH: 219
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-Delta62

<400> SEQUENCE: 110

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160
```

```
Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg
    210                 215


<210> SEQ ID NO 111
<211> LENGTH: 203
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-Delta78

<400> SEQUENCE: 111

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly
        195                 200


<210> SEQ ID NO 112
<211> LENGTH: 189
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-Delta92

<400> SEQUENCE: 112

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
```

```
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg
            180                 185
```

<210> SEQ ID NO 113
<211> LENGTH: 171
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-Delta110

<400> SEQUENCE: 113

```
Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys
                165                 170
```

<210> SEQ ID NO 114

<211> LENGTH: 167
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-Delta114

<400> SEQUENCE: 114

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu
                165

<210> SEQ ID NO 115
<211> LENGTH: 344
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-FL-CD28

<400> SEQUENCE: 115

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
130 135 140

Gly Gly Ala Leu Trp Leu Gly Val Leu Arg Leu Leu Leu Phe Lys Leu
145 150 155 160

Leu Leu Phe Asp Leu Leu Leu Thr Cys Ser Cys Leu Cys Asp Pro Ala
165 170 175

Gly Pro Leu Pro Ser Pro Ala Thr Thr Thr Arg Leu Arg Ala Leu Gly
180 185 190

Ser His Arg Leu His Pro Ala Thr Glu Thr Gly Gly Arg Glu Ala Thr
195 200 205

Ser Ser Pro Arg Pro Gln Pro Arg Asp Arg Arg Trp Gly Asp Thr Pro
210 215 220

Pro Gly Arg Lys Pro Gly Ser Pro Val Trp Gly Glu Gly Ser Tyr Leu
225 230 235 240

Ser Ser Tyr Pro Thr Cys Pro Ala Gln Ala Trp Cys Ser Arg Ser Arg
245 250 255

Leu Arg Ala Pro Ser Ser Ser Leu Gly Ala Phe Phe Arg Gly Asp Leu
260 265 270

Pro Pro Pro Leu Gln Ala Gly Ala Ala Ala Ser Gly Gly Val Leu Ala
275 280 285

Cys Tyr Ser Leu Leu Val Thr Val Ala Phe Ile Ile Phe Trp Val Arg
290 295 300

Ser Lys Arg Ser Arg Gly Gly His Ser Asp Tyr Met Asn Met Thr Pro
305 310 315 320

Arg Arg Pro Gly Pro Thr Arg Lys His Tyr Gln Pro Tyr Ala Pro Pro
325 330 335

Arg Asp Phe Ala Ala Tyr Arg Ser
340

<210> SEQ ID NO 116
<211> LENGTH: 311
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-FL-CD8

<400> SEQUENCE: 116

Met Ala Gly Thr Trp Leu Leu Leu Leu Leu Ala Leu Gly Cys Pro Ala
1 5 10 15

Leu Pro Thr Gly Val Gly Gly Thr Pro Phe Pro Ser Leu Ala Pro Pro
20 25 30

Ile Met Leu Leu Val Asp Gly Lys Gln Gln Met Val Val Val Cys Leu
35 40 45

Val Leu Asp Val Ala Pro Pro Gly Leu Asp Ser Pro Ile Trp Phe Ser
50 55 60

Ala Gly Asn Gly Ser Ala Leu Asp Ala Phe Thr Tyr Gly Pro Ser Pro
65 70 75 80

Ala Thr Asp Gly Thr Trp Thr Asn Leu Ala His Leu Ser Leu Pro Ser
85 90 95

Glu Glu Leu Ala Ser Trp Glu Pro Leu Val Cys His Thr Gly Pro Gly
100 105 110

Ala Glu Gly His Ser Arg Ser Thr Gln Pro Met His Leu Ser Gly Glu
115 120 125

Ala Ser Thr Ala Arg Thr Cys Pro Gln Glu Pro Leu Arg Gly Thr Pro 130 135 140

Gly Gly Ala Leu Trp Leu Gly Val Leu Arg Leu Leu Leu Phe Lys Leu
145 150 155 160

Leu Leu Phe Asp Leu Leu Leu Thr Cys Ser Cys Leu Cys Asp Pro Ala
165 170 175

Gly Pro Leu Pro Ser Pro Ala Thr Thr Thr Arg Leu Arg Ala Leu Gly
180 185 190

Ser His Arg Leu His Pro Ala Thr Glu Thr Gly Gly Arg Glu Ala Thr
195 200 205

Ser Ser Pro Arg Pro Gln Pro Arg Asp Arg Arg Trp Gly Asp Thr Pro
210 215 220

Pro Gly Arg Lys Pro Gly Ser Pro Val Trp Gly Glu Gly Ser Tyr Leu
225 230 235 240

Ser Ser Tyr Pro Thr Cys Pro Ala Gln Ala Trp Cys Ser Arg Ser Arg
245 250 255

Leu Arg Ala Pro Ser Ser Ser Leu Gly Ala Phe Phe Arg Gly Asp Leu
260 265 270

Pro Pro Pro Leu Gln Ala Gly Ala Ala Ala Ser His Arg Asn Arg Arg
275 280 285

Arg Val Cys Lys Cys Pro Arg Pro Val Val Lys Ser Gly Asp Lys Pro
290 295 300

Ser Leu Ser Ala Arg Tyr Val
305 310

<210> SEQ ID NO 117
<211> LENGTH: 325
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-FL-41BB

<400> SEQUENCE: 117

Met Ala Gly Thr Trp Leu Leu Leu Leu Leu Ala Leu Gly Cys Pro Ala
1 5 10 15

Leu Pro Thr Gly Val Gly Gly Thr Pro Phe Pro Ser Leu Ala Pro Pro
20 25 30

Ile Met Leu Leu Val Asp Gly Lys Gln Gln Met Val Val Val Cys Leu
35 40 45

Val Leu Asp Val Ala Pro Pro Gly Leu Asp Ser Pro Ile Trp Phe Ser
50 55 60

Ala Gly Asn Gly Ser Ala Leu Asp Ala Phe Thr Tyr Gly Pro Ser Pro
65 70 75 80

Ala Thr Asp Gly Thr Trp Thr Asn Leu Ala His Leu Ser Leu Pro Ser
85 90 95

Glu Glu Leu Ala Ser Trp Glu Pro Leu Val Cys His Thr Gly Pro Gly
100 105 110

Ala Glu Gly His Ser Arg Ser Thr Gln Pro Met His Leu Ser Gly Glu
115 120 125

Ala Ser Thr Ala Arg Thr Cys Pro Gln Glu Pro Leu Arg Gly Thr Pro
130 135 140

Gly Gly Ala Leu Trp Leu Gly Val Leu Arg Leu Leu Leu Phe Lys Leu
145 150 155 160

Leu Leu Phe Asp Leu Leu Leu Thr Cys Ser Cys Leu Cys Asp Pro Ala
165 170 175

-continued

```
Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Ser Leu Gly Ala Phe Phe Arg Gly Asp Leu
            260                 265                 270

Pro Pro Pro Leu Gln Ala Gly Ala Ala Gly Ser Lys Arg Gly Arg Lys
        275                 280                 285

Lys Leu Leu Tyr Ile Phe Lys Gln Pro Phe Met Arg Pro Val Gln Thr
    290                 295                 300

Thr Gln Glu Glu Asp Gly Cys Ser Cys Arg Phe Pro Glu Glu Glu Glu
305                 310                 315                 320

Gly Gly Cys Glu Leu
                325


<210> SEQ ID NO 118
<211> LENGTH: 296
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-Delta48-CD28

<400> SEQUENCE: 118

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190
```

```
Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Ala Ser Gly Gly Val Leu Ala
225                 230                 235                 240

Cys Tyr Ser Leu Leu Val Thr Val Ala Phe Ile Ile Phe Trp Val Arg
                245                 250                 255

Ser Lys Arg Ser Arg Gly Gly His Ser Asp Tyr Met Asn Met Thr Pro
            260                 265                 270

Arg Arg Pro Gly Pro Thr Arg Lys His Tyr Gln Pro Tyr Ala Pro Pro
        275                 280                 285

Arg Asp Phe Ala Ala Tyr Arg Ser
    290                 295


<210> SEQ ID NO 119
<211> LENGTH: 263
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-Delta48-CD8

<400> SEQUENCE: 119

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Ala Ser His Arg Asn Arg Arg
225                 230                 235                 240

Arg Val Cys Lys Cys Pro Arg Pro Val Val Lys Ser Gly Asp Lys Pro
```

```
                245                 250                 255

Ser Leu Ser Ala Arg Tyr Val
            260


<210> SEQ ID NO 120
<211> LENGTH: 277
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha-Delta48-41BB

<400> SEQUENCE: 120

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Gly Ser Lys Arg Gly Arg Lys
225                 230                 235                 240

Lys Leu Leu Tyr Ile Phe Lys Gln Pro Phe Met Arg Pro Val Gln Thr
                245                 250                 255

Thr Gln Glu Glu Asp Gly Cys Ser Cys Arg Phe Pro Glu Glu Glu Glu
            260                 265                 270

Gly Gly Cys Glu Leu
        275


<210> SEQ ID NO 121
<211> LENGTH: 172
<212> TYPE: PRT
<213> ORGANISM: Artificial sequence
<220> FEATURE:
<223> OTHER INFORMATION: Synthetic polypeptide
<220> FEATURE:
```

<223> OTHER INFORMATION: pTalpha-Delta114-TCRalpha.IC

<400> SEQUENCE: 121

```
Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Arg Leu Trp Ser Ser
                165                 170
```

<210> SEQ ID NO 122
<211> LENGTH: 173
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha.EC-TCRalpha. TM. IC

<400> SEQUENCE: 122

```
Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Leu Ser Val Ile Gly Phe Arg Ile Leu Leu Leu Lys Val Ala
145                 150                 155                 160
```

Gly Phe Asn Leu Leu Met Thr Leu Arg Leu Trp Ser Ser
165 170

<210> SEQ ID NO 123
<211> LENGTH: 233
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha.EC-Delta48-1xMUT

<400> SEQUENCE: 123

Met Ala Gly Thr Trp Leu Leu Leu Leu Leu Ala Leu Gly Cys Pro Ala
1 5 10 15

Leu Pro Thr Gly Val Gly Gly Thr Pro Phe Pro Ser Leu Ala Pro Pro
20 25 30

Ile Met Leu Leu Val Asp Gly Lys Gln Gln Met Val Val Val Cys Leu
35 40 45

Val Leu Asp Val Ala Pro Pro Gly Leu Asp Ser Pro Ile Arg Phe Ser
50 55 60

Ala Gly Asn Gly Ser Ala Leu Asp Ala Phe Thr Tyr Gly Pro Ser Pro
65 70 75 80

Ala Thr Asp Gly Thr Trp Thr Asn Leu Ala His Leu Ser Leu Pro Ser
85 90 95

Glu Glu Leu Ala Ser Trp Glu Pro Leu Val Cys His Thr Gly Pro Gly
100 105 110

Ala Glu Gly His Ser Arg Ser Thr Gln Pro Met His Leu Ser Gly Glu
115 120 125

Ala Ser Thr Ala Arg Thr Cys Pro Gln Glu Pro Leu Arg Gly Thr Pro
130 135 140

Gly Gly Ala Leu Trp Leu Gly Val Leu Arg Leu Leu Leu Phe Lys Leu
145 150 155 160

Leu Leu Phe Asp Leu Leu Leu Thr Cys Ser Cys Leu Cys Asp Pro Ala
165 170 175

Gly Pro Leu Pro Ser Pro Ala Thr Thr Thr Arg Leu Arg Ala Leu Gly
180 185 190

Ser His Arg Leu His Pro Ala Thr Glu Thr Gly Gly Arg Glu Ala Thr
195 200 205

Ser Ser Pro Arg Pro Gln Pro Arg Asp Arg Arg Trp Gly Asp Thr Pro
210 215 220

Pro Gly Arg Lys Pro Gly Ser Pro Val
225 230

<210> SEQ ID NO 124
<211> LENGTH: 233
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: pTalpha.EC-Delta48-4xMUT

<400> SEQUENCE: 124

Met Ala Gly Thr Trp Leu Leu Leu Leu Leu Ala Leu Gly Cys Pro Ala
1 5 10 15

Leu Pro Thr Gly Val Gly Gly Thr Pro Phe Pro Ser Leu Ala Pro Pro
20 25 30

Ile Met Leu Leu Val Ala Gly Ala Gln Gln Met Val Val Val Cys Leu

```
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Ala Ser Thr Gln Pro Met His Leu Ser Gly Glu
        115                 120                 125

Ala Ser Thr Ala Ala Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val
225                 230
```

<210> SEQ ID NO 125
<211> LENGTH: 9
<212> TYPE: PRT
<213> ORGANISM: Unknown
<220> FEATURE:
<223> OTHER INFORMATION: “LAGLIDAG” family motif endonuclease sequence

<400> SEQUENCE: 125

```
Leu Ala Gly Leu Ile Asp Ala Asp Gly
1               5
```

<210> SEQ ID NO 126
<211> LENGTH: 30
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Forward adaptator sequence

<400> SEQUENCE: 126

```
ccatctcatc cctgcgtgtc tccgactcag                                        30
```

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for GR exon 2

<400> SEQUENCE: 127

```
ggttcattta acaagctgcc                                                   20
```

-continued

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for GR exon 3

<400> SEQUENCE: 128
gcattctgac tatgccgtga 20

<210> SEQ ID NO 129
<211> LENGTH: 29
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for GR exon 5

<400> SEQUENCE: 129
tcagcaggcc actacaggag tctcacaag 29

<210> SEQ ID NO 130
<211> LENGTH: 30
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Reverse adaptator sequence

<400> SEQUENCE: 130
cctatcccct gtgtgccttg gcagtctcag 30

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific reverse sequence for GR exon 2

<400> SEQUENCE: 131
agccagtgag ggtgaagacg 20

<210> SEQ ID NO 132
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific reverse sequence for GR exon 3

<400> SEQUENCE: 132
gggctttgca tataaatgga a 21

<210> SEQ ID NO 133
<211> LENGTH: 29
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific reverse sequence for GR exon 5

<400> SEQUENCE: 133
ctgactctcc ccttcatagt ccccagaac 29

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for CD52

<400> SEQUENCE: 134
cagatctgca gaaaggaagc 20

<210> SEQ ID NO 135
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for TRAC

<400> SEQUENCE: 135
atcactggca tctggactcc a 21

<210> SEQ ID NO 136
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for TRBC1

<400> SEQUENCE: 136
agagccccta ccagaaccag ac 22

<210> SEQ ID NO 137
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for TRBC2

<400> SEQUENCE: 137
ggacctagta acataattgt gc 22

<210> SEQ ID NO 138
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Endogenous locus specific reverse sequence for CD52

<400> SEQUENCE: 138
cctgttggag tccatctgct g 21

<210> SEQ ID NO 139
<211> LENGTH: 20

<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Endogenous locus specific reverse sequence for TRAC

<400> SEQUENCE: 139
cctcatgtct agcacagttt 20

<210> SEQ ID NO 140
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Endogenous locus specific reverse sequence for TRBC1 and TRBC2

<400> SEQUENCE: 140
accagctcag ctccacgtgg t 21

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for CTLA4_T01

<400> SEQUENCE: 141
ctctacttcc tgaagacctg 20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for CTLA4_T03/T04

<400> SEQUENCE: 142
acagttgaga gatggagggg 20

<210> SEQ ID NO 143
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for PDCD1_T01

<400> SEQUENCE: 143
ccacagaggt aggtgccgc 19

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Locus specific forward sequence for PDCD1_T03

<400> SEQUENCE: 144
gacagagatg ccggtcacca 20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Endogenous locus specific reverse sequence for CTLA4_T01

<400> SEQUENCE: 145
tggaatacag agccagccaa 20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Endogenous locus specific reverse sequence for CTLA4_T03/T04

<400> SEQUENCE: 146
ggtgcccgtg cagatggaat 20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Endogenous locus specific reverse sequence for PDCD1_T01

<400> SEQUENCE: 147
ggctctgcag tggaggccag 20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Endogenous locus specific reverse sequence for PDCD1_T03

<400> SEQUENCE: 148
ggacaacgcc accttcacct 20

<210> SEQ ID NO 149
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 149
ttgtcccaca gatatcc 17

<210> SEQ ID NO 150

<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 150
ttcctcctac tcaccat 17

<210> SEQ ID NO 151
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 151
ttgctctcac cagtata 17

<210> SEQ ID NO 152
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 152
tcactcttac ctggacc 17

<210> SEQ ID NO 153
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 153
tctcagatga tacaccc 17

<210> SEQ ID NO 154
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 154
tgatcccaca gaaatac 17

<210> SEQ ID NO 155
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 155
ttcctctaac ctgtatt 17

<210> SEQ ID NO 156
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 156
tagtccccca gatatga 17

<210> SEQ ID NO 157
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 157
ttgtcacaca tataccg 17

<210> SEQ ID NO 158
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 158
taactcttac ctgtagt 17

<210> SEQ ID NO 159
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 159
ttactccaac taactat 17

<210> SEQ ID NO 160
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 160
tggctcatac ctgtagt 17

<210> SEQ ID NO 161
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 161
ttgctcatac atgtgca 17

<210> SEQ ID NO 162
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 162
ttgtcccaca gacattc 17

<210> SEQ ID NO 163
<211> LENGTH: 17
<212> TYPE: DNA

<213> ORGANISM: Artificial sequence
<220> FEATURE:
<223> OTHER INFORMATION: Synthetic oligonucleotide

<400> SEQUENCE: 163
tcacacctgg tacatag 17

<210> SEQ ID NO 164
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 164
ttgtcccaca gctaccc 17

<210> SEQ ID NO 165
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 165
tctcaactga aacaagg 17

<210> SEQ ID NO 166
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 166
ccgtgtacca gctgaga 17

<210> SEQ ID NO 167
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 167
ggtacaggta agagcaa 17

<210> SEQ ID NO 168
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 168
ttttcaggta agtgcaa 17

<210> SEQ ID NO 169
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 169
cctacaggtt aagggcca 18

<210> SEQ ID NO 170
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 170
agtacaggca tgagcca 17

<210> SEQ ID NO 171
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 171
gcatttctgt gggatca 17

<210> SEQ ID NO 172
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 172
gatccaggta aggtcaa 17

<210> SEQ ID NO 173
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 173
aaggtgtgga tgaggaa 17

<210> SEQ ID NO 174
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 174
tggtatttgt gtgacaa 17

<210> SEQ ID NO 175
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 175
agatttctct ggggcaa 17

<210> SEQ ID NO 176
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 176
ccgtttaccg gcttaga 17

<210> SEQ ID NO 177
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 177
aggatgaggt ggaggaa 17

<210> SEQ ID NO 178
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 178
atgctgtgta ggtggta 17

<210> SEQ ID NO 179
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 179
ccacgtagca gctggga 17

<210> SEQ ID NO 180
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 180
gtgtttagta gggggaa 17

<210> SEQ ID NO 181
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 181
gagtctttgt aggacaa 17

<210> SEQ ID NO 182
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 182
tgtaatgtca agagcaa 17

<210> SEQ ID NO 183
<211> LENGTH: 109
<212> TYPE: DNA
<213> ORGANISM: homo sapiens
<220> FEATURE:

<400> SEQUENCE: 183
catgtcctaa ccctgatcct cttgtcccac agatatccag aaccctgacc ctgccgtgta 60
ccagctgaga gactctaaat ccagtgacaa gtcctattca ccgattttg 109

<210> SEQ ID NO 184
<211> LENGTH: 92
<212> TYPE: DNA
<213> ORGANISM: homo sapiens
<220> FEATURE:

<400> SEQUENCE: 184
catgtcctaa ccctgatcct cttgtcccac agatatccgt gtaccagctg agagactcta 60
aatccagtga caagtcctat tcaccgattt tg 92

<210> SEQ ID NO 185
<211> LENGTH: 100
<212> TYPE: DNA
<213> ORGANISM: homo sapiens
<220> FEATURE:

<400> SEQUENCE: 185
catgtcctaa ccctgatcct cttgtcccac agatatccag atatccgtgt accagctgag 60
agactctaaa tccagtgaca agtcctattc accgattttg 100

<210> SEQ ID NO 186
<211> LENGTH: 78
<212> TYPE: DNA
<213> ORGANISM: homo sapiens
<220> FEATURE:

<400> SEQUENCE: 186
catgtcctaa ccctcgatcc tgccgtgtac cagctgagag actctaaatc cagtgacaag 60
tcctattcac cgattttg 78

<210> SEQ ID NO 187
<211> LENGTH: 104
<212> TYPE: DNA
<213> ORGANISM: homo sapiens
<220> FEATURE:

<400> SEQUENCE: 187
catgtcctaa ccctgatcct cttgtcccac agatatccag aaccctgacc gtgtaccagc 60
tgagagactc taaatccagt gacaagtcct attcaccgat tttg 104

<210> SEQ ID NO 188
<211> LENGTH: 97
<212> TYPE: DNA
<213> ORGANISM: homo sapiens
<220> FEATURE:

<400> SEQUENCE: 188
catgtcctaa ccctgatcct cttgtcccac agatatccag aaccctgacc agctgagaga 60
ctctaaatcc agtgacaagt cctattcacc gattttg 97

<210> SEQ ID NO 189

<211> LENGTH: 45
<212> TYPE: DNA
<213> ORGANISM: homo sapiens
<220> FEATURE:

<400> SEQUENCE: 189
catgtcctaa ccctgatcct cttgtcccac agatatccag atttg 45

<210> SEQ ID NO 190
<211> LENGTH: 72
<212> TYPE: DNA
<213> ORGANISM: homo sapiens
<220> FEATURE:

<400> SEQUENCE: 190
catgtcctaa ccctgatcct cttgtcccac agagactcta aatccagtga caagtcctat 60
tcaccgattt tg 72

<210> SEQ ID NO 191
<211> LENGTH: 102
<212> TYPE: DNA
<213> ORGANISM: homo sapiens
<220> FEATURE:

<400> SEQUENCE: 191
catgtcctaa ccctgatcct cttgtcccac agatatccag aacctgccgt gtaccagctg 60
agagactcta aatccagtga caagtcctat tcaccgattt tg 102

<210> SEQ ID NO 192
<211> LENGTH: 82
<212> TYPE: DNA
<213> ORGANISM: homo sapiens
<220> FEATURE:

<400> SEQUENCE: 192
catgtcctaa ccctgatcct cttgtcccac agaccagctg agagactcta aatccagtga 60
caagtcctat tcaccgattt tg 82

<210> SEQ ID NO 193
<211> LENGTH: 121
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: scFV-fragment 4G7 (antigen: human CD19)VH

<400> SEQUENCE: 193

Glu Val Gln Leu Gln Gln Ser Gly Pro Glu Leu Ile Lys Pro Gly Ala
1 5 10 15

Ser Val Lys Met Ser Cys Lys Ala Ser Gly Tyr Thr Phe Thr Ser Tyr
20 25 30

Val Met His Trp Val Lys Gln Lys Pro Gly Gln Gly Leu Glu Trp Ile
35 40 45

Gly Tyr Ile Asn Pro Tyr Asn Asp Gly Thr Lys Tyr Asn Glu Lys Phe
50 55 60

Lys Gly Lys Ala Thr Leu Thr Ser Asp Lys Ser Ser Ser Thr Ala Tyr
65 70 75 80

Met Glu Leu Ser Ser Leu Thr Ser Glu Asp Ser Ala Val Tyr Tyr Cys
85 90 95

Ala Arg Gly Thr Tyr Tyr Tyr Gly Ser Arg Val Phe Asp Tyr Trp Gly

```
            100                 105                 110

Gln Gly Thr Thr Leu Thr Val Ser Ser
        115                 120


<210> SEQ ID NO 194
<211> LENGTH: 115
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: scFV 4G7 VL

<400> SEQUENCE: 194

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ala Asp
        115


<210> SEQ ID NO 195
<211> LENGTH: 251
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: scFV 4G7

<400> SEQUENCE: 195

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser Gly Gly Gly Gly Ser Gly Gly
        115                 120                 125

Gly Gly Ser Gly Gly Gly Gly Ser Asp Ile Val Met Thr Gln Ala Ala
    130                 135                 140
```

Pro Ser Ile Pro Val Thr Pro Gly Glu Ser Val Ser Ile Ser Cys Arg
145 150 155 160

Ser Ser Lys Ser Leu Leu Asn Ser Asn Gly Asn Thr Tyr Leu Tyr Trp
165 170 175

Phe Leu Gln Arg Pro Gly Gln Ser Pro Gln Leu Leu Ile Tyr Arg Met
180 185 190

Ser Asn Leu Ala Ser Gly Val Pro Asp Arg Phe Ser Gly Ser Gly Ser
195 200 205

Gly Thr Ala Phe Thr Leu Arg Ile Ser Arg Val Glu Ala Glu Asp Val
210 215 220

Gly Val Tyr Tyr Cys Met Gln His Leu Glu Tyr Pro Phe Thr Phe Gly
225 230 235 240

Ala Gly Thr Lys Leu Glu Leu Lys Arg Ala Asp
245 250

<210> SEQ ID NO 196
<211> LENGTH: 45
<212> TYPE: PRT
<213> ORGANISM: homo sapiens
<220> FEATURE:
<223> OTHER INFORMATION: Synthetic polypeptide
<220> FEATURE:
<223> OTHER INFORMATION: Fragment of CD8 alpha chain isoform 1 precursor

<400> SEQUENCE: 196

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 197
<211> LENGTH: 112
<212> TYPE: PRT
<213> ORGANISM: homo sapiens
<220> FEATURE:
<223> OTHER INFORMATION: Synthetic polypeptide
<220> FEATURE:
<223> OTHER INFORMATION: Fragment of CD3 zeta chain

<400> SEQUENCE: 197

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 198
<211> LENGTH: 21

<212> TYPE: PRT
<213> ORGANISM: homo sapiens
<220> FEATURE:
<223> OTHER INFORMATION: Activation motif of FcRI epsilon gamma chain

<400> SEQUENCE: 198

```
Asp Gly Val Tyr Thr Gly Leu Ser Thr Arg Asn Gln Glu Thr Tyr Glu
1               5                   10                  15

Thr Leu Lys His Glu
            20
```

<210> SEQ ID NO 199
<211> LENGTH: 17
<212> TYPE: PRT
<213> ORGANISM: homo sapiens
<220> FEATURE:
<223> OTHER INFORMATION: Activation motif of FcRI epsilon beta chain

<400> SEQUENCE: 199

```
Asp Arg Val Tyr Glu Glu Leu Asn Ile Tyr Ser Ala Thr Tyr Ser Glu
1               5                   10                  15

Leu
```

<210> SEQ ID NO 200
<211> LENGTH: 42
<212> TYPE: PRT
<213> ORGANISM: homo sapiens
<220> FEATURE:
<223> OTHER INFORMATION: Fragment of 4-1BB ligand receptor

<400> SEQUENCE: 200

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 201
<211> LENGTH: 41
<212> TYPE: PRT
<213> ORGANISM: homo sapiens
<220> FEATURE:
<223> OTHER INFORMATION: Fragment of surface glycoprotein CD28

<400> SEQUENCE: 201

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 202
<211> LENGTH: 257
<212> TYPE: PRT
<213> ORGANISM: homo sapiens
<220> FEATURE:
<223> OTHER INFORMATION: Epsilon receptor subunit alpha precursor

<400> SEQUENCE: 202

```
Met Ala Pro Ala Met Glu Ser Pro Thr Leu Leu Cys Val Ala Leu Leu
1               5                   10                  15
```

```
Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Phe Phe Ile
        195                 200                 205

Pro Leu Leu Val Val Ile Leu Phe Ala Val Asp Thr Gly Leu Phe Ile
    210                 215                 220

Ser Thr Gln Gln Gln Val Thr Phe Leu Leu Lys Ile Lys Arg Thr Arg
225                 230                 235                 240

Lys Gly Phe Arg Leu Leu Asn Pro His Pro Lys Pro Asn Pro Lys Asn
                245                 250                 255

Asn


<210> SEQ ID NO 203
<211> LENGTH: 244
<212> TYPE: PRT
<213> ORGANISM: homo sapiens
<220> FEATURE:
<223> OTHER INFORMATION: Epsilon receptor subunit beta isoform 1

<400> SEQUENCE: 203

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
```

```
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu Asp Arg Val Tyr Glu Glu Leu Asn Ile
    210                 215                 220

Tyr Ser Ala Thr Tyr Ser Glu Leu Glu Asp Pro Gly Glu Met Ser Pro
225                 230                 235                 240

Pro Ile Asp Leu


<210> SEQ ID NO 204
<211> LENGTH: 86
<212> TYPE: PRT
<213> ORGANISM: homo sapiens
<220> FEATURE:
<223> OTHER INFORMATION: Epsilon receptor subunit gamma precursor

<400> SEQUENCE: 204

Met Ile Pro Ala Val Val Leu Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85


<210> SEQ ID NO 205
<211> LENGTH: 25
<212> TYPE: PRT
<213> ORGANISM: homo sapiens
<220> FEATURE:
<223> OTHER INFORMATION: Signal peptide of Fc epsilon RI alpha chain

<400> SEQUENCE: 205

Met Ala Pro Ala Met Glu Ser Pro Thr Leu Leu Cys Val Ala Leu Leu
1               5                   10                  15

Phe Phe Ala Pro Asp Gly Val Leu Ala
            20                  25


<210> SEQ ID NO 206
<211> LENGTH: 373
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: FcRI alpha 4g7scFV-CD8 chain of multichain CAR
```

<400> SEQUENCE: 206

```
Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
            340                 345                 350

Lys Arg Thr Arg Lys Gly Phe Arg Leu Leu Asn Pro His Pro Lys Pro
        355                 360                 365

Asn Pro Lys Asn Asn
    370
```

<210> SEQ ID NO 207
<211> LENGTH: 415
<212> TYPE: PRT
<213> ORGANISM: Artificial sequence

```
<220> FEATURE:
<223> OTHER INFORMATION: Synthetic polypeptide
<220> FEATURE:
<223> OTHER INFORMATION: FcRI alpha-4g7scFV-CD8-4-1BB chain of
      multichain CAR

<400> SEQUENCE: 207

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
            340                 345                 350

Lys Arg Thr Arg Lys Gly Phe Arg Leu Leu Asn Pro His Pro Lys Pro
        355                 360                 365

Asn Pro Lys Asn Asn Lys Arg Gly Arg Lys Lys Leu Leu Tyr Ile Phe
    370                 375                 380
```

```
Lys Gln Pro Phe Met Arg Pro Val Gln Thr Thr Gln Glu Glu Asp Gly
385                 390                 395                 400

Cys Ser Cys Arg Phe Pro Glu Glu Glu Glu Gly Gly Cys Glu Leu
                405                 410                 415


<210> SEQ ID NO 208
<211> LENGTH: 257
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: FcRI beta-deltaITAM-41BB chain of multichain
      CAR

<400> SEQUENCE: 208

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu


<210> SEQ ID NO 209
<211> LENGTH: 369
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: FcRbeta-deltaITAM-41BB-CD3zeta chain of
```

multichain CAR

<400> SEQUENCE: 209

Met Asp Thr Glu Ser Asn Arg Arg Ala Asn Leu Ala Leu Pro Gln Glu
1 5 10 15

Pro Ser Ser Val Pro Ala Phe Glu Val Leu Glu Ile Ser Pro Gln Glu
20 25 30

Val Ser Ser Gly Arg Leu Leu Lys Ser Ala Ser Ser Pro Pro Leu His
35 40 45

Thr Trp Leu Thr Val Leu Lys Lys Glu Gln Glu Phe Leu Gly Val Thr
50 55 60

Gln Ile Leu Thr Ala Met Ile Cys Leu Cys Phe Gly Thr Val Val Cys
65 70 75 80

Ser Val Leu Asp Ile Ser His Ile Glu Gly Asp Ile Phe Ser Ser Phe
85 90 95

Lys Ala Gly Tyr Pro Phe Trp Gly Ala Ile Phe Phe Ser Ile Ser Gly
100 105 110

Met Leu Ser Ile Ile Ser Glu Arg Arg Asn Ala Thr Tyr Leu Val Arg
115 120 125

Gly Ser Leu Gly Ala Asn Thr Ala Ser Ser Ile Ala Gly Gly Thr Gly
130 135 140

Ile Thr Ile Leu Ile Ile Asn Leu Lys Lys Ser Leu Ala Tyr Ile His
145 150 155 160

Ile His Ser Cys Gln Lys Phe Phe Glu Thr Lys Cys Phe Met Ala Ser
165 170 175

Phe Ser Thr Glu Ile Val Val Met Met Leu Phe Leu Thr Ile Leu Gly
180 185 190

Leu Gly Ser Ala Val Ser Leu Thr Ile Cys Gly Ala Gly Glu Glu Leu
195 200 205

Lys Gly Asn Lys Val Pro Glu Lys Arg Gly Arg Lys Lys Leu Leu Tyr
210 215 220

Ile Phe Lys Gln Pro Phe Met Arg Pro Val Gln Thr Thr Gln Glu Glu
225 230 235 240

Asp Gly Cys Ser Cys Arg Phe Pro Glu Glu Glu Glu Gly Gly Cys Glu
245 250 255

Leu Arg Val Lys Phe Ser Arg Ser Ala Asp Ala Pro Ala Tyr Gln Gln
260 265 270

Gly Gln Asn Gln Leu Tyr Asn Glu Leu Asn Leu Gly Arg Arg Glu Glu
275 280 285

Tyr Asp Val Leu Asp Lys Arg Arg Gly Arg Asp Pro Glu Met Gly Gly
290 295 300

Lys Pro Arg Arg Lys Asn Pro Gln Glu Gly Leu Tyr Asn Glu Leu Gln
305 310 315 320

Lys Asp Lys Met Ala Glu Ala Tyr Ser Glu Ile Gly Met Lys Gly Glu
325 330 335

Arg Arg Arg Gly Lys Gly His Asp Gly Leu Tyr Gln Gly Leu Ser Thr
340 345 350

Ala Thr Lys Asp Thr Tyr Asp Ala Leu His Met Gln Ala Leu Pro Pro
355 360 365

Arg

<210> SEQ ID NO 210
<211> LENGTH: 286
<212> TYPE: PRT

<213> ORGANISM: Artificial sequence
<220> FEATURE:
<223> OTHER INFORMATION: Synthetic polypeptide
<220> FEATURE:
<223> OTHER INFORMATION: FcRbeta-41BB chain of the multi-chain CAR

<400> SEQUENCE: 210

```
Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu Asp Arg Val Tyr Glu Glu Leu Asn Ile
    210                 215                 220

Tyr Ser Ala Thr Tyr Ser Glu Leu Glu Asp Pro Gly Glu Met Ser Pro
225                 230                 235                 240

Pro Ile Asp Leu Lys Arg Gly Arg Lys Lys Leu Leu Tyr Ile Phe Lys
                245                 250                 255

Gln Pro Phe Met Arg Pro Val Gln Thr Thr Gln Glu Glu Asp Gly Cys
            260                 265                 270

Ser Cys Arg Phe Pro Glu Glu Glu Glu Gly Gly Cys Glu Leu
        275                 280                 285
```

<210> SEQ ID NO 211
<211> LENGTH: 327
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: FcRbeta-deltaITAM-CD3zeta chain of the multi-chain CAR

<400> SEQUENCE: 211

```
Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
```

```
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu Arg Val Lys Phe Ser Arg Ser Ala Asp
    210                 215                 220

Ala Pro Ala Tyr Gln Gln Gly Gln Asn Gln Leu Tyr Asn Glu Leu Asn
225                 230                 235                 240

Leu Gly Arg Arg Glu Glu Tyr Asp Val Leu Asp Lys Arg Arg Gly Arg
                245                 250                 255

Asp Pro Glu Met Gly Gly Lys Pro Arg Arg Lys Asn Pro Gln Glu Gly
            260                 265                 270

Leu Tyr Asn Glu Leu Gln Lys Asp Lys Met Ala Glu Ala Tyr Ser Glu
        275                 280                 285

Ile Gly Met Lys Gly Glu Arg Arg Arg Gly Lys Gly His Asp Gly Leu
    290                 295                 300

Tyr Gln Gly Leu Ser Thr Ala Thr Lys Asp Thr Tyr Asp Ala Leu His
305                 310                 315                 320

Met Gln Ala Leu Pro Pro Arg
                325


<210> SEQ ID NO 212
<211> LENGTH: 215
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: FcRgamma-delta ITAM-41BB-CD3zeta chain of
      multi-chain CAR

<400> SEQUENCE: 212

Met Ile Pro Ala Val Val Leu Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
```

```
        35                  40                  45

Gln Val Arg Lys Ala Ala Ile Thr Ser Tyr Glu Lys Ser Lys Arg Gly
    50                  55                  60

Arg Lys Lys Leu Leu Tyr Ile Phe Lys Gln Pro Phe Met Arg Pro Val
65                  70                  75                  80

Gln Thr Thr Gln Glu Glu Asp Gly Cys Ser Cys Arg Phe Pro Glu Glu
                85                  90                  95

Glu Glu Gly Gly Cys Glu Leu Arg Val Lys Phe Ser Arg Ser Ala Asp
            100                 105                 110

Ala Pro Ala Tyr Gln Gln Gly Gln Asn Gln Leu Tyr Asn Glu Leu Asn
        115                 120                 125

Leu Gly Arg Arg Glu Glu Tyr Asp Val Leu Asp Lys Arg Arg Gly Arg
    130                 135                 140

Asp Pro Glu Met Gly Gly Lys Pro Arg Arg Lys Asn Pro Gln Glu Gly
145                 150                 155                 160

Leu Tyr Asn Glu Leu Gln Lys Asp Lys Met Ala Glu Ala Tyr Ser Glu
                165                 170                 175

Ile Gly Met Lys Gly Glu Arg Arg Arg Gly Lys Gly His Asp Gly Leu
            180                 185                 190

Tyr Gln Gly Leu Ser Thr Ala Thr Lys Asp Thr Tyr Asp Ala Leu His
        195                 200                 205

Met Gln Ala Leu Pro Pro Arg
    210                 215


<210> SEQ ID NO 213
<211> LENGTH: 173
<212> TYPE: PRT
<213> ORGANISM: Artificial sequence
<220> FEATURE:
<223> OTHER INFORMATION: Synthetic polypeptide
<220> FEATURE:
<223> OTHER INFORMATION: FcRgamma-deltaITAM-CD3zeta chain of multi-chain
      CAR

<400> SEQUENCE: 213

Met Ile Pro Ala Val Val Leu Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Arg Val Lys
    50                  55                  60

Phe Ser Arg Ser Ala Asp Ala Pro Ala Tyr Gln Gln Gly Gln Asn Gln
65                  70                  75                  80

Leu Tyr Asn Glu Leu Asn Leu Gly Arg Arg Glu Glu Tyr Asp Val Leu
                85                  90                  95

Asp Lys Arg Arg Gly Arg Asp Pro Glu Met Gly Gly Lys Pro Arg Arg
            100                 105                 110

Lys Asn Pro Gln Glu Gly Leu Tyr Asn Glu Leu Gln Lys Asp Lys Met
        115                 120                 125

Ala Glu Ala Tyr Ser Glu Ile Gly Met Lys Gly Glu Arg Arg Arg Gly
    130                 135                 140

Lys Gly His Asp Gly Leu Tyr Gln Gly Leu Ser Thr Ala Thr Lys Asp
145                 150                 155                 160

Thr Tyr Asp Ala Leu His Met Gln Ala Leu Pro Pro Arg
```

165 170

<210> SEQ ID NO 214
<211> LENGTH: 1119
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRgamma-CD3zeta chain of multi-chain CAR

<400> SEQUENCE: 214
atggctcctg ccatggaatc ccctactcta ctgtgtgtag ccttactgtt cttcgctcca 60
gatggcgtgt tagcagaggt gcagttgcag cagtcagggc cagagttgat taagcccgga 120
gcctccgtca agatgtcctg caaggccagc gggtacactt tcaccagcta cgtcatgcat 180
tgggtgaagc agaagccagg ccaggggctt gagtggattg ggtacatcaa cccctacaac 240
gacgggacca aatacaacga gaaattcaag ggcaaagcca cactcacctc cgataagtcc 300
tcctctaccg cctacatgga gctcagctcc ctgacctccg aggatagcgc tgtgtattac 360
tgcgcaaggg gcacatacta ctatggctct agggtgttcg actactgggg gcagggcact 420
actctcacag tgagctcagg cggaggaggc agtggcggag gggaagtgg gggcggcggc 480 agcgatattg tcatgaccca ggcagcccct agtatccctg tgactccagg cgagagcgtg 540
agcatcagct gccggtccag caagagcctg ctgaacagta acggaaacac atacctctac 600
tggtttctgc agaggcccgg ccagagccct cagctgctga tttaccgcat gtcaaatctt 660
gcctctgggg tgcccgatag atttagtggg agcggatccg gcacagcttt tacattgcgg 720
atctccagag tcgaggccga agacgtgggg gtctattact gtatgcaaca cctggaatac 780
ccctttacct tcggagccgg cacaaagctg gagctgaagc gggctgacac cacaaccccc 840
gctccaaggc cccctacccc cgcaccaact attgcctccc agccactctc actgcggcct 900
gaggcctgtc ggcccgctgc tggaggcgca gtgcatacaa ggggcctcga tttcgcctgc 960
gattttttta tcccattgtt ggtggtgatt ctgtttgctg tggacacagg attatttatc 1020
tcaactcagc agcaggtcac atttctcttg aagattaaga gaaccaggaa aggcttcaga 1080
cttctgaacc cacatcctaa gccaaacccc aaaaacaac 1119

<210> SEQ ID NO 215
<211> LENGTH: 1119
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRalpha-4g7scFV-CD8 chain of multichain CAR

<400> SEQUENCE: 215
atggctcctg ccatggaatc ccctactcta ctgtgtgtag ccttactgtt cttcgctcca 60
gatggcgtgt tagcagaggt gcagttgcag cagtcagggc cagagttgat taagcccgga 120
gcctccgtca agatgtcctg caaggccagc gggtacactt tcaccagcta cgtcatgcat 180
tgggtgaagc agaagccagg ccaggggctt gagtggattg ggtacatcaa cccctacaac 240
gacgggacca aatacaacga gaaattcaag ggcaaagcca cactcacctc cgataagtcc 300
tcctctaccg cctacatgga gctcagctcc ctgacctccg aggatagcgc tgtgtattac 360
tgcgcaaggg gcacatacta ctatggctct agggtgttcg actactgggg gcagggcact 420
actctcacag tgagctcagg cggaggaggc agtggcggag gggaagtgg gggcggcggc 480 agcgatattg tcatgaccca ggcagcccct agtatccctg tgactccagg cgagagcgtg 540
agcatcagct gccggtccag caagagcctg ctgaacagta acggaaacac atacctctac 600
tggtttctgc agaggcccgg ccagagccct cagctgctga tttaccgcat gtcaaatctt 660
gcctctgggg tgcccgatag atttagtggg agcggatccg gcacagcttt tacattgcgg 720
atctccagag tcgaggccga agacgtgggg gtctattact gtatgcaaca cctggaatac 780
ccctttacct tcggagccgg cacaaagctg gagctgaagc gggctgacac cacaaccccc 840
gctccaaggc cccctacccc cgcaccaact attgcctccc agccactctc actgcggcct 900
gaggcctgtc ggcccgctgc tggaggcgca gtgcatacaa ggggcctcga tttcgcctgc 960
gattttttta tcccattgtt ggtggtgatt ctgtttgctg tggacacagg attatttatc 1020
tcaactcagc agcaggtcac atttctcttg aagattaaga gaaccaggaa aggcttcaga 1080
cttctgaacc cacatcctaa gccaaacccc aaaaacaac 1119

<210> SEQ ID NO 216
<211> LENGTH: 1245
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRalpha-4g7scFV-CD8-4-1BB chain of multichain CAR

<400> SEQUENCE: 216
atggctcctg ccatggaatc ccctactcta ctgtgtgtag ccttactgtt cttcgctcca 60
gatggcgtgt tagcagaggt gcagttgcag cagtcagggc cagagttgat taagcccgga 120
gcctccgtca agatgtcctg caaggccagc gggtacactt tcaccagcta cgtcatgcat 180
tgggtgaagc agaagccagg ccaggggctt gagtggattg ggtacatcaa cccctacaac 240
gacgggacca aatacaacga gaaattcaag ggcaaagcca cactcacctc cgataagtcc 300
tcctctaccg cctacatgga gctcagctcc ctgacctccg aggatagcgc tgtgtattac 360
tgcgcaaggg gcacatacta ctatggctct agggtgttcg actactgggg gcagggcact 420
actctcacag tgagctcagg cggaggaggc agtggcggag gggaagtggg gggcggcggc 480
agcgatattg tcatgaccca ggcagcccct agtatccctg tgactccagg cgagagcgtg 540
agcatcagct gccggtccag caagagcctg ctgaacagta acggaaacac atacctctac 600
tggtttctgc agaggcccgg ccagagccct cagctgctga tttaccgcat gtcaaatctt 660
gcctctgggg tgcccgatag atttagtggg agcggatccg gcacagcttt tacattgcgg 720
atctccagag tcgaggccga agacgtgggg gtctattact gtatgcaaca cctggaatac 780
ccctttacct tcggagccgg cacaaagctg gagctgaagc gggctgacac cacaaccccc 840
gctccaaggc cccctacccc cgcaccaact attgcctccc agccactctc actgcggcct 900
gaggcctgtc ggcccgctgc tggaggcgca gtgcatacaa ggggcctcga tttcgcctgc 960
gattttttta tcccattgtt ggtggtgatt ctgtttgctg tggacacagg attatttatc 1020
tcaactcagc agcaggtcac atttctcttg aagattaaga gaaccaggaa aggcttcaga 1080
cttctgaacc cacatcctaa gccaaacccc aaaaacaaca aacggggccg gaagaagctc 1140
ctctacattt ttaagcagcc tttcatgcgg ccagtgcaga caacccaaga ggaggatggg 1200
tgttcctgca gattccctga ggaagaggaa ggcgggtgcg agctg 1245

<210> SEQ ID NO 217
<211> LENGTH: 771
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRbeta-deltaITAM-41BB chain of multichain CAR

<400> SEQUENCE: 217

```
atggacacag aaagtaatag gagagcaaat cttgctctcc cacaggagcc ttccagtgtg      60

cctgcatttg aagtcttgga aatatctccc caggaagtat cttcaggcag actattgaag     120

tcggcctcat ccccaccact gcatacatgg ctgacagttt tgaaaaaaga gcaggagttc     180

ctgggggtaa cacaaattct gactgctatg atatgccttt gttttggaac agttgtctgc     240

tctgtacttg atatttcaca cattgaggga gacatttttt catcatttaa agcaggttat     300

ccattctggg gagccatatt tttttctatt tctggaatgt tgtcaattat atctgaaagg     360

agaaatgcaa catatctggt gagaggaagc ctgggagcaa acactgccag cagcatagct     420

gggggaacgg gaattaccat cctgatcatc aacctgaaga agagcttggc ctatatccac     480

atccacagtt gccagaaatt ttttgagacc aagtgcttta tggcttcctt ttccactgaa     540

attgtagtga tgatgctgtt tctcaccatt ctgggacttg gtagtgctgt gtcactcaca     600

atctgtggag ctggggaaga actcaaagga aacaaggttc cagagaaacg gggccggaag     660

aagctcctct acatttttaa gcagcctttc atgcggccag tgcagacaac ccaagaggag     720

gatgggtgtt cctgcagatt ccctgaggaa gaggaaggcg ggtgcgagct g              771
```

<210> SEQ ID NO 218
<211> LENGTH: 1107
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRbeta-deltaITAM-41BB-CD3zeta chain of multichain CAR

<400> SEQUENCE: 218

```
atggacacag aaagtaatag gagagcaaat cttgctctcc cacaggagcc ttccagtgtg      60

cctgcatttg aagtcttgga aatatctccc caggaagtat cttcaggcag actattgaag     120

tcggcctcat ccccaccact gcatacatgg ctgacagttt tgaaaaaaga gcaggagttc     180

ctgggggtaa cacaaattct gactgctatg atatgccttt gttttggaac agttgtctgc     240

tctgtacttg atatttcaca cattgaggga gacatttttt catcatttaa agcaggttat     300

ccattctggg gagccatatt tttttctatt tctggaatgt tgtcaattat atctgaaagg     360

agaaatgcaa catatctggt gagaggaagc ctgggagcaa acactgccag cagcatagct     420

gggggaacgg gaattaccat cctgatcatc aacctgaaga agagcttggc ctatatccac     480

atccacagtt gccagaaatt ttttgagacc aagtgcttta tggcttcctt ttccactgaa     540

attgtagtga tgatgctgtt tctcaccatt ctgggacttg gtagtgctgt gtcactcaca     600

atctgtggag ctggggaaga actcaaagga aacaaggttc cagagaaacg gggccggaag     660

aagctcctct acatttttaa gcagcctttc atgcggccag tgcagacaac ccaagaggag     720

gatgggtgtt cctgcagatt ccctgaggaa gaggaaggcg ggtgcgagct gagagtgaag     780

ttctccagga gcgcagatgc ccccgcctat caacagggcc agaaccagct ctacaacgag     840

cttaacctcg ggaggcgcga agaatacgac gtgttggata agagaagggg gcgggacccc     900
```

```
gagatgggag gaaagccccg gaggaagaac cctcaggagg gcctgtacaa cgagctgcag    960

aaggataaga tggccgaggc ctactcagag atcgggatga agggggagcg gcgccgcggg   1020

aaggggcacg atgggctcta ccaggggctg agcacagcca caaaggacac atacgacgcc   1080

ttgcacatgc aggcccttcc accccgg                                       1107
```

<210> SEQ ID NO 219
<211> LENGTH: 858
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRbeta-41BB chain of multi-chain CAR

<400> SEQUENCE: 219

```
atggacacag aaagtaatag gagagcaaat cttgctctcc cacaggagcc ttccagtgtg     60

cctgcatttg aagtcttgga aatatctccc caggaagtat cttcaggcag actattgaag    120

tcggcctcat ccccaccact gcatacatgg ctgacagttt tgaaaaaaga gcaggagttc    180

ctgggggtaa cacaaattct gactgctatg atatgccttt gttttggaac agttgtctgc    240

tctgtacttg atatttcaca cattgaggga gacatttttt catcatttaa agcaggttat    300

ccattctggg gagccatatt tttttctatt tctggaatgt tgtcaattat atctgaaagg    360

agaaatgcaa catatctggt gagaggaagc ctgggagcaa acactgccag cagcatagct    420

gggggaacgg gaattaccat cctgatcatc aacctgaaga agagcttggc ctatatccac    480

atccacagtt gccagaaatt ttttgagacc aagtgcttta tggcttcctt ttccactgaa    540

attgtagtga tgatgctgtt tctcaccatt ctgggacttg gtagtgctgt gtcactcaca    600

atctgtggag ctggggaaga actcaaagga aacaaggttc cagaggatcg tgtttatgaa    660

gaattaaaca tatattcagc tacttacagt gagttggaag acccagggga aatgtctcct    720

cccattgatt taaaacgggg ccggaagaag ctcctctaca tttttaagca gcctttcatg    780

cggccagtgc agacaaccca agaggaggat gggtgttcct gcagattccc tgaggaagag    840

gaaggcgggt gcgagctg                                                  858
```

<210> SEQ ID NO 220
<211> LENGTH: 981
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRbeta-deltaITAM-CD3zeta chain of multi-chain
      CAR

<400> SEQUENCE: 220

```
atggacacag aaagtaatag gagagcaaat cttgctctcc cacaggagcc ttccagtgtg     60

cctgcatttg aagtcttgga aatatctccc caggaagtat cttcaggcag actattgaag    120

tcggcctcat ccccaccact gcatacatgg ctgacagttt tgaaaaaaga gcaggagttc    180

ctgggggtaa cacaaattct gactgctatg atatgccttt gttttggaac agttgtctgc    240

tctgtacttg atatttcaca cattgaggga gacatttttt catcatttaa agcaggttat    300

ccattctggg gagccatatt tttttctatt tctggaatgt tgtcaattat atctgaaagg    360

agaaatgcaa catatctggt gagaggaagc ctgggagcaa acactgccag cagcatagct    420

gggggaacgg gaattaccat cctgatcatc aacctgaaga agagcttggc ctatatccac    480
```

atccacagtt gccagaaatt ttttgagacc aagtgcttta tggcttcctt ttccactgaa 540
attgtagtga tgatgctgtt tctcaccatt ctgggacttg gtagtgctgt gtcactcaca 600
atctgtggag ctggggaaga actcaaagga aacaaggttc cagagagagt gaagttctcc 660
aggagcgcag atgcccccgc ctatcaacag ggccagaacc agctctacaa cgagcttaac 720
ctcgggaggc gcgaagaata cgacgtgttg gataagagaa gggggcggga ccccgagatg 780
ggaggaaagc cccggaggaa gaaccctcag gagggcctgt acaacgagct gcagaaggat 840
aagatggccg aggcctactc agagatcggg atgaaggggg agcggcgccg cgggaagggg 900
cacgatgggc tctaccaggg gctgagcaca gccacaaagg acacatacga cgccttgcac 960
atgcaggccc ttccaccccg g 981

<210> SEQ ID NO 221
<211> LENGTH: 648
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRgamma-delta ITAM-41BB-CD3zeta chain of multi-chain CAR

<400> SEQUENCE: 221
atgattccag cagtggtctt gctcttactc cttttggttg aacaagcagc ggccctggga 60
gagcctcagc tctgctatat cctggatgcc atcctgtttc tgtatggaat tgtcctcacc 120
ctcctctact gtcgactgaa gatccaagtg cgaaaggcag ctataaccag ctatgagaaa 180
tcaaaacggg gccggaagaa gctcctctac atttttaagc agcctttcat gcggccagtg 240
cagacaaccc aagaggagga tgggtgttcc tgcagattcc ctgaggaaga ggaaggcggg 300
tgcgagctga gagtgaagtt ctccaggagc gcagatgccc ccgcctatca acagggccag 360
aaccagctct acaacgagct taacctcggg aggcgcgaag aatacgacgt gttggataag 420
agaagggggc gggaccccga gatgggagga aagccccgga ggaagaaccc tcaggagggc 480
ctgtacaacg agctgcagaa ggataagatg gccgaggcct actcagagat cgggatgaag 540
ggggagcggc gccgcgggaa ggggcacgat gggctctacc aggggctgag cacagccaca 600
aaggacacat acgacgcctt gcacatgcag gcccttccac cccggtga 648

<210> SEQ ID NO 222
<211> LENGTH: 522
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRgamma-deltaITAM-CD3zeta chain of multi-chain CAR

<400> SEQUENCE: 222
atgattccag cagtggtctt gctcttactc cttttggttg aacaagcagc ggccctggga 60
gagcctcagc tctgctatat cctggatgcc atcctgtttc tgtatggaat tgtcctcacc 120
ctcctctact gtcgactgaa gatccaagtg cgaaaggcag ctataaccag ctatgagaaa 180
tcaagagtga agttctccag gagcgcagat gcccccgcct atcaacaggg ccagaaccag 240
ctctacaacg agcttaacct cgggaggcgc gaagaatacg acgtgttgga taagagaagg 300
gggcgggacc ccgagatggg aggaaagccc cggaggaaga accctcagga gggcctgtac 360
aacgagctgc agaaggataa gatggccgag gcctactcag agatcgggat gaagggggag 420
cggcgccgcg ggaaggggca cgatgggctc taccaggggc tgagcacagc cacaaaggac 480
acatacgacg ccttgcacat gcaggccctt ccaccccggt ga 522

<210> SEQ ID NO 223
<211> LENGTH: 597
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: FcRgamma-CD3zeta chain of multi-chain CAR

<400> SEQUENCE: 223
atgattccag cagtggtctt gctcttactc cttttggttg aacaagcagc ggccctggga 60
gagcctcagc tctgctatat cctggatgcc atcctgtttc tgtatggaat tgtcctcacc 120
ctcctctact gtcgactgaa gatccaagtg cgaaaggcag ctataaccag ctatgagaaa 180
tcagatggtg tttacacggg cctgagcacc aggaaccagg agacttacga gactctgaag 240
catgagaaac caccacagag agtgaagttc tccaggagcg cagatgcccc cgcctatcaa 300
cagggccaga accagctcta caacgagctt aacctcggga ggcgcgaaga atacgacgtg 360
ttggataaga gaagggggcg ggaccccgag atgggaggaa agccccggag gaagaaccct 420
caggagggcc tgtacaacga gctgcagaag gataagatgg ccgaggccta ctcagagatc 480
gggatgaagg gggagcggcg ccgcgggaag gggcacgatg ggctctacca ggggctgagc 540
acagccacaa aggacacata cgacgccttg cacatgcagg cccttccacc ccggtga 597

<210> SEQ ID NO 224
<211> LENGTH: 2247
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: csm1

<400> SEQUENCE: 224
atggctcctg ccatggaatc ccctactcta ctgtgtgtag ccttactgtt cttcgctcca 60
gatggcgtgt tagcagaggt gcagttgcag cagtcagggc cagagttgat taagcccgga 120
gcctccgtca agatgtcctg caaggccagc gggtacactt tcaccagcta cgtcatgcat 180
tgggtgaagc agaagccagg ccaggggctt gagtggattg ggtacatcaa cccctacaac 240
gacgggacca aatacaacga gaaattcaag ggcaaagcca cactcacctc cgataagtcc 300
tcctctaccg cctacatgga gctcagctcc ctgacctccg aggatagcgc tgtgtattac 360
tgcgcaaggg gcacatacta ctatggctct agggtgttcg actactgggg gcagggcact 420
actctcacag tgagctcagg cggaggaggc agtggcggag gggaagtggg gggcggcggc 480
agcgatattg tcatgaccca ggcagcccct agtatccctg tgactccagg cgagagcgtg 540
agcatcagct gccggtccag caagagcctg ctgaacagta acggaaacac atacctctac 600
tggtttctgc agaggcccgg ccagagccct cagctgctga tttaccgcat gtcaaatctt 660
gcctctgggg tgcccgatag atttagtggg agcggatccg gcacagcttt tacattgcgg 720
atctccagag tcgaggccga agacgtgggg gtctattact gtatgcaaca cctggaatac 780
ccctttacct tcggagccgg cacaaagctg gagctgaagc gggctgacac cacaaccccc 840
gctccaaggc cccctacccc cgcaccaact attgcctccc agccactctc actgcggcct 900
gaggcctgtc ggcccgctgc tggaggcgca gtgcatacaa ggggcctcga tttcgcctgc 960 gatttttta tcccattgtt ggtggtgatt ctgtttgctg tggacacagg attatttatc 1020
tcaactcagc agcaggtcac atttctcttg aagattaaga gaaccaggaa aggcttcaga 1080
cttctgaacc cacatcctaa gccaaacccc aaaaacaaca gagccgaggg cagaggcagc 1140
ctgctgacct gcggcgacgt ggaggagaac ccaggcccca tggacacaga aagtaatagg 1200
agagcaaatc ttgctctccc acaggagcct tccagtgtgc ctgcatttga agtcttggaa 1260
atatctcccc aggaagtatc ttcaggcaga ctattgaagt cggcctcatc cccaccactg 1320
catacatggc tgacagtttt gaaaaaagag caggagttcc tgggggtaac acaaattctg 1380
actgctatga tatgcctttg ttttggaaca gttgtctgct ctgtacttga tatttcacac 1440
attgagggag acattttttc atcatttaaa gcaggttatc cattctgggg agccatattt 1500
ttttctattt ctggaatgtt gtcaattata tctgaaagga gaaatgcaac atatctggtg 1560
agaggaagcc tgggagcaaa cactgccagc agcatagctg gggaacggg aattaccatc 1620 ctgatcatca acctgaagaa gagcttggcc tatatccaca tccacagttg ccagaaattt 1680
tttgagacca agtgctttat ggcttccttt tccactgaaa ttgtagtgat gatgctgttt 1740
ctcaccattc tgggacttgg tagtgctgtg tcactcacaa tctgtggagc tggggaagaa 1800
ctcaaaggaa acaaggttcc agaggatcgt gtttatgaag aattaaacat atattcagct 1860
acttacagtg agttggaaga cccaggggaa atgtctcctc ccattgattt aggttctggc 1920
gtgaaacaga ctttgaattt tgaccttctc aagttggcgg gagacgtgga gtccaaccca 1980
gggcccatga ttccagcagt ggtcttgctc ttactccttt tggttgaaca agcagcggcc 2040
ctgggagagc ctcagctctg ctatatcctg gatgccatcc tgtttctgta tggaattgtc 2100
ctcaccctcc tctactgtcg actgaagatc caagtgcgaa aggcagctat aaccagctat 2160
gagaaatcag atggtgttta cacgggcctg agcaccagga accaggagac ttacgagact 2220
ctgaagcatg agaaaccacc acagtga 2247

<210> SEQ ID NO 225
<211> LENGTH: 2634
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: csm2

<400> SEQUENCE: 225
atggctcctg ccatggaatc ccctactcta ctgtgtgtag ccttactgtt cttcgctcca 60
gatggcgtgt tagcagaggt gcagttgcag cagtcagggc cagagttgat taagcccgga 120
gcctccgtca agatgtcctg caaggccagc gggtacactt tcaccagcta cgtcatgcat 180
tgggtgaagc agaagccagg ccaggggctt gagtggattg ggtacatcaa cccctacaac 240
gacgggacca aatacaacga gaaattcaag ggcaaagcca cactcacctc cgataagtcc 300
tcctctaccg cctacatgga gctcagctcc ctgacctccg aggatagcgc tgtgtattac 360
tgcgcaaggg gcacatacta ctatggctct agggtgttcg actactgggg gcagggcact 420
actctcacag tgagctcagg cggaggaggc agtggcggag gggaagtgg gggcggcggc 480 agcgatattg tcatgaccca ggcagcccct agtatccctg tgactccagg cgagagcgtg 540
agcatcagct gccggtccag caagagcctg ctgaacagta acggaaacac atacctctac 600

-continued

```
tggtttctgc agaggcccgg ccagagccct cagctgctga tttaccgcat gtcaaatctt    660

gcctctgggg tgcccgatag atttagtggg agcggatccg gcacagcttt tacattgcgg    720

atctccagag tcgaggccga agacgtgggg gtctattact gtatgcaaca cctggaatac    780

ccctttacct tcggagccgg cacaaagctg gagctgaagc gggctgacac cacaaccccc    840

gctccaaggc cccctacccc cgcaccaact attgcctccc agccactctc actgcggcct    900

gaggcctgtc ggcccgctgc tggaggcgca gtgcatacaa ggggcctcga tttcgcctgc    960

gattttttta tcccattgtt ggtggtgatt ctgtttgctg tggacacagg attatttatc   1020

tcaactcagc agcaggtcac atttctcttg aagattaaga gaaccaggaa aggcttcaga   1080

cttctgaacc cacatcctaa gccaaacccc aaaaacaaca gagccgaggg cagaggcagc   1140

ctgctgacct gcggcgacgt ggaggagaac ccaggcccca tggacacaga aagtaatagg   1200

agagcaaatc ttgctctccc acaggagcct tccagtgtgc ctgcatttga agtcttggaa   1260

atatctcccc aggaagtatc ttcaggcaga ctattgaagt cggcctcatc cccaccactg   1320

catacatggc tgacagtttt gaaaaaagag caggagttcc tgggggtaac acaaattctg   1380

actgctatga tatgcctttg ttttggaaca gttgtctgct ctgtacttga tatttcacac   1440

attgagggag acattttttc atcatttaaa gcaggttatc cattctgggg agccatattt   1500

ttttctattt ctggaatgtt gtcaattata tctgaaagga gaaatgcaac atatctggtg   1560

agaggaagcc tgggagcaaa cactgccagc agcatagctg gggaacggg aattaccatc   1620

ctgatcatca acctgaagaa gagcttggcc tatatccaca tccacagttg ccagaaattt   1680

tttgagacca agtgctttat ggcttccttt tccactgaaa ttgtagtgat gatgctgttt   1740

ctcaccattc tgggacttgg tagtgctgtg tcactcacaa tctgtggagc tggggaagaa   1800

ctcaaaggaa acaaggttcc agaggatcgt gtttatgaag aattaaacat atattcagct   1860

acttacagtg agttggaaga cccaggggaa atgtctcctc ccattgattt aggttctggc   1920

gtgaaacaga ctttgaattt tgaccttctc aagttggcgg gagacgtgga gtccaaccca   1980

gggcccatga ttccagcagt ggtcttgctc ttactccttt tggttgaaca agcagcggcc   2040

ctgggagagc ctcagctctg ctatatcctg gatgccatcc tgtttctgta tggaattgtc   2100

ctcaccctcc tctactgtcg actgaagatc caagtgcgaa aggcagctat aaccagctat   2160

gagaaatcaa aacggggccg gaagaagctc ctctacattt ttaagcagcc tttcatgcgg   2220

ccagtgcaga caacccaaga ggaggatggg tgttcctgca gattccctga ggaagaggaa   2280

ggcgggtgcg agctgagagt gaagttctcc aggagcgcag atgcccccgc ctatcaacag   2340

ggccagaacc agctctacaa cgagcttaac ctcgggaggc gcgaagaata cgacgtgttg   2400

gataagagaa gggggcggga ccccgagatg ggaggaaagc cccggaggaa gaaccctcag   2460

gagggcctgt acaacgagct gcagaaggat aagatggccg aggcctactc agagatcggg   2520

atgaaggggg agcggcgccg cgggaagggg cacgatgggc tctaccaggg gctgagcaca   2580

gccacaaagg acacatacga cgccttgcac atgcaggccc ttccaccccg gtga         2634
```

<210> SEQ ID NO 226
<211> LENGTH: 2547
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: csm4

<400> SEQUENCE: 226

-continued

```
atggctcctg ccatggaatc ccctactcta ctgtgtgtag ccttactgtt cttcgctcca     60
gatggcgtgt tagcagaggt gcagttgcag cagtcagggc cagagttgat taagcccgga    120
gcctccgtca agatgtcctg caaggccagc gggtacactt tcaccagcta cgtcatgcat    180
tgggtgaagc agaagccagg ccaggggctt gagtggattg ggtacatcaa cccctacaac    240
gacgggacca aatacaacga gaaattcaag ggcaaagcca cactcacctc cgataagtcc    300
tcctctaccg cctacatgga gctcagctcc ctgacctccg aggatagcgc tgtgtattac    360
tgcgcaaggg gcacatacta ctatggctct agggtgttcg actactgggg gcagggcact    420
actctcacag tgagctcagg cggaggaggc agtggcggag gggaagtgg gggcggcggc     480
agcgatattg tcatgaccca ggcagcccct agtatccctg tgactccagg cgagagcgtg    540
agcatcagct gccggtccag caagagcctg ctgaacagta acggaaacac atacctctac    600
tggtttctgc agaggcccgg ccagagccct cagctgctga tttaccgcat gtcaaatctt    660
gcctctgggg tgcccgatag atttagtggg agcggatccg gcacagcttt tacattgcgg    720
atctccagag tcgaggccga agacgtgggg gtctattact gtatgcaaca cctggaatac    780
ccctttacct tcggagccgg cacaaagctg gagctgaagc gggctgacac cacaaccccc    840
gctccaaggc cccctacccc cgcaccaact attgcctccc agccactctc actgcggcct    900
gaggcctgtc ggcccgctgc tggaggcgca gtgcatacaa ggggcctcga tttcgcctgc    960
gattttttta tcccattgtt ggtggtgatt ctgtttgctg tggacacagg attatttatc   1020
tcaactcagc agcaggtcac atttctcttg aagattaaga gaaccaggaa aggcttcaga   1080
cttctgaacc cacatcctaa gccaaacccc aaaaacaaca gagccgaggg cagaggcagc   1140
ctgctgacct gcggcgacgt ggaggagaac ccaggcccca tggacacaga aagtaatagg   1200
agagcaaatc ttgctctccc acaggagcct tccagtgtgc ctgcatttga agtcttggaa   1260
atatctcccc aggaagtatc ttcaggcaga ctattgaagt cggcctcatc cccaccactg   1320
catacatggc tgacagtttt gaaaaaagag caggagttcc tgggggtaac acaaattctg   1380
actgctatga tatgcctttg ttttggaaca gttgtctgct ctgtacttga tatttcacac   1440
attgagggag acatttttc atcatttaaa gcaggttatc cattctgggg agccatattt    1500
ttttctattt ctggaatgtt gtcaattata tctgaaagga gaaatgcaac atatctggtg   1560
agaggaagcc tgggagcaaa cactgccagc agcatagctg gggaacggg aattaccatc    1620
ctgatcatca acctgaagaa gagcttggcc tatatccaca tccacagttg ccagaaattt   1680
tttgagacca agtgctttat ggcttccttt tccactgaaa ttgtagtgat gatgctgttt   1740
ctcaccattc tgggacttgg tagtgctgtg tcactcacaa tctgtggagc tggggaagaa   1800
ctcaaaggaa acaaggttcc agagaaacgg ggccggaaga agctcctcta catttttaag   1860
cagcctttca tgcggccagt gcagacaacc caagaggagg atgggtgttc ctgcagattc   1920
cctgaggaag aggaaggcgg gtgcgagctg ggttctggcg tgaaacagac tttgaatttt   1980
gaccttctca agttggcggg agacgtggag tccaacccag ggcccatgat tccagcagtg   2040
gtcttgctct tactcctttt ggttgaacaa gcagcggccc tgggagagcc tcagctctgc   2100
tatatcctgg atgccatcct gtttctgtat ggaattgtcc tcaccctcct ctactgtcga   2160
ctgaagatcc aagtgcgaaa ggcagctata accagctatg agaaatcaag agtgaagttc   2220
tccaggagcg cagatgcccc cgcctatcaa cagggccaga accagctcta caacgagctt   2280
aacctcggga ggcgcgaaga atacgacgtg ttggataaga gaagggggcg ggaccccgag   2340
```

```
atgggaggaa agccccggag gaagaaccct caggagggcc tgtacaacga gctgcagaag   2400

gataagatgg ccgaggccta ctcagagatc gggatgaagg gggagcggcg ccgcgggaag   2460

gggcacgatg ggctctacca ggggctgagc acagccacaa aggacacata cgacgccttg   2520

cacatgcagg cccttccacc ccggtga                                       2547


<210> SEQ ID NO 227
<211> LENGTH: 2622
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: csm5

<400> SEQUENCE: 227

atggctcctg ccatggaatc ccctactcta ctgtgtgtag ccttactgtt cttcgctcca     60

gatggcgtgt tagcagaggt gcagttgcag cagtcagggc cagagttgat taagcccgga    120

gcctccgtca agatgtcctg caaggccagc gggtacactt tcaccagcta cgtcatgcat    180

tgggtgaagc agaagccagg ccaggggctt gagtggattg ggtacatcaa cccctacaac    240

gacgggacca aatacaacga gaaattcaag ggcaaagcca cactcacctc cgataagtcc    300

tcctctaccg cctacatgga gctcagctcc ctgacctccg aggatagcgc tgtgtattac    360

tgcgcaaggg gcacatacta ctatggctct agggtgttcg actactgggg gcagggcact    420

actctcacag tgagctcagg cggaggaggc agtggcggag gggaagtgg gggcggcggc    480

agcgatattg tcatgaccca ggcagcccct agtatccctg tgactccagg cgagagcgtg    540

agcatcagct gccggtccag caagagcctg ctgaacagta acggaaacac atacctctac    600

tggtttctgc agaggcccgg ccagagccct cagctgctga tttaccgcat gtcaaatctt    660

gcctctgggg tgcccgatag atttagtggg agcggatccg gcacagcttt tacattgcgg    720

atctccagag tcgaggccga agacgtgggg gtctattact gtatgcaaca cctggaatac    780

ccctttacct tcggagccgg cacaaagctg gagctgaagc gggctgacac cacaacccc    840

gctccaaggc cccctacccc cgcaccaact attgcctccc agccactctc actgcggcct    900

gaggcctgtc ggcccgctgc tggaggcgca gtgcatacaa ggggcctcga tttcgcctgc    960

gattttttta tcccattgtt ggtggtgatt ctgtttgctg tggacacagg attatttatc   1020

tcaactcagc agcaggtcac atttctcttg aagattaaga gaaccaggaa aggcttcaga   1080

cttctgaacc cacatcctaa gccaaacccc aaaaacaaca gagccgaggg cagaggcagc   1140

ctgctgacct gcggcgacgt ggaggagaac ccaggcccca tggacacaga aagtaatagg   1200

agagcaaatc ttgctctccc acaggagcct tccagtgtgc ctgcatttga agtcttggaa   1260

atatctcccc aggaagtatc ttcaggcaga ctattgaagt cggcctcatc cccaccactg   1320

catacatggc tgacagtttt gaaaaaagag caggagttcc tgggggtaac acaaattctg   1380

actgctatga tatgcctttg ttttggaaca gttgtctgct ctgtacttga tatttcacac   1440

attgagggag acattttttc atcatttaaa gcaggttatc cattctgggg agccatattt   1500

ttttctattt ctggaatgtt gtcaattata tctgaaagga gaaatgcaac atatctggtg   1560

agaggaagcc tgggagcaaa cactgccagc agcatagctg gggaacggg aattaccatc   1620

ctgatcatca acctgaagaa gagcttggcc tatatccaca tccacagttg ccagaaattt   1680

tttgagacca agtgctttat ggcttccttt tccactgaaa ttgtagtgat gatgctgttt   1740

ctcaccattc tgggacttgg tagtgctgtg tcactcacaa tctgtggagc tggggaagaa   1800
```

ctcaaaggaa acaaggttcc agagaaacgg ggccggaaga agctcctcta catttttaag 1860
cagcctttca tgcggccagt gcagacaacc caagaggagg atgggtgttc ctgcagattc 1920
cctgaggaag aggaaggcgg gtgcgagctg agagtgaagt tctccaggag cgcagatgcc 1980
cccgcctatc aacagggcca gaaccagctc tacaacgagc ttaacctcgg gaggcgcgaa 2040
gaatacgacg tgttggataa gagaaggggg cgggaccccg agatgggagg aaagccccgg 2100
aggaagaacc ctcaggaggg cctgtacaac gagctgcaga aggataagat ggccgaggcc 2160
tactcagaga tcgggatgaa gggggagcgg cgccgcggga aggggcacga tgggctctac 2220
caggggctga gcacagccac aaaggacaca tacgacgcct tgcacatgca ggcccttcca 2280
ccccggggtt ctggcgtgaa acagactttg aattttgacc ttctcaagtt ggcgggagac 2340
gtggagtcca acccagggcc catgattcca gcagtggtct tgctcttact ccttttggtt 2400
gaacaagcag cggccctggg agagcctcag ctctgctata tcctggatgc catcctgttt 2460
ctgtatggaa ttgtcctcac cctcctctac tgtcgactga agatccaagt gcgaaaggca 2520
gctataacca gctatgagaa atcagatggt gtttacacgg gcctgagcac caggaaccag 2580
gagacttacg agactctgaa gcatgagaaa ccaccacagt ga 2622

<210> SEQ ID NO 228
<211> LENGTH: 2709
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: csm6

<400> SEQUENCE: 228
atggctcctg ccatggaatc ccctactcta ctgtgtgtag ccttactgtt cttcgctcca 60
gatggcgtgt tagcagaggt gcagttgcag cagtcagggc cagagttgat taagcccgga 120
gcctccgtca agatgtcctg caaggccagc gggtacactt tcaccagcta cgtcatgcat 180
tgggtgaagc agaagccagg ccaggggctt gagtggattg ggtacatcaa cccctacaac 240
gacgggacca aatacaacga gaaattcaag ggcaaagcca cactcacctc cgataagtcc 300
tcctctaccg cctacatgga gctcagctcc ctgacctccg aggatagcgc tgtgtattac 360
tgcgcaaggg gcacatacta ctatggctct agggtgttcg actactgggg gcagggcact 420
actctcacag tgagctcagg cggaggaggc agtggcggag gggggaagtgg gggcggcggc 480 agcgatattg tcatgaccca ggcagcccct agtatccctg tgactccagg cgagagcgtg 540
agcatcagct gccggtccag caagagcctg ctgaacagta acggaaacac atacctctac 600
tggtttctgc agaggcccgg ccagagccct cagctgctga tttaccgcat gtcaaatctt 660
gcctctgggg tgcccgatag atttagtggg agcggatccg gcacagcttt tacattgcgg 720
atctccagag tcgaggccga agacgtgggg gtctattact gtatgcaaca cctggaatac 780
ccctttacct tcggagccgg cacaaagctg gagctgaagc gggctgacac cacaaccccc 840
gctccaaggc cccctacccc cgcaccaact attgcctccc agccactctc actgcggcct 900
gaggcctgtc ggcccgctgc tggaggcgca gtgcatacaa ggggcctcga tttcgcctgc 960
gattttttta tcccattgtt ggtggtgatt ctgtttgctg tggacacagg attatttatc 1020
tcaactcagc agcaggtcac atttctcttg aagattaaga gaaccaggaa aggcttcaga 1080
cttctgaacc cacatcctaa gccaaacccc aaaaacaaca gagccgaggg cagaggcagc 1140
ctgctgacct gcggcgacgt ggaggagaac ccaggcccca tggacacaga aagtaatagg 1200
agagcaaatc ttgctctccc acaggagcct tccagtgtgc ctgcatttga agtcttggaa 1260
atatctcccc aggaagtatc ttcaggcaga ctattgaagt cggcctcatc cccaccactg 1320
catacatggc tgacagtttt gaaaaaagag caggagttcc tgggggtaac acaaattctg 1380
actgctatga tatgcctttg ttttggaaca gttgtctgct ctgtacttga tatttcacac 1440
attgagggag acattttttc atcatttaaa gcaggttatc cattctgggg agccatattt 1500
ttttctattt ctggaatgtt gtcaattata tctgaaagga gaaatgcaac atatctggtg 1560
agaggaagcc tgggagcaaa cactgccagc agcatagctg gggaacggg aattaccatc 1620 ctgatcatca acctgaagaa gagcttggcc tatatccaca tccacagttg ccagaaattt 1680
tttgagacca agtgctttat ggcttccttt tccactgaaa ttgtagtgat gatgctgttt 1740
ctcaccattc tgggacttgg tagtgctgtg tcactcacaa tctgtggagc tggggaagaa 1800
ctcaaaggaa acaaggttcc agaggatcgt gtttatgaag aattaaacat atattcagct 1860
acttacagtg agttggaaga cccaggggaa atgtctcctc ccattgattt aaaacggggc 1920
cggaagaagc tcctctacat ttttaagcag cctttcatgc ggccagtgca gacaacccaa 1980
gaggaggatg ggtgttcctg cagattccct gaggaagagg aaggcgggtg cgagctgggt 2040
tctggcgtga aacagacttt gaattttgac cttctcaagt tggcgggaga cgtggagtcc 2100
aacccagggc ccatgattcc agcagtggtc ttgctcttac tccttttggt tgaacaagca 2160
gcggccctgg gagagcctca gctctgctat atcctggatg ccatcctgtt tctgtatgga 2220
attgtcctca ccctcctcta ctgtcgactg aagatccaag tgcgaaaggc agctataacc 2280
agctatgaga aatcagatgg tgtttacacg ggcctgagca ccaggaacca ggagacttac 2340
gagactctga agcatgagaa accaccacag agagtgaagt tctccaggag cgcagatgcc 2400
cccgcctatc aacagggcca gaaccagctc tacaacgagc ttaacctcgg gaggcgcgaa 2460
gaatacgacg tgttggataa gagaaggggg cgggaccccg agatgggagg aaagccccgg 2520
aggaagaacc ctcaggaggg cctgtacaac gagctgcaga aggataagat ggccgaggcc 2580
tactcagaga tcgggatgaa gggggagcgg cgccgcggga aggggcacga tgggctctac 2640
caggggctga gcacagccac aaaggacaca tacgacgcct tgcacatgca ggcccttcca 2700
ccccggtga 2709

<210> SEQ ID NO 229
<211> LENGTH: 2373
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: csm7

<400> SEQUENCE: 229
atggctcctg ccatggaatc ccctactcta ctgtgtgtag ccttactgtt cttcgctcca 60
gatggcgtgt tagcagaggt gcagttgcag cagtcagggc cagagttgat taagcccgga 120
gcctccgtca agatgtcctg caaggccagc gggtacactt tcaccagcta cgtcatgcat 180
tgggtgaagc agaagccagg ccaggggctt gagtggattg ggtacatcaa cccctacaac 240
gacgggacca aatacaacga gaaattcaag ggcaaagcca cactcacctc cgataagtcc 300
tcctctaccg cctacatgga gctcagctcc ctgacctccg aggatagcgc tgtgtattac 360
tgcgcaaggg gcacatacta ctatggctct agggtgttcg actactgggg gcagggcact 420

-continued

```
actctcacag tgagctcagg cggaggaggc agtggcggag ggggaagtgg gggcggcggc     480
agcgatattg tcatgaccca ggcagcccct agtatccctg tgactccagg cgagagcgtg     540
agcatcagct gccggtccag caagagcctg ctgaacagta acggaaacac atacctctac     600
tggtttctgc agaggcccgg ccagagccct cagctgctga tttaccgcat gtcaaatctt     660
gcctctgggg tgcccgatag atttagtggg agcggatccg gcacagcttt tacattgcgg     720
atctccagag tcgaggccga agacgtgggg gtctattact gtatgcaaca cctggaatac     780
ccctttacct tcggagccgg cacaaagctg gagctgaagc gggctgacac cacaaccccc     840
gctccaaggc cccctacccc cgcaccaact attgcctccc agccactctc actgcggcct     900
gaggcctgtc ggcccgctgc tggaggcgca gtgcatacaa ggggcctcga tttcgcctgc     960
gatttttta tcccattgtt ggtggtgatt ctgtttgctg tggacacagg attatttatc    1020
tcaactcagc agcaggtcac atttctcttg aagattaaga gaaccaggaa aggcttcaga    1080
cttctgaacc cacatcctaa gccaaacccc aaaaacaaca aacggggccg gaagaagctc    1140
ctctacattt ttaagcagcc tttcatgcgg ccagtgcaga caacccaaga ggaggatggg    1200
tgttcctgca gattccctga ggaagaggaa ggcgggtgcg agctgagagc cgagggcaga    1260
ggcagcctgc tgacctgcgg cgacgtggag gagaacccag gccccatgga cacagaaagt    1320
aataggagag caaatcttgc tctcccacag gagccttcca gtgtgcctgc atttgaagtc    1380
ttggaaatat ctccccagga agtatcttca ggcagactat tgaagtcggc ctcatcccca    1440
ccactgcata catggctgac agttttgaaa aaagagcagg agttcctggg ggtaacacaa    1500
attctgactg ctatgatatg cctttgtttt ggaacagttg tctgctctgt acttgatatt    1560
tcacacattg agggagacat tttttcatca tttaaagcag gttatccatt ctggggagcc    1620
atattttttt ctatttctgg aatgttgtca attatatctg aaaggagaaa tgcaacatat    1680
ctggtgagag gaagcctggg agcaaacact gccagcagca tagctggggg aacgggaatt    1740
accatcctga tcatcaacct gaagaagagc ttggcctata tccacatcca cagttgccag    1800
aaatttttg agaccaagtg ctttatggct tccttttcca ctgaaattgt agtgatgatg    1860
ctgtttctca ccattctggg acttggtagt gctgtgtcac tcacaatctg tggagctggg    1920
gaagaactca aaggaaacaa ggttccagag gatcgtgttt atgaagaatt aaacatatat    1980
tcagctactt acagtgagtt ggaagaccca ggggaaatgt ctcctcccat tgatttaggt    2040
tctggcgtga aacagacttt gaattttgac cttctcaagt tggcgggaga cgtggagtcc    2100
aacccagggc ccatgattcc agcagtggtc ttgctcttac tccttttggt tgaacaagca    2160
gcggccctgg gagagcctca gctctgctat atcctggatg ccatcctgtt tctgtatgga    2220
attgtcctca ccctcctcta ctgtcgactg aagatccaag tgcgaaaggc agctataacc    2280
agctatgaga aatcagatgg tgtttacacg ggcctgagca ccaggaacca ggagacttac    2340
gagactctga agcatgagaa accaccacag tga                                2373
```

<210> SEQ ID NO 230
<211> LENGTH: 2622
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: csm8

<400> SEQUENCE: 230

-continued

```
atggctcctg ccatggaatc ccctactcta ctgtgtgtag ccttactgtt cttcgctcca     60
gatggcgtgt tagcagaggt gcagttgcag cagtcagggc cagagttgat taagcccgga    120
gcctccgtca agatgtcctg caaggccagc gggtacactt tcaccagcta cgtcatgcat    180
tgggtgaagc agaagccagg ccaggggctt gagtggattg ggtacatcaa cccctacaac    240
gacgggacca aatacaacga gaaattcaag ggcaaagcca cactcacctc cgataagtcc    300
tcctctaccg cctacatgga gctcagctcc ctgacctccg aggatagcgc tgtgtattac    360
tgcgcaaggg gcacatacta ctatggctct agggtgttcg actactgggg gcagggcact    420
actctcacag tgagctcagg cggaggaggc agtggcggag ggggaagtgg gggcggcggc    480
agcgatattg tcatgaccca ggcagcccct agtatccctg tgactccagg cgagagcgtg    540
agcatcagct gccggtccag caagagcctg ctgaacagta acggaaacac atacctctac    600
tggtttctgc agaggcccgg ccagagccct cagctgctga tttaccgcat gtcaaatctt    660
gcctctgggg tgcccgatag atttagtggg agcggatccg gcacagcttt tacattgcgg    720
atctccagag tcgaggccga agacgtgggg gtctattact gtatgcaaca cctggaatac    780
ccctttacct tcggagccgg cacaaagctg gagctgaagc gggctgacac cacaaccccc    840
gctccaaggc cccctaccc cgcaccaact attgcctccc agccactctc actgcggcct    900
gaggcctgtc ggcccgctgc tggaggcgca gtgcatacaa ggggcctcga tttcgcctgc    960
gatttttta tcccattgtt ggtggtgatt ctgtttgctg tggacacagg attatttatc   1020
tcaactcagc agcaggtcac atttctcttg aagattaaga gaaccaggaa aggcttcaga   1080
cttctgaacc cacatcctaa gccaaacccc aaaaacaaca aacggggccg gaagaagctc   1140
ctctacattt ttaagcagcc tttcatgcgg ccagtgcaga caacccaaga ggaggatggg   1200
tgttcctgca gattccctga ggaagaggaa ggcgggtgcg agctgagagc cgagggcaga   1260
ggcagcctgc tgacctgcgg cgacgtggag gagaacccag gccccatgga cacagaaagt   1320
aataggagag caaatcttgc tctcccacag gagccttcca gtgtgcctgc atttgaagtc   1380
ttggaaatat ctccccagga agtatcttca ggcagactat tgaagtcggc ctcatcccca   1440
ccactgcata catggctgac agttttgaaa aaagagcagg agttcctggg ggtaacacaa   1500
attctgactg ctatgatatg cctttgtttt ggaacagttg tctgctctgt acttgatatt   1560
tcacacattg agggagacat tttttcatca tttaaagcag gttatccatt ctggggagcc   1620
atattttttt ctatttctgg aatgttgtca attatatctg aaaggagaaa tgcaacatat   1680
ctggtgagag gaagcctggg agcaaacact gccagcagca tagctggggg aacgggaatt   1740
accatcctga tcatcaacct gaagaagagc ttggcctata tccacatcca cagttgccag   1800
aaattttttg agaccaagtg ctttatggct tccttttcca ctgaaattgt agtgatgatg   1860
ctgtttctca ccattctggg acttggtagt gctgtgtcac tcacaatctg tggagctggg   1920
gaagaactca aaggaaacaa ggttccagag agagtgaagt tctccaggag cgcagatgcc   1980
cccgcctatc aacagggcca gaaccagctc tacaacgagc ttaacctcgg gaggcgcgaa   2040
gaatacgacg tgttggataa gagaaggggg cgggaccccg agatgggagg aaagccccgg   2100
aggaagaacc ctcaggaggg cctgtacaac gagctgcaga aggataagat ggccgaggcc   2160
tactcagaga tcgggatgaa gggggagcgg cgccgcggga aggggcacga tgggctctac   2220
caggggctga gcacagccac aaaggacaca tacgacgcct tgcacatgca ggcccttcca   2280
ccccggggtt ctggcgtgaa acagactttg aattttgacc ttctcaagtt ggcgggagac   2340
gtggagtcca acccagggcc catgattcca gcagtggtct tgctcttact ccttttggtt   2400
```

-continued gaacaagcag cggccctggg agagcctcag ctctgctata tcctggatgc catcctgttt 2460
ctgtatggaa ttgtcctcac cctcctctac tgtcgactga agatccaagt gcgaaaggca 2520
gctataacca gctatgagaa atcagatggt gtttacacgg gcctgagcac caggaaccag 2580
gagacttacg agactctgaa gcatgagaaa ccaccacagt ga 2622

<210> SEQ ID NO 231
<211> LENGTH: 2709
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: csm9

<400> SEQUENCE: 231
atggctcctg ccatggaatc ccctactcta ctgtgtgtag ccttactgtt cttcgctcca 60
gatggcgtgt tagcagaggt gcagttgcag cagtcagggc cagagttgat taagcccgga 120
gcctccgtca agatgtcctg caaggccagc gggtacactt tcaccagcta cgtcatgcat 180
tgggtgaagc agaagccagg ccaggggctt gagtggattg ggtacatcaa cccctacaac 240
gacgggacca aatacaacga gaaattcaag ggcaaagcca cactcacctc cgataagtcc 300
tcctctaccg cctacatgga gctcagctcc ctgacctccg aggatagcgc tgtgtattac 360
tgcgcaaggg gcacatacta ctatggctct agggtgttcg actactgggg gcagggcact 420
actctcacag tgagctcagg cggaggaggc agtggcggag gggaagtgg gggcggcggc 480 agcgatattg tcatgaccca ggcagcccct agtatccctg tgactccagg cgagagcgtg 540
agcatcagct gccggtccag caagagcctg ctgaacagta acggaaacac atacctctac 600
tggtttctgc agaggcccgg ccagagccct cagctgctga tttaccgcat gtcaaatctt 660
gcctctgggg tgcccgatag atttagtggg agcggatccg gcacagcttt tacattgcgg 720
atctccagag tcgaggccga agacgtgggg gtctattact gtatgcaaca cctggaatac 780
ccctttacct tcggagccgg cacaaagctg gagctgaagc gggctgacac cacaaccccc 840
gctccaaggc cccctacccc cgcaccaact attgcctccc agccactctc actgcggcct 900
gaggcctgtc ggcccgctgc tggaggcgca gtgcatacaa ggggcctcga tttcgcctgc 960 gatttttta tcccattgtt ggtggtgatt ctgtttgctg tggacacagg attatttatc 1020
tcaactcagc agcaggtcac atttctcttg aagattaaga gaaccaggaa aggcttcaga 1080
cttctgaacc cacatcctaa gccaaacccc aaaaacaaca aacggggccg gaagaagctc 1140
ctctacattt ttaagcagcc tttcatgcgg ccagtgcaga caacccaaga ggaggatggg 1200
tgttcctgca gattccctga ggaagaggaa ggcgggtgcg agctgagagc cgagggcaga 1260
ggcagcctgc tgacctgcgg cgacgtggag gagaacccag gccccatgga cacagaaagt 1320
aataggagag caaatcttgc tctcccacag gagccttcca gtgtgcctgc atttgaagtc 1380
ttggaaatat ctccccagga agtatcttca ggcagactat tgaagtcggc ctcatcccca 1440
ccactgcata catggctgac agttttgaaa aaagagcagg agttcctggg ggtaacacaa 1500
attctgactg ctatgatatg cctttgtttt ggaacagttg tctgctctgt acttgatatt 1560
tcacacattg agggagacat tttttcatca tttaaagcag gttatccatt ctggggagcc 1620
atattttttt ctatttctgg aatgttgtca attatatctg aaaggagaaa tgcaacatat 1680
ctggtgagag gaagcctggg agcaaacact gccagcagca tagctggggg aacgggaatt 1740

-continued accatcctga tcatcaacct gaagaagagc ttggcctata tccacatcca cagttgccag 1800
aaattttttg agaccaagtg ctttatggct tccttttcca ctgaaattgt agtgatgatg 1860
ctgtttctca ccattctggg acttggtagt gctgtgtcac tcacaatctg tggagctggg 1920
gaagaactca aaggaaacaa ggttccagag gatcgtgttt atgaagaatt aaacatatat 1980
tcagctactt acagtgagtt ggaagaccca ggggaaatgt ctcctcccat tgatttaggt 2040
tctggcgtga aacagacttt gaattttgac cttctcaagt tggcgggaga cgtggagtcc 2100
aacccagggc ccatgattcc agcagtggtc ttgctcttac tccttttggt tgaacaagca 2160
gcggccctgg gagagcctca gctctgctat atcctggatg ccatcctgtt tctgtatgga 2220
attgtcctca ccctcctcta ctgtcgactg aagatccaag tgcgaaaggc agctataacc 2280
agctatgaga aatcagatgg tgtttacacg ggcctgagca ccaggaacca ggagacttac 2340
gagactctga agcatgagaa accaccacag agagtgaagt tctccaggag cgcagatgcc 2400
cccgcctatc aacagggcca gaaccagctc tacaacgagc ttaacctcgg gaggcgcgaa 2460
gaatacgacg tgttggataa gagaaggggg cgggaccccg agatgggagg aaagccccgg 2520
aggaagaacc ctcaggaggg cctgtacaac gagctgcaga aggataagat ggccgaggcc 2580
tactcagaga tcgggatgaa gggggagcgg cgccgcggga aggggcacga tgggctctac 2640
caggggctga gcacagccac aaaggacaca tacgacgcct tgcacatgca ggcccttcca 2700
ccccggtga 2709

<210> SEQ ID NO 232
<211> LENGTH: 2670
<212> TYPE: DNA
<213> ORGANISM: Artificial sequence
<220> FEATURE:
<223> OTHER INFORMATION: Synthetic polynucleotide
<220> FEATURE:
<223> OTHER INFORMATION: csm10

<400> SEQUENCE: 232
atggctcctg ccatggaatc ccctactcta ctgtgtgtag ccttactgtt cttcgctcca 60
gatggcgtgt tagcagaggt gcagttgcag cagtcagggc cagagttgat taagcccgga 120
gcctccgtca agatgtcctg caaggccagc gggtacactt tcaccagcta cgtcatgcat 180
tgggtgaagc agaagccagg ccaggggctt gagtggattg ggtacatcaa cccctacaac 240
gacgggacca aatacaacga gaaattcaag ggcaaagcca cactcacctc cgataagtcc 300
tcctctaccg cctacatgga gctcagctcc ctgacctccg aggatagcgc tgtgtattac 360
tgcgcaaggg gcacatacta ctatggctct agggtgttcg actactgggg gcagggcact 420
actctcacag tgagctcagg cggaggaggc agtggcggag gggggaagtgg gggcggcggc 480 agcgatattg tcatgaccca ggcagcccct agtatccctg tgactccagg cgagagcgtg 540
agcatcagct gccggtccag caagagcctg ctgaacagta acggaaacac atacctctac 600
tggtttctgc agaggcccgg ccagagccct cagctgctga tttaccgcat gtcaaatctt 660
gcctctgggg tgcccgatag atttagtggg agcggatccg gcacagcttt tacattgcgg 720
atctccagag tcgaggccga agacgtgggg gtctattact gtatgcaaca cctggaatac 780
ccctttacct tcggagccgg cacaaagctg gagctgaagc gggctgacac cacaaccccc 840
gctccaaggc cccctacccc cgcaccaact attgcctccc agccactctc actgcggcct 900
gaggcctgtc ggcccgctgc tggaggcgca gtgcatacaa ggggcctcga tttcgcctgc 960 gatttttta tcccattgtt ggtggtgatt ctgtttgctg tggacacagg attatttatc 1020

-continued

```
tcaactcagc agcaggtcac atttctcttg aagattaaga gaaccaggaa aggcttcaga   1080
cttctgaacc cacatcctaa gccaaacccc aaaaacaacc ggagcaagcg gagcagaggc   1140
ggccacagcg actacatgaa catgaccccc agacggcctg gccccacccg gaagcactac   1200
cagccctacg ccccacccag ggactttgcc gcctaccggt ccagagccga gggcagaggc   1260
agcctgctga cctgcggcga cgtggaggag aacccaggcc ccatggacac agaaagtaat   1320
aggagagcaa atcttgctct cccacaggag ccttccagtg tgcctgcatt tgaagtcttg   1380
gaaatatctc cccaggaagt atcttcaggc agactattga agtcggcctc atccccacca   1440
ctgcatacat ggctgacagt tttgaaaaaa gagcaggagt tcctgggggt aacacaaatt   1500
ctgactgcta tgatatgcct ttgttttgga acagttgtct gctctgtact tgatatttca   1560
cacattgagg gagacatttt ttcatcattt aaagcaggtt atccattctg ggagccata    1620
tttttttcta tttctggaat gttgtcaatt atatctgaaa ggagaaatgc aacatatctg   1680
gtgagaggaa gcctgggagc aaacactgcc agcagcatag ctgggggaac gggaattacc   1740
atcctgatca tcaacctgaa gaagagcttg gcctatatcc acatccacag ttgccagaaa   1800
tttttgaga ccaagtgctt tatggcttcc ttttccactg aaattgtagt gatgatgctg    1860
tttctcacca ttctgggact tggtagtgct gtgtcactca caatctgtgg agctggggaa   1920
gaactcaaag gaaacaaggt tccagagaaa cggggccgga agaagctcct ctacatttt    1980
aagcagcctt tcatgcggcc agtgcagaca acccaagagg aggatgggtg ttcctgcaga   2040
ttccctgagg aagaggaagg cgggtgcgag ctgggttctg gcgtgaaaca gactttgaat   2100
tttgaccttc tcaagttggc gggagacgtg gagtccaacc cagggcccat gattccagca   2160
gtggtcttgc tcttactcct tttggttgaa caagcagcgg ccctgggaga gcctcagctc   2220
tgctatatcc tggatgccat cctgtttctg tatggaattg tcctcaccct cctctactgt   2280
cgactgaaga tccaagtgcg aaaggcagct ataaccagct atgagaaatc aagagtgaag   2340
ttctccagga gcgcagatgc ccccgcctat caacagggcc agaaccagct ctacaacgag   2400
cttaacctcg ggaggcgcga agaatacgac gtgttggata agagaagggg gcgggacccc   2460
gagatgggag gaaagccccg gaggaagaac cctcaggagg gcctgtacaa cgagctgcag   2520
aaggataaga tggccgaggc ctactcagag atcgggatga agggggagcg gcgccgcggg   2580
aaggggcacg atgggctcta ccagggggctg agcacagcca caaaggacac atacgacgcc   2640
ttgcacatgc aggcccttcc accccggtga                                    2670
```